US009394368B2

(12) United States Patent
Brogdon et al.

(10) Patent No.: US 9,394,368 B2
(45) Date of Patent: Jul. 19, 2016

(54) TREATMENT OF CANCER USING HUMANIZED ANTI-EGFRVIII CHIMERIC ANTIGEN RECEPTOR

(71) Applicants: Jennifer Brogdon, Cambridge, MA (US); Laura Alexandra Johnson, Ardmore, PA (US); Carl H. June, Merion Station, PA (US); Andreas Loew, Cambridge, MA (US); Marcela Maus, Bryn Mawr, PA (US); John Scholler, Narberth, PA (US); Hideho Okada, Pittsburgh, PA (US)

(72) Inventors: Jennifer Brogdon, Cambridge, MA (US); Laura Alexandra Johnson, Ardmore, PA (US); Carl H. June, Merion Station, PA (US); Andreas Loew, Cambridge, MA (US); Marcela Maus, Bryn Mawr, PA (US); John Scholler, Narberth, PA (US); Hideho Okada, Pittsburgh, PA (US)

(73) Assignees: NOVARTIS AG, Basel (CH); THE TRUSTEES OF THE UNIVERSITY OF PENNSYLVANIA, Philadelphia, PA (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/184,924

(22) Filed: Feb. 20, 2014

(65) Prior Publication Data

US 2014/0322275 A1 Oct. 30, 2014

Related U.S. Application Data

(60) Provisional application No. 61/888,255, filed on Oct. 8, 2013, provisional application No. 61/767,071, filed on Feb. 20, 2013.

(51) Int. Cl.

| | |
|---|---|
| ***C12N 15/62*** | (2006.01) |
| ***C12N 15/63*** | (2006.01) |
| ***C07K 16/28*** | (2006.01) |
| ***A61K 38/00*** | (2006.01) |
| ***C07K 16/30*** | (2006.01) |
| ***A61K 35/17*** | (2015.01) |
| *A61K 39/00* | (2006.01) |

(52) U.S. Cl.

CPC ............. *C07K 16/2863* (2013.01); *A61K 35/17* (2013.01); *A61K 38/00* (2013.01); *C07K 16/3053* (2013.01); *A61K 2039/505* (2013.01); *C07K 2317/21* (2013.01); *C07K 2317/24* (2013.01); *C07K 2317/34* (2013.01); *C07K 2317/622* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,906,936 | A | 5/1999 | Eshhar et al. |
| 6,103,521 | A | 8/2000 | Capon et al. |
| 6,407,213 | B1 | 6/2002 | Carter et al. |
| 7,049,136 | B2 | 5/2006 | Seed et al. |
| 7,052,906 | B1 | 5/2006 | Lawson et al. |
| 7,129,332 | B2 | 10/2006 | Pastan et al. |
| 7,320,787 | B2 | 1/2008 | Seed et al. |
| 7,446,190 | B2 | 11/2008 | Sadelain et al. |
| 7,628,986 | B2 | 12/2009 | Weber et al. |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,252,914 | B2 | 8/2012 | Zhang et al. |
| 8,389,282 | B2 | 3/2013 | Sadelain et al. |
| 8,399,645 | B2 | 3/2013 | Campana et al. |
| 8,637,307 | B2 | 1/2014 | June et al. |
| 8,722,400 | B2 | 5/2014 | Riley et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 2003/0060444 | A1 | 3/2003 | Finney et al. |
| 2003/0148982 | A1 | 8/2003 | Brenner et al. |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2005/0113564 | A1 | 5/2005 | Campana et al. |
| 2005/0129671 | A1 | 6/2005 | Cooper et al. |
| 2007/0036773 | A1 | 2/2007 | Cooper et al. |

(Continued)

FOREIGN PATENT DOCUMENTS

| | | | |
|---|---|---|---|
| CN | 103113470 | A | 5/2013 |
| EP | 0871495 | A1 | 10/1998 |

(Continued)

OTHER PUBLICATIONS

Paul, W.E. Fundamental Immunology, 3rd Edition, 1993, pp. 292-295.*

(Continued)

*Primary Examiner* — Michael Pak

(74) *Attorney, Agent, or Firm* — Lando & Anastasi, LLP

(57) ABSTRACT

The invention provides compositions and methods for treating diseases associated with expression of EGFRvIII. The invention also relates to chimeric antigen receptor (CAR) specific to EGFRvIII, vectors encoding the same, and recombinant T cells comprising the anti-EGFRvIII CAR. The invention also includes methods of administering a genetically modified T cell expressing a CAR that comprises an anti-EGFRvIII binding domain.

38 Claims, 23 Drawing Sheets

(56) References Cited

U.S. PATENT DOCUMENTS

| | | | |
|---|---|---|---|
| 2008/0131415 | A1 | 6/2008 | Riddell et al. |
| 2010/0105136 | A1 | 4/2010 | Carter et al. |
| 2011/0052554 | A1 | 3/2011 | Zakrzewski et al. |
| 2012/0148552 | A1 | 6/2012 | Jensen |
| 2012/0321667 | A1 | 12/2012 | Sentman |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0287748 | A1 | 10/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0242049 | A1 | 8/2014 | Choi et al. |
| 2014/0271635 | A1 | 9/2014 | Brogdon et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0370045 | A1 | 12/2014 | June et al. |
| 2015/0017141 | A1 | 1/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0283178 | A1 | 10/2015 | June et al. |
| 2015/0290244 | A1 | 10/2015 | June et al. |

FOREIGN PATENT DOCUMENTS

| | | | |
|---|---|---|---|
| EP | 1226244 | A2 | 7/2002 |
| EP | 2694549 | A1 | 2/2014 |
| WO | 9623814 | A1 | 8/1996 |
| WO | 9624671 | A1 | 8/1996 |
| WO | 9723613 | A2 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 01062931 | A2 | 8/2001 |
| WO | 0233101 | A1 | 4/2002 |
| WO | 03057171 | A2 | 7/2003 |
| WO | 2005019429 | A2 | 3/2005 |
| WO | 20051118788 | A2 | 12/2005 |
| WO | 2006060878 | A1 | 6/2006 |
| WO | 2008045437 | A2 | 4/2008 |
| WO | 2010025177 | A1 | 3/2010 |
| WO | 2011059836 | A2 | 5/2011 |
| WO | 2011097477 | A1 | 8/2011 |
| WO | 2012058460 | A2 | 5/2012 |
| WO | 2012079000 | A1 | 6/2012 |
| WO | 2012082841 | A2 | 6/2012 |
| WO | 20121099973 | A2 | 7/2012 |
| WO | 2012127464 | A2 | 9/2012 |
| WO | 2012129514 | A1 | 9/2012 |
| WO | 2012135854 | A2 | 10/2012 |
| WO | 2012138475 | A1 | 10/2012 |
| WO | 2012138858 | A1 | 10/2012 |
| WO | 2013019615 | A2 | 2/2013 |
| WO | 2013026833 | A1 | 2/2013 |
| WO | 2013026837 | A1 | 2/2013 |
| WO | 2013033626 | A2 | 3/2013 |
| WO | 2013040371 | A2 | 3/2013 |
| WO | 2013040557 | A2 | 3/2013 |
| WO | 2013074916 | A1 | 5/2013 |
| WO | 2013/126712 | A1 | 8/2013 |
| WO | 2013123061 | A1 | 8/2013 |
| WO | 2013126726 | A1 | 8/2013 |
| WO | 2013126729 | A1 | 8/2013 |
| WO | 2013126733 | A1 | 8/2013 |
| WO | 2013185552 | A1 | 12/2013 |
| WO | 2014/011984 | A1 | 1/2014 |
| WO | 2014/011987 | A1 | 1/2014 |
| WO | 2014/011993 | A2 | 1/2014 |
| WO | 2014/012001 | A2 | 1/2014 |
| WO | 2014011988 | A2 | 1/2014 |
| WO | 2014011996 | A1 | 1/2014 |
| WO | 2014031687 | A1 | 2/2014 |
| WO | 2014039513 | A2 | 3/2014 |
| WO | 2014/055442 | A2 | 4/2014 |
| WO | 2014055657 | A1 | 4/2014 |
| WO | 2014100385 | A1 | 6/2014 |
| WO | 2014124143 | A1 | 8/2014 |
| WO | 2014130657 | A1 | 8/2014 |
| WO | 2014/145252 | A2 | 9/2014 |
| WO | 2015090229 | A1 | 6/2015 |
| WO | 2015090230 | A1 | 6/2015 |
| WO | 2015112626 | A1 | 7/2015 |
| WO | 2015/142661 | A1 | 9/2015 |
| WO | 2015142675 | A2 | 9/2015 |
| WO | 2015157252 | A1 | 10/2015 |

OTHER PUBLICATIONS

MacCallum R.M. et al, Antibody-antigen interactions: Contact analysis and binding site topography. J. Mol. Biol., 1998, vol. 262, p. 732-745.*

Casset F, et al. A peptide mimetic of an anti-CD4 monoclonal antibody by rational design. Biochemical and Biophysical Research Communications, 2003, vol. 307, p. 198-205.*

Bendig, M.M. Humanization of rodent monoclonal antibodies by CDR grafting. Methods: A Companion to Methods in Enzymology, 1995; vol. 8, p. 83-93.*

Beers, et al., "Immunotoxins with Increased Activity against Epidermal Growth Factor Receptor vIII-expressing Cells Produced by Antibody Phage Display" Clinical Cancer Research, 6:2835-2843 (2000).

Bullain, et al., "Genetically engineered T cells to target EGFRvIII expressing glioblastoma" J Neurooncol, 94:373-382 (2009).

Gupta, et al., "Development of an EGFRvIII specific recombinant antibody" BMC Biotechnology, 10(72):1-13 (2010).

International Search Report for International Application No. PCT/US2014/017364, mailed Jul. 8, 2014.

Lorimer, et al., "Recombinant immunotoxins specific for a mutant epidermal growth factor receptor: Targeting with a single chain antibody variable domain isolated by phage display" Proc. Natl. Acad. Sci. USA, 93:14815-14820 (1996).

Morgan, et al., "Recognition of Glioma Stem Cells by Genetically Modified T Cells Targeting EGFRvIII and Development of Adoptive Cell Therapy for Glioma" Human Gene Therapy, 23:1043-1053 (2012).

Nakayashiki, et al., "Production of a Single-chain Variable Fragment Antibody Recognizing Type III Mutant Epidermal Growth Factor Receptor" Jpn. J. Cancer Res., 91:1035-1043 (2000).

Ohno, et al., "Expression of miR-17-92 enhances anti-tumor activity of T-cells transduced with the anti-EGFRvIII chimeric antigen receptor in mice bearing human GBM xenografts" Journal of ImmunoTherapy of Cancer, 1:21 (2013).

Ohno, et al., "Retrovirally engineered T-cell-based immunotherapy targeting type III variant epidermal growth factor receptor, a glioma-associated antigen" Cancer Science, 101(12):2518-2524 (2010).

Okamoto, et al., "Monoclonal antibody against the fusion junction of a deletion-mutant epidermal growth factor receptor" British Journal of Cancer, 73:1366-1372 (1996).

Sampson, et al., "EGFRvIII mCAR-Modified T-Cell Therapy Cures Mice with Established Intracerebral Glioma and Generates Host Immunity against Tumor-Antigen Loss" Clinical Cancer Research, 20(4):972-984 (2013).

Singh, et al., "Third Generation Chimeric Antigen Receptors Containing CD137 or CD134 Signaling Endodomains Augment CD19-Specific T-Cell Effector Function" Blood: Ash Annual Meeting Abstracts; 114:22 (2009).

Brentjens et al. "Genetically Targeted T Cells Eradicate Systemic Acute Lymphoblastic Leukemia Xenografts", Clinical Cancer Research(2007) vol. 13, No. 18, pp. 5426-5435.

(56) References Cited

OTHER PUBLICATIONS

Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Friedmann-Morvinski et al., "Redirected primary T cells harboring a chimeric receptor require costimulation for their antigen-specific activation," Blood 105: 3087-3093 (2005).
Geiger et al., "Integrated src kinase and constimulatory activity enhances signal transduction through single-chain chimeric receptors in T lymphocytes," Blood 98(8): 2364-2371 (2001).
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Irving et al., "The cytoplasmic domain of the T cell receptor zeta chain is sufficient to couple to receptor-associated signal transduction pathways," Cell 64: 891-901 (1991).
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kwon et al., "cDNA sequences of two inducible T-cell genes". Proc. Natl. Acad. Sci. U.S.A. 86(6): 1963-1967 (1989).
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
NCBI accession HM_852952 accessed Sep. 29, 2015 from http://www.ncbi.nlm.nih.gov/nuccore/hm852952.
Porter et al. "Chimeric Antigen Receptor-Modified T Cells in Chronic Lymphoid Leukemia", The New England Journal of Medicine (2011) vol. 365 No. 8 pp. 725-733.
Romeo et al., "Cellular immunity to HIV activated by CD4 fused to T cell or Fc receptor polypeptides," Cell 64:1037-1046 (1991).
Sadelain et al., "Targeting Tumours with Genetically Enhanced T Lymphocytes," Nature Reviews: Cancer 3: 35-45 (2003).
Shirasu et al., "Functional Design of Chimeric T-Cell Antigen Receptors for Adoptive Immunotherapy of Cancer: Architecture and Outcomes," AntiCancer Res. 32: 2377-2384 (2012).

* cited by examiner

TREATMENT OF CANCER USING HUMANIZED ANTI-EGFRVIII CHIMERIC ANTIGEN RECEPTOR

This application claims priority to U.S. Ser. No. 61/888,255 filed Oct. 8, 2013 and U.S. Ser. No. 61/767,071, filed Feb. 20, 2013, the entire contents of each of these applications is incorporated herein by reference.

STATEMENT REGARDING FEDERALLY SPONSORED RESEARCH OR DEVELOPMENT

This invention was made with government support under 2R01 NS055140 and 1P01 CA1322714 awarded by the National Institute of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Feb. 11, 2014, is named N2067-7000WO_SL.txt and is 224,156 bytes in size.

FIELD OF THE INVENTION

The present invention relates generally to the use of T cells engineered to express a Chimeric Antigen Receptor (CAR) to treat a disease associated with expression of Epidermal Growth Factor Receptor III.

BACKGROUND OF THE INVENTION

Although the central nervous system (CNS) is often considered to be immunologically privileged (Okada et al., 2009, Crit Rev Immunol 29:1-42), recent vaccine studies in patients with malignant glioma demonstrated positive results (Aguilar et al., 2012, Curr Treat Options Oncol 13:437-450; Ruzevick, et al., 2012, Neurosurg Clin N Am 23:459-470; 15; and Okada et al., 2011, J Clin Oncol 29:330-336). However, vaccine efficacy, which relies on intact host-immune activity, can suffer from systemic suppression of immunity due to tumor expression of immunosuppressive cytokines as well as chemo- and radiotherapy. On the other hand, adoptive cell transfer (ACT) therapy with autologous T-cells, especially with T-cells transduced with Chimeric Antigen Receptors (CARs), has shown promise in pilot hematologic cancer trials (Kalos et al., 2011, Sci Transl Med 3(95):95ra73; and Porter et al., 2011, New England Journal of Medicine 365:725-733).

Enhanced expression of epidermal growth factor receptor (EGFR) is frequently detected in a variety of carcinomas, including breast, lung, head and neck, as well as glioblastoma. Spontaneous rearrangements within the EGF receptor gene were first identified in primary human glioblastoma tumors, and in nearly all cases the alterations have been reported in tumors with EGFR amplification. Three different types of mutants result from these rearrangements. The most common of these is the Type III EGF deletion-mutant receptor (EGFRvIII), which is characterized by the deletion of exons 2-7 in the EGFR mRNA. These deletions correspond to cDNA nucleotides 275-1075, which encode amino acids 6-276, presumably through alternative splicing or rearrangements. Deletion of 801 bp within the extracellular domain of the EGFR gene causes an in-frame truncation of the normal EGFR protein, resulting in a 145-kDa receptor, thereby creating a tumor specific and immunogenic epitope (reviewed in Hatanpaa et al., 2010, Neoplasia 12:675-684; Mukasa et al., 2010, Proc Natl Acad Sci USA 107:2616-2621). EGFRvIII expression has been seen in many tumor types, including glioblastoma multiforme (GBM), but is rarely observed in normal tissue. EGFRvIII is expressed in 24% to 67% of GBM cases, and in patients surviving ≥1 year, the expression of EGFRvIII is an independent negative prognostic indicator (Heimberger et al., 2005, Clin. Cancer Res. 11:1462-1466; Heimberger et al., 2005, J Transl. Med 3:38).

SUMMARY OF THE INVENTION

The invention provides, among other things, compositions and methods for controlling an immune response in patients by providing optimized and/or humanized antibodies or antibody fragments (e.g., scFv) that bind Epidermal Growth Factor Receptor III (EGFRvIII) integrated into a Chimeric Antigen Receptor (CAR) construct. In some embodiments, the invention pertains to the use of T cells engineered to express an antibody or antibody fragment that bind EGFRvIII, e.g., a humanized antibody or antibody fragment that binds EGFRvIII, integrated into a CAR to treat a cancer associated with expression of EGFRvIII. In some aspects, the invention pertains to adoptive cell transfer that may be particularly suitable for patients with glioma because the specificity, number, and functional phenotype of cells prepared ex vivo can be manipulated and controlled far better than native T-cells induced by in vivo immunization.

Accordingly, in one aspect, the invention pertains to an isolated nucleic acid molecule encoding a chimeric antigen receptor (CAR), wherein the CAR comprises an antibody or antibody fragment which includes an anti-EGFRvIII binding domain (e.g., a humanized antibody or antibody fragment that specifically binds to EGFRvIII), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-EGFRvIII binding domain described herein (e.g., a humanized antibody or antibody fragment that specifically binds to EGFRvIII as described herein), a transmembrane domain described herein, and an intracellular signaling domain described herein (e.g., an intracellular signaling domain comprising a costimulatory domain and/or a primary signaling domain).

In one embodiment, the encoded anti-EGFRvIII binding domain comprises one or more (e.g., all three) light chain complementary determining region 1 (LC CDR1), light chain complementary determining region 2 (LC CDR2), and light chain complementary determining region 3 (LC CDR3) of an anti-EGFRvIII binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-EGFRvIII binding domain described herein, e.g., a humanized anti-EGFRvIII binding domain comprising one or more, e.g., all three, LC CDRs and one or more, e.g., all three, HC CDRs. In one embodiment, the encoded anti-EGFRvIII binding domain comprises a light chain variable region described herein (e.g., in Table 2 or SEQ ID NO:11) and/or a heavy chain variable region described herein (e.g., in Table 2 or SEQ ID NO:11). In one embodiment, the encoded anti-EGFRvIII binding domain is a scFv comprising a light chain and a heavy chain of an amino acid sequence of Table 2 or SEQ ID NO:11. In an embodiment, the anti-EGFRvIII binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2 or SEQ ID NO:11, or a sequence with 95-99% identity with an amino acid sequence of Table 2 or SEQ ID NO:11; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2 or SEQ ID NO:11, or a sequence with 95-99% identity to an amino acid sequence of Table 2 or SEQ ID NO:11. In one embodiment, the anti-EGFRvIII binding domain comprises a sequence selected from a group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof. In one embodiment, the nucleic acid sequence encoding the anti-EGFRvIII binding domain comprises a sequence of SEQ ID NO:68. In one embodiment, the nucleic acid sequence encoding the anti-EGFRvIII binding domain comprises a sequence selected from a group consisting of SEQ ID NO:39, SEQ ID NO:45, SEQ ID NO:51, SEQ ID NO:57, SEQ ID NO:63, SEQ ID NO:69, SEQ ID NO:75, SEQ ID NO:81, and SEQ ID NO:98, or a sequence with 95-99% identify thereof. In one embodiment, the encoded anti-EGFRvIII binding domain is a scFv, and a light chain variable region comprising an amino acid sequence described herein, e.g., in Table 2 or SEQ ID NO:11, is attached to a heavy chain variable region comprising an amino acid sequence described herein, e.g., in Table 2 or SEQ ID NO:11, via a linker, e.g., a linker described herein. In one embodiment, the encoded anti-EGFRvIII binding domain includes a ($Gly_4$-Ser)n linker, wherein n is 1, 2, 3, 4, 5, or 6, preferably 4 (SEQ ID NO: 110). The light chain variable region and heavy chain variable region of a scFv can be, e.g., in any of the following orientations: light chain variable region-linker-heavy chain variable region or heavy chain variable region-linker-light chain variable region.

In one embodiment, the encoded CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises a sequence of SEQ ID NO: 15. In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:15, or a sequence with 95-99% identity to an amino acid sequence of SEQ ID NO:15. In one embodiment, the nucleic acid sequence encoding the transmembrane domain comprises a sequence of SEQ ID NO:8, or a sequence with 95-99% identify thereof.

In one embodiment, the encoded anti-EGFRvIII binding domain is connected to the transmembrane domain by a hinge region, e.g., a hinge region described herein. In one embodiment, the encoded hinge region comprises SEQ ID NO:14 or SEQ ID NO:104 or SEQ ID NO:106 or SEQ ID NO:108, or a sequence with 95-99% identity thereof. In one embodiment, the nucleic acid sequence encoding the hinge region comprises a sequence of SEQ ID NO:7, or SEQ ID NO:105 or SEQ ID NO:107 or SEQ ID NO:109 or a sequence with 95-99% identify thereof.

In one embodiment, the isolated nucleic acid molecule further comprises a sequence encoding a costimulatory domain, e.g., a costimulatory domain described herein. In one embodiment, the encoded costimulatory domain comprises a functional signaling domain of a protein selected from the group consisting of OX40, CD2, CD27, CD28, CDS, ICAM-1, LFA-1 (CD11a/CD18), ICOS (CD278), and 4-1BB (CD137). In one embodiment, the encoded costimulatory domain comprises a sequence of SEQ ID NO:16. In one embodiment, the encoded costimulatory domain comprises a sequence of SEQ ID NO:102. In one embodiment, the encoded costimulatory domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:102, or a sequence with 95-99% identity to an amino acid sequence of SEQ ID NO:16 or SEQ ID NO:102. In one embodiment, the nucleic acid sequence encoding the costimulatory domain comprises a sequence of SEQ ID NO:9, or a sequence with 95-99% identify thereof.

In one embodiment, the isolated nucleic acid molecule further comprises a sequence encoding an intracellular signaling domain, e.g., an intracellular signaling domain described herein. In one embodiment, the encoded intracellular signaling domain comprises a functional signaling domain of 4-1BB and/or a functional signaling domain of CD3 zeta. In one embodiment, the encoded intracellular signaling domain comprises a functional signaling domain of CD27 and/or a functional signaling domain of CD3 zeta. In one embodiment, the encoded intracellular signaling domain comprises the sequence of SEQ ID NO: 16 or SEQ ID NO: 102 and/or the sequence of SEQ ID NO: 17 or SEQ ID NO:99. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:16 and/or an amino acid sequence of SEQ ID NO:17 or SEQ ID NO:99, or a sequence with 95-99% identity to an amino acid sequence of SEQ ID NO:16 or SEQ ID NO:102 and/or an amino acid sequence of SEQ ID NO:17 or SEQ ID NO:99. In one embodiment, the encoded intracellular signaling domain comprises the sequence of SEQ ID NO: 16 or SEQ ID NO:102 and the sequence of SEQ ID NO: 17 or SEQ ID NO:99, wherein the sequences comprising the intracellular signaling domain are expressed in the same frame and as a single polypeptide chain. In one embodiment, the nucleic acid sequence encoding the intracellular signaling domain comprises a sequence of SEQ ID NO:9 or SEQ ID NO:103, or a sequence with 95-99% identify thereof, and/or a sequence of SEQ ID NO:10 or SEQ ID NO:100, or a sequence with 95-99% identity thereof.

In another aspect, the invention pertains to an isolated nucleic acid molecule encoding a CAR construct comprising a leader sequence, e.g., a leader sequence described herein, e.g., of SEQ ID NO: 13, an anti-EGFRvIII binding domain described herein, e.g., an anti-EGFRvIII binding domain comprising a LC CDR1, a LC CDR2, a LC CDR3, a HC CDR1, a HC CDR2 and a HC CDR3 described herein, e.g., an anti-EGFRvIII binding domain described in Table 2 or SEQ ID NO:11, or a sequence with 95-99% identify thereof, a hinge region described herein, e.g., of SEQ ID NO:14 or SEQ ID NO:104 or SEQ ID NO:106 or SEQ ID NO:108, a transmembrane domain described herein, e.g., having a sequence of SEQ ID NO: 15, and an intracellular signaling domain, e.g., an intracellular signaling domain described herein. In one embodiment, the encoded intracellular signaling domain comprises a costimulatory domain, e.g., a costimulatory domain described herein, e.g., a 4-1BB costimulatory domain having a sequence of SEQ ID NO:16, and/or a primary signaling domain, e.g., a primary signaling domain described herein, e.g., a CD3 zeta stimulatory domain having a sequence of SEQ ID NO:17 or SEQ ID NO:99. In one embodiment, the encoded intracellular signaling domain comprises a costimulatory domain, e.g., a costimulatory domain described herein, e.g., a CD27 costimulatory domain having a sequence of SEQ ID NO:102, and/or a primary signaling domain, e.g., a primary signaling domain described herein, e.g., a CD3 zeta stimulatory domain having a sequence of SEQ ID NO:17 or SEQ ID NO:99. In one embodiment, the encoded intracellular signaling domain comprises a costimulatory domain, e.g., a costimulatory domain described herein, e.g., a 4-1BB costimulatory domain having a sequence of SEQ ID NO:16, and a primary signaling domain, e.g., a primary signaling domain described herein, e.g., a CD3 zeta stimulatory domain having a sequence of SEQ ID NO:17 or SEQ ID NO:99. In one embodiment, the encoded intracellular signaling domain comprises a costimulatory domain, e.g., a costimulatory domain described herein, e.g., a CD27 costimulatory domain having a sequence of SEQ ID NO:102, and a primary signaling domain, e.g., a primary signaling domain described herein, e.g., a CD3 zeta stimulatory domain having a sequence of SEQ ID NO:17 or SEQ ID NO:99. In one embodiment, the isolated nucleic acid molecule encoding the CAR construct includes a leader sequence encoded by the nucleic acid sequence of SEQ ID NO:6, or a sequence with 95-99% identity thereto. In one embodiment, the isolated nucleic acid molecule encoding the CAR construct includes an anti-EGFR binding domain sequence encoded by the nucleic acid sequence of SEQ ID NO:39, SEQ ID NO:45, SEQ ID NO:51, SEQ ID NO:57, SEQ ID NO:63, SEQ ID NO:69, SEQ ID NO:75, SEQ ID NO:81, or SEQ ID NO:98, or a sequence with 95-99% identity thereto. In one embodiment, the isolated nucleic acid molecule encoding the CAR construct includes an anti-EGFR binding domain sequence encoded by the nucleic acid sequence of SEQ ID NO:69, or a sequence with 95-99% identity thereto. In one embodiment, the isolated nucleic acid molecule encoding the CAR construct includes an anti-EGFR binding domain sequence encoded by the nucleic acid sequence of SEQ ID NO:4, or a sequence with 95-99% identity thereto. In one embodiment, the isolated nucleic acid molecule encoding the CAR construct includes a transmembrane sequence encoded by the nucleic acid sequence of SEQ ID NO:8, or a sequence with 95-99% identity thereto. In one embodiment, the isolated nucleic acid molecule encoding the CAR construct includes an intracellular signaling domain sequence encoded by the nucleic acid sequence of SEQ ID NO:9, or a sequence with 95-99% identity thereto and/or a nucleic acid sequence of SEQ ID NO:10, or a sequence with 95-99% identity thereto.

In one embodiment, the isolated nucleic acid molecule comprises (e.g., consists of) a nucleic acid encoding a CAR amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90, or an amino acid sequence having 85%, 90%, 95%, 96%, 97%, 98% or 99% identity to an amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90. In one embodiment, the isolated nucleic acid molecule comprises (e.g., consists of) a nucleic acid encoding a CAR amino acid sequence of SEQ ID NO:1, or SEQ ID NO:2, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:1, or SEQ ID NO:2, or an amino acid sequence having 85%, 90%, 95%, 96%, 97%, 98% or 99% identity to an amino acid sequence of SEQ ID NO:1 or SEQ ID NO:2.

In one embodiment, the isolated nucleic acid molecule comprises (e.g., consists of) a nucleic acid sequence of SEQ ID NO:42, SEQ ID NO:48, SEQ ID NO:54, SEQ ID NO:60, SEQ ID NO:66, SEQ ID NO:72, SEQ ID NO:78, SEQ ID NO:84, or SEQ ID NO:89 or a nucleic acid sequence having 85%, 90%, 95%, 96%, 97%, 98% or 99% identity to a nucleic acid sequence of SEQ ID NO:42, SEQ ID NO:48, SEQ ID NO:54, SEQ ID NO:60, SEQ ID NO:66, SEQ ID NO:72, SEQ ID NO:78, SEQ ID NO:84, or SEQ ID NO:89. In one embodiment, the isolated nucleic acid molecule comprises (e.g., consists of) a nucleic acid sequence of SEQ ID NO:18, or SEQ ID NO:19, or a nucleic acid sequence having 85%, 90%, 95%, 96%, 97%, 98% or 99% identity to a nucleic acid sequence of SEQ ID NO:18 or SEQ ID NO:19.

In one aspect, the invention pertains to an isolated nucleic acid molecule encoding an anti-EGFRvIII binding domain, wherein the anti-EGFRvIII binding domain comprises one or more (e.g., all three) light chain complementary determining region 1 (LC CDR1), light chain complementary determining region 2 (LC CDR2), and light chain complementary determining region 3 (LC CDR3) of an anti-EGFRvIII binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-EGFRvIII binding domain described herein, e.g., a humanized anti-EGFRvIII binding domain comprising one or more, e.g., all three, LC CDRs and one or more, e.g., all three, HC CDRs. In one embodiment, the encoded anti-EGFRvIII binding domain comprises a light chain variable region described herein (e.g., in SEQ ID NO:38, 44, 50, 56, 62, 68, 74 or 80) and/or a heavy chain variable region described herein (e.g., in SEQ ID NO:38, 44, 50, 56, 62, 68, 74 or 80). In one embodiment, the encoded anti-EGFRvIII binding domain is a scFv comprising a light chain and a heavy chain of an amino acid sequence of in SEQ ID NO:38, 44, 50, 56, 62, 68, 74 or 80. In an embodiment, the anti-EGFRvIII binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in SEQ ID NO:38, 44, 50, 56, 62, 68, 74 or 80, or a sequence with 95-99% identity with an amino acid sequence of SEQ ID NO:38, 44, 50, 56, 62, 68, 74 or 80; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in SEQ ID NO:38, 44, 50, 56, 62, 68, 74 or 80, or a sequence with 95-99% identity to an amino acid sequence in SEQ ID NO:38, 44, 50, 56, 62, 68, 74 or 80. In one embodiment, the anti-EGFRvIII binding domain comprises a sequence selected from a group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof. In one embodiment, the nucleic acid sequence encoding the anti-EGFRvIII binding domain comprises a sequence selected from a group consisting of SEQ ID NO:39, SEQ ID NO:45, SEQ ID NO:51, SEQ ID NO:57, SEQ ID NO:63, SEQ ID NO:69, SEQ ID NO:75, SEQ ID NO:81, and SEQ ID NO:98, or a sequence with 95-99% identify thereof. In one embodiment, the encoded anti-EGFRvIII binding domain is a scFv, and a light chain variable region comprising an amino acid sequence described herein, e.g., in Table 2, is attached to a heavy chain variable region comprising an amino acid sequence described herein, e.g., in Table 2, via a linker, e.g., a linker described herein. In one embodiment, the encoded anti-EGFRvIII binding domain includes a ($Gly_4$-Ser)n linker, wherein n is 1, 2, 3, 4, 5, or 6, preferably 4 (SEQ ID NO: 110). The light chain variable region and heavy chain variable region of a scFv can be, e.g., in any of the following orientations: light chain variable region-linker-heavy chain variable region or heavy chain variable region-linker-light chain variable region.

In another aspect, the invention pertains to an isolated polypeptide molecule encoded by the nucleic acid molecule. In one embodiment, the isolated polypeptide molecule comprises a sequence selected from the group consisting of SEQ ID NO:43, SEQ ID NO:49, SEQ ID NO:55, SEQ ID NO:61, SEQ ID NO:67, SEQ ID NO:73, SEQ ID NO:79, SEQ ID NO:85 and SEQ ID NO:90, or a sequence with 95-99% identify thereof. In one embodiment, the isolated polypeptide comprises a sequence of SEQ ID NO:73, or a sequence with 95-99% identify thereof. In one embodiment, the isolated polypeptide comprises a sequence of SEQ ID NO:79, or a sequence with 95-99% identify thereof.

In another aspect, the invention pertains to an isolated chimeric antigen receptor (CAR) molecule comprising an anti-EGFRvIII binding domain (e.g., a humanized antibody or antibody fragment that specifically binds to EGFRvIII), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-EGFRvIII binding domain described herein (e.g., a humanized antibody or antibody fragment that specifically binds to EGFRvIII as described herein), a transmembrane domain described herein, and an intracellular signaling domain described herein (e.g., an intracellular signaling domain comprising a costimulatory domain and/or a primary signaling domain described herein).

In one embodiment, the anti-EGFRvIII binding domain comprises one or more (e.g., all three) light chain complementary determining region 1 (LC CDR1), light chain complementary determining region 2 (LC CDR2), and light chain complementary determining region 3 (LC CDR3) of an anti-EGFRvIII binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-EGFRvIII binding domain described herein, e.g., a humanized anti-EGFRvIII binding domain comprising one or more, e.g., all three, LC CDRs and one or more, e.g., all three, HC CDRs. In one embodiment, the anti-EGFRvIII binding domain comprises a light chain variable region described herein (e.g., in Table 2 or SEQ ID NO:11) and/or a heavy chain variable region described herein (e.g., in Table 2 or SEQ ID NO:11). In one embodiment, the anti-EGFRvIII binding domain is a scFv comprising a light chain and a heavy chain of an amino acid sequence listed in Table 2 or SEQ ID NO:11. In an embodiment, the anti-EGFRvIII binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 2 or SEQ ID NO:11, or a sequence with 95-99% identity with an amino acid sequence provided in Table 2 or SEQ ID NO:11; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 2 or SEQ ID NO:11, or a sequence with 95-99% identity to an amino acid sequence provided in Table 2 or SEQ ID NO:11. In one embodiment, the anti-EGFRvIII binding domain comprises a sequence selected from a group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof. In one embodiment, the anti-EGFRvIII binding domain is a scFv, and a light chain variable region comprising an amino acid sequence described herein, e.g., in Table 2 or SEQ ID NO:11, is attached to a heavy chain variable region comprising an amino acid sequence described herein, e.g., in Table 2 or SEQ ID NO:11, via a linker, e.g., a linker described herein. In one embodiment, the anti-EGFRvIII binding domain includes a ($Gly_4$-Ser)n linker, wherein n is 1, 2, 3, 4, 5, or 6, preferably 4 (SEQ ID NO: 110). The light chain variable region and heavy chain variable region of a scFv can be, e.g., in any of the following orientations: light chain variable region-linker-heavy chain variable region or heavy chain variable region-linker-light chain variable region.

In one embodiment, the isolated CAR molecule comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:15. In one embodiment, the transmembrane domain comprises an amino acid sequence having at least one, two or three modifications (e.g., substitutions) but not more than 20, 10 or 5 modifications (e.g., substitutions) of an amino acid sequence of SEQ ID NO:15, or a sequence with 95-99% identity to an amino acid sequence of SEQ ID NO:15.

In one embodiment, the anti-EGFRvIII binding domain is connected to the transmembrane domain by a hinge region, e.g., a hinge region described herein. In one embodiment, the encoded hinge region comprises SEQ ID NO:14 or SEQ ID NO:104 or SEQ ID NO:106 or SEQ ID NO:108, or a sequence with 95-99% identity thereof.

In one embodiment, the isolated CAR molecule further comprises a sequence encoding a costimulatory domain, e.g., a costimulatory domain described herein. In one embodiment, the costimulatory domain comprises a functional signaling domain of a protein selected from the group consisting of OX40, CD2, CD27, CD28, CD5, ICAM-1, LFA-1 (CD11a/CD18) and 4-1BB (CD137). In one embodiment, the costimulatory domain comprises a sequence of SEQ ID NO:16 or SEQ ID NO:102. In one embodiment, the costimulatory domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:102, or a sequence with 95-99% identity to an amino acid sequence of SEQ ID NO:16 or SEQ ID NO:102. In one embodiment, the isolated CAR molecule further comprises a sequence encoding an intracellular signaling domain, e.g., an intracellular signaling domain described herein. In one embodiment, the intracellular signaling domain comprises a functional signaling domain of 4-1BB or CD27 and/or a functional signaling domain of CD3 zeta. In one embodiment, the intracellular signaling domain comprises the sequence of SEQ ID NO: 16 or SEQ ID NO:102 and/or the sequence of SEQ ID NO:17. In one embodiment, the intracellular signaling domain comprises the sequence of SEQ ID NO: 16 or SEQ ID NO:102 and/or the sequence of SEQ ID NO:99. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:16 or SEQ ID NO:102 and/or an amino acid sequence of SEQ ID NO:17 or SEQ ID NO:99, or a sequence with 95-99% identity to an amino acid sequence of SEQ ID NO:16 or SEQ ID NO:102 and/or an amino acid sequence of SEQ ID NO:17 or SEQ ID NO:99. In one embodiment, the intracellular signaling domain comprises the sequence of SEQ ID NO: 16 or SEQ ID NO:102 and the sequence of SEQ ID NO: 17 or SEQ ID NO:99, wherein the sequences comprising the intracellular signaling domain are expressed in the same frame and as a single polypeptide chain.

In one embodiment, the isolated CAR molecule further comprises a leader sequence, e.g., a leader sequence described herein. In one embodiment, the leader sequence comprises an amino acid sequence of SEQ ID NO: 13, or a sequence with 95-99% identity to an amino acid sequence of SEQ ID NO:13.

In another aspect, the invention pertains to an isolated CAR molecule comprising a leader sequence, e.g., a leader sequence described herein, e.g., a leader sequence of SEQ ID NO: 13, or having 95-99% identity thereof, an anti-EGFRvIII binding domain described herein, e.g., an anti-EGFRvIII binding domain comprising a LC CDR1, a LC CDR2, a LC CDR3, a HC CDR1, a HC CDR2 and a HC CDR3 described herein, e.g., an anti-EGFRvIII binding domain described in Table 2 or SEQ ID NO:11, or a sequence with 95-99% identify thereof, a hinge region, e.g., a hinge region described herein, e.g., a hinge region of SEQ ID NO:14 or SEQ ID NO:104 or SEQ ID NO:106 or SEQ ID NO:108, or having 95-99% identity thereof, a transmembrane domain, e.g., a transmembrane domain described herein, e.g., a transmembrane domain having a sequence of SEQ ID NO: 15 or a sequence having 95-99% identity thereof, an intracellular signaling domain, e.g., an intracellular signaling domain described herein (e.g., an intracellular signaling domain comprising a costimulatory domain and/or a primary signaling domain). In one embodiment, the intracellular signaling domain comprises a costimulatory domain, e.g., a costimulatory domain described herein, e.g., a 4-1BB costimulatory domain having a sequence of SEQ ID NO:16 or a CD27 costimulatory domain having a sequence of SEQ ID NO:102, or having 95-99% identity thereof, and/or a primary signaling domain, e.g., a primary signaling domain described herein, e.g., a CD3 zeta stimulatory domain having a sequence of SEQ ID NO:17 or SEQ ID NO:99, or having 95-99% identity thereof. In one embodiment, the intracellular signaling domain comprises a costimulatory domain, e.g., a costimulatory domain described herein, e.g., a 4-1BB costimulatory domain having a sequence of SEQ ID NO:16 or a CD27 costimulatory domain having a sequence of SEQ ID NO:102, and/a primary signaling domain, e.g., a primary signaling domain described herein, e.g., a CD3 zeta stimulatory domain having a sequence of SEQ ID NO:17 or SEQ ID NO:99.

In one embodiment, the isolated CAR molecule comprises (e.g., consists of) an amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90, or an amino acid sequence having 85%, 90%, 95%, 96%, 97%, 98% or 99% identity to an amino acid sequence of SEQ ID NO:43, SEQ ID NO:49, SEQ ID NO:55, SEQ ID NO:61, SEQ ID NO:67, SEQ ID NO:73, SEQ ID NO:79, SEQ ID NO:85, or SEQ ID NO:90. In one embodiment, the isolated CAR molecule comprises (e.g., consists of) an amino acid sequence of SEQ ID NO:1, orSEQ ID NO:2, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:1 or SEQ ID NO:2, or an amino acid sequence having 85%, 90%, 95%, 96%, 97%, 98% or 99% identity to an amino acid sequence of SEQ ID NO:1 or SEQ ID NO:2. In one embodiment, the isolated CAR molecule comprises (e.g., consists of) an amino acid sequence of SEQ ID NO:73, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:73, or an amino acid sequence having 85%, 90%, 95%, 96%, 97%, 98% or 99% identity to an amino acid sequence of SEQ ID NO:73. In one embodiment, the isolated CAR molecule comprises (e.g., consists of) an amino acid sequence of SEQ ID NO:79, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:79, or an amino acid sequence having 85%, 90%, 95%, 96%, 97%, 98% or 99% identity to an amino acid sequence of SEQ ID NO:79.

In one aspect, the invention pertains to an anti-EGFRvIII binding domain comprising one or more (e.g., all three) light chain complementary determining region 1 (LC CDR1), light chain complementary determining region 2 (LC CDR2), and light chain complementary determining region 3 (LC CDR3) of an anti-EGFRvIII binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-EGFRvIII binding domain described herein, e.g., a humanized anti-EGFRvIII binding domain comprising one or more, e.g., all three, LC CDRs and one or more, e.g., all three, HC CDRs. In one embodiment, the anti-EGFRvIII binding domain comprises a light chain variable region described herein (e.g., in SEQ ID NO:38, 44, 50, 56, 62, 68, 74 or 80) and/or a heavy chain variable region described herein (e.g. in SEQ ID NO:38, 44, 50, 56, 62, 68, 74 or 80). In one embodiment, the anti-EGFRvIII binding domain is a scFv comprising a light chain and a heavy chain of an amino acid sequence of in SEQ ID NO:38, 44, 50, 56, 62, 68, 74 or 80. In an embodiment, the anti-EGFRvIII binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided, in SEQ ID NO:38, 44, 50, 56, 62, 68, 74 or 80 or a sequence with 95-99% identity with an amino acid sequence in SEQ ID NO:38, 44, 50, 56, 62, 68, 74 or 80; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in SEQ ID NO:38, 44, 50, 56, 62, 68, 74 or 80, or a sequence with 95-99% identity to an amino acid sequence in SEQ ID NO:38, 44, 50, 56, 62, 68, 74 or 80. In one embodiment, the anti-EGFRvIII binding domain comprises a sequence selected from a group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof. In one embodiment, the anti-EGFRvIII binding domain is a scFv, and a light chain variable region comprising an amino acid sequence described herein, e.g., in Table 2, is attached to a heavy chain variable region comprising an amino acid sequence described herein, e.g., in Table 2, via a linker, e.g., a linker described herein. In one embodiment, the anti-EGFRvIII binding domain includes a ($Gly_4$-Ser)n linker, wherein n is 1, 2, 3, 4, 5, or 6, preferably 4 (SEQ ID NO: 110). The light chain variable region and heavy chain variable region of a scFv can be, e.g., in any of the following orientations: light chain variable region-linker-heavy chain variable region or heavy chain variable region-linker-light chain variable region.

In another aspect, the invention pertains to a vector comprising a nucleic acid molecule described herein, e.g., a nucleic acid molecule encoding a CAR described herein. In one embodiment, the vector is selected from the group consisting of a DNA, a RNA, a plasmid, a lentivirus vector, adenoviral vector, or a retrovirus vector.

In one embodiment, the vector is a lentivirus vector. In one embodiment, the vector further comprises a promoter. In one embodiment, the promoter is an EF-1 promoter. In one embodiment, the EF-1 promoter comprises a sequence of SEQ ID NO: 97.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases (SEQ ID NO: 111). In one embodiment, the nucleic acid sequence in the vector further comprises a 3'UTR, e.g., a 3' UTR described herein, e.g., comprising at least one repeat of a 3'UTR derived from human beta-globulin.

In another aspect, the invention pertains to a cell comprising a vector described herein. In one embodiment, the cell is a cell described herein, e.g., a human T cell, e.g., a human T cell described herein. In one embodiment, the human T cell is a CD8+ T cell.

In another aspect, the invention pertains to a method of making a cell comprising transducing a cell described herein, e.g., a T cell described herein, with a vector of comprising a nucleic acid encoding a CAR, e.g., a CAR described herein.

The present invention also provides a method of generating a population of RNA-engineered cells, e.g., cells described herein, e.g., T cells, transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a mammal comprising administering to the mammal an effective amount of a cell expressing a CAR molecule, e.g., a cell expressing a CAR molecule described herein. In one embodiment, the cell is an autologous T cell. In one embodiment, the cell is an allogeneic T cell. In one embodiment, the mammal is a human.

In another aspect, the invention pertains to a method of treating a mammal having a disease associated with expression of EGFRvIII (e.g., a proliferative disease, a precancerous condition, and a noncancer related indication associated with the expression of EGFRvIII) comprising administering to the mammal an effective amount of the cells expressing a CAR molecule, e.g., a CAR molecule described herein.

In one embodiment, the disease is a disease described herein. In one embodiment, the disease associated with EGFRvIII is a glioblastoma. In one embodiment, the disease associated with EGFRvIII is a cancer, e.g., a cancer selected from the group consisting of glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, atypical teratoid/rhabdoid tumor, lung cancer (e.g., non-small cell lung carcinomas) breast, prostate, ovarian, colorectal and bladder carcinoma and any combination thereof, and metastases of any of the cancers.

In one embodiment, the cells expressing a CAR molecule, e.g., a CAR molecule described herein, are administered in combination with an agent that increases the efficacy of a cell expressing a CAR molecule, e.g., an agent described herein.

In one embodiment, the cells expressing a CAR molecule, e.g., a CAR molecule described herein, are administered in combination with an agent that ameliorates one or more side effect associated with administration of a cell expressing a CAR molecule, e.g., an agent described herein.

In one embodiment, the cells expressing a CAR molecule, e.g., a CAR molecule described herein, are administered in combination with an agent that treats the disease associated with EGFRvIII, e.g., an agent described herein.

In one embodiment, the cells expressing a CAR molecule, e.g., a CAR molecule described herein, are administered at a dose and/or dosing schedule described herein.

In one embodiment, the cells expressing a CAR molecule, e.g., a CAR molecule described herein, are administered as a first line treatment for the disease, e.g., the cancer, e.g., the cancer described herein. In another embodiment, the cells expressing a CAR molecule, e.g., a CAR molecule described herein, are administered as a second, third, fourth line treatment for the disease, e.g., the cancer, e.g., the cancer described herein.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament, e.g., as described herein.

In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing EGFRvIII, e.g., a disease expressing EGFRvIII as described herein.

BRIEF DESCRIPTION OF THE DRAWINGS

FIG. 1A depicts the 3C10-CAR expressing vector pELNS-3C10-CAR; and FIG. 1B depicts the miR-17-92-expressing lentiviral vector;

DETAILED DESCRIPTION

Definitions

Figure 1A:
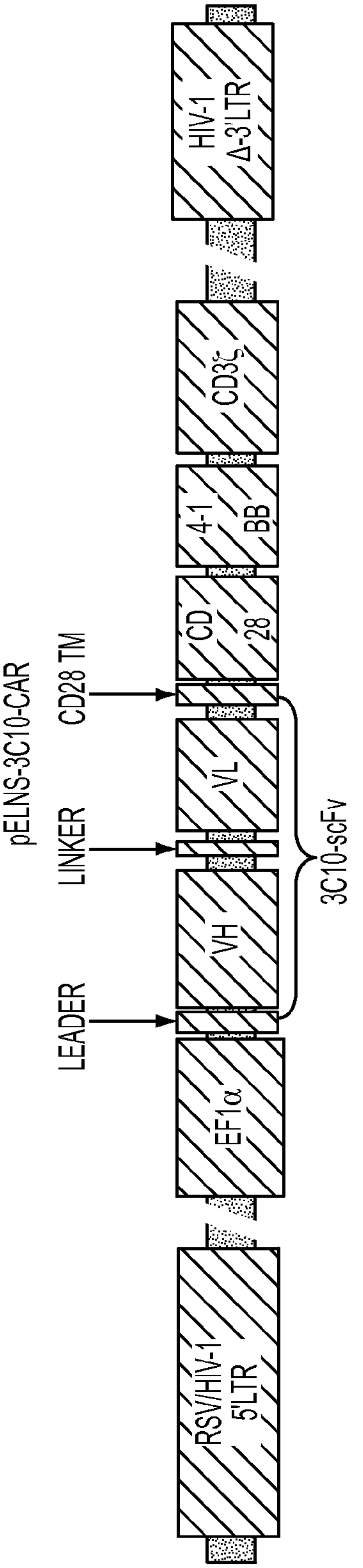
FIGS. 1A and 1B are a series of schematic diagrams of lentiviral vectors for 3C10-CAR and miR-17-92.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from 4-1BB (i.e., CD137) and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

The term "EGFR" refers to any mammalian mature full-length epidermal growth factor receptor, including human and non-human forms. The 1186 amino acid human EGFR is described in Ullrich et al., Nature 309:418-425 (1984)) and GenBank Accession No. AF125253 and SwissProt Acc No P00533-2.

The term "EGFRvIII" refers to Epidermal growth factor receptor variant III. EGFRvIII is the most common variant of EGFR observed in human tumors but is rarely observed in normal tissue. This protein results from the in-frame deletion of exons 2-7 and the generation of a novel glycine residue at the junction of exons 1 and 8 within the extra-cellular domain of the EGFR, thereby creating a tumor specific epitope. EGFRvIII is expressed in 24% to 67% of GBM, but not in normal tissues. EGFRvIII is also known as type III mutant, delta-EGFR, EGFRde2-7, and ΔEGFR and is described in U.S. Pat. Nos. 6,455,498, 6,127,126, 5,981,725, 5,814,317, 5,710,010, 5,401,828, and 5,212,290. Expression of EGFRvIII may result from a chromosomal deletion, and may also result from aberrant alternative splicing. See Sugawa et al., 1990, Proc. Natl. Acad. Sci. 87:8602-8606.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', $F(ab')_2$, and Fv fragments, scFv antibody fragments, linear antibodies, single domain antibodies such as sdAb (either VL or VH), camelid VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, New York; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refer to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and, include but are not limited to, glioblastoma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "disease associated with expression of EGFRvIII" as used herein includes, but is not limited to, a disease associated with expression of EGFRvIII or condition associated with cells which express EGFRvIII including, tumor cells of various cancers such as, e.g., glioblastoma (including glioblastoma stem cells); breast, ovarian, and non-small cell lung carcinomas; head and neck squamous cell carcinoma; medulloblastoma, colorectal cancer, prostate cancer, and bladder carcinoma. Without being bound to a particular theory or mechanism, it is believed that by eliciting an antigen-specific response against EGFRvIII, the CARs disclosed herein provide for one or more of the following: targeting and destroying EGFRvIII-expressing tumor cells, reducing or eliminating tumors, facilitating infiltration of immune cells to the tumor site, and enhancing/extending anti-tumor responses. Because EGFRvIII is not expressed at detectable levels in normal (i.e., non-cancerous) tissue, it is contemplated that the inventive CARs advantageously substantially avoid targeting/destroying normal tissues and cells.

The term "conservative sequence modifications" is intended to refer to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. In a specific CAR of the invention, the intracellular signaling domain in any one or more CARS of the invention comprises an intracellular signaling sequence, e.g., a primary signaling sequence of CD3-zeta. In a specific CAR of the invention, the primary signaling sequence of CD3-zeta is the sequence provided as SEQ ID NO:17 or the equivalent residues from a non-human species, e.g., mouse, rodent, monkey, ape and the like. In a specific CAR of the invention, the primary signaling sequence of CD3-zeta is the sequence provided as SEQ ID NO:99 or the equivalent residues from a non-human species, e.g., mouse, rodent, monkey, ape and the like.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:17. In one aspect, the "zeta stimulatory domain" or a "CD3-zeta stimulatory domain" is the sequence provided as SEQ ID NO:99.

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, BTLA and a Toll ligand receptor, as well as OX40, CD2, CD27, CD28, CDS, ICAM-1, LFA-1 (CD11a/CD18) and 4-1BB (CD137).

A costimulatory intracellular signaling domain can be derived from the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" refers to member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the sequence provided as SEQ ID NO:16 or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" as used herein refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibodies/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "human" antibody refers to fully human antibodies as well as effectively human antibodies. "Fully human" refers to an immunoglobulin, such as an antibody or antibody fragment, where the whole molecule is of human origin or consists of an amino acid sequence identical to a human form of the antibody or immunoglobulin. An "effectively human" antibody is an antibody that includes a sufficient number of human amino acid positions such that the antibody does not elicit an immunogenic response in a normal human.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive promoter" refers to a nucleotide sequence which, when operably linked with a polynucleotide which encodes or specifies a gene product, causes the gene product to be produced in a cell under most or all physiological conditions of the cell.

The term "inducible promoter" refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific promoter" refers to a nucleotide sequence which, when operably linked with a polynucleotide encodes or specified by a gene, causes the gene product to be produced in a cell substantially only if the cell is a cell of the tissue type corresponding to the promoter.

The term "flexible polypeptide linker" or "linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)n (SEQ ID NO: 112), where n is a positive integer equal to or greater than 1. For example, n=1, n=2, n=3. n=4, n=5 and n=6, n=7, n=8, n=9 and n=10. In one embodiment, the flexible polypeptide linkers include, but are not limited to, (Gly4 Ser)4 (SEQ ID NO: 113) or (Gly4 Ser)3 (SEQ ID NO: 114). In another embodiment, the linkers include multiple repeats of (Gly2Ser), (GlySer) or (Gly3Ser) (SEQ ID NO: 112). Also included within the scope of the invention are linkers described in WO2012/138475, incorporated herein by reference).

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 115), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, non-Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions of matter and methods of use for the treatment of a disease such as cancer using an anti-EGFRvIII chimeric antigen receptors (CAR).

In one aspect, the invention provides a number of chimeric antigen receptors comprising an antibody or antibody fragment engineered to specifically bind to an EGFRvIII protein. In one aspect, the invention provides a cell (e.g., T cell) engineered to express a CAR, wherein the CAR T cell ("CART") exhibits an antitumor property. In one aspect a cell is transformed with the CAR and the CAR is expressed on the cell surface. In some embodiments, the cell (e.g., T cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell) is transfected with a nucleic acid, e.g., mRNA, cDNA, DNA, encoding a CAR. In some such embodiments, the cell may transiently express the CAR.

In one aspect, the EGFRvIII protein binding portion of the CAR is a scFv antibody fragment. In one aspect such antibody fragments are functional in that they retain the equivalent binding affinity, e.g., they bind the same antigen with comparable efficacy, as the IgG antibody from which it is derived. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the EGFRvIII antigen binding domain of the CAR is a murine scFv antibody fragment. In another aspect, the EGFRvIII antigen binding domain of the CAR is a scFv antibody fragment that is humanized compared to the murine sequence of the scFv from which it is derived. Generation of an exemplary parental murine monoclonal antibody against EGFRvIII (3C10) is disclosed in Okamoto et al. (British J. Cancer 1996, 73:1366-1372). An exemplary fully human antibody against EGFRvIII (139) is disclosed in Morgan et al. (2012) Human Gene Therapy, 23: 1043-1953, incorporated herein by reference. In one aspect, the scFv for the murine sequence comprises SEQ ID NO: 11. Humanization of this mouse scFv may be desired for the clinical setting, where the mouse-specific residues may induce a human-anti-mouse antigen (HAMA) response in patients who receive EGFRvIII treatment, e.g., treatment with T cells transduced with the EGFRvIII construct.

In one aspect, the anti-EGFRvIII binding domain portion of a CAR is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the anti-EGFRvIII binding domain of a CAR is a humanized anti-EGFRvIII binding domain. For example, in one embodiment, the anti-EGFRvIII binding domain comprises the scFv portion provided in SEQ ID NO:38. In one aspect, the humanized anti-EGFRvIII binding domain comprises the scFv portion provided in SEQ ID NO:44. In one aspect, the humanized anti-EGFRvIII binding domain comprises the scFv portion provided in SEQ ID NO:50. In one aspect, the humanized anti-EGFRvIII binding domain comprises the scFv portion provided in SEQ ID NO:56. In one aspect, the humanized anti-EGFRvIII binding domain comprises the scFv portion provided in SEQ ID NO:62. In one aspect, the humanized anti-EGFRvIII binding domain comprises the scFv portion provided in SEQ ID NO:68. In one aspect, the humanized anti-EGFRvIII binding domain comprises the scFv portion provided in SEQ ID NO:74. In one aspect, the humanized anti-EGFRvIII binding domain comprises the scFv portion provided in SEQ ID NO:80. In one aspect, the humanized anti-EGFRvIII binding domain comprises the scFv portion provided in SEQ ID NO:86.

In one aspect, a CAR disclosed herein includes an antigen binding domain of a specific antibody with an intracellular signaling domain. For example, in some aspects, the intracellular signaling domain includes, but is not limited to, CD3-zeta chain, 4-1BB and CD28 signaling modules and combinations thereof.

In one aspect, the antigen binding domain binds to EGFRvIII. In one aspect, the CAR comprises the sequence provided in SEQ ID NO:43. In one aspect, the CAR comprises the sequence provided in SEQ ID NO:49. In one aspect, the CAR comprises the sequence provided in SEQ ID NO:55. In one aspect, the CAR comprises the sequence provided in SEQ ID NO:61. In one aspect, the CAR comprises the sequence provided in SEQ ID NO:67. In one aspect, the CAR comprises the sequence provided in SEQ ID NO:73. In one aspect, the CAR comprises the sequence provided in SEQ ID NO:79. In one aspect, the CAR comprises the sequence provided in SEQ ID NO:85.

In one aspect, CAR comprises at least one intracellular signaling domain selected from the group consisting of a CD137 (4-1BB) signaling domain, a CD28 signaling domain, a CD3zeta signal domain, and any combination thereof. In one aspect, the CAR comprises at least one intracellular signaling domain of one or more costimulatory molecule(s) other than a CD137 (4-1BB) or CD28, a CD3zeta signal domain, and any combination thereof.

Furthermore, the present invention provides CAR compositions and their use in medicaments or methods for treating, among other diseases, cancer or any malignancy or autoimmune diseases involving cells or tissues which express EGFRvIII.

The present invention also provides compositions and methods for overexpression of miR-17-92, e.g., in a CAR-expressing cell, e.g., a T cell. In one aspect, transgene-derived overexpression of miR-17-92 provides a CAR-transduced T-cell with improved resistance against tumor-induced immunosuppression and chemotherapy, thereby promoting long-lasting therapeutic effects.

Chimeric Antigen Receptor (CAR)

The present invention encompasses a recombinant DNA construct comprising sequences encoding a CAR, wherein the CAR comprises an antibody fragment that binds specifically to EGFRvIII, e.g., a human antibody fragment that specifically binds to EGFRvIII. In one aspect, the EGFRvIII is human EGFRvIII, and the nucleic acid sequence encoding the antibody fragment is contiguous with, and in the same reading frame as a nucleic acid sequence encoding an intracellular signaling domain. The intracellular signaling domain can comprise a costimulatory signaling domain and/or a primary signaling domain, e.g., a zeta chain. The costimulatory signaling domain refers to a portion of the CAR comprising at least a portion of the intracellular domain of a costimulatory molecule.

In specific aspects, a CAR construct of the invention comprises a scFv domain selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, wherein the scFv may be preceded by an optional leader sequence such as provided in SEQ ID NO: 13, and followed by an optional hinge sequence such as provided in SEQ ID NO:14 or SEQ ID NO:104 or SEQ ID NO:106 or SEQ ID NO:108, a transmembrane region such as provided in SEQ ID NO:15, an intracellular signalling domain that includes SEQ ID NO:16 or SEQ ID NO:102 and a CD3 zeta sequence that includes SEQ ID NO:17 or SEQ ID NO:99, wherein the domains are contiguous with and in the same reading frame to form a single fusion protein. Also included in the invention is a nucleotide sequence that encodes the polypeptide of each of the scFv fragments selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO: 86, and each of the domains of SEQ ID NOS: 13-17. Also included in the invention is a nucleotide sequence that encodes the polypeptide of each of the scFv fragments selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO: 86, and each of the domains of SEQ ID NOS: 13-16 and SEQ ID NO:99. In one aspect, the EGFRvIII CAR construct comprises an optional leader sequence, an extracellular antigen binding domain that specifically binds EGFRvIII, a hinge, a transmembrane domain, and an intracellular stimulatory domain. In one aspect, the EGFRvIII CAR construct comprises an optional leader sequence, an extracellular antigen binding domain that specifically binds EGFRvIII, a hinge, a transmembrane domain, an intracellular signaling domain that includes a costimulatory domain and a primary stimulatory domain. Specific EGFRvIII CAR constructs containing a humanized scFv domain are provided in SEQ ID NO:43, SEQ ID NO:49, SEQ ID NO:55, SEQ ID NO:61, SEQ ID NO:67, SEQ ID NO:73, SEQ ID NO:79, SEQ ID NO:85, and SEQ ID NO:90. Specific EGFRvIII CAR constructs containing a murine scFv domain is provided in SEQ ID NO:1 and SEQ ID NO:2.

An exemplary leader sequence is provided as SEQ ID NO: 13. An exemplary hinge/spacer sequence is provided as SEQ ID NO: 14 or SEQ ID NO:104 or SEQ ID NO:106 or SEQ ID NO:108. An exemplary transmembrane domain sequence is provided as SEQ ID NO:15. An exemplary sequence of a costimulatory domain of the 4-1BB protein is provided as SEQ ID NO: 16. An exemplary sequence of a costimulatory domain of the CD27 protein is provided as SEQ ID NO:102. An exemplary primary signaling domain of a CD3zeta domain sequence is provided as SEQ ID NO: 17. Another exemplary primary signaling domain of a CD3zeta domain sequence is provided as SEQ ID NO:99.

In one aspect, the present invention encompasses a recombinant nucleic acid construct comprising a nucleic acid molecule encoding a CAR, wherein the nucleic acid molecule comprises the nucleic acid sequence encoding an anti-EGFRvIII binding domain, e.g., described herein, that is contiguous with, and in the same reading frame as a nucleic acid sequence encoding an intracellular signaling domain. In one aspect, the anti-EGFRvIII binding domain is selected from one or more of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86. In one aspect, the anti-EGFRvIII binding domain is encoded by a nucleotide sequence provided in a sequence selected from the group consisting of SEQ ID NO: 39, SEQ ID NO: 45, SEQ ID NO: 51, SEQ ID NO: 57, SEQ ID NO: 63, SEQ ID NO: 69, SEQ ID NO: 75, SEQ ID NO: 81, and SEQ ID NO:98. In one aspect, the anti-EGFRvIII binding domain is encoded by SEQ ID NO: 39. In one aspect, the anti-EGFRvIII binding domain is encoded by SEQ ID NO: 45. In one aspect, the anti-EGFRvIII binding domain is encoded by SEQ ID NO: 51. In one aspect, the anti-EGFRvIII binding domain is encoded by SEQ ID NO: 57. In one aspect, the anti-EGFRvIII binding domain is encoded by SEQ ID NO: 63. In one aspect, the anti-EGFRvIII binding domain is encoded by SEQ ID NO: 69. In one aspect, the anti-EGFRvIII binding domain is encoded by SEQ ID NO: 75. In one aspect, the anti-EGFRvIII binding domain is encoded by SEQ ID NO: 81.

In one aspect, the present invention encompasses a recombinant nucleic acid construct comprising a nucleic acid molecule encoding a CAR, wherein the nucleic acid molecule comprises a nucleic acid sequence encoding an anti-EGFRvIII binding domain selected from the group consisting of SEQ ID NO:42, SEQ ID NO:48, SEQ ID NO:54, SEQ ID NO:60, SEQ ID NO:66, SEQ ID NO:72, SEQ ID NO:78, SEQ ID NO:84, and SEQ ID NO:90 wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of intracellular signaling domains of CD3-zeta, CD28, 4-1BB, and the like. In one aspect the nucleic acid construct comprises SEQ ID NO: 42. In one aspect the nucleic acid sequence of a CAR construct is SEQ ID NO:48. In one aspect the nucleic acid construct comprises SEQ ID NO:54. In one aspect the nucleic acid construct comprises SEQ ID NO:60. In one aspect the nucleic acid construct comprises SEQ ID NO:66. In one aspect the nucleic acid construct comprises SEQ ID NO:72. In one aspect the nucleic acid construct comprises SEQ ID NO:78. In one aspect the nucleic acid construct comprises SEQ ID NO:84.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one embodiment, the template includes sequences for the CAR. In an embodiment, an RNA CAR vector is transduced into a T cell by electroporation.

Antigen Binding Domain

In one aspect, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR.

In one aspect, the portion of the CAR comprising the antigen binding domain comprises an antigen binding domain that targets EGFRvIII. In one aspect, the antigen binding domain targets human EGFRvIII. For example, a mouse monoclonal antibody (IgG2b) 3C10 was produced against EGFRvIII by immunization of mice with a 14 amino acid peptide (LEEKKGNYVVTDHC; SEQ ID NO:101) including the EGFRvIII-specific fusion junction and demonstrated highly specific recognition of EGFRvIII without any detectable binding to wild-type EGFR (Okamoto et al, British J. Cancer 1996, 73:1366-1372). Accordingly, in some embodiments, the antigen binding domain targets an amino acid sequence, e.g., an amino acid sequence comprising an added glycine residue, within the EGFvIII fusion junction domain. In some embodiments, the antigen binding domain targets an one or more amino acid sequence in the amino acid sequence of SEQ ID NO:101.

The antigen binding domain can be any domain that binds to the antigen including, but not limited to, a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

Thus, in one aspect, the antigen binding domain comprises a human antibody or an antibody fragment. In another aspect, the antigen binding domain comprises a humanized antibody or antibody fragment. In one embodiment, the anti-EGFRvIII binding domain comprises one or more (e.g., one, two, or all three) light chain complementary determining region 1 (LC CDR1), light chain complementary determining region 2 (LC CDR2), and light chain complementary determining region 3 (LC CDR3) of an anti-EGFRvIII binding domain described herein, and one or more (e.g., one, two, or all three) heavy chain complementary determining region 1 (HC CDR1), heavy chain complementary determining region 2 (HC CDR2), and heavy chain complementary determining region 3 (HC CDR3) of an anti-EGFRvIII binding domain described herein. In one embodiment, the anti-EGFRvIII binding domain comprises a light chain variable region described herein and/or a heavy chain variable region described herein. In one embodiment, the anti-EGFRvIII binding domain is a scFv comprising a light chain variable region and a heavy chain variable region of an amino acid sequence, e.g., a light chain variable region and heavy chain variable region described herein. In an embodiment, the anti-EGFRvIII binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 85-99% (e.g., 90-99%, or 95-99%) identity to an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 85-99% (e.g., 90-99%, or 95-99%) identity to an amino acid sequence provided herein. In one aspect, the antigen binding domain comprises one or more sequence selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86. In one aspect the humanized CAR is selected from one or more sequence selected from the group consisting of SEQ ID NO:43, SEQ ID NO:49, SEQ ID NO:55, SEQ ID NO:61, SEQ ID NO:67, SEQ ID NO:73, SEQ ID NO:79, SEQ ID NO:85, and SEQ ID NO:90.

In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5): 489-498; Studnicka et al., 1994, Protein Engineering, 7(6): 805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., 2002, J. Immunol., 169:1119-25; Caldas et al., 2000, Protein Eng., 13(5):353-60; Morea et al., 2000, Methods, 20:267-79; Baca et al., 1997, J. Biol. Chem., 272:10678-84; Roguska et al., 1996, Protein Eng., 9(10):895-904; Couto et al., 1995, Cancer Res., 55:5973s-5977; Couto et al., 1995, Cancer Res., 55(8): 1717-22; Sandhu 1994 Gene, 150(2):409-10; and Pedersen et al., 1994, J. Mol. Biol., 235(3):959-73, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6): 805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Carter et al., Proc. Natl. Acad. Sci. USA, 89:4285 (1992); Presta et al., J. Immunol., 151:2623 (1993), the contents of which are incorporated herein by reference herein in their entirety).

In some aspects, the portion of a CAR composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

In one aspect, the anti-EGFRvIII binding domain is, for example, a Fv, a Fab, or a (Fab')2, or a bi-functional (e.g. bi-specific) hybrid antibody (e.g., Lanzavecchia et al., Eur. J. Immunol. 17, 105 (1987)). In one aspect, an antibody fragment provided herein is a scFv. In one aspect, the scFv binds an EGFRvIII protein but not wild type EGFR. In some instances, a human scFv may also be derived from a yeast display library.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$ (SEQ ID NO: 37), where n is a positive integer equal to or greater than 1. In one embodiment, the linker can be $(Gly_4Ser)_4$ (SEQ ID NO: 113) or $(Gly_4Ser)_3$ (SEQ ID NO: 114). Variation in the linker length may retain or enhance activity, giving rise to superior efficacy in activity studies.

Stability and Mutations

The stability of an anti-EGFRvIII binding domain, e.g., scFv molecules (e.g., soluble scFv), can be evaluated in reference to the biophysical properties (e.g., thermal stability) of a conventional control scFv molecule or a full length antibody. In one embodiment, the humanized scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the anti-EGFRvIII binding domain, e.g., scFv, is subsequently conferred to the entire EGFRvIII CAR construct, leading to improved therapeutic properties of the EGFRvIII CAR construct. The thermal stability of the anti-EGFRvIII binding domain, e.g., scFv, can be improved by at least about 2° C. or 3° C. as compared to a conventional antibody. In one embodiment, the anti-EGFRvIII binding domain, e.g., scFv, has a 1° C. improved thermal stability as compared to a conventional antibody. In another embodiment, the anti-EGFRvIII binding domain, e.g., scFv, has a 2° C. improved thermal stability as compared to a conventional antibody. In another embodiment, the anti-EGFRvIII binding domain, e.g., scFv, has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through humanization or direct mutagenesis of the soluble scFv) alter the stability of the scFv and improve the overall stability of the scFv and the EGFRvIII CAR construct. Stability of the humanized scFv is compared against the murine scFv using measurements such as Tm, temperature denaturation and temperature aggregation. The binding capacity of the mutant scFvs can be determined using assays described in the Examples.

In one embodiment, the anti-EGFRvIII binding domain, e.g., scFv, comprises at least one mutation arising from the humanization process such that the mutated scFv confers improved stability to the EGFRvIII construct. In another embodiment, the anti-EGFRvIII binding domain, e.g., scFv, comprises at least 1, 2, 3, 4, 5, 6, 7, 8, 9, 10 mutations arising from the humanization process such that the mutated scFv confers improved stability to the EGFRvIII construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g. a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of anti-EGFRvIII binding domain, e.g., scFv, variants may be created using methods known in the art. Anti-EGFRvIII binding domain, e.g., scFv, expression may be induced and the anti-EGFRvIII binding domain, e.g., scFv, may be subjected to thermal challenge. The challenged test samples may be assayed for binding and those anti-EGFRvIII binding domains, e.g., scFvs, which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an anti-EGFRvIII binding domain, e.g., scFv, are about 40° C., 41° C., 42° C., 43° C., 44° C., 45° C., 46° C., 47° C., 48° C., 49° C., 50° C., 51° C., 52° C., 53° C., 54° C., 55° C., 56°

C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the $T_C$ value) at which 50% of the composition retains its activity (e.g. binding activity).

In addition, mutations to the anti-EGFRvIII binding domain, e.g., scFv, alter the thermal stability of the anti-EGFRvIII binding domain, e.g., scFv, compared with the unmutated anti-EGFRvIII binding domain, e.g., scFv. When the humanized anti-EGFRvIII binding domain, e.g., scFv, is incorporated into an anti-EGFRvIII CAR construct, the anti-EGFRvIII binding domain, e.g., humanized scFv confers thermal stability to the overall anti-EGFRvIII CAR construct. In one embodiment, the anti-EGFRvIII binding domain, e.g., scFv, comprises a single mutation that confers thermal stability to the anti-EGFRvIII binding domain, e.g., scFv. In another embodiment, the anti-EGFRvIII binding domain, e.g., scFv, comprises multiple mutations that confer thermal stability to the anti-EGFRvIII binding domain, e.g., scFv. In one embodiment, the multiple mutations in the anti-EGFRvIII binding domain, e.g., scFv, have an additive effect on thermal stability of the anti-EGFRvIII binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the anti-EGFRvIII antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM 120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-EGFRvIII binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-EGFRvIII binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CART cell surface. In a different aspect, the amino acid sequence of the transmembrane domain may be modified or substituted so as to minimize interactions with the binding domains of the native binding partner present in the same CART.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:14. In one aspect, the transmembrane domain comprises (e.g., consists of) a transmembrane domain of SEQ ID NO: 15.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGKM (SEQ ID NO:104). In some embodiments, the hinge or spacer comprises a hinge encoded by a nucleotide sequence of GAGAGCAAGTACGGCCCTCCCTGCCCCCCTTGCCCTGCCCCCGAGTTCCTGGGCGGACCCAGCGTGTTCCTGTTCCCCCCCAAGCCCAAGGACACCCTGATGATCAGCCGGACCCCCGAGGTGACCTGTGTGGTGGTGGACGTGTCCCAGGAGGACCCCGAGGTCCAGTTCAACTGGTACGTGGACGGCGTGGAGGTGCACAACGCCAAGACCAAGCCCCGGGAGGAGCAGTTCAATAGCACCTACCGGGTGGTGTCCGTGCTGACCGTGCTGCACCAGGACTGGCTGAACGGCAAGGAATACAAGTGTAAGGTGTCCAACAAGGGCCTGCCCAGCAGCATCGAGAAAACCATCAGCAAGGCCAAGGGCCAGCCTCGGGAGCCCCAGGTGTACACCCTGCCCCCTAGCCAAGAGGAGATGACCAAGAACCAGGTGTCCCTGACCTGCCTGGTGAAGGGCTTCTACCCCAGCGACATCGCCGTGGAGTGGGAGAGCAACGGCCAGCCCGAGAACAACTACAAGACCACCCCCCCTGTGCTGGACAGCGACGGCAGCTTCTTCCTGTACAGCCGGCTGACCGTGGACAAGAGCCGGTGGCAGGAGGGCAACGTCTTTAGCTGCTCCGTGATGCACGAGGCCCTGCACAACCACTACACCCAGAAGAGCCTGAGCCTGTCCCTGGGCAAGATG (SEQ ID NO:105).

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQEERETKTPECPSHTQPLGVYLLTPAVQDLWLRDKATFTCFVVGSDLKDAHLTWEVAGKVPTGGVEEGLLERHSNGSQSQHSRLTLPRSLWNAGTSVTCTLNHPSLPPQRLMALREPAAQAPVKLSLNLLASSDPPEAASWLLCEVSGFSPPNILLMWLEDQREVNTSGFAPARPPPQPGSTTFWAWSVLRVPAPPSPQPATYTCVVSHEDSRTLLNASRSLEVSYVTDH (SEQ ID NO:106). In some embodiments, the hinge or spacer comprises a hinge encoded by a nucleotide sequence of AGGTGGCCCGAAAGTCCCAAGGCCCAGGCATCTAGTGTTCCTACTGCACAGCCCCAGGCAGAAGGCAGCCTAGCCAAAGCTACTACTGCACCTGCCACTACGCGCAATACTGGCCGTGGCGGGGAGGAGAAGAAAAAGGAGAAAGAGAAAGAAGAACAGGAAGAGAGGGAGACCAAGACCCCTGAATGTCCATCCCATACCCAGCCGCTGGGCGTCTATCTCTTGACTCCCGCAGTACAGGACTTGTGGCTTAGAGATAAGGCCACCTTTACATGTTTCGTCGTGGGCTCTGACCTGAAGGATGCCCATTTGACTTGGGAGGTTGCCGGAAAGGTACCCACAGGGGGGGTTGAGGAAGGGTTGCTGGAGCGCCATTCCAATGGCTCTCAGAGCCAGCACTCAAGACTCACCCTTCCGAGATCCCTGTGGAACGCCGGGACCTCTGTCACATGTACTCTAAATCATCCTAGCCTGCCCCCACAGCGTCTGATGGCCCTTAGAGAGCCAGCCGCCCAGGCACCAGTTAAGCTTAGCCTGAATCTGCTCGCCAGTAGTGATCCCCCAGAGGCCGCCAGCTGGCTCTTATGCGAAGTGTCCGGCTTTAGCCCGCCCAACATCTTGCTCATGTGGCTGGAGGACCAGCGAGAAGTGAACACCAGCGGCTTCGCTCCAGCCCGGCCCCCACCCCAGCCGGGTTCTACCACATTCTGGGCCTGGAGTGTCTTAAGGGTCCCAGCACCACCTAGCCCCCAGCCAGCCACATACACCTGTGTTGTGTCCCATGAAGATAGCAGGACCCTGCTAAATGCTTCTAGGAGTCTGGAGGTTTCCTACGTGACTGACCATT (SEQ ID NO:107).

In one aspect, the transmembrane domain may be recombinant, in which case it will comprise predominantly hydrophobic residues such as leucine and valine. In one aspect, a triplet of phenylalanine, tryptophan and valine can be found at each end of a recombinant transmembrane domain.

Optionally, a short oligo- or polypeptide linker, e.g., between 2 and 10 amino acids in length, may form the linkage between the transmembrane domain and the cytoplasmic region of the CAR. A glycine-serine doublet is an example of a suitable linker. For example, in one aspect, the linker comprises the amino acid sequence of GGGGSGGGGS (SEQ ID NO:108). In some embodiments, the linker is encoded by a nucleotide sequence of GGTGGCGGAGGTTCTGGAGGTGGAGGTTCC (SEQ ID NO:109).

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic signaling domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, and CD66d. In one embodiment, a CAR of the invention, e.g., a CAR selected from the group consisting of SEQ ID NO:43, SEQ ID NO:49, SEQ ID NO:55, SEQ ID NO:61, SEQ ID NO:67, SEQ ID NO:73, SEQ ID NO:79, and SEQ ID NO:85, comprises a intracellular signaling domain, e.g., a primary signaling domain, of CD3-zeta. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of a CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signalling domain is designed to comprise the signaling domain of CD3-zeta and the signaling domain of 4-1BB. In one aspect, the signaling domain of 4-1BB is a signaling domain of SEQ ID NO: 16. In one aspect, the signaling domain of CD3-zeta is a signaling domain of SEQ ID NO: 17.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRY-SCPREEEGSTIPIQEDYRKPEPACSP (SEQ ID NO:102). In one aspect, the signalling domain of CD27 is encoded by a nucleic acid sequence of AGGAGTAAGAGGAGCAG-GCTCCTGCACAGTGACTACATGAACAT-GACTCCCCGCC GCCCCGGGCCCACCCGCAAGCAT-TACCAGCCCTATGCCCCACCACGCGACTTCGCA GCCTATCGCTCC (SEQ ID NO:103).

In one aspect, the CAR-expressing cell described herein can further comprise a second CAR, e.g., a second CAR that includes a different antigen binding domain, e.g., to the same target (EGFRvIII) or a different target.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-EGFRvIII binding domain described herein, and a second cell expressing a CAR having a different anti-EGFRvIII binding domain, e.g., an anti-EGFRvIII binding domain described herein that differs from the anti-EGFRvIII binding domain in the CAR expressed by the first cell. As another example, the population of CAR-expressing cells can include a first cell expressing a CAR that includes an anti-EGFRvIII binding domain, e.g., as described herein, and a second cell expressing a CAR that includes an antigen binding domain to a target other than EGFRvIII. In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-EGFRvIII domain described herein, and a second cell expressing another agent, e.g., an agent which enhances the activity of a CAR-expressing cell. For example, in one embodiment, the agent can be an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 116). RNA so produced can efficiently transfect different kinds of cells. In one aspect, the template includes sequences for the CAR.

In one aspect the EGFRvIII CAR is encoded by a messenger RNA (mRNA). In one aspect the mRNA encoding the EGFRvIII CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. “Substantially complementary,” as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. “Forward primers” are primers that contain a region of nucleotides that are substantially complementary to nucleotides on the DNA template that are upstream of the DNA sequence that is to be amplified. “Upstream” is used herein to refer to a location 5, to the DNA sequence to be amplified relative to the coding strand. “Reverse primers” are primers that contain a region of nucleotides that are substantially complementary to a double-stranded DNA template that are downstream of the DNA sequence that is to be amplified. “Downstream” is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3'

UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 117) (size can be 50-5000 T (SEQ ID NO: 118)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 119).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides (SEQ ID NO: 120) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a CAR

The present invention provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises a anti-EGFRvIII binding domain (e.g., a humanized anti-EGFRvIII binding domain), a transmembrane domain, and an intracellular signaling domain comprising a stimulatory domain, e.g., a costimulatory signaling domain and/or a primary signaling domain, e.g., zeta chain. In one embodiment, the anti-EGFRvIII binding domain is an anti-EGFRvIII binding domain described herein, e.g., an anti-EGFRvIII binding domain which comprises a sequence selected from a group consisting of SEQ ID NO:38, SEQ ID NO:44, SEQ ID NO:50, SEQ ID NO:56, SEQ ID NO:62, SEQ ID NO:68, SEQ ID NO:74, and SEQ ID NO:80, or a sequence with 95-99% identify thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18), ICOS (CD278), and 4-1BB (CD137). In one embodiment, the costimulatory domain comprises a sequence of SEQ ID NO:16, or a sequence with 95-99% identity thereof. In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 15, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises the sequence of SEQ ID NO: 16 or SEQ ID NO:102, or a sequence with 95-99% identity thereof, and the sequence of SEQ ID NO: 17 or SEQ ID NO:99, or a sequence with 95-99% identity thereof, wherein the sequences comprising the intracellular signaling domain are expressed in the same frame and as a single polypeptide chain. In one embodiment, the anti-EGFRvIII binding domain is connected to the transmembrane domain by a hinge region, e.g., a hinge described herein. In one embodiment, the hinge region comprises SEQ ID NO:14 or SEQ ID NO:104 or SEQ ID NO:106 or SEQ ID NO:108, or a sequence with 95-99% identity thereof.

In another aspect, the invention pertains to an isolated nucleic acid molecule encoding a CAR construct comprising a leader sequence of SEQ ID NO: 13, a scFv domain having a sequence selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86 (or a sequence with 95-99% identify thereof), a hinge region of SEQ ID NO:14 or SEQ ID NO:104 or SEQ ID NO:106 or SEQ ID NO:108 (or a sequence with 95-99% identity thereof), a transmembrane domain having a sequence of SEQ ID NO: 15 (or a sequence with 95-99% identity thereof), a 4-1BB costimulatory domain having a sequence of SEQ ID NO:16 or a CD27 costimulatory domain having a sequence of SEQ ID NO:102 (or a sequence with 95-99% identity thereof), and a CD3 zeta stimulatory domain having a sequence of SEQ ID NO:17 or SEQ ID NO:99 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:43, SEQ ID NO:49, SEQ ID NO:55, SEQ ID NO:61, SEQ ID NO:67, SEQ ID NO:73, SEQ ID NO:79, SEQ ID NO:85, and SEQ ID NO:90 or a sequence with 95-99% identify thereof. In one embodiment, the isolated polypeptide comprises a sequence of SEQ ID NO:73, or a sequence with 95-99% identify thereof. In one embodiment, the isolated polypeptide comprises a sequence of SEQ ID NO:79, or a sequence with 95-99% identify thereof.

In another aspect, the invention pertains to a nucleic acid molecule encoding a chimeric antigen receptor (CAR) molecule that comprises an anti-EGFRvIII binding domain, a transmembrane domain, and an intracellular signaling domain comprising a stimulatory domain, and wherein said anti-EGFRvIII binding domain comprises a sequence selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CDS, ICAM-1, LFA-1 (CD11a/CD18) and 4-1BB (CD137). In one embodiment, the costimulatory domain comprises a sequence of SEQ ID NO:16. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD 154. In one embodiment, the transmembrane domain comprises a sequence of SEQ ID NO:15. In one embodiment, the intracellular signaling domain comprises a functional signaling domain of 4-1BB and a functional signaling domain of zeta. In one embodiment, the intracellular signaling domain comprises the sequence of SEQ ID NO: 16 and the sequence of SEQ ID NO: 17, wherein the sequences comprising the intracellular signaling domain are expressed in the same frame and as a single polypeptide chain. In one embodiment, the anti-EGFRvIII binding domain is connected to the transmembrane domain by a hinge region. In one embodiment, the hinge region comprises SEQ ID NO:14. In one embodiment, the hinge region comprises SEQ ID NO:104 or SEQ ID NO:106 or SEQ ID NO:108

In another aspect, the invention pertains to an encoded CAR molecule comprising a leader sequence of SEQ ID NO: 13, a scFv domain having a sequence selected from the group consisting of SEQ ID NO:38, SEQ ID NO:44, SEQ ID NO:50, SEQ ID NO:56, SEQ ID NO:62, SEQ ID NO:68, SEQ ID NO:74, SEQ ID NO:80, and SEQ ID NO:86, or a sequence with 95-99% identify thereof, a hinge region of SEQ ID NO:14 or SEQ ID NO:104 or SEQ ID NO:106 or SEQ ID NO:108, a transmembrane domain having a sequence of SEQ ID NO: 15, a 4-1BB costimulatory domain having a sequence of SEQ ID NO:16 or a CD27 costimulatory domain having a sequence of SEQ ID NO:102, and a CD3 zeta stimulatory domain having a sequence of SEQ ID NO:17 or SEQ ID NO:99. In one embodiment, the encoded CAR molecule comprises a sequence selected from a group consisting of SEQ ID NO:43, SEQ ID NO:49, SEQ ID NO:55, SEQ ID NO:61, SEQ ID NO:67, SEQ ID NO:73, SEQ ID NO:79, SEQ ID NO:85, and SEQ ID NO:90, or a sequence with 95-99% identify thereof. In one embodiment, the encoded CAR molecule comprises a sequence of SEQ ID NO:73, or a sequence with 95-99% identify thereof. In one embodiment, the isolated CAR molecule comprises a sequence of SEQ ID NO:79, or a sequence with 95-99% identify thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art.

The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a nanoparticle, e.g., a liposome or other suitable sub-micron sized delivery system. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is $5\times10^6$/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, 10^4 to 10^9 T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a EGFRvIII CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a EGFRvIII CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1a, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either $EGFRvIII^+$ U-87 cells (U-87-EGFRvIII), wild-type U-87 cells (U-87 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/ml. $GFP^+$ T cells are enumerated by flow cytometry using bead-based counting. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter following stimulation with αCD3/αCD28 coated magnetic beads on day 0, and transduction with the indicated CAR on day 1.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with target cells, such asU87MG, BHK or CHO cells expressing EGFRvIII or EGFR wildtype (wt) or CD32 and CD137 (KT32-BBL) for a final T-cell: target cell ratio of 1:1. Anti-CD3 (clone OKT3) and anti-CD28 (clone 9.3) monoclonal antibodies are added to cultures with KT32-BBL cells to serve as a positive control for stimulating T-cell proliferation since these signals support long-term $CD8^+$ T cell expansion ex vivo. T cells are enumerated in cultures using CountBright™ fluorescent beads (Invitrogen, Carlsbad, Calif.) and flow cytometry as described by the manufacturer. $CAR^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant EGFRvIII protein and a secondary avidin-PE conjugate. CD4+ and $CD8^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACS-calibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (U87MG, BHK or CHO cells expressing EGFRvIII or EGFR wildtype (wt) are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}Cr$ is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition. Alternative cytotoxicity assays may also be used, such as flow based cytotoxicity assays, as described in Example 8.

Click beetle red and click beetle green luciferase can be used to simultaneously follow tumor progression and T cell trafficking, as each use the same luciferin substrate but emit light at the opposite ends of the visible light spectrum.

Other assays, including those described in the Example section herein as well as those that are known in the art can also be used to evaluate the EGFRvIII CAR constructs of the invention.

Therapeutic Application for EGFRvIII Expressing Diseases and Disorders

EGFRvIII is a tumor specific, ligand-independent, constitutively active variant of the epidermal growth factor receptor. The present invention provides compositions and methods for treating diseases and disorders associated with EGFRvIII. An example of a disease or disorder associated with EGFRvIII is glioma.

Glioma refers to a cancer of the central nervous system that begins in glial cells (e.g., cells that surround and support nerve cells and includes oligodendrocytes, astrocytes, microglia, and ependymal cells). Gliomas are particularly serious in terms of both incidence and malignancy, and are classified into seven or more types such as glioblastoma and anaplastic astrocytoma according to their detailed pathological tissue type. Disease stage (tumor size, presence of distal metastasis) and histological malignancy are used when determining the degree of malignancy of primary brain tumors. Histological malignancy is classified into four levels, i.e., G1 to G4 according to the Guidelines for the Treatment of Brain Tumors ((2002) Kanehara & Co., Ltd.), and these correspond to WHO1 to WHO4, respectively. The larger the number, the higher the degree of malignancy. For example, the malignancy of glioblastoma is G4 (WHO4), while the malignancy of anaplastic astrocytoma is G3 (WHO3), and both G3 and G4 are classified as malignant. Thus, according to some embodiments, the methods of this invention target malignant gliomas. In other aspects the invention targets glioblastoma multiforme (GBM). In further embodiments, the compositions and methods of the present invention may be used in the treatment of other gliomas including, but not limited to, anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor.

Glioblastoma is the most common primary brain tumor in adults. More than half of the 18,000 patients diagnosed with malignant primary brain tumors in US each year have glioblastoma multiforme. Glioblastoma multiforme is an anaplastic, highly cellular tumor, with high proliferation indices, microvascular proliferation and focal necrosis. Signs and symptoms depend on several factors (size, rate of growth, localization of the tumor within the brain) and are mainly represented by headache, seizures, neurological deficits, changes in mental status. Glioblastoma multiforme prognosis remains dismal. Survival time is less than 2 years for the majority of patients. Karnofsky performance status (KPS) is one of the most important prognostic factors: patients with KPS>70 are alive at 18 months in approx 18% of cases, compared with 13% of patients with lower KPS scores. Primary glioblastoma multiforme develops de novo from glial cells, typically has a clinical history of less than six months, is more common in older patients and presents small-cell histology. Secondary glioblastoma multiforme develops over months or years from pre-existing low-grade astrocytomas, predominantly affects younger people and presents giant-cell histology.

Malignant gliomas are also known as high grade gliomas. They can affect the brain and the spinal cord. In some aspects, compositions and methods of the present invention may be used to treat subjects carrying a brain malignant glioma, for example, one that is chosen among anaplastic astrocytoma (AA), glioblastoma multiform (GBM), anaplastic oligodendroglioma (AO) and anaplastic oligoastrocytoma (AOA). In some aspects, compositions and methods of the present invention may be used to treat subjects carrying a glioblastoma multiforme (GBM).

Glioblastoma multiforme is the most malignant stage of astrocytoma, with survival times of less than 2 years for most patients. Histologically, these tumors are characterized by high proliferation indices, endothelial proliferation and focal necrosis. The highly proliferative nature of these lesions likely results from multiple mitogenic effects. One of the hallmarks of GBM is endothelial proliferation. A host of angiogenic growth factors and their receptors are found in GBMs.

There are biologic subsets of astrocytomas, which may reflect the clinical heterogeneity observed in these tumors. These subsets include brain stem gliomas, which are a form of pediatric diffuse, fibrillary astrocytoma that often follow a malignant course. Brain stem GBMs share genetic features with those adult GBMs that affect younger patients. Pleiomorphic xanthoastrocytoma (PXA) is a superficial, low-grade astrocytic tumor that predominantly affects young adults. While these tumors have a bizarre histological appearance, they are typically slow-growing tumors that may be amenable to surgical cure. Some PXAs, however, may recur as GBM. Pilocytic astrocytoma is the most common astrocytic tumor of childhood and differs clinically and histopathologically from the diffuse, fibrillary astrocytoma that affects adults. Pilocytic astrocytomas do not have the same genomic alterations as diffuse, fibrillary astrocytomas. Subependymal giant cell astrocytomas (SEGA) are periventricular, low-grade astrocytic tumors that are usually associated with tuberous sclerosis (TS), and are histologically identical to the so-called "candle-gutterings" that line the ventricles of TS patients. Similar to the other tumorous lesions in TS, these are slowly-growing and may be more akin to hamartomas than true neoplasms. Desmoplastic cerebral astrocytoma of infancy (DCAI) and desmoplastic infantile ganglioglioma (DIGG) are large, superficial, usually cystic, benign astrocytomas that affect children in the first year or two of life.

Oligodendrogliomas and oligoastrocytomas (mixed gliomas) are diffuse, primarily CNS glial tumors that are clinically and biologically most closely related to the diffuse, fibrillary astrocytomas. The tumors, however, are far less common than astrocytomas and have generally better prognoses than the diffuse astrocytomas. Oligodendrogliomas and oligoastrocytomas may progress, either to WHO grade III anaplastic oligodendroglioma or anaplastic oligoastrocytoma, or to WHO grade IV GBM. Thus, the genetic changes that lead to oligodendroglial tumors constitute yet another pathway to GBM.

Ependymomas are a clinically diverse group of gliomas that vary from aggressive intraventricular tumors of children to benign spinal cord tumors in adults. Transitions of ependymoma to GBM are rare. Choroid plexus tumors are also a varied group of tumors that preferentially occur in the ventricular system, ranging from aggressive supratentorial intraventricular tumors of children to benign cerebellopontine angle tumors of adults. Choroid plexus tumors have been reported occasionally in patients with Li-Fraumeni syndrome and von Hippel-Lindau (VHL) disease.

Medulloblastomas are malignant, primitive tumors that arise in the posterior fossa, primarily in children. These tumors also occur in young adults. Medulloblastomas often are surgically resected with subsequent treatment with chemotherapy and/or radiation. They may recur locally or occasionally as drop metastasis from the posterior fossa to the spine. Meningiomas are common intracranial tumors that arise in the meninges and compress the underlying brain. Although typically considered benign and only rarely frankly malignant, management of these tumors often poses clinical challenges. Histological grades of meningiomas vary with the majority benign, WHO grade I/IV (82%); less commonly atypical, WHO II/IV (15%); and infrequently they occur as anaplastic or malignant, WHO grade III/IV (3%).

Schwannomas are benign tumors that arise on peripheral nerves. Schwannomas may arise on cranial nerves, particularly the vestibular portion of the eighth cranial nerve (vestibular schwannomas, acoustic neuromas) where they present as cerebellopontine angle masses. Hemangioblastomas are tumors of uncertain origin that are composed of endothelial cells, pericytes and so-called stromal cells. These benign tumors most frequently occur in the cerebellum and spinal cord of young adults. Multiple hemangioblastomas are characteristic of von Hippel-Lindau disease (VHL). Hemangiopericytomas (HPCs) are dural tumors which may display locally aggressive behavior and may metastasize. The histogenesis of dural-based hemangiopericytoma (HPC) has long been debated, with some authors classifying it as a distinct entity and others classifying it as a subtype of meningioma.

The symptoms of both primary and metastatic brain tumors often depend on the location in the brain and the size of the tumor. Since various regions of the brain are responsible for specific functions, clinical symptoms will vary a great deal. Tumors in the frontal lobe of the brain may cause weakness and paralysis, mood disturbances, difficulty thinking, confusion and disorientation, and wide emotional mood swings. Parietal lobe tumors may cause seizures, numbness or paralysis, difficulty with handwriting, inability to perform simple mathematical problems, difficulty with certain movements, and loss of the sense of touch. Tumors in the occipital lobe can cause loss of vision in half of each visual field, visual hallucinations, and seizures. Temporal lobe tumors can cause seizures, perceptual and spatial disturbances, and receptive aphasia. If a tumor occurs in the cerebellum, the person may have ataxia, loss of coordination, headaches, and vomiting. Tumors in the hypothalamus may cause emotional changes, and changes in the perception of hot and cold. In addition, hypothalamic tumors may affect growth and nutrition in children. With the exception of the cerebellum, a tumor on one side of the brain causes symptoms and impairment on the opposite side of the body.

Compositions and methods of the present invention may be used to treat a subject who has been characterized as having cells or tissues expressing EGFRvIII, or is suspected of having cells or tissues expressing EGFRvIII. For example, subjects benefiting from treatment according to the invention include subjects with a glioma, or subjects suspected of having a glioma, for example, as evidenced by the presence of one or more of headaches, nausea and vomiting, seizures, loss of vision, pain, weakness, numbness in the extremities, and/or cranial nerve disorders as a result of increased intracranial pressure. In particular embodiments, the glioma being treated is glioblastoma multiforme. In accordance with this embodiment, the glioblastoma multiforme can be in the brain or spinal cord.

The present invention provides methods for inhibiting the proliferation or reducing an EGFRvIII-expressing cell population, the methods comprising contacting a population of cells comprising an EGFRvIII-expressing cell with a CAR-expressing cell described herein, e.g., a T cell, that binds to the EGFRvIII-expressing cell. In a specific embodiment, the present invention provides methods for inhibiting the proliferation or reducing the population of cancer cells expressing EGFRvIII, the methods comprising contacting the EGFRvIII-expressing cancer cell population with invention CAR-expressing cell described herein, e.g., a T cell, that binds to the EGFRvIII-expressing cell. In another embodiment, the present invention provides methods for inhibiting the proliferation or reducing the population of cancer cells expressing EGFRvIII, the methods comprising contacting the EGFRvIII-expressing cancer cell population with an EGFRvIII CART cell of the invention that binds to the EGFRvIII-expressing cell. In certain embodiments, the EGFRvIII CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model glioma or another cancer associated with EGFRvIII-expressing cells relative to a negative control. In one aspect, the subject is a human.

The present invention also provides methods for preventing, treating and/or managing a disorder associated with EGFRvIII-expressing cells (e.g., a glioblastoma), the methods comprising administering to a subject in need an EGFRvIII CART cell described herein that binds to the EGFRvIII-expressing cell. In one aspect, the subject is a human.

The present invention provides methods for preventing relapse of cancer associated with EGFRvIII-expressing cells, the methods comprising administering to a subject in need thereof an EGFRvIII CART cell described herein that binds to the EGFRvIII-expressing cell. In another embodiment, the methods comprise administering to the subject in need thereof an effective amount of an EGFRvIII CART cell described herein that binds to the EGFRvIII-expressing cell in combination with an effective amount of another therapy.

In one aspect, the invention pertains to a vector comprising an EGFRvIII CAR operably linked to promoter for expression in mammalian T cells. In one aspect, the invention provides a recombinant T cell expressing the EGFRvIII CAR for use in treating EGFRvIII-expressing tumors. The recombinant T cell expressing the anti-EGFRvIII CAR is termed an EGFRvIII CART. In one aspect, the EGFRvIII CART of the invention is capable of contacting a tumor cell with at least one EGFRvIII CAR of the invention expressed on its surface such that the EGFRvIII CART is activated in response to the antigen and the CART targets the tumor cell and growth of the tumor is inhibited.

In one aspect, the invention pertains to a method of inhibiting growth of a EGFRvIII-expressing tumor cell, comprising contacting the tumor cell with an EGFRvIII CAR T cell described herein such that the CART is activated in response to the antigen and targets the cancer cell, wherein the growth of the tumor is inhibited. In one aspect, the activated CART targets and kills the cancer cell.

In one aspect, the invention pertains to a method of treating cancer in a subject. The method comprises administering to the subject an EGFRvIII CAR T cell described herein such that the cancer is treated in the subject. An example of a cancer that is treatable by the EGFRvIII CAR T cell of the invention is a cancer associated with expression of EGFRvIII. In one aspect, the cancer associated with expression of EGFRvIII is a glioblastoma.

In one aspect, cancer associated with EGFRvIII is selected from the group consisting of glioblastoma multiforme (GBM), anaplastic astrocytoma, giant cell glioblastoma, gliosarcoma, anaplastic oligodendroglioma, anaplastic ependymoma, choroid plexus carcinoma, anaplastic ganglioglioma, pineoblastoma, medulloepithelioma, ependymoblastoma, medulloblastoma, supratentorial primitive neuroectodermal tumor, and atypical teratoid/rhabdoid tumor, non-small cell lung carcinomas, lung, breast, prostate, ovarian, colorectal and bladder carcinoma and any combination thereof.

The invention includes a type of cellular therapy where T cells are genetically modified to express a chimeric antigen receptor (CAR) and the CAR T cell is infused to a recipient in need thereof. The infused cell is able to kill tumor cells in the recipient. In some embodiments, the CAR-modified T cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

In one aspect, the CAR-modified T cells described herein may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (e.g., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with expression of EGFRvIII. In certain aspects, the cells of the invention are used in the treatment of patients at risk for developing diseases, disorders and conditions associated with expression of EGFRvIII. Thus, the present invention provides methods for the treatment or prevention of diseases, disorders and conditions associated with expression of EGFRvIII comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations or other drug treatments, e.g., described herein.

The present invention also provides methods for inhibiting the proliferation or reducing an EGFRvIII-expressing cell population, the methods comprising contacting a population of cells comprising an EGFRvIII-expressing cell with an EGFRvIII CART cell described herein that binds to the EGFRvIII-expressing cell. In a specific aspect, the present invention provides methods for inhibiting the proliferation or reducing the population of cancer cells expressing EGFRvIII, the methods comprising contacting the EGFRvIII-expressing cancer cell population with an EGFRvIII CART cell described herein that binds to the EGFRvIII-expressing cell. In one aspect, the present invention provides methods for inhibiting the proliferation or reducing the population of cancer cells expressing EGFRvIII, the methods comprising contacting the EGFRvIII-expressing cancer cell population with an EGFRvIII CART cell described herein that binds to the EGFRvIII-expressing cell. In certain aspects, the EGFRvIII CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for glioma or another cancer associated with EGFRvIII-expressing cells relative to a negative control. In one aspect, the subject is a human.

The present invention also provides methods for preventing, treating and/or managing a disease associated with EGFRvIII-expressing cells (e.g., glioblastoma), the methods comprising administering to a subject in need an EGFRvIII CART cell described herein that binds to the EGFRvIII-expressing cell. In one aspect, the subject is a human.

The present invention provides methods for preventing relapse of cancer associated with EGFRvIII-expressing cells, the methods comprising administering to a subject in need thereof an EGFRvIII CART cell described herein that binds to the EGFRvIII-expressing cell. In one aspect, the methods comprise administering to the subject in need thereof an effective amount of an EGFRvIII CART cell described herein that binds to the EGFRvIII-expressing cell in combination with an effective amount of another therapy.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. Exemplary immunotherapy approaches for malignant glioma are disclosed in Johnson et al. 2010 Curr Neurol Neurosci Rep 10:259-266. In some embodiments, a CAR-expressing cell described herein may be used in a treatment regimen in combination an agent targets extracellular matrix proteins, such as tenscin, e.g., an anti-tenascin antibody, e.g., a $^{211}$At-labeled anti-tenascin antibody. In some embodiments, a CAR-expressing cell described herein may be used in a treatment regimen in combination with an immunomodulatory agent, such as interferon alpha, interferon beta, TGF-β2 peptide inhibitor, or poly-ICLC. In some embodiments, a CAR-expressing cell described herein may be used in a treatment regimen in combination with a WT1 transcription factor peptide vaccine, such as that described in Izumoto et al. 2008 J Neurosurg 108:963-971.

In one embodiment, a CAR-expressing cell described herein can be used in combination with a chemotherapeutic agent. Exemplary chemotherapeutic agents include an alkylating agent, a platinum based agent, an angiogenesis inhibitor (e.g., a VEGF pathway inhibitor, a tyrosine kinase inhibitor (e.g., an EGF pathway inhibitor), an mTOR inhibitor.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents include, without limitation, carboplatin, cisplatin, and oxaliplatin.

Exemplary angiogenesis inhibitors include, without limitation A6 (Angstrom Pharmacueticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP O2) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharaceuticals), Combretastatin (Oxigene), CP-751,871(Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974(Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089(Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518(Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230(Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary Vascular Endothelial Growth Factor (VEGF) receptor inhibitors include, but are not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors include, without limitation tyrphostin 46, EKB-569, erlotinib (Tarceva®), gefitinib (Iressa®), erbitux, nimotuzumab, lapatinib (Tykerb®), cetuximab (anti-EGFR mAb), $^{188}$Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

Exemplary mTor inhibitors include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.$0^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and $N^2$-[1,4-dioxo-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

Exemplary Phosphoinositide 3-kinase (PI3K) inhibitors include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho [1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to. 8-[4-(1-Aminocyclobutyl)phenyl]-9-phenyl-1,2,4-triazolo [3,4-f][1,6]naphthyridin-3(2H)-one (MK-2206, CAS 1032349-93-1); Perifosine (KRX0401); 4-Dodecyl-N-1,3,4-thiadiazol-2-yl -benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Tricirbine (6-Amino-4-methyl-8-(β-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)methyl]-1-(7H-pyrrolo [2,3-d]pyrimidin-4-yl)-4-piperidinamine (CCT128930, CAS 885499-61-6); 4-(4-Chlorophenyl)-4-[4-(1H pyrazol-4-yl) phenyl]-piperidine (AT7867, CAS 857531-00-1); and Archexin (RX-0201, CAS 663232-27-7).

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a CAR-expressing cell described herein to a subject and further administering an agent to manage elevated levels of a soluble factor resulting from treatment with a CAR-expressing cell. In one embodiment, the soluble factor elevated in the subject is one or more of IFN-γ, TNFα, IL-2 and IL-6. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is entanercept. An example of an IL-6 inhibitor is Tocilizumab (toc).

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675, 206).).

PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are available in the art and may be used combination with a CD123 CAR described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649. The agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., the polypeptide that is associated with a positive signal is CD28, ICOS, and fragments thereof, e.g., an intracellular signaling domain of CD28 and/or ICOS. In one embodiment, the fusion protein is expressed by the same cell that expressed the CAR. In another embodiment, the fusion protein is expressed by a cell, e.g., a T cell that does not express an anti-EGFRvIII CAR.

In one embodiment, the agent which enhances activity of a CAR-expressing cell described herein is miR-17-92.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the T cell compositions of the present invention are administered by i.v. injection. The compositions of T cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1

Redirected Autologous T Cells Engineered to Express EGFRvIII-Targeted Chimeric Antigen Receptor in Patients Diagnosed with EGFRvIII+ Glioblastoma The following experiments were designed to address whether human T cells re-directed to the surface protein EGFRvIII with an antibody-based chimeric antigen receptor (CAR) would be effective in eliminating an EGFRvIII+ model of glioblastoma multiforme in NSG mice. In addition, experiments were designed to evaluate engraftment and persistence of these cells. Three different forms of CARs are tested, encompassing two different single-chain variable fragments (the portion of the CAR binding to the EGFRvIII antigen), and the intracellular signaling domains (4-1BB and CD3 zeta with and without CD28).

The immunodeficient NOD/scid/γcnull (NSG) mouse is an excellent xenotransplantation model to engraft human tumor cell lines (the brain tumor line U87, which are EGFR+ and has versions engineered to be EGFRvIII+) and human T cells. Following engraftment, the human T cells can be maintained in NSG mice for approximately 2 months, or until fatal xenogeneic GVHD (xGVHD) develops, which depends on the dose and donor of human T cells infused.

Briefly, a novel CAR (3C10 CAR) using the lentiviral platform was created incorporating a scFv derived from anti-EGFRvIII monoclonal antibody 3C10. This CAR has been tested in vitro and in xenogeneic mouse models. NOD/scid/γc(−/−) (NSG) mouse models have been widely used for pre-clinical assessments of CAR therapy, including evaluation of long-term persistence of infused human T-cells. NSG mice bearing Day 7 U87-EGFRvIII tumors in the brain received i.p. injections of temozolomide (1 mg/dose) daily on Days 7-11 and i.v. infusions of: $2\times10^6$ human T-cells ex vivo transduced with 3C10 CAR or mock enhance green fluorescence protein (EGFP)-vector on Days 7 and 17. On Day 21, BLI signals were undetectable in all mice that received CAR-transduced T-cells, while mice treated with the mock-transduced T-cells show regrowth of the tumor in 4 of 5 mice following the transient anti-tumor effect by temozolomide. In a separate experiment, mice treated with CAR-T-cells were sacrificed on Day 21, and the infiltration of CAR-transduced T-cells was evaluated by immunohistochemistry using biotin-conjugated anti-F(ab')$_2$ mAb (specific for the 3C10CAR) and streptavidin-Phycoerythrin (PE). i.v. infused CAR-T-cells appeared to heavily infiltrate the tumor based on the intense PE signals while the control tissue stained with streptavidin-PE but without the anti-F(ab')$_2$ mAb showed background signals only.

The materials and methods employed in these experiments are now.

Materials and Methods

NSG Mouse Model

A colony of immunodeficient NOD/scid/γcnull (NSG) mice was recently established. NSG mice lack T and B cells, natural killer cells, and also have impaired dendritic cell function. It has been confirmed that engraftment of activated T cells was superior in NSG mice over the previous NOD/scid/β2Mnull mouse model. Therefore the NSG model was used for the human xenotransplantation experiments.

Structure and Characteristics of the Biological System

Although many of the monoclonal and polyclonal Abs directed against EGFRvIII have cross reactivity to wild type EGFR or other non-specific proteins, a monoclonal antibody (mAb) 3C10, which was originally developed by immunization of mice with a 14 amino acid peptide including the EGFRvIII-specific fusion junction, demonstrated highly specific recognition of EGFRvIII with negligible detectable binding to wild-type EGFR (Okamoto et al., 1996 *Br J Cancer* 73:1366-1372). A research-grade lentiviral vector was used for the transduction of the T cells.

Cell Preparation for Mouse Infusion

The cells for infusion into mice are human T cells. Human mononuclear cell enriched apheresis products are obtained by leukapheresis of healthy volunteer donors by the University of Pennsylvania Human Immunology Core. All specimens are collected under a University Institutional Review Board-approved protocol, and informed written consent is obtained from each donor. T cells are negatively selected using a RosetteSep human T cell enrichment cocktail (Stemcell Technologies, Vancouver, Canada). T cells are transferred to TRP laboratory where they are activated with research grade CD3/28 beads and expanded in RPMI with Glutamine, 10% FBS, 20 mM Hepes, 100 U/ml Penicillin and 100 ug/ml Streptomycin. Vector transduction occurs 24 hours later with packaged lentivectors added directly to activated cultures. Cells are debeaded on day 5 and expansion is monitored with a Coulter Multisizer 3(Beckman Coulter, Fullerton, Calif.) for changes in size (fl) and total cell counts, maintaining concentration between 0.7E6 to 2E6 cells/ml. Transduction efficiency for CAR-transduced T cells is tested by flow cytometry by staining with either goat anti-mouse antibody (GAM, for 3C10-based CARs) or goat-anti-human (GAH, for 139-based CAR). Mice are infused with 1 million CAR+ T cells per mouse by tail vein injection on day 0 of the study.

Temozolomide (TMZ) Treatment

Mice bearing i.c. U87-EGFRvIII tumor and receiving CAR+ T cells on day 0 subsequently receive intraperitoneal (i.p.) injections of TMZ on days 0-4 (daily for 5 days): TMZ is resolved in DMEM at 6.67 mg/ml. Each mouse receives 50 uL TMZ solution (333 microgram/dose; approximately 17 mg/kg/dose) by i.p. injections.

Clinical Grade CART

The CART-EGFRvIII T cells are prepared in the clinical cell and vaccine production facility (CVPF), and the cell product is autologous T lymphocytes. CD3+ T-cells are enriched from a leukapheresis product by depletion of monocytes via counterflow centrifugal elutriation. On day 0, the manufacturing process is initiated with activation of the enriched T-cells using anti-CD3/CD28 mAb coated magnetic beads. The T cell culture is exposed to the EGFRvIII CAR lentivirus vector and expanded. The T-cell manufacturing process initiates in a static tissue culture (day 0 to day 5), followed by transfer to a Wave bioreactor if needed for additional expansion under perfusion conditions. At the end of the culture, cells are depleted of magnetic beads, washed, concentrated, and cryopreserved. The modified T cell product is cryopreserved in cryobags in a volume dependent on the cell number (at a final concentration of maximum $10^8$/ml) using a controlled-rate freezer. Cryopreserved EGFRvIII CAR T-cell products are stored in a monitored freezer at ≤−130° C. The results of the experiments are now described.

Eradication of Intracranial EGFRvIII-Expressing Glioblastoma by CAR-T-Cells

Glioblastoma (GBM) is the most common and the most malignant primary brain tumors, and responsible for approximately 12,000 cancer-related deaths in the US each year. Patients with GBM have a median survival of sorter than 15 months following treatment with a combination of chemotherapy (temozolomide) with radiotherapy (RT). Adoptive cell transfer (ACT) therapy with autologous T-cells, especially with T-cells transduced with chimeric antigen receptors (CARs), has shown promise in recent hematologic cancer trials. ACT with CART cells may be particularly suitable for patients with GBM because the specificity, number, and functional phenotype of cells prepared ex vivo can be manipulated and controlled better than native T-cells induced by in vivo immunization.

Epidermal growth factor receptor variant III (EGFRvIII) is the most common variant of the EGFR observed in human tumors but is rarely observed in normal tissue. This protein results from the in-frame deletion of exons 2-7 and the generation of a novel glycine residue at the junction of exons 1 and 8 within the extra-cellular domain of the EGFR, thereby creating a tumor-specific epitope. EGFRvIII is expressed in 24% to 67% of GBM, but not in normal tissues.

Figure 6:
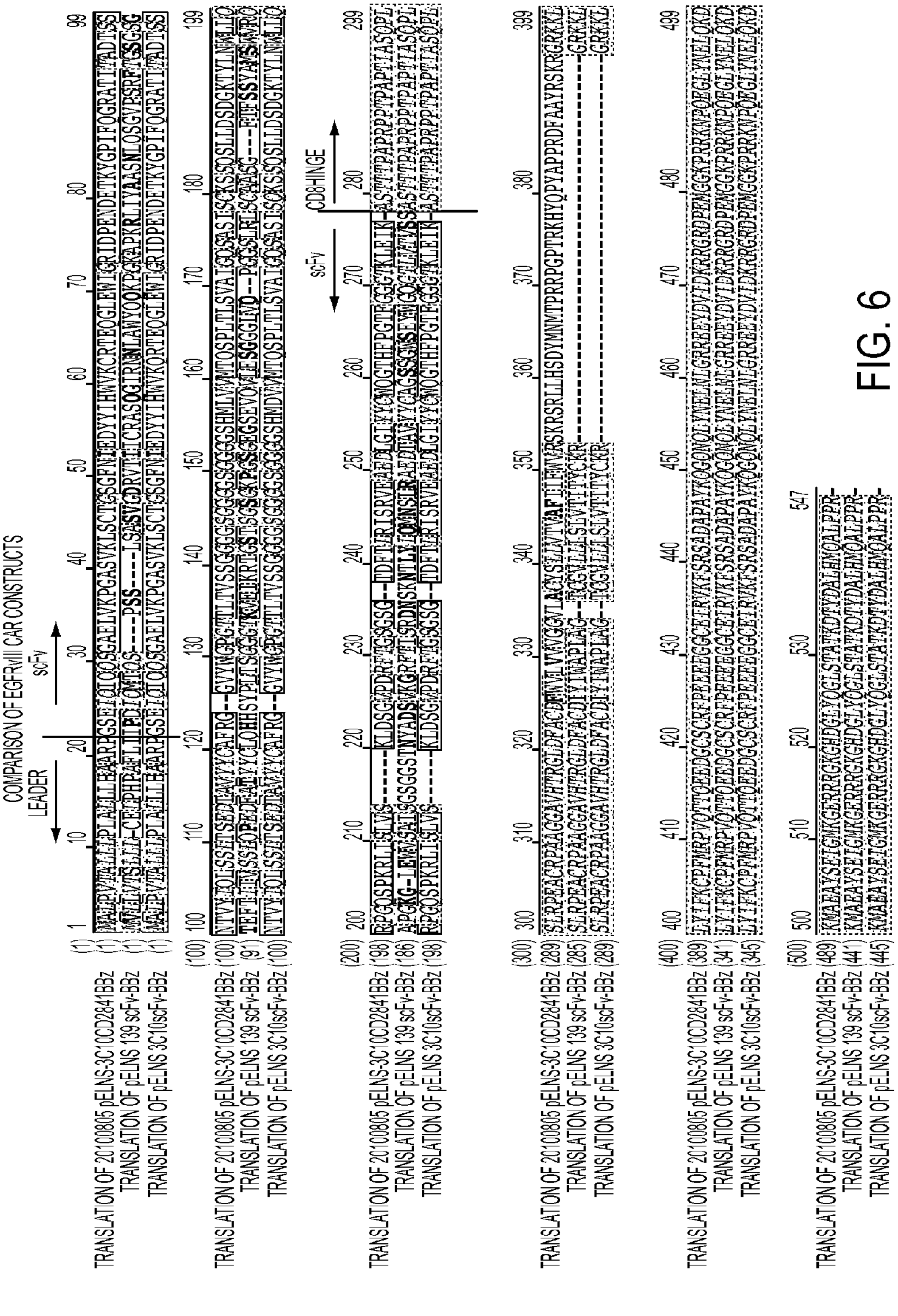
FIG. 6 is an image showing the comparison of the representative EGFRvIII CARs (SEQ ID NOS 1, 121, and 2, respectively, in order of appearance)
Figure 7A:
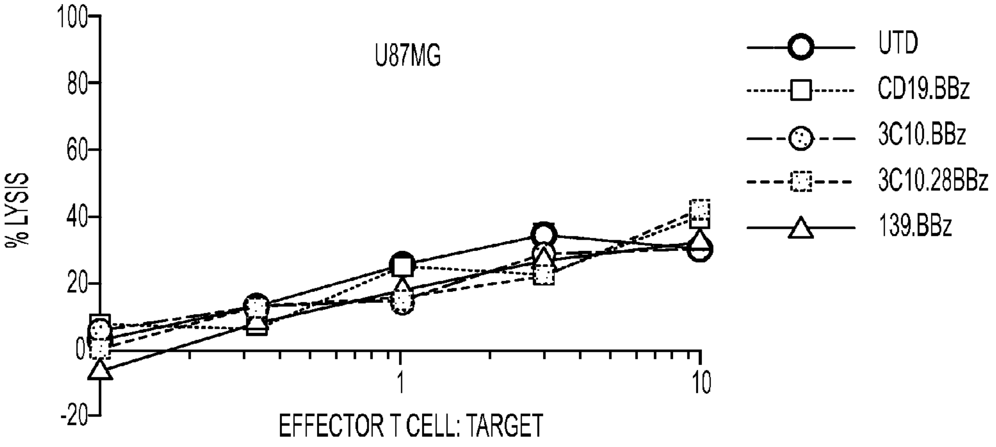
FIGS. 7A and 7B are images showing that human T-cells transduced with EGFRvIII CARs exhibited specific and potent lysis of EGFRvIII-expressing U87 human GBM cells (U87-EGFRvIII)
Figure 7B:
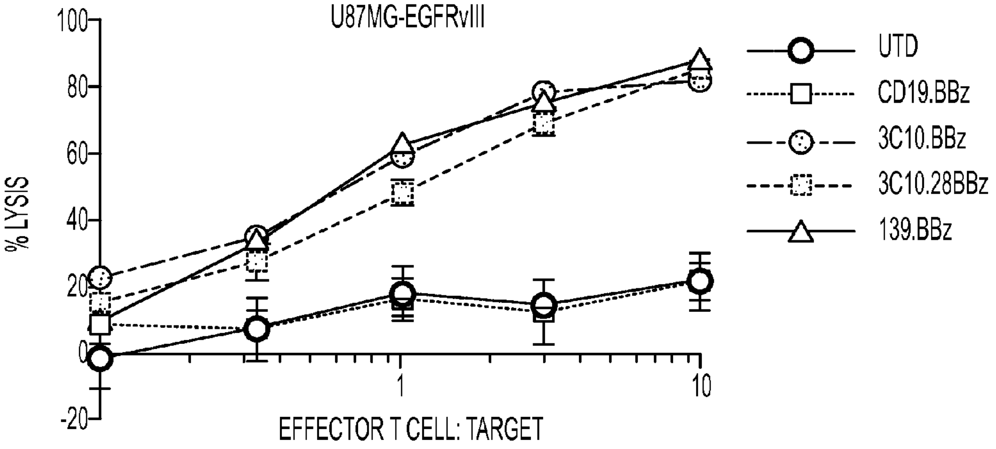
Figure 8:
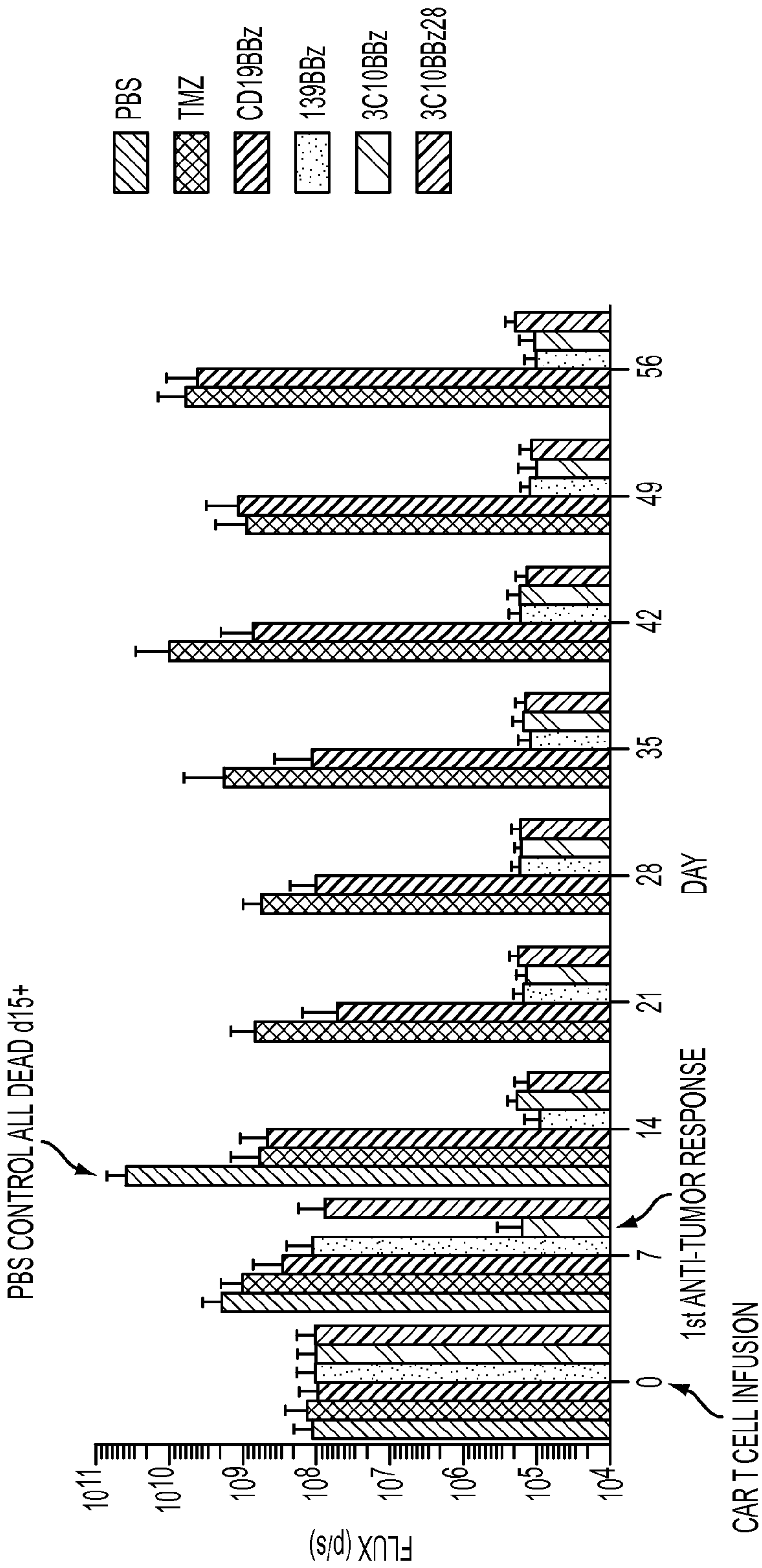
FIG. 8 is a graph showing that all anti-EGFRvIII CARTs clear tumor cells, but construct 3C10.BBz CART clears tumors most rapidly by day 7.

To develop effective CAR therapy for GBM, three novel lentiviral CAR constructs targeting EGFRvIII were generated. Each of these vectors encode a single-chain variable fragment (scFv) derived from EGFRvIII-specific murine monoclonal antibodies (mAbs) 3C10 or EGFRvIII-specific humanized monoclonal antibodies (mAbs) designated "139" (FIG. 6). The 3C10 scFv was coupled with CD8a hinge, 4-1BB and CD3ζ domains with or without CD28 trans-membrane and intracellular domains (3C10BBz28-CAR and 3C10BBz-CAR, respectively). The 139 scFv was coupled with CD8a hinge, 4-1BB and CD3ζ domains (139BBz-CAR). Human T-cells transduced with each of these CARs demonstrated specific and potent lysis of EGFRvIII-expressing U87 human GBM cells (U87-EGFRvIII); see FIGS. 7A and 7B. Immunocompromised NOD/scid/γc(−/−) (NSG) mice bearing Day 7 U87-EGFRvIII tumors in the brain received intravenous infusions of $1\times10^6$ human T-cells transduced ex vivo with: 1) 139BBz-CAR; 2) 3C10BBz-CAR; 3) 3C10BBz28-CAR; 4) control CD19BBz-CAR targeting human CD 19. These mice also received intraperitoneal injections of temozolomide (330 mcg/dose) daily on Days 7-11. The tumor growth was monitored by bioluminescence imaging (BLI) as the U87-EGFRvIII cells also express luciferase. All mice treated with only saline died by Day 21 due to rapid tumor growth, and temozolomide treatment without ACT inhibited but did not eradicate the U87-EGFRvIII tumors. Mice receiving CD19BBz-CAR-T-cells and temozolomide demonstrated some allogeneic responses against U87-EGFRvIII, but the tumors continued to grow in these mice. On the other hand, in all mice receiving 139BBz-CAR-, 3C10BBz-CAR-, or 3C10BBz28-CAR-transduced T-cells, the BLI signals diminished to under baseline levels by Day 21, suggesting total tumor eradication (FIG. 8). Importantly, mice receiving 3C10BBz-CART cells cleared the tumor faster than either the 3C10BBz28 or 139BBz CART cells, suggesting the combination of 3C10 with BBz might afford a better response in patients. The tumor growth and peripheral immune responses were monitored to determine whether any of the three EGFRvIII-CAR vectors are superior to the others for long-term anti-tumor effects.

The results presented herein strongly support development of a Phase I clinical trial of ACT with EGFRvIII-targeting CAR-T-cells in GBM patients who concurrently receive standard of care chemotherapy with temozolomide.

Clinical Design

A single-arm open-label pilot study was designed to determine the safety, tolerability and engraftment potential of CART-EGFRvIII T cells in patients with EGFRvIII+ newly diagnosed GBMs. Generally, all subjects are dosed with autologous CART-EGFRvIII T cells. Eligible subjects are leukapheresed to obtain large numbers of peripheral blood mononuclear cells (PBMC) for CART-EGFRvIII manufacturing. The T cells are purified from the PBMC, transduced with the humanized 3C10-CAR lentiviral vector, expanded in vitro and cryopreserved in appropriate dose aliquots. Cells to be infused are thawed at the bedside immediately prior to infusion on day 0.

Subjects are subjected to blood tests to assess safety, and engraftment and persistence of the CART EGFRvIII cells at regular intervals through week 4 (day 28). The subsets of circulating T-cells that contain the 3C10-CAR vector are assessed at various times after infusion and compared to the baseline sample. After day 28, subjects are evaluated monthly until 6 months with a medical history, a physical examination, brain MRI and blood tests or as per standard of care.

Research blood tests are conducted concurrent with these visits. After the six months, patients are followed every 2 months for two years. After the two-year timepoint, subjects enter a roll-over study for annual follow-up by phone and questionnaire for an additional thirteen years to assess for the diagnosis of long-term health problems, such as development of new malignancy, as required by FDA regulations pertaining to gene transfer studies.

Without wishing to be bound by any particular theory, it is believed that because of the highly restricted expression of the EGFRvIII protein, there is no anticipation of any kind of off-tumor on-target activation of T cells. Preferably, only one infusion of the CART-EGFRvIII is administered, and therefore do not anticipate allergic-type responses either. However, one toxicity that may be encountered is bystander inflammation from T cell activation at the site of tumor. Symptoms and signs of brain edema will be closely monitored and managed. In some embodiments, bystander inflammation from T cell activation can be treated by administration of an anti-inflammatory agent, such as a steroid agent.

Example 2

Co-transduction of miR-17-92 Enhances Anti-tumor Activity of T-Cells Transduced with the Anti-EGFRvIII Chimeric Antigen Receptor in Mice Bearing Human Glioblastoma Xenografts miR-17-92 expression confers type-1 phenotype and enhanced survival of T-cells. It has been reported that that miR-17-92 is down-regulated in T-cells derived from glioblastoma (GBM) patients. To improve the efficacy of adoptive transfer therapy against GBM using T-cells transduced with Chimeric Antigen Receptors (CAR-T-cells), a novel lentiviral vectors for miR-17-92 and a CAR consisting of epidermal growth factor receptor variant III (EGFRvIII)-specific single-chain variable fragment (scFv) coupled to the T-cell receptor CD3ζ chain signaling module and co-stimulatory motifs of CD137 (4-1BB) and CD28 in tandem (pELNS-3C10-CAR) was constructed. In addition to antigen-specific and potent cytotoxic activities against U87 GBM cells stably expressing EGFRvIII (U87-EGFRvIII), CAR-T-cells co-transduced with miR-17-92 exhibited improved resistance to T-cell suppressing effects of transforming growth factor (TGF)-β and temozolomide compared with CAR-T-cells without miR-17-92 co-transduction. In mice bearing intracranial U87-EGFRvIII xenografts, CAR-T-cells with or without transgene-derived miR-17-92 expression demonstrated similar levels of potent therapeutic effects without demonstrating any uncontrolled growth of CAR-T-cells. However, when these mice were re-challenged with U87-EGFRvIII cells in the brains, mice receiving co-transduced CAR-T-cells exhibited improved protection compared with mice treated with CAR-T-cells without miR-17-92 co-transduction. These data support miR-17-92 can be integrated in the CAR to improve the efficacy in patients with GBM.

The results of the experiments are now described.

Construction of Lentiviral Vectors for EGFRvIII-Specific CAR and miR-17-92

Figure 1B:
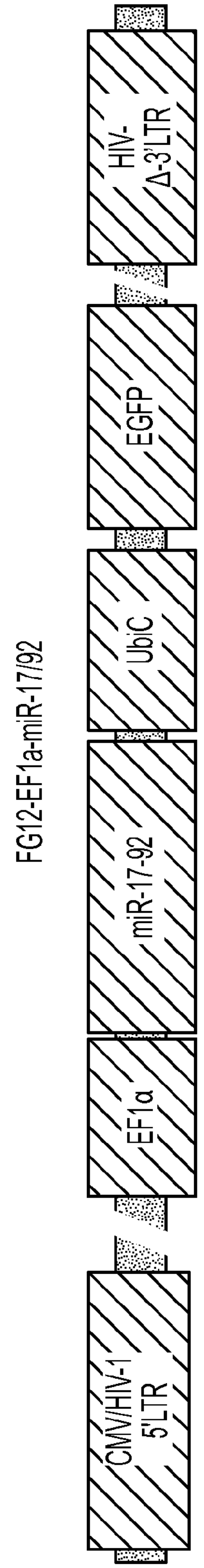

A lentiviral vector for a CAR that recognizes the EGFRvIII through a single-chain variable fragment (scFv) derived from human EGFRvIII-specific monoclonal antibody (mAb) 3C10 (pELNS-3C10-CAR was generated (See FIG. 1A). In this construct, the EF-1α promoter drives the CAR fusion protein integrating the 3C10-derived scFv, CD28 trans-membrane (TM) as well as 4-1BB and intracellular domains (ICD) and CD3ζ domains. A lentiviral miR-17-92 construct using the FG12-based self-inactivating (SIN) vector (FG12-EF1a-miR-17/92 was also created (See FIG. 1B). In this vector, the EF-1αpromoter drives miR-17-92 and the human UbiC promoter drives enhanced green fluorescence protein (EGFP) marker gene for tracking of transduced cells. Abbreviations used in the schema: RSV/HIV-1 5'LTR; Hybrid RSV promoter-R/U5 long terminal repeat, EF-1α; Human elongation factor 1α-subunit promoter, VH; Variable region in the heavy chain of the 3C10 immunoglobulin, VL; Variable region in the light chain of the 3C10 immunoglobulin, HIV-1 Δ-3'LTR; Self-inactivating 3' long terminal repeat with deletion in U3 region, CMV/HIV-1 5'LTR Hybrid CMV promoter-R/U5 long terminal repeat, UbiC; Ubiquitin C promoter.

In Vitro Characterization of Human T-Cells Transduced with the CAR and miR-17-92

Figure 2A:
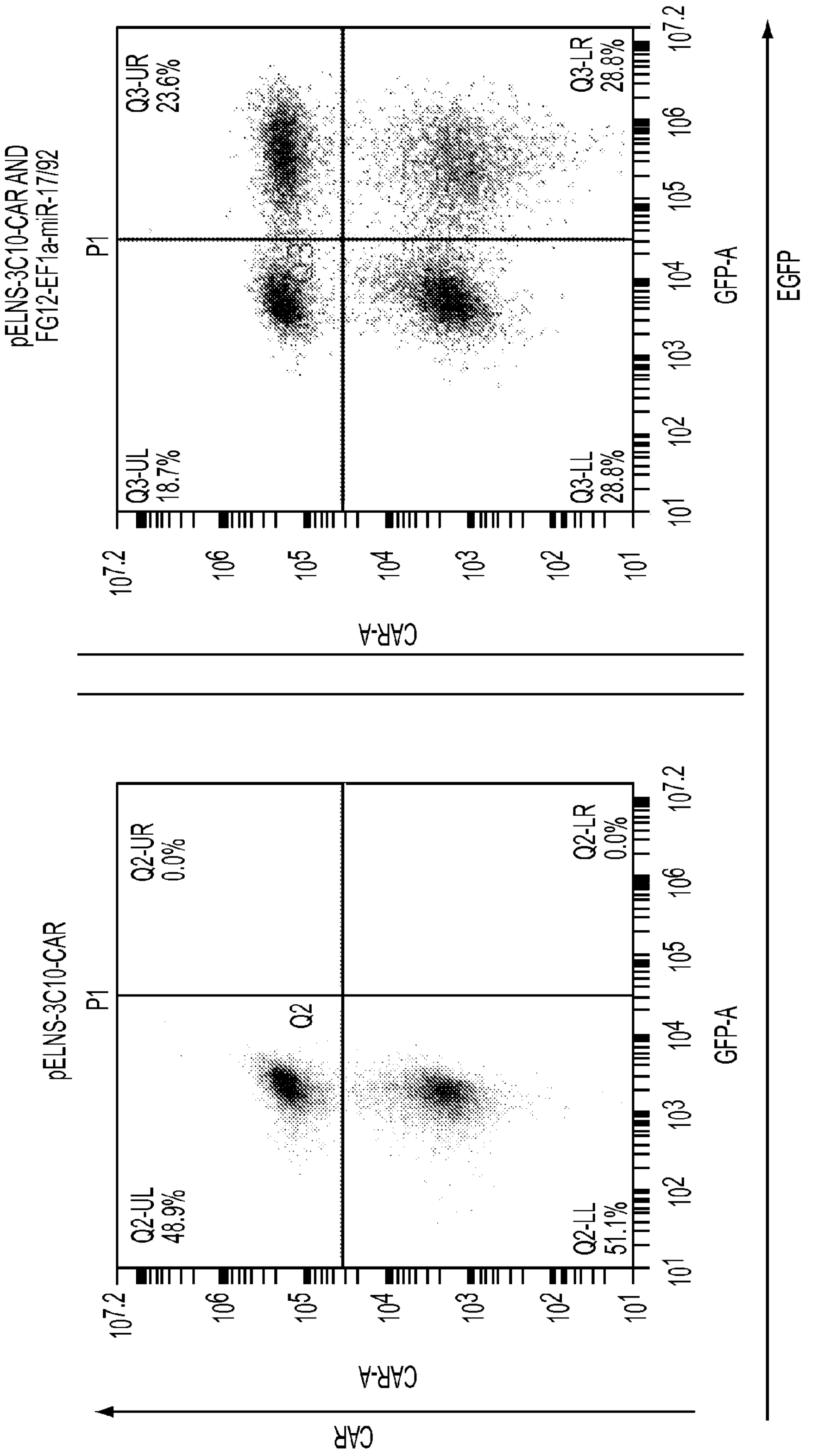
FIGS. 2A through 2C are a series of images showing the functional expression of lentivirally transduced 3C10-CAR and miR-17-92 in human T cells. CD3+ T cells that were transduced with pELNS-3C10-CAR alone or both pELNS-3C10-CAR and FG12-EF1a-miR-17/92.

Healthy donor-derived $CD3^+$ T-cells were transduced with pELNS-3C10-CAR, and the cells were evaluated for expression levels of the transgene by flow cytometry for expression of 3C10-CAR and miR-17-92 by anti-mouse $(Fab')_2$ antibody and EGFP, respectively (FIG. 2A, Left). Using anti-mouse $F(ab')_2$ Ab, which is specific for the 3C10-derived scFv on human T-cells, nearly half (48.9%) of the T-cells expressing the 3C10-derived scFv on their surface were detected.

Figure 2B:
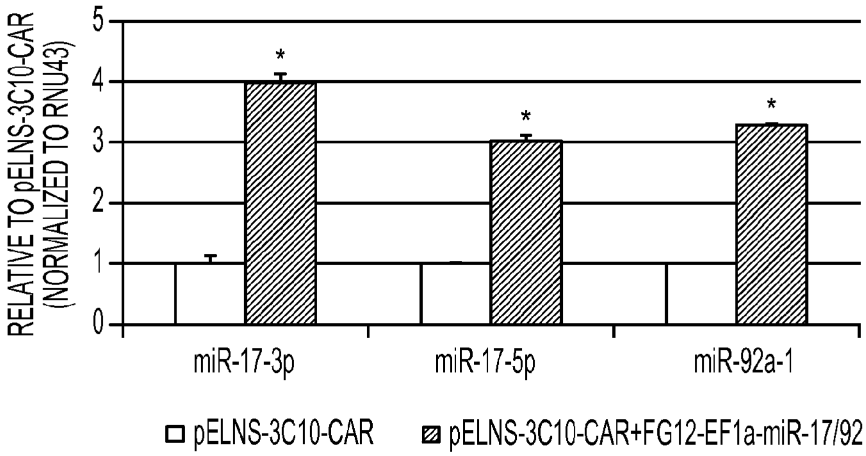
Figure 2C:
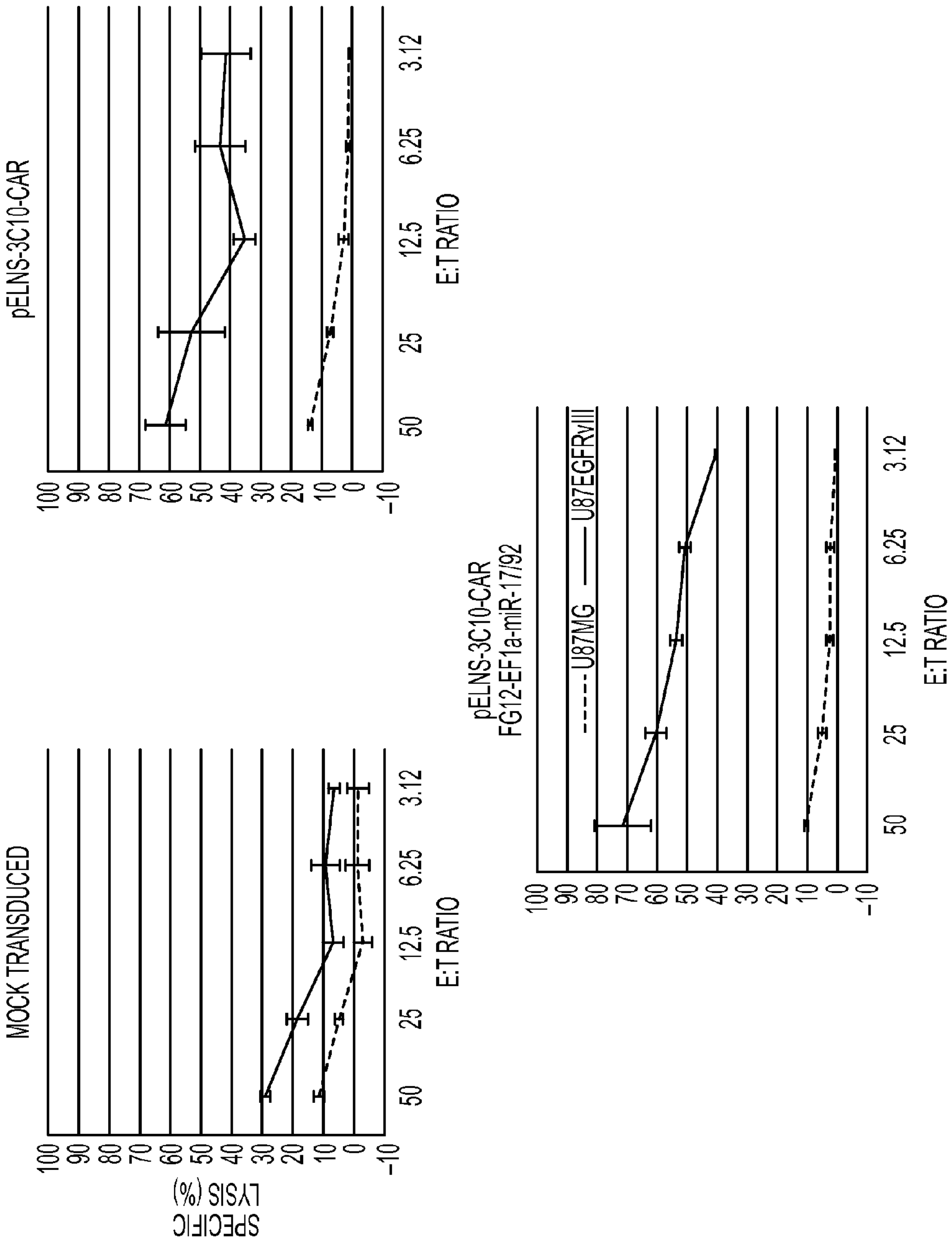

To obtain human T-cells expressing both the CAR and transgene-derived miR-17-92, $CD3^+$ T-cells were co-transduced with pELNS-3C10-CAR and FG12-EF1a-miR-17/92 by sequential infection of the two lentiviral vectors. At 24 hours after the initial transduction with pELNS-3C10-CAR, the T-cells were transduced with FG12-EF1a-miR-17-92. It was observed that approximately a quarter (23.6%) of the total T-cells expressed both CAR and EGFP (FIG. 2A, Right). For subsequent in vitro studies, CAR-transduced T-cells (CAR-T-cells) were enriched using biotinylated anti-mouse $F(ab')_2$ Ab and anti-biotin MACS. Based on the efficiency of co-transduction (FIG. 2A, Right), at least 50% of the CAR-T-cells also expressed EGFR (hence the transgene-derived miR-17-92). By real-time PCR, 3-4 fold higher expression of miR-17-92 was detected in the $F(ab')_2$ Ab-enriched, miR-17-92-co-transduced CAR-T-cells compared with T-cells transduced with the CAR alone (FIG. 2B). FIG. 2B demonstrates the expression levels of the miR-17-92 cluster members, miR-17-3p, miR-17-5p and miR-92a-1 in transduced T cells measured by qRT-PCR. Mean±SD values of 3 replicate measurements from one of three experiments with similar results are depicted. * indicates $p<0.05$ between the two groups using student t test. FIG. 2C depicts EGFRvIII specific cytotoxic activities of transduced T cells evaluated by a 12-h 51Cr-release assay at various E:T ratios against 51Cr-labeled U87-EGFRvIII or control U87 cells. Control cells were Mock (EGFP)-transduced T-cells. Values indicate mean±SD in triplicated wells.

While the mock-transduced T-cells showed only background levels of lysis against both parental U87 (EGFRvIII-negative) and U87-EGFRvIII cells, T-cells transduced with the CAR demonstrated potent and specific lysis of EGFRvIII-expressing U87 human GBM cells (U87-EGFRvIII) with only background levels of cytotoxic effects against parental U87 cells (FIG. 2C). In these 12h $^{51}Cr$-release assays, co-transduction of CAR-T-cells with miR-17-92 did not significantly enhance their specific cytotoxic activity against U87-EGFRvIII target cells.

miR-17-92 Co-transduction Confers Enhanced IFN-γ release and Resistance to Suppressive Effects by TGF-β and Temozolomide (TMZ—Standard of Care Therapy)

In a previous study (Sasaki et al., 2010, J. Transl Med 8:17), $CD4^+$ T cells derived from miR-17-92 transgenic mice demonstrated increased IFN-γ production when compared with counterparts derived from wild type mice; and transfection of human Jurkat T cells with miR-17-92 lead to enhanced resistance to activation-induced cell death (AICD).

Experiments were conducted to evaluate whether co-transduction of CAR-T-cells with miR-17-92 confers improved IFN-γ production, cell proliferation and lesser degrees of apoptotic death when they are exposed to a chemotherapy agent TMZ or an immuno-suppressive cytokine TGF-β.

Figure 3A:
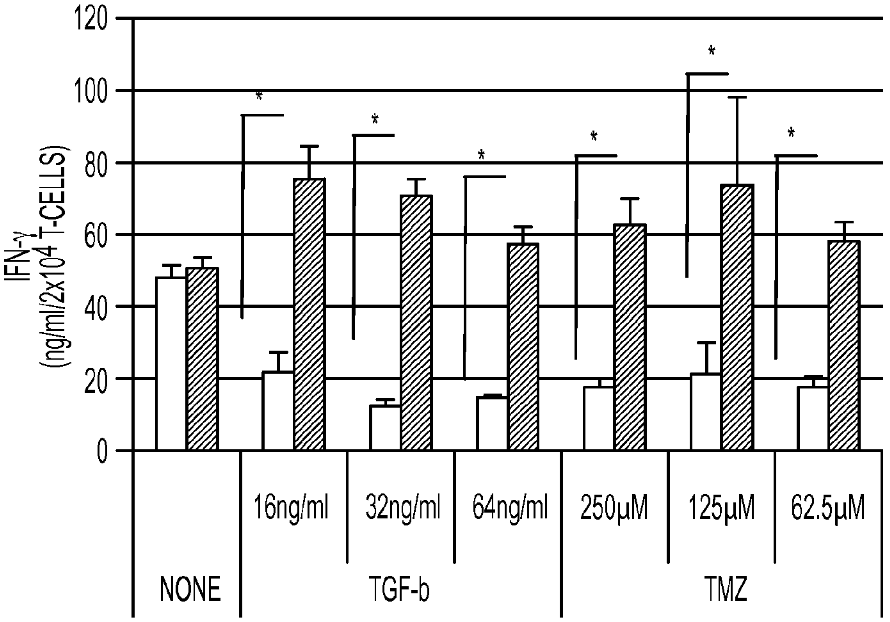
FIGS. 3A through 3D are a series of images demonstrating that co-expression of miR17-92 in CAR-T-cells confers resistance to suppressive effects of TGF-β and TMZ. CAR-T-cells (open bars) and those co-transduced with miR-17-92 (closed bars) were co-cultured with an APCs expressing EGFRvIII in the presence of indicated concentrations of TGF-β and TMZ.
Figure 3B:
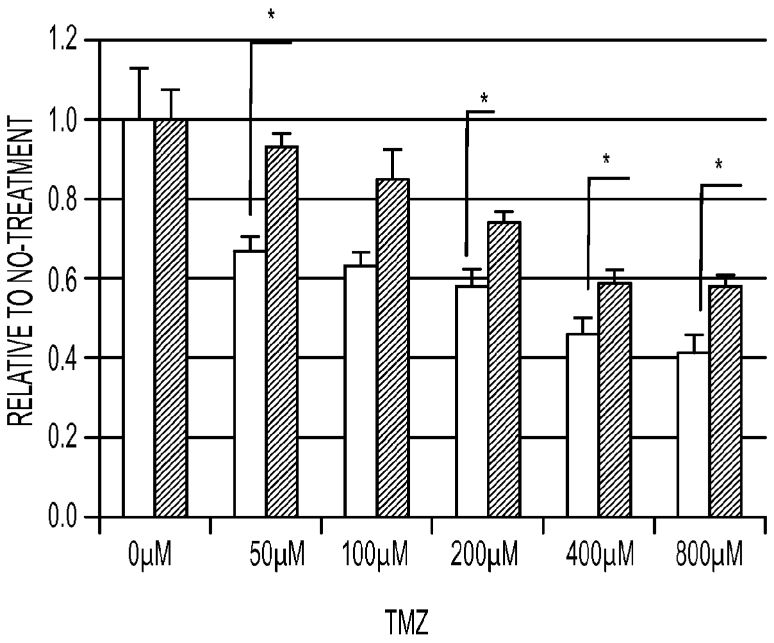
Figure 3C:
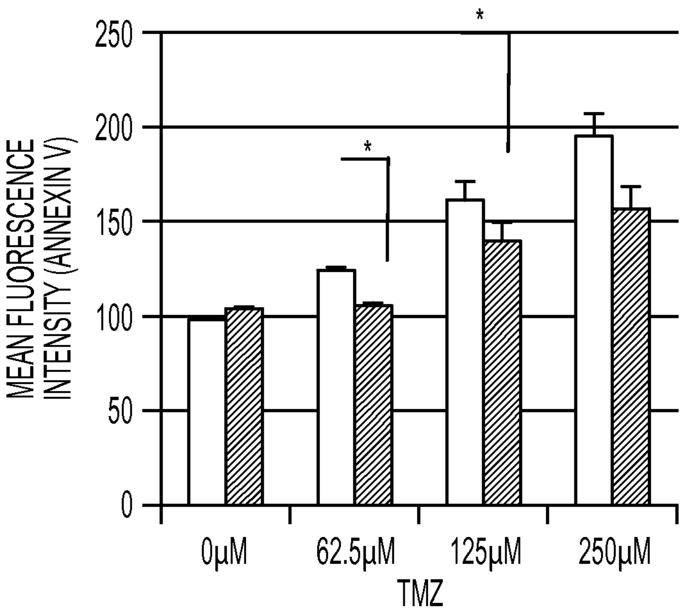
Figure 3D:
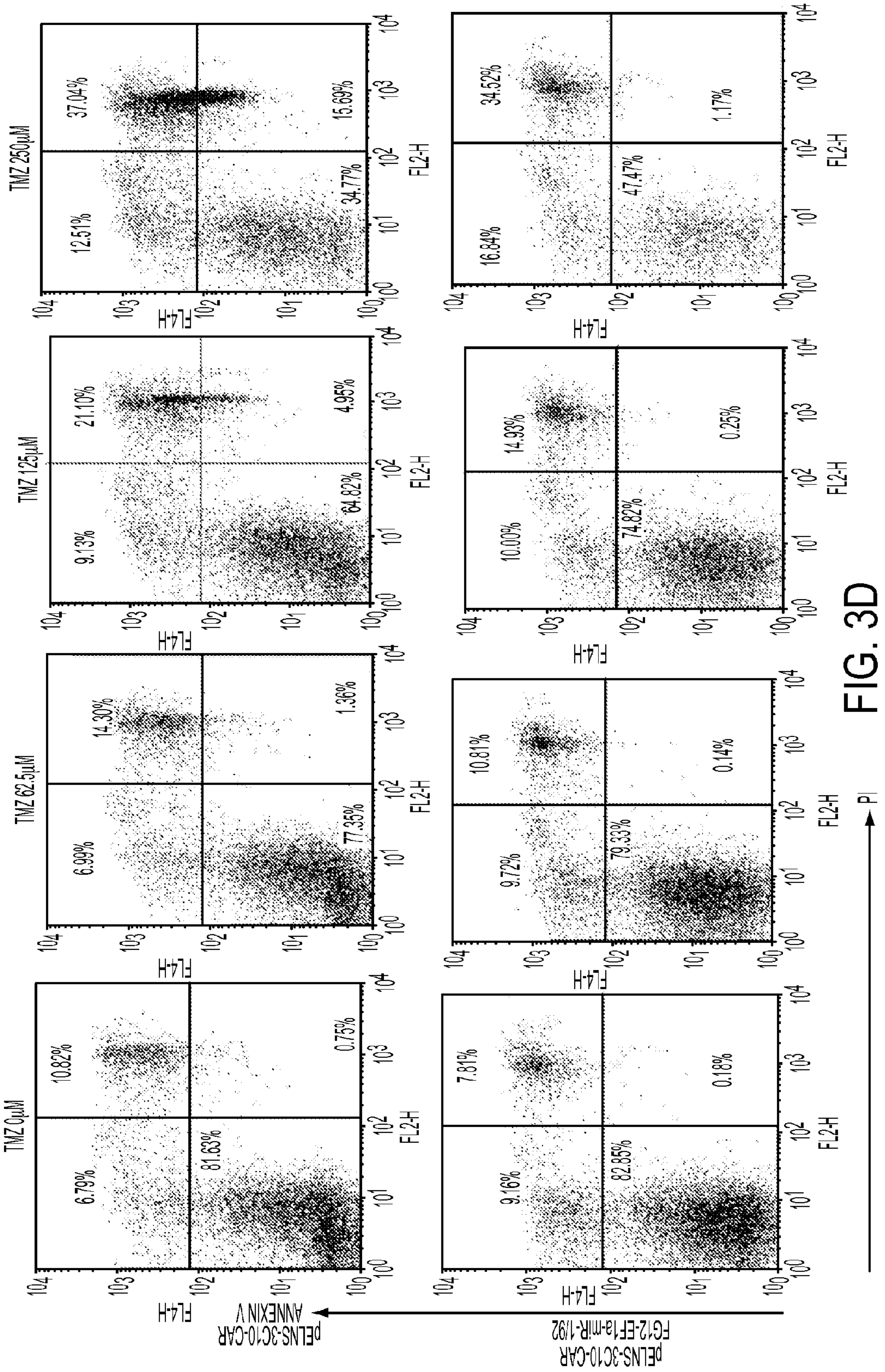

When CAR-T-cells were stimulated with EGFRvIII-transduced artificial Antigen-Presenting Cells (aAPCs) without TGF-β or TMZ, the cells expressed similar levels of IFN-γ with or without co-transduction. However, when the cells were exposed to escalating doses of TGF-β or TMZ, CAR-T-cells without miR-17-92 co-transduction produced significantly reduced levels of IFN-γ, while the co-transduced CAR-T-cells maintained high level production of IFN-γ (FIG. 3A). Open bars and closed bars represent results from CAR-T-cells (without miR-17-72) and miR-17-92 co-transduced CAR-T cells, respectively. FIG. 3A shows IFN-γ produced by the transduced T cells during the 25 last 24 h of 96 h co-culture. FIG. 3B shows relative proliferation levels between the groups were evaluated by WST1 assay following the 3-day co-culture course. FIGS. 3C and 3D show apoptotic death of CAR-T-cells evaluated by Annexin-V and PI. FIG. 3C show mean fluorescent intensity for Annexin-V on CAR-T-cells exposed to TMZ. Values indicate mean±SD in triplicate wells. (* indicates $P<0.05$) FIG. 3D show flow cytometric histograms for Annexin-V+ and/or PI+ in one of the three experiments with similar results.

Experiments were conducted to evaluate the effects of miR-17-92 co-transduction on proliferation of CAR-T-cells in the presence of TMZ in culture. Experiments were designed to induce the proliferation of CAR-T-cells with EGFRvIII-expressing aAPC and the proliferation was evaluated by WST-1 assay (FIG. 3B). Without TMZ, miR-17-92-co-transduced CAR-T-cells demonstrated a trend toward a faster proliferation rate compared with control CAR-T-cells, but the difference was not significant. To specifically evaluate the impact of TMZ on the CAR-T-cell proliferation, in FIG. 3B, the proliferation rate of the cells in each group was depicted relative to the proliferation of the same cells without TMZ. When increasing concentrations of TMZ are added in the culture, the degrees of growth suppression was significantly less in the miR-17-92 co-transduced CAR-T-cells compared with the control CAR-T-cells.

Experiments were conducted to evaluate whether miR-17-92-co-transduction would render CAR-T-cells more resistant to TMZ-induced apoptosis. To this end, flow-cytometric assessments of Annexin $V^+$ and propidium iodide $(PI)^+$ CAR-T-cells were conducted in increasing concentrations of TMZ (FIGS. 3C and 3D). It was observed that a dose-dependent increase of both early apoptotic (Annexin $V^+PI^-$), apoptotic/necrotic (Annexin $V^+PI^+$) and necrotic (Annexin $V^-PI^+$) cells, and miR-17-92-co-transduced CAR-T-cells demonstrated lesser degrees of the apoptotic changes compared with control CAR-T-cells.

Figure 4A:
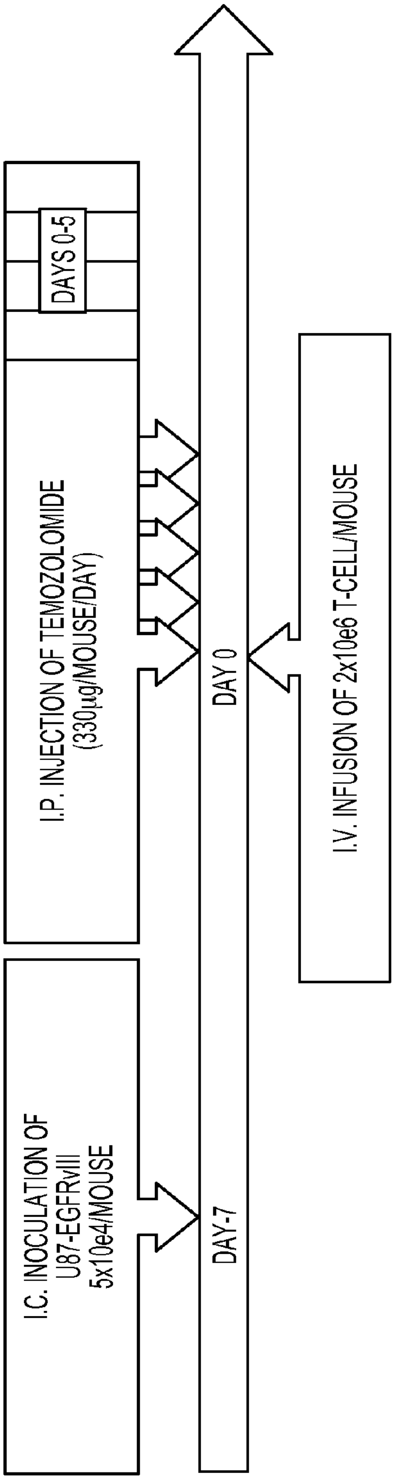
FIGS. 4A and 4B are images depicting robust therapeutic effects of CAR-T-cells in mice bearing U87-EGFRvIII tumors.
Figure 4B:
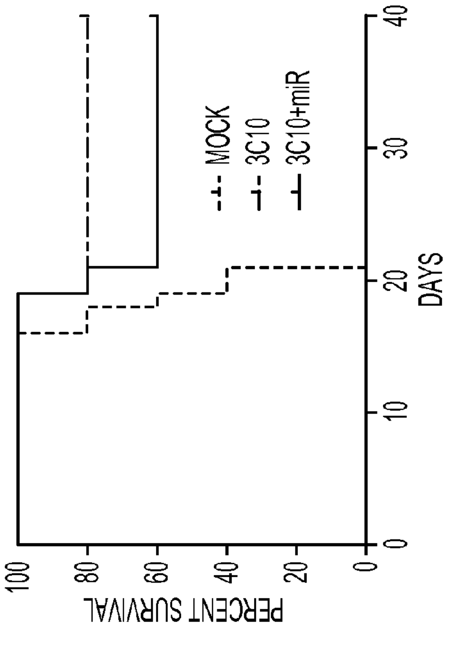
Figure 5A:
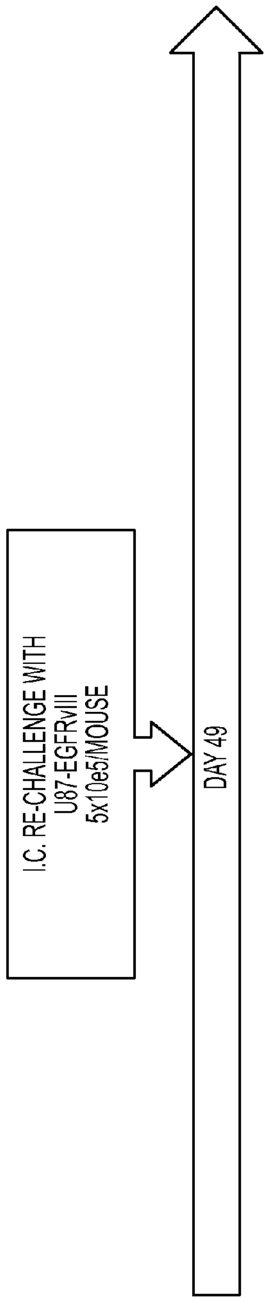
FIGS. 5A through 5C are a series of images demonstrating that co-transduced miR-17-92 in CAR-T cells confers improved protection against re-challenged glioma cells.
Figure 5B:
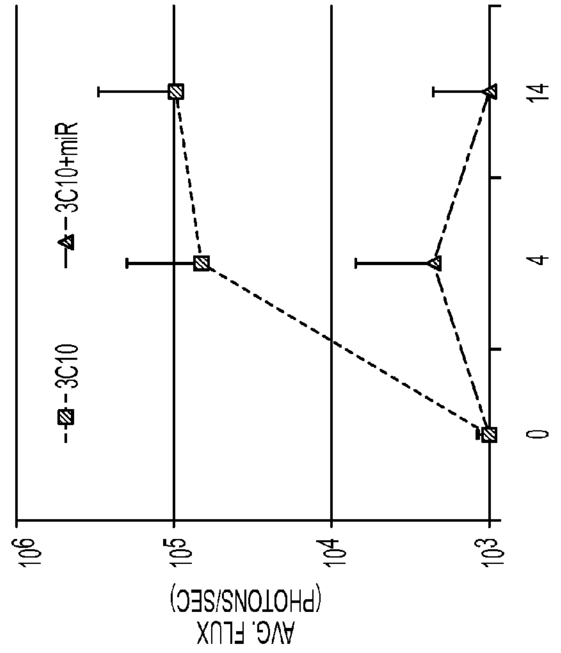
Figure 5C:
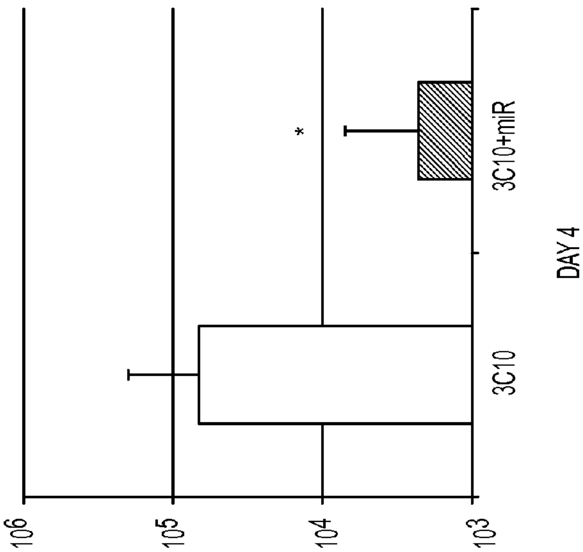

Intravenous Injection of CAR-T-Cells in Combination with TMZ Leads to Complete Remission of Established U87-EGFRvIII Tumors in NSG Mice Experiments were conducted to evaluate the efficacy of CAR-T-cells in immunocompromised NOD/scid/γc(−/−) (NSG) mice bearing established (Day 7) intracranial U87-EGFRvIII tumors. Mice received a single intravenous (i.v.) infusion of miR-17-92 co-transduced CAR-T-cells, CAR-T-cells without co-transduction of miR-17-92, or mock-transduced T-cells ($2\times10^6$/mouse) via the tail vein. As newly diagnosed GBM patients routinely receive TMZ therapy, experiments were designed to administer intraperitoneal (i.p.) daily injections of TMZ for 5 days starting on the day of T-cell infusion (FIG. 4A). FIG. 4B shows a Kaplan-Meier analysis. Median survival of the mice treated with CAR-T cells (with or without co-transduction of miR-17-92) was significantly greater compared the mice with mock transduced T cells ($p<0.05$). TMZ treatment itself was ineffective as all the control mice receiving TMZ and mock-transduced T-cells died within 3 weeks (day 21) after the T-cell infusion (FIG. 4B). Although one of five mice with CAR-T-cells and two of five mice with miR-17-92 co-transduced CAR-T-cells died for the tumor progression by day 22, all the other mice in these groups survived longer than 40 days. Results are from one of two independent experiments with similar results. There was not a statistically significant difference in survival of the mice receiving miR-17-92-co-transduced CAR-T-cells vs. CAR-T-cells without miR-17-92 co-transduction (log-rank test: $p=0.5485$).

miR-17-92 Co-transduced CAR-T-Cells Confers a Persistent Protection Against U87-EGFRvIII Tumors in Mice To determine whether CAR-T-cells infused in the mice in the experiment presented in FIG. 4 can provide long-term protection of the hosts against the U87-EGFRvIII tumors, the survivors were re-challenged with inoculation of U87-EGFRvIII cells in the contra-lateral hemisphere of the brain on Day 49 (FIG. 5). While the re-challenged tumor cells grew in all three mice treated with CAR-T-cells, none of the mice treated with miR-17-92-co-transduced CAR-T-cells demonstrated BLI signals beyond the background levels. These results strongly suggest that co-transduction of miR-17-92 cluster confers long-term persistence of the CAR-T-cells, thereby providing prolonged protection of the host against the tumor growth. Longitudinal measurements of tumor-derived mean photon flux±SD from the 2 groups of mice. The background luminescence level (up to 10^3 p/s) was defined based on the levels observed in non-tumor-bearing mice imaged in parallel with tumor-bearing mice in treatment groups miR-17-92 can be Integrated in the CAR to Improve Efficacy The results presented herein demonstrate the effects of miR-17-92 co-expression in T-cells transduced with the novel anti-EGFRvIII-CAR (3C10-CAR) integrating 3C10 scFv with CD3ζ chain, CD137 (4-1BB) and CD28. The present results show that co-expression of miR-17-92 confers improved resistance to T-cell growth-suppressing effects of TGF-β and temozolomide. In vivo, T-cells co-transduced with both 3C10-CAR and miR-17-92 demonstrated more persistent therapeutic effects compared with T-cells transduced with 3C10-CAR alone.

Lentiviral transduction of miR-17-92 in the present study confers ectopic over-expression of the miR-cluster in transduced T-cells. In physiological conditions, however, expression levels of endogenous miR-17-92 in T-cells appear to be tightly regulated. In human $CD8^+$ T cells, miR-17-92 expression is detected high levels in naïve cells but diminishes as the cells differentiate (Salaun et al., 2011, J Transl Med 9:44). In a mouse model of lymphocytic choriomeningitis virus infection, miR-17-92 is strongly up-regulated following T-cell activation, however down-regulated after clonal expansion, and further silenced during memory development (Wu et al., 2012, Proc Natl Acad Sci USA 109:9965-9970). In this referenced study, miR-17-92 is necessary for the rapid T-cell expansion and their IFN-γ expression. However, overexpression of miR-17-92 skews the differentiation toward short-lived terminal effector cells. Failure to down-regulate miR- 17-92 leads to a gradual loss of memory cells and defective central memory cell development (Wu et al., 2012, Proc Natl Acad Sci USA 109:9965-9970). These observations are not necessarily consistent with the results presented herein as persistence of miR-17-92-co-transduced CAR-T-cells and their efficient ability to protect the hosts from the re-challenged U87-EGFRvIII cells was observed. Without wishing to be bound by any particular theory, it is believed that this observation is attributable to the combinatory effects of the co-stimulatory molecules provided in the CAR and the miR-17-92.

Although miR-17-92 has been described as an oncogenic miR (van Haaften and Agami, 2010, Genes & Development 24:1-4), miR-17-92 overexpression itself is known not to be oncogenic in lymphocytes (Xiao et al., 2008, Nat Immunol 9:405-414). Indeed, uncontrolled proliferation of miR-17-92-transduced T-cells in the current study was not observed. Nonetheless, as an alternative approach for better safety assurance, transient transduction of T-cells with miR-17-92 itself, instead of lentiviral stable transfer, and multiple injection of those T-cells may represent a reasonable approach without the associated safety concerns of integrating viral vectors (Zhao et al., 2010, Cancer Research 70:9053-9061).

In regard to the EGFRvIII-targeting CARs for therapy of GBM, recently, Morgan et al. evaluated scFv sequences derived from seven different anti-EGFRvIII mAbs, including 3C10 and human 139, in γ-retroviral CARs (Morgan et al., 2012, Hum Gene Ther 23:1043-1053). The in vitro characterization of those CARs revealed the 3C10 and the 139 as two of the three clones that yielded specific IFN-γ production in response to EGFRvIII-expressing target cells, but not cells expressing the wild-type EGFR gene.

It is also important to recognize that EGFRvIII is expressed only in a population of GBM patients and fractions of the GBM cells even in "EGFRvIII-positive" cases (Heimberger et al., 2005, Clin. Cancer Res. 11:1462-1466). Immunotherapy targeting EGFRvIII as the single target will likely result in the outgrowth of GBM cells that have down-regulated the immunotherapy-targeted antigen (Sampson et al, 2010, J Clin Oncol 28:4722-4729). A number of previous studies have developed CARs against GBM-associated antigens, such as IL-13Rα2 (Kong et al., 2012, Clin Cancer Res 18:5949-5960; Kahlon et al., 2004, Cancer Res. 64:9160-9166), HER-2 (Ahmed et al., 2010, Clinical Cancer Research 16:474-485) and EphA2 (Chow, K. K. et al. T Cells Redirected to EphA2 for the Immunotherapy of Glioblastoma. Mol Ther (2012). Without wishing to be bound by any particular theory, it is believed that effective CAR therapy should ultimately employ T-cells that are able to resist GBM-induced suppression mechanisms and target multiple antigens, so that the infused T-cells will exhibit effective and sustained therapeutic effects against GBM with heterogenous antigen-expression profiles.

The results presented herein demonstrate the benefits of using T-cells co-transduced with pELNS-3C10-CAR and FG12-EF1a-miR-17/92. As an alternative approach to achieve co-expression of the CAR and miR-17-92 transgene, a pELNS-based lentiviral vector that expresses both 3C10-CAR gene and miR-17-92 gene as a single transcript was constructed. Use of this single "tandem" vector may have an advantage in terms of relatively simple transduction procedures and straightforward regulatory processes compared with the two vector-based approach. Furthermore, all T-cells that express the CAR should also express miR-17-92. However, it was found that the transduction efficiency of the "tandem" vector is lower than that by the two vector approach likely because the titer of lentivirus decreases as the size of insert increases. As discussed elsewhere herein, lentiviral transduction of 3C10-CAR gene and electroporation of miR-17-92 in combination may be a feasible strategy.

In the present study, it was also found that 40% to 60% of $CD3^+$ CAR-T-cells were $CD4^+$, and that $CD4^+$ CAR-T-cells effectively lysed U87-EGFRvIII cells in an EGFRvIII-specific manner. It has been reported that $Perforin^+$ $CD4^+$ T-cells mediate cytotoxic activities via the perforin/granzyme B pathway, but not the Fas/FasL pathway (Porakishvili et al., 2004, Haematologica 89:435-443). Hence, it is believed that the $CD4^+$ CAR-T-cells in the current study expressed perforin and granzyme B to mediate the observed lytic activities against U87-EGFRvIII cells.

In summary, the current study provides a strong foundation for evaluation of CAR therapy integrating miR-17-92.

Example 3

CAR Sequences

Murine monoclonal antibody (mAb) 3C10 was originally developed by immunization of mice with a 14 amino acid peptide (PEP3) including the EGFRvIII-specific fusion junction and demonstrated highly specific recognition of EGFRvIII without any detectable binding to wild-type EGFR (Okamoto et al, British J. Cancer 1996, 73:1366-1372). Subsequently, a single-chain variable fragment (scFv) of mAb 3C10 was produced and cDNA for the 3C10 scFv was obtained. While avidity and/or antigen-specificity of the original mAbs can be often lost in scFv forms, the 3C10 scFv retained its selective reactivity with the EGFRvIII-specific epitope (Nakayashiki et al., Jpn. J. Cancer Res. 2000, 91:1035-1043).

An EGFRvIII CAR was constructed by cloning the 3C10scFv (mouse) with CD28, 4-1BB, and CD3 zeta into the pELNS lentiviral backbone plasmid (EF1 promoter). Another EGFRvIII CAR was generated by cloning the 3C10scFv into a CD8ahinge/CD8TM/4-1BB/CD3zeta pELNS lentiviral backbone, which is expressed by EF1a promoter.

```
3C10scFv-CD28BBzeta CAR (Amino Acid)
                                                      (SEQ ID NO: 1)
MALPVTALLLPLALLLHAARPGSEIQLQQSGAELVKPGASVKLSCTGSGFNIEDY
YIHWVKQRTEQGLEWIGRIDPENDETKYGPIFQGRATITADTSSNTVYLQLSSLTS
EDTAVYYCAFRGGVYWGPGTTLTVSSGGGGSGGGGSGGGGSHMDVVMTQSPL
TLSVAIGQSASISCKSSQSLLDSDGKTYLNWLLQRPGQSPKRLISLVSKLDSGVPDRFTG
SGSGTDFTLRISRVEAEDLGIYYCWQGTHFPGTFGGGTKLEIKASTTTPAPR
PPTPAPTIASQPLSLRPEACRPAAGGAVHTRGLDFACDFWVLVVVGGVLACYSL
LVTVAFIIFWVRSKRSRLLHSDYMNMTPRRPGPTRKHYQPYAPPRDFAAYRSKR
GRKKLLYIFKQPFMRPVQTTQEEDGCSCRFPEEEEGGCELRVKFSRSADAPAYKQ
GQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR
```

-continued

```
3C10scFv-BBz CAR (Amino Acid)
                                                    (SEQ ID NO: 2)
MALPVTALLLPLALLLHAARPGSEIQLQQSGAELVKPGASVKLSCTGSGFNIE
DYYIHWVKQRTEQGLEWIGRIDPENDETKYGPIFQGRATITADTSSNTVYLQLSSLTSE
DTAVYYCAFRGGVYWGPGTTLTVSSGGGGSGGGGSGGGGSHMDVVMTQSPL
TLSVAIGQSASISCKSSQSLLDSDGKTYLNWLLQRPGQSPKRLISLVS KLDSGVPD
RFTGSGSGTDFTLRISRVEAEDLGIYYCWQGTHFPGTFGGGTKLEIKASTTTPAPR
PPTPAPTIASQPLSLRPEACRPAAGGAVHTRGLDFACDIYIWAPLAGTCGVLLLSL
VITLYCKRGRKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

3C10scFv-CD28BBzeta CAR (Nucleic Acid)
                                                    (SEQ ID NO: 18)
atggccttaccagtgaccgccttgctcctgccgctggccttgctgctccacgccgccaggccgggatccgagattcagctgcag
caatctggggcagaacttgtgaagccaggggcctcagtcaagctgtcctgcacaggttctggcttcaacattgaagactactatat
tcactgggtgaagcagaggactgaacagggcctggaatggattggaaggattgatcctgagaatgatgaaactaaatatggccc
aatattccagggcagggccactataacagcagacacatcctccaacacagtctacctgcaactcagcagcctgacatctgagga
cactgccgtctattactgtgcctttcgcggtggagtctactggggccaggaaccactctcacagtctcctcaggaggtggtggttccggt
ggtggtggttccggaggtggtggttcacatatggatgttgtgatgacccagtctccactcactctatcggttgccattggac
aatcagcctccatctcttgcaagtcaagtcagagcctcttagatagtgatggaaagacatatttgaattggttgttacagaggccaggccagt
ctccaaagcgcctaatctctctggtgtctaaactggactctggagtccctgacaggttcactggcagtggatcagggac
agatttcacactgagaatcagcagagtggaggctgaggatttgggaatttattattgctggcaaggtacacattttcctgggacgtt
cggtggagggaccaagctggagataaaagctagcaccacgacgccagcgccgcgaccaccaacaccggcgcccaccatcg
cgtcgcagcccctgtccctgcgcccagaggcgtgccggccagcggcggggggcgcagtgcacacgagggggctggacttcgcctgt
gattttgggtgctggtggtggttggtggagtcctggcttgctatagcttgctagtaacagtggcctttattattttctgggtg
aggagtaagaggagcaggctcctgcacagtgactacatgaacatgactccccgccgccccgggcccacccgcaagcattacc
agccctatgccccaccacgcgacttcgcagcctatcgctccaaacggggcagaaagaaactcctgtatatattcaaacaaccatt
tatgagaccagtacaaactactcaagaggaagatggctgtagctgccgatttccagaagaagaagaaggaggatgtgaactga
gagtgaagttcagcaggagcgcagacgcccccgcgtacaagcagggccagaaccagctctataacgagctcaatctaggacgaagag
aggagtacgatgttttggacaagagacgtggccgggaccctgagatggggggaaagccgagaaggaagaaccct
caggaaggcctgtacaatgaactgcagaaagataagatggcggaggcctacagtgagattgggatgaaaggcgagcgccgg
aggggcaaggggcacgatggcctttaccagggtctcagtacagccaccaaggacacctacgacgcccttcacatgcaggccc
tgccccctcgc

3C10scFv-BBz CAR (Nucleic Acid)
                                                    (SEQ ID NO: 19)
Atggccttaccagtgaccgccttgctcctgccgctggccttgctgctccacgccgccaggccgggatccgagattcagctgca
gcaatctggggcagaacttgtgaagccaggggcctcagtcaagctgtcctgcacaggttctggcttcaacattgaagactactat
attcactgggtgaagcagaggactgaacagggcctggaatggattggaaggattgatcctgagaatgatgaaactaaatatggc
ccaatattccagggcagggccactataacagcagacacatcctccaacacagtctacctgcaactcagcagcctgacatctgaggacact
gccgtctattactgtgcctttcgcggtggagtctactggggccaggaaccactctcacagtctcctcaggaggtggtg
gttccggtggtggtggttccggaggtggtggttcacatatggatgttgtgatgacccagtctccactcactctatcggttgccattg
gacaatcagcctccatctcttgcaagtcaagtcagagcctcttagatagtgatggaaagacatatttgaattggttgttacagaggc
caggccagtctccaaagcgcctaatctctctggtgtctaaactggactctggagtccctgacaggttcactggcagtggatcagg
gacagatttcacactgagaatcagcagagtggaggctgaggatttgggaatttattattgctggcaaggtacacattttcctgggacgttcg
gtggagggaccaagctggagataaaagctagcaccacgacgccagcgccgcgaccaccaacaccggcgcccacc
atcgcgtcgcagcccctgtccctgcgcccagaggcgtgccggccagcggcggggggcgcagtgcacacgagggggctgg
acttcgcctgtgatatctacatctgggcgcccttggccgggacttgtggggtccttctcctgtcactggttatcaccctttactgcaa
acggggcagaaagaaactcctgtatatattcaaacaaccatttatgagaccagtacaaactactcaagaggaagatggctgtagc
tgccgatttccagaagaagaagaaggaggatgtgaactgagagtgaagttcagcaggagcgcagacgcccccgcgtacaagcaggg
ccagaaccagctctataacgagctcaatctaggacgaagagaggagtacgatgttttggacaagagacgtggccggg
accctgagatggggggaaagccgagaaggaagaaccctcaggaaggcctgtacaatgaactgcagaaagataagatggcggaggcc
tacagtgagattgggatgaaaggcgagcgccggaggggcaaggggcacgatggcctttaccagggtctcagtacagccaccaagga
cacctacgacgcccttcacatgcaggccctgccccctcgc
```

The scFv fragment termed "139" is a human antibody to EGFRvIII (Morgan et al., 2012 Hum Gene Ther 23(10): 1043-53). An EGFRvIII CAR comprising the 139 scFv was generated by initially synthesizing the 139 scFv. The sequence for the 139 scFv was cloned with a leader sequence, CD8 hinge, transmembrane (TM) domain, and the desired signaling domains. For example, the sequence for the 139 scFv was cloned with the signaling domains for 4-1BB and CD3 zeta. The CAR construct (139scFv-BBZ) is expressed from the pELNS vector for lentivirus production.

```
139scFv-BBz CAR (Amino Acid)
                                                    (SEQ ID NO: 3)
MALPVTALLLPLALLLHAARPGSDIQMTQSPSSLSASVGDRVTITCRASQGIRNNL
AWYQQKPGKAPKRLIYAASNLQSGVPSRFTGSGSGTEFTLIVSSLQPEDFATYYC
LQHHSYPLTSGGGTKVEIKRTGSTSGSGKPGSGEGSEVQVLESGGGLVQPGGSLR
LSCAASGFTFSSYAMSWVRQAPGKGLEWVSAISGSGGSTNYADSVKGRFTISRD
NSKNTLYLQMNSLRAEDTAVYYCAGSSGWSEYWGQGTLVTVSSASTTTPAPRP
PTPAPTIASQPLSLRPEACRPAAGGAVHTRGLDFACDIYIWAPLAGTCGVLLLSLV
ITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR
```

-continued

139scFv-BBz CAR (Nucleic Acid)

(SEQ ID NO: 20)

Atggccttaccagtgaccgccttgctcctgccgctggccttgctgctccacgccgccaggccgggatccgacatccagatgacccaga
gccctagcagcctgagcgccagcgtgggcgacagagtgaccatcacctgtcgggccagccagggcatcagaaaca
acctggcctggtatcagcagaagcccggcaaggcccccaagagactgatctacgctgccagcaatctgcagagcggcgtgcc
cagcagattcaccggaagcggctccggcaccgagttcaccctgatcgtgtccagcctgcagcccgaggacttcgccacctact
actgcctgcagcaccacagctaccctctgaccagcggcggaggcaccaaggtggagatcaagcggaccggcagcaccagc
ggcagcggcaagcctggcagcggcgagggaagcgaggtccaggtgctggaatctggcggcggactggtgcagcctggcggcagc
ctgagactgagctgtgccgccagcggcttcaccttcagcagctacgccatgtcttgggtccggcaggctcctggaaag
ggcctggaatgggtgtccgccatcagcggctctggcggctccaccaactacgccgacagcgtgaagggccggttcaccatcagccgg
gacaacagcaagaacaccctgtatctgcagatgaacagcctgagagccgaggacaccgccgtgtactactgtgccgg
cagcagcgggtggagcgagtactggggccagggcacactggtcacagtgtctagcgctagcaccacgacgccagcgccgc
gaccaccaacaccggcgcccaccatcgcgtcgcagcccctgtccctgcgcccagaggcgtgccggccagcggcgggggg
cgcagtgcacacgagggggctggacttcgcctgtgatatctacatctgggcgcccttggccgggacttgtggggtccttctcctgtcactg
gttatcaccctttactgcaaacggggcagaaagaaactcctgtatatattcaaacaaccatttatgagaccagtacaaactactcaagagga
agatggctgtagctgccgatttccagaagaagaagaaggaggatgtgaactgagagtgaagttcagcaggagcgcagacgcccccgc
gtacaagcagggccagaaccagctctataacgagctcaatctaggacgaagagaggagtacgatgttttggacaagagacgtggccgg
gaccctgagatggggggaaagccgagaaggaagaaccctcaggaaggcctgtacaatgaactgcagaaagataagatggcggagg
cctacagtgagattgggatgaaaggcgagcgccggaggggcaaggggcacgatggcctttaccagggtctcagtacagccaccaag
gacacctacgacgcccttcacatgcaggccctgccccctcgct Car Components

NUCLEIC ACID SEQUENCES:

3C10 scFv Nucleotide Sequence (Mouse);

(SEQ ID NO: 4)

GAGATTCAGCTGCAGCAATCTGGGGCAGAACTTGTGAAGCCAGGGGCCTCAGTCA
AGCTGTCCTGCACAGGTTCTGGCTTCAACATTGAAGACTACTATATTCACTGGGTG
AAGCAGAGGACTGAACAGGGCCTGGAATGGATTGGAAGGATTGATCCTGAGAATG
ATGAAACTAAATATGGCCCAATATTCCAGGGCAGGGCCACTATAACAGCAGACAC
ATCCTCCAACACAGTCTACCTGCAACTCAGCAGCCTGACATCTGAGGACACTGCCG
TCTATTACTGTGCCTTTCGCGGTGGAGTCTACTGGGGGCCAGGAACCACTCTCACA
GTCTCCTCAGGAGGTGGTGGTTCCGGTGGTGGTGGTTCCGGAGGTGGTGGTTCACA
TATGGATGTTGTGATGACCCAGTCTCCACTCACTCTATCGGTTGCCATTGGACAATC
AGCCTCCATCTCTTGCAAGTCAAGTCAGAGCCTCTTAGATAGTGATGGAAAGACAT
ATTTGAATTGGTTGTTACAGAGGCCAGGCCAGTCTCCAAAGCGCCTAATCTCTCTG
GTGTCTAAACTGGACTCTGGAGTCCCTGACAGGTTCACTGGCAGTGGATCAGGGAC
AGATTTCACACTGAGAATCAGCAGAGTGGAGGCTGAGGATTTGGGAATTTATTATT
GCTGGCAAGGTACACATTTTCCTGGGACGTTCGGTGGAGGGACCAAGCTGGAGAT
AAAA 139 scFv Nucleotide Sequence (Humanized);

(SEQ ID NO: 5)

GACATCCAGATGACCCAGAGCCCTAGCAGCCTGAGCGCCAGCGTGGGCGACAGAG
TGACCATCACCTGTCGGGCCAGCCAGGGCATCAGAAACAACCTGGCCTGGTATCA
GCAGAAGCCCGGCAAGGCCCCCAAGAGACTGATCTACGCTGCCAGCAATCTGCAG
AGCGGCGTGCCCAGCAGATTCACCGGAAGCGGCTCCGGCACCGAGTTCACCCTGA
TCGTGTCCAGCCTGCAGCCCGAGGACTTCGCCACCTACTACTGCCTGCAGCACCAC
AGCTACCCTCTGACCAGCGGCGGAGGCACCAAGGTGGAGATCAAGCGGACCGGCA
GCACCAGCGGCAGCGGCAAGCCTGGCAGCGGCGAGGGAAGCGAGGTCCAGGTGCT
GGAATCTGGCGGCGGACTGGTGCAGCCTGGCGGCAGCCTGAGACTGAGCTGTGCC
GCCAGCGGCTTCACCTTCAGCAGCTACGCCATGTCTTGGGTCCGGCAGGCTCCTGG
AAAGGGCCTGGAATGGGTGTCCGCCATCAGCGGCTCTGGCGGCTCCACCAACTAC
GCCGACAGCGTGAAGGGCCGGTTCACCATCAGCCGGGACAACAGCAAGAACACCC
TGTATCTGCAGATGAACAGCCTGAGAGCCGAGGACACCGCCGTGTACTACTGTGCC
GGCAGCAGCGGGTGGAGCGAGTACTGGGGCCAGGGCACACTGGTCACAGTGTCTA
GC leader (nucleic acid sequence);

(SEQ ID NO: 6)

ATGGCCTTACCAGTGACCGCCTTGCTCCTGCCGCTGGCCTTGCTGCTCCACGC
CGCCAGGCCG hinge (nucleic acid sequence);

(SEQ ID NO: 7)

ACCACGACGCCAGCGCCGCGACCACCAACACCGGCGCCCACCATCGCGTCGC
AGCCCCTGTCCCTGCGCCCAGAGGCGTGCCGGCCAGCGGCGGGGGGCGCAGT
GCACACGAGGGGGCTGGACTTCGCCTGTGAT transmembrane (nucleic acid sequence);

(SEQ ID NO: 8)

ATCTACATCTGGGCGCCCTTGGCCGGGACTTGTGGGGTCCTTCTCCTGTCACT
GGTTATCACCCTTTACTGC 4-1BB Intracellular domain (nucleic acid sequence);

(SEQ ID NO: 9)

AAACGGGGCAGAAAGAAACTCCTGTATATATTCAAACAACCATTTATGAGAC
CAGTACAAACTACTCAAGAGGAAGATGGCTGTAGCTGCCGATTTCCAGAAGAAGA
AGAAGGAGGATGTGAACTG

-continued

CD3 zeta (nucleic acid sequence);

(SEQ ID NO: 10)

AGAGTGAAGTTCAGCAGGAGCGCAGACGCCCCCGCGTACAAGCAGGGCCAG
AACCAGCTCTATAACGAGCTCAATCTAGGACGAAGAGAGGAGTACGATGTTT
TGGACAAGAGACGTGGCCGGGACCCTGAGATGGGGGGAAAGCCGAGAAGGA
AGAACCCTCAGGAAGGCCTGTACAATGAACTGCAGAAAGATAAGATGGCGG
AGGCCTACAGTGAGATTGGGATGAAAGGCGAGCGCCGGAGGGGCAAGGGGC
ACGATGGCCTTTACCAGGGTCTCAGTACAGCCACCAAGGACACCTACGACGC
CCTTCACATGCAGGCCCTGCCCCCTCGC

CD3 zeta (nucleic acid sequence; NCBI Reference Sequence NM_000734.3);

(SEQ ID NO: 100)

AGAGTGAAGTTCAGCAGGAGCGCAGACGCCCCCGCGTACCAGCAGGGCCAG
AACCAGCTCTATAACGAGCTCAATCTAGGACGAAGAGAGGAGTACGATGTTT
TGGACAAGAGACGTGGCCGGGACCCTGAGATGGGGGGAAAGCCGAGAAGGA
AGAACCCTCAGGAAGGCCTGTACAATGAACTGCAGAAAGATAAGATGGCGG
AGGCCTACAGTGAGATTGGGATGAAAGGCGAGCGCCGGAGGGGCAAGGGGC
ACGATGGCCTTTACCAGGGTCTCAGTACAGCCACCAAGGACACCTACGACGC
CCTTCACATGCAGGCCCTGCCCCCTCGC

AMINO ACID SEQUENCES:

3C10 scFv Amino Sequence (Mouse);

(SEQ ID NO: 11)

EIQLQQSGAELVKPGASVKLSCTGSGFNIEDYYIHWVKQRTEQGLEWIGRIDPEN
DETKYGPIFQGRATITADTSSNTVYLQLSSLTSEDTAVYYCAFRGGVYWGPGTTL
TVSSGGGGSGGGGSGGGGSHMDVVMTQSPLTLSVAIGQSASISCKSSQSLLDSDG
KTYLNWLLQRPGQSPKRLISLVSKLDSGVPDRFTGSGSGTDFTLRISRVEAEDLGI
YYCWQGTHFPGTFGGGTKLEIK 139 scFv Amino Sequence (Human);

(SEQ ID NO: 12)

DIQMTQSPSSLSASVGDRVTITCRASQGIRNNLAWYQQKPGKAPKRLIYAASNLQ
SGVPSRFTGSGSGTEFTLIVSSLQPEDFATYYCLQHHSYPLTSGGGTKVEIKRTGS
TSGSGKPGSGEGSEVQVLESGGGLVQPGGSLRLSCAASGFTFSSYAMSWVRQAP
GKGLEWVSAISGSGGSTNYADSVKGRFTISRDNSKNTLYLQMNSLRAEDTAVYY
CAGSSGWSEYWGQGTLVTVSS leader (amino acid sequence)

(SEQ ID NO: 13)

MALPVTALLLPLALLLHAARP hinge (amino acid sequence)

(SEQ ID NO: 14)

TTTPAPRPPTPAPTIASQPLSLRPEACRPAAGGAVHTRGLDFACD transmembrane (amino acid sequence)

(SEQ ID NO: 15)

IYIWAPLAGTCGVLLLSLVITLYC 4-1BB Intracellular domain (amino acid sequence)

(SEQ ID NO: 16)

KRGRKKLLYIFKQPFMRPVQTTQEEDGCSCRFPEEEEGGCEL

CD3 zeta domain (amino acid sequence)

(SEQ ID NO: 17)

RVKFSRSADAPAYKQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR

CD3 zeta domain (amino acid sequence; NCBI Reference Sequence NM_000734.3)

(SEQ ID NO: 99)

RVKFSRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR

The nucleotide encoding the polypeptide of SEQ ID NO:11 is provided as SEQ ID NO:4. The nucleotide encoding the polypeptide of SEQ ID NO:12 is provided as SEQ ID NO:5. The nucleotide encoding the polypeptide of SEQ ID NO:13 is provided as SEQ ID NO:6. The nucleotide encoding the polypeptide of SEQ ID NO:14 is provided as SEQ ID NO:7. The nucleotide encoding the polypeptide of SEQ ID NO:15 is provided as SEQ ID NO:8. The nucleotide encoding the polypeptide of SEQ ID NO:16 is provided as SEQ ID NO:9. The nucleotide encoding the polypeptide of SEQ ID NO:17 is provided as SEQ ID NO:10. The nucleotide encoding the polypeptide of SEQ ID NO:1 is provided as SEQ ID NO:18. The nucleotide encoding the polypeptide of SEQ ID NO:2 is provided as SEQ ID NO:19. The nucleotide encoding the polypeptide of SEQ ID NO:3 is provided as SEQ ID NO:20. The nucleotide encoding the polypeptide of SEQ ID NO:99 is provided as SEQ ID NO:100.

Example 4

Predicted CDR Designations for the EGFRvIIICAR

The predicted CDR designations for the EGFRvIII CAR under Kabat are as follows:

VH:

(SEQ ID NO: 21)

EIQLQQSGAELVKPGASVKLSCTGSGFNIEDYYIHWVKQRTEQGLEWIG
RIDPENDETKYGPIFQGRATITADTSSNTVYLQLSSLTSEDTAVYYCAF
RGGVYWGPGTTLTVSS;;

-continued wherein CDR1 is DYYIH (SEQ ID NO: 22), CDR2 is RID PENDETKYGPIFQG (SEQ ID NO: 23), and CDR3 is RGGVY (SEQ ID NO: 24).

VL:

(SEQ ID NO: 25)
DVVMTQSPLTLSVAIGQSASISCKSSQSLLDSDGKTYLNWLLQRPGQSPK RLISLVSKLDSGVPDRFTGSGSGTDFTLRISRVEAEDLGIYYCWQGTHFP GTFGGGTKLEIK;;

wherein CDR1 is KSSQSLLDSDGKTYLN (SEQ ID NO: 26), CDR2 is LVSKLDS (SEQ ID NO: 27), and CDR3 is WQGTH FPGT (SEQ ID NO: 28).

The predicted CDR designations for the EGFRvIII CAR under Chothia are as follows:

VH:

(SEQ ID NO: 29)
EIQLQQSGAELVKPGASVKLSCTGSGFNIEDYYIHWVKQRTEQGLEWIG RIDPENDETKYGPIFQGRATITADTSSNTVYLQLSSLTSEDTAVYYCAF RGGVYWGPGTTLTVSS;;

wherein CDR1 is GFNIEDY (SEQ ID NO: 30), CDR2 is DPENDE (SEQ ID NO: 31), and CDR3 is RGGVY (SEQ ID NO: 32).

VL:

(SEQ ID NO: 33)
DVVMTQSPLTLSVAIGQSASISCKSSQSLLDSDGKTYLNWLLQRPGQSPK RLISLVSKLDSGVPDRFTGSGSGTDFTLRISRVEAEDLGIYYCWQGTHFP GTFGGGTKLEIK;;

wherein CDR1 is SQSLLDSDGKTY (SEQ ID NO: 34), CDR2 is LVS (SEQ ID NO: 35), and CDR3 is GTHFPG (SEQ ID NO: 36).

Example 5

Humanization of Murine Anti-EGFRvIII Antibody

Humanization of murine EGFRvIII antibody is desired for the clinical setting, where the mouse-specific residues may induce a human-anti-mouse antigen (HAMA) response in patients who receive treatment with T cells transduced with the murine CAR construct. VH and VL sequences of hybridoma derived murine EGFRvIII antibody were extracted from published literature (Morgan et al. (2012) Human Gene Therapy, 23: 1043-1953, Supra). Humanization was accomplished by grafting CDR regions from murine EGFRvIII antibody onto human germline acceptor frameworks VH1_1-f or VH5_5a as well as VK2_A17 or VK4_B3 (vBASE database). In addition to the CDR regions, several framework residues, i.e. VK2 #36, #49, VK4 #2, #36, #46, #49, VH1 #2, #24, #76, #94 and VH5 #2, #24, #73, #76, #94, thought to support the structural integrity of the CDR regions were retained from the murine sequence. Further, the human J elements JH6 and JK4 were used for the heavy and light chain, respectively. The resulting amino acid sequences of the humanized antibody were designated VK2_A17/Hz1 and VK4_B3/Hz1 for the light-chains and VH1_1-f/Hz1, VH5_5-a/Hz1 for the heavy chains shown in FIG. 9. The residue numbering follows Kabat (Kabat E. A. et al, 1991, supra). For CDR definitions, both Kabat as well as Chothia et al, 1987 supra) were used. Frame work residues retained from mouse EGFRvIII are shown boxed bold/italic, CDR residues are underlined.

Figure 9:
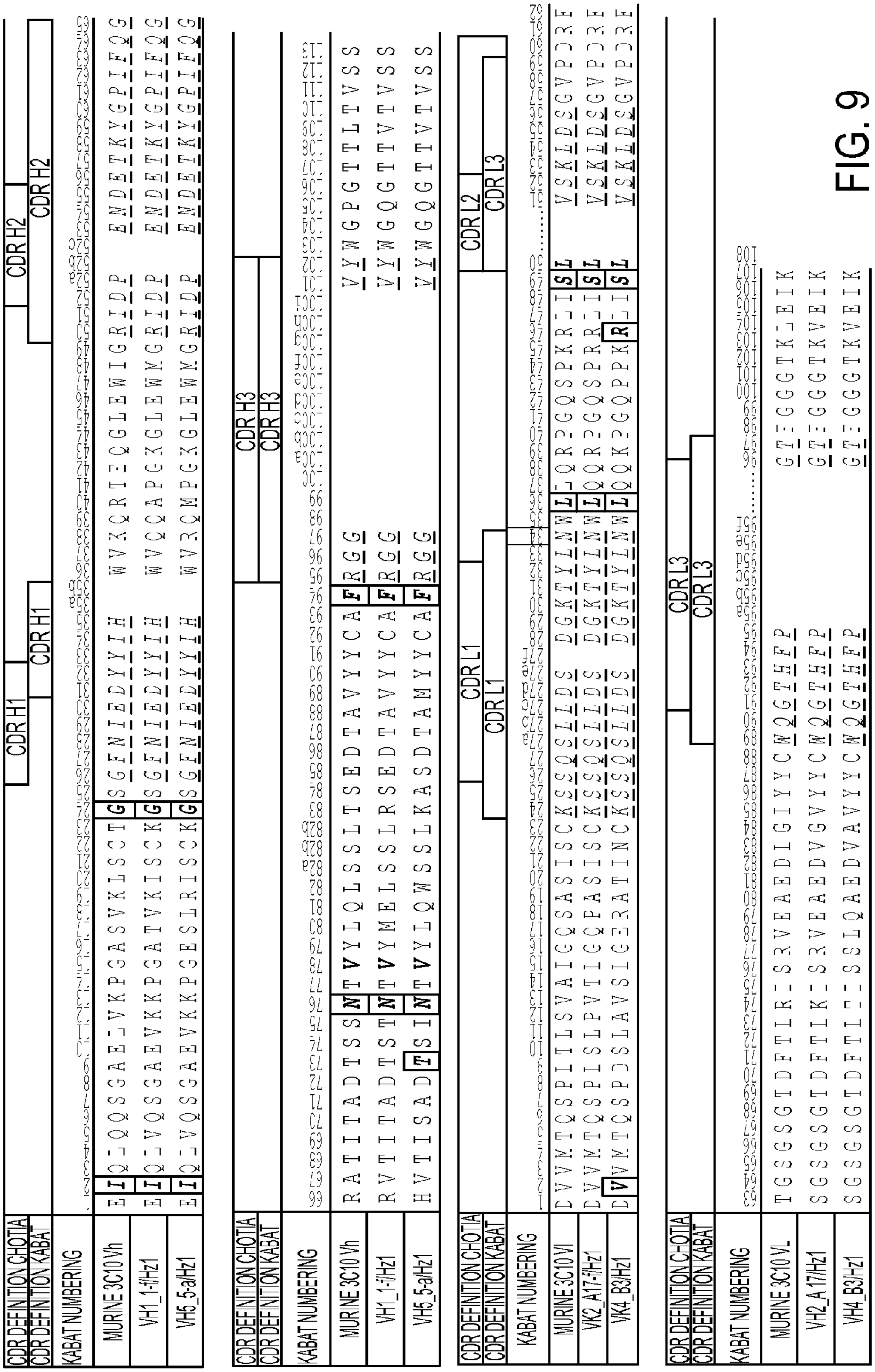
FIG. 9 is a table showing the VH and VL sequences of humanized EGFRvIII (SEQ ID NOS 122-127, respectively, in order of appearance)

Based on the humanized light and heavy chain sequences as shown in FIG. 9, a total of 8 framework combinations were used to generate soluble scFv's for further validation. The order in which the VL and VH domains appear in the scFv was varied (i.e., VL-VH, or VH-VL orientation), and four copies of the "$G_4S$" subunit (SEQ ID NO: 37), in which each subunit comprises the sequence GGGGS (SEQ ID NO:37) was used to connect the frameworks. FIG. 9 discloses the CDR's in the VH and VL sequences calculated by Kabat et al and Chothia et al. (Supra).

Cloning:

DNA sequences coding for mouse and humanized VL and VH domains were obtained, and the codons for the constructs were optimized for expression in cells from *Homo sapiens.*

Sequences coding for VL and VH domain were subcloned into expression vectors suitable for secretion in mammalian cells. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Example 6

Characterization of Humanized Anti-EGFRvIII Soluble scFv Fragments

Soluble scFv fragments were generated described above using standard molecule biology techniques. These soluble scFvs were used in characterization studies to examine the stability, cell surface expression, and binding properties of the scFvs.

scFv Expression and Purification

For transfection of each scFv construct, approximately 3e8 293F cells were transfected with 100 μg of plasmid using PEI as the transfection reagent at the ratio of 3:1 (PEI:DNA). The cells were grown in 100 ml EXPi293 Expression media (Invitrogen) in a shaker flask at 37° C., 125 rpm, 8% $CO_2$. The culture was harvested after six days and used for protein purification.

293F cells were harvested by spinning down at 3500 g for 20 minutes. The supernatant was collected and filtered through VacuCap90 PF Filter Unit (w/0.8/0.2 μm Super Membrane, PALL). Around 400 ul of Ni-NTA agarose beads (Qiagen) were added to the supernatant. The mixture was rotated and incubated for 4 hrs at 4° C. It was loaded onto a purification column and washed with washing buffer with 20 mM Histidine. The protein was eluted with 500 μl elution buffer with 300 mM Histidine. The samples were dialyzed against PBS buffer at 4 C overnight. Protein samples were quantified using nanodrop 2000 c.

$EC_{50}$ by FACS Binding of Purified scFv's to Cells Expressing Either Human EGFR Wild Type or EGFRvIII The following experiments were conducted to demonstrate that all the humanized EGFRvIII scFv variants have comparable binding to EGFRvIII, but no binding to wild type EGFR.

HEK293F suspension cells were transiently transfected with either wild type hEGFR or hEGFRvIII and were harvested 2 days after transfection. Approximately 5e5 cells/per well were transferred to a BD Falcon 96 well plate. The cells were spun down at 900 rpm (Sorval Legend XT centrifuge) for 3 minutes. The supernatant was removed. Anti-EGFRvIII scFv protein samples were diluted in DPBS with 5% FBS. The samples were added into the wells, mixed and incubated for 1 hour. The cells were washed twice in the DPBS with 5% FBS. The cells were incubated with anti-poly His PE (R&D) for 1 hour, washed twice before FACS analysis (LSRII from BD Biosciences).

Figure 10:
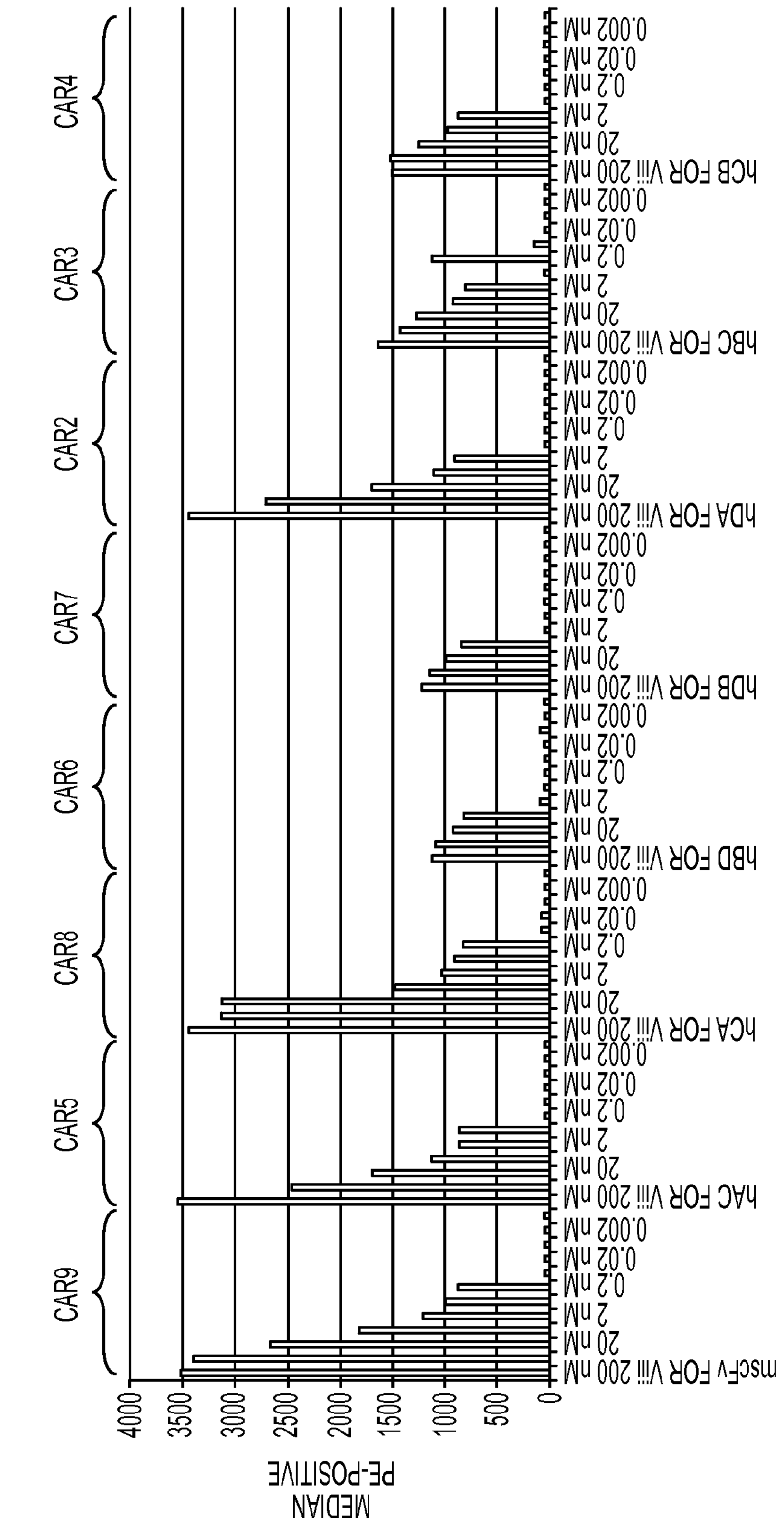
FIG. 10 is a graph showing in vitro binding of soluble humanized scFv constructs binding to EGFRvIII+cell line.
Figure 11:
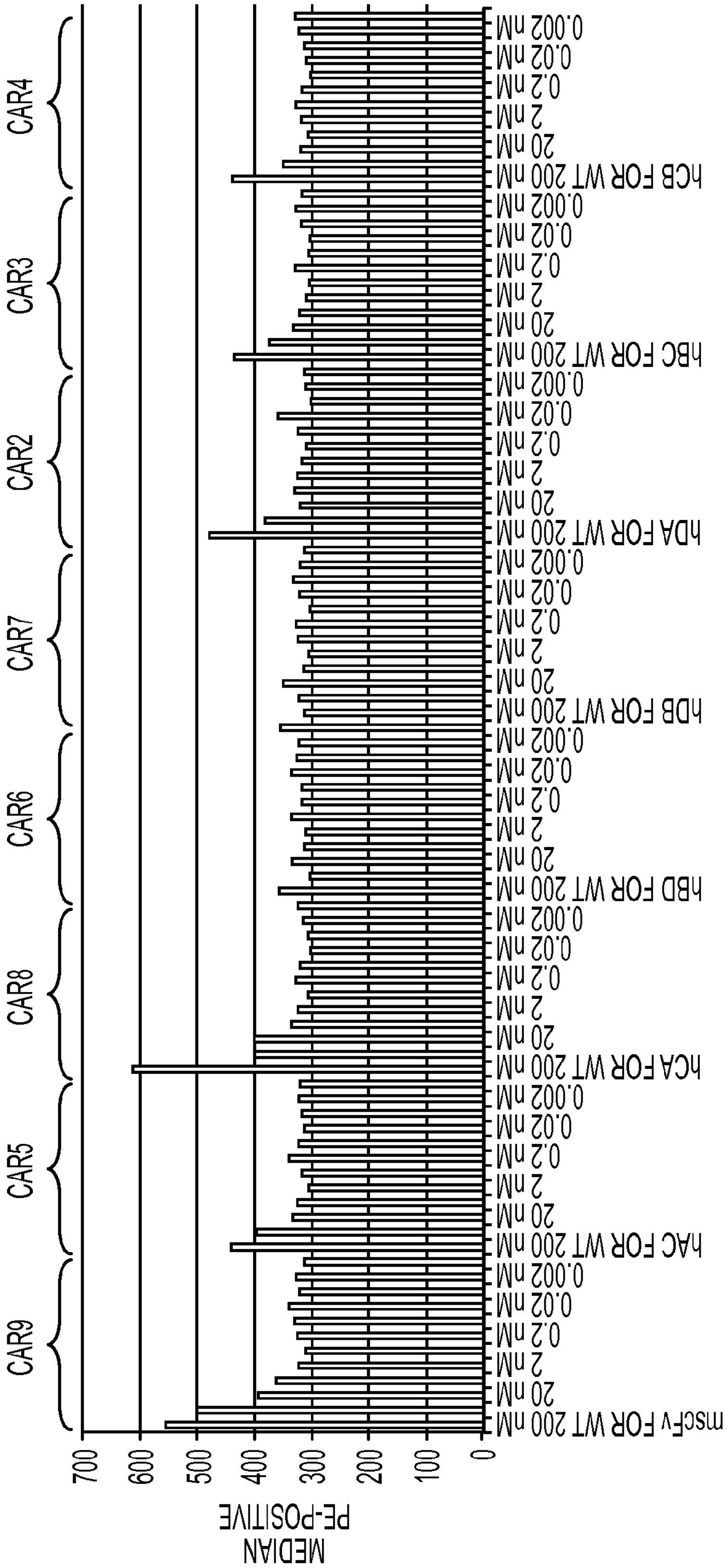
FIG. 11 is a graph showing in vitro binding of soluble humanized scFv constructs binding to EGFR wild type cell line, with clone 73 (also referred to as CAR6) and clone 74 (also referred to as CAR7) showing a safer profile.

The $EC_{50}$ of mouse scFv (m3C10) for hEGFRvIII was determined to be ~5 nM as shown in FIG. 10. All the humanized EGFRvIII scFv variants showed $EC_{50}$ values in the single digit to low double digit nM $EC_{50}$s range (5-50 nM), Moreover, no appreciable binding of constructs 2173 and 2174 to wild type EGFR expressing cell lines was detected indicating an improved safety profile compared to murine 3C10, as shown in FIG. 11. Based on these studies, clone 2173 was selected for further clinical characterization, as shown in Example 8

Example 7

Humanized EGFRvIII CAR Constructs

ScFv to be used in the final CAR constructs were derived from the humanized framework sequences described in Example 1. The order in which the VL and VH domains appear in the scFv was varied (i.e., VL-VH, or VH-VL orientation). A $(G4S)_4$ (SEQ ID NO: 113), linker was used to connect the variable domains to create the scFvs shown in Table 1.

TABLE 1

Humanized EGFRvIII scFv constructs showing VH and VL orientation and linker length (Table discloses “G4S” as SEQ ID NO: 37)

| construct ID | Length aa | annotation |
|---|---|---|
| 108358 | 277 | VH1-VK4, 4G4S |
| 108359 | 277 | VK4-VH1, 4G4S |

TABLE 1-continued

Humanized EGFRvIII scFv constructs showing VH and VL orientation and linker length (Table discloses “G4S” as SEQ ID NO: 37)

| construct ID | Length aa | annotation |
|---|---|---|
| 108360 | 277 | VH5-VK2, 4G4S |
| 108361 | 277 | VK2-VH5, 4G4S |
| 107276 | 277 | VH1-VK2, 4G4S |
| 111046 | 278 | VH5-VK4, 4G4S |
| 111048 | 278 | VK4-VH5, 4G4S |
| 107277 | 277 | VK2-VH1, 4G4S |
| 107275 | | |
| mEGFRvIII 3C10 | 274 | VH-VL, 3G4S + HM |
| EGFRvIII 139 | 269 | VL-VH, |

The sequences of the humanized scFv fragments are provided below in Table 2 (SEQ ID NO:38, SEQ ID NO:44, SEQ ID NO:50, SEQ ID NO:56, SEQ ID NO:62, SEQ ID NO:68, SEQ ID NO:74, and SEQ ID NO:80). These scFv fragments were used with additional sequences, SEQ ID NOs: 13-17, to generate full CAR constructs with SEQ ID NOs: SEQ ID NO:43, SEQ ID NO:49, SEQ ID NO:55, SEQ ID NO:61, SEQ ID NO:67, SEQ ID NO:73, SEQ ID NO:79, and SEQ ID NO:85.

These clones all contained a Q/K residue change in the signal domain of the co-stimulatory domain derived from CD3zeta chain.

TABLE 2

Humanized EGFRvIII CAR Constructs

| Name | SEQ ID NO: | Sequence |
|---|---|---|
| | | CAR 1 |
| CAR1 scFv domain | 38 | eiqlvqsgaevkkpgatvkisckgsgfniedyyihwvqqapgkglewmgridpendet<br>kygpifqgrvtitadtstntvymelsslrsedtavyycafrggvywgqgttvtvssggggsg<br>gggsggggsggggsdvvmtqspdslavslgeratinckssqslldsdgktylnwlqqkpg<br>qppkrlislvskldsgvpdrfsgsgsgtdftltisslqaedvavyycwqgthfpgtfgggtkv<br>eik |
| CAR1 scFv domain nt | 39 | gaaatccagctggtccaatcgggagctgaggtcaagaagccgggagccaccgtcaagatct<br>catgcaaggggtcgggattcaacatcgaggactactacattcactgggtgcagcaagctccg<br>ggaaaaggcctggaatggatgggcagaatcgacccagaaaacgacgaaactaagtacgga<br>ccgattttccaaggaagagtgactatcaccgccgatacttcaaccaataccgtctacatggaac<br>tgagctcgctccggtccgaagatactgcagtgtattactgtgcctttcgcggaggggtgtactg<br>gggccaaggaactactgtcactgtctcgtcaggaggcggagggtcgggaggaggcgggag<br>cggaggcggtggctcgggtggcggaggaagcgacgtggtgatgacccagtccccggactc<br>cctcgccgtgagcctcggagagagggcgactatcaattgcaagtcgtcccagtcacttctgga<br>ttccgatggtaaaacgtacctcaactggctgcagcaaaagccagggcagccacccaaacggt<br>tgatctcccttgtgtccaaactggatagcggagtgcctgaccgcttctcgggttccggtagcgg<br>gaccgacttcaccctgacgatcagctcactgcaggcggaggacgtggcagtgtactactgct<br>ggcagggaacccacttccctggcacctttggaggtggcaccaaggtggagatcaag |
| CAR1 Soluble scFv - nt | 40 | atggccctccctgtcaccgccctgctgcttccgctggctcttctgctccacgccgctcggcccg<br>aaatccagctggtccaatcgggagctgaggtcaagaagccgggagccaccgtcaagatctc<br>atgcaaggggtcgggattcaacatcgaggactactacattcactgggtgcagcaagctccgg<br>gaaaaggcctggaatggatgggcagaatcgacccagaaaacgacgaaactaagtacggac<br>cgattttccaaggaagagtgactatcaccgccgatacttcaaccaataccgtctacatggaact<br>gagctcgctccggtccgaagatactgcagtgtattactgtgcctttcgcggaggggtgtactgg<br>ggccaaggaactactgtcactgtctcgtcaggaggcggagggtcgggaggaggcgggagc<br>ggaggcggtggctcgggtggcggaggaagcgacgtggtgatgacccagtccccggactcc<br>ctcgccgtgagcctcggagagagggcgactatcaattgcaagtcgtcccagtcacttctggatt<br>ccgatggtaaaacgtacctcaactggctgcagcaaaagccagggcagccacccaaacggtt<br>gatctcccttgtgtccaaactggatagcggagtgcctgaccgcttctcgggttccggtagcggg<br>accgacttcaccctgacgatcagctcactgcaggcggaggacgtggcagtgtactactgctg<br>gcagggaacccacttccctggcacctttggaggtggcaccaaggtggagatcaagggatcg<br>caccaccatcaccatcatcatcac |

TABLE 2-continued

Humanized EGFRvIII CAR Constructs

| Name | SEQ ID NO: | Sequence |
|---|---|---|
| CAR1<br>Soluble<br>scFv - aa | 41 | Malpvtalllplalllhaarpeiqlvqsgaevkkpgatvkisckgsgfniedyyihwvqqap<br>gkglewmgridpendetkygpifqgrvtitadtstntvymelsslrsedtavyycafrggvy<br>wgqgttvtvssggggsggggsggggsggggsdvvmtqspdslavslgeratinckssqsl<br>ldsdgktylnwlqqkpgqppkrlislvskldsgvpdrfsgsgsgtdftltisslqaedvavyy<br>cwqgthfpgtfgggtkveikgshhhhhhhh |
| CAR 1 -<br>Full - nt<br>lentivirus | 42 | atggccctccctgtcaccgccctgctgcttccgctggctcttctgctccacgccgctcggcccg<br>agatccagctggtgcagtcgggagctgaagtcaaaaagcctggcgcaaccgtcaagatctcg<br>tgcaaaggatcagggttcaacatcgaggactactacatccattgggtgcaacaggcacccgg<br>aaaaggcctggagtggatggggaggattgacccagaaaatgacgaaaccaagtacggacc<br>gatcttccaaggacgggtgaccatcacggctgacacttccactaacaccgtctacatggaact<br>ctcgagccttcgctcggaagataccgcggtgtactactgcgcctttagaggtggagtctactgg<br>ggacaagggactaccgtcaccgtgtcgtcaggtggcggaggatcaggcggaggcggctcc<br>ggtggaggaggaagcggaggaggtggctccgacgtggtgatgacgcagtcaccggactcc<br>ttggcggtgagcctgggtgaacgcgccactatcaactgcaagagctcccagagcttgctgga<br>ctccgatggaaagacttatctcaattggctgcaacagaagcctggccagccgccaaagagac<br>tcatctcactggtgagcaagctggatagcggagtgccagatcggttttcgggatcgggctcag<br>gcaccgacttcaccctgactatttcctccctccaagccgaggatgtggccgtctactactgttgg<br>caggggactcacttcccggggaccttcggtggaggcactaaggtggagatcaaaaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 1 -<br>Full - aa | 43 | malpvtalllplalllhaarpeiqlvqsgaevkkpgatvkisckgsgfnie**dyyih**wvqqap<br>gkglewmg**ridpendetkygpifqg**rvtitadtstntvymelsslrsedtavyycaf**rgg**<br>**v**ywgqgttvtvssggggsggggsggggsggggsdvvmtqspdslavslgeratinc**kss**<br>**qslldsdgktyln**wlqqkpgqppkrlis**lvsklds**gvpdrfsgsgsgtdftltisslqaedva<br>vyyc**wqgthfpgt**fgggtkveikttpaprpptpaptiasqplslrpeacrpaaggavhtrg<br>ldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrk<br>npqeglynelqkdkmaeayseigmkgerrrgkghdglyqglstatkdtydalhmqalppr |
| | | CAR 2 |
| CAR2<br>scFv<br>domain | 44 | dvvmtqspdslavslgeratinckssqslldsdgktylnwlqqkpgqppkrlislvskldsg<br>vpdrfsgsgsgtdftltisslqaedvavyycwqgthfpgtfgggtkveikggggsggggsg<br>gggsggggseiqlvqsgaevkkpgatvkisckgsgfniedyyihwvqqapgkglewm<br>gridpendetkygpifqgrvtitadtstntvymelsslrsedtavyycafrggvywgqgttvt<br>vss |
| CAR2<br>scFv<br>domain - nt | 45 | gatgtcgtgatgacccagtccccagactccctcgcagtgtccttgggagaacgggccaccatc<br>aactgcaaatcgagccagtcactgctggactcagacggaaagacctacctcaactggctgca<br>gcagaagcctggccagccaccgaagcgcctgatctccctggtgtccaagctggactcgggc<br>gtcccggacaggtttagcggtagcggctcgggaaccgacttcactctgaccattagctcgctc<br>caagctgaagatgtggcggtctactactgctggcaggggacccacttccccgggacctttggc<br>ggaggaactaaagtcgaaatcaaaggaggaggcggatcaggtggaggaggcagcggagg<br>aggagggagcggcggtggcggctccgaaattcaacttgtgcaatccggtgccgaggtgaag<br>aaacctggtgccactgtcaagatctcgtgtaagggatcgggattcaatatcgaggactactaca<br>tccactgggtgcaacaggcgccaggaaagggattggagtggatgggtcgcatcgacccgga<br>aaacgatgagactaagtacggaccgatcttccaaggccgggtcacgatcactgcggatacct<br>ccactaataccgtgtatatggagctctcgtcactgagaagcgaagatacggccgtgtactactg<br>cgcattcagaggaggtgtgtactggggccagggaactactgtgaccgtgtcgtcg |
| CAR2 -<br>Soluble<br>scFv - nt | 46 | atggccctccctgtcaccgccctgctgcttccgctggctcttctgctccacgccgctcggcccg<br>atgtcgtgatgacccagtccccagactccctcgcagtgtccttgggagaacgggccaccatca<br>actgcaaatcgagccagtcactgctggactcagacggaaagacctacctcaactggctgcag<br>cagaagcctggccagccaccgaagcgcctgatctccctggtgtccaagctggactcgggcgt<br>cccggacaggtttagcggtagcggctcgggaaccgacttcactctgaccattagctcgctcca<br>agctgaagatgtggcggtctactactgctggcaggggacccacttccccgggacctttggcg<br>gaggaactaaagtcgaaatcaaaggaggaggcggatcaggtggaggaggcagcggagga<br>ggagggagcggcggtggcggctccgaaattcaacttgtgcaatccggtgccgaggtgaaga<br>aacctggtgccactgtcaagatctcgtgtaagggatcgggattcaatatcgaggactactacat<br>ccactgggtgcaacaggcgccaggaaagggattggagtggatgggtcgcatcgacccgga |

TABLE 2-continued

Humanized EGFRvIII CAR Constructs

| Name | SEQ ID NO: | Sequence |
|---|---|---|
| | | aaacgatgagactaagtacggaccgatcttccaaggccgggtcacgatcactgcggatacct<br>ccactaataccgtgtatatggagctctcgtcactgagaagcgaagatacggccgtgtactactg<br>cgcattcagaggaggtgtgtactggggccagggaactactgtgaccgtgtcgtcggggtcac<br>atcaccaccatcatcatcaccac |
| CAR2 - Soluble scFv - aa | 47 | malpvtalllplalllhaarpdvvmtqspdslavslgeratinckssqslldsdgktylnwlqq<br>kpgqppkrlislvskldsgvpdrfsgsgsgtdftltisslqaedvavyycwqgthfpgtfggg<br>tkveikggggsggggsggggsggggseiqlvqsgaevkkpgatvkisckgsgfniedyyi<br>hwvqqapgkglewmgridpendetkygpifqgrvtitadtstntvymelsslrsedtavy<br>ycafrggvywgqgttvtvssgshhhhhhhh |
| CAR 2 - Full - nt | 48 | atggccctccctgtcaccgccctgctgcttccgctggctcttctgctccacgccgctcggcccg<br>acgtggtcatgactcaaagcccagattccttggctgtctcccttggagaaagagcaacgatcaa<br>ttgcaaaagctcgcagtccctgttggactccgatggaaaaacctacctcaactggctgcagca<br>gaagccgggacaaccaccaaagcggctgatttccctcgtgtccaagctggacagcggcgtg<br>ccggatcgcttctcgggcagcggctcgggaaccgattttactctcactatttcgtcactgcaagc<br>ggaggacgtggcggtgtattactgctggcagggcactcacttcccgggtacttttggtggagg<br>taccaaagtcgaaatcaagggtggaggcgggagcggaggaggcgggtcgggaggagga<br>ggatcgggtggcggaggctcagaaatccagctggtgcagtcaggtgccgaagtgaagaag<br>cctggggccacggtgaagatctcgtgcaaggggagcggattcaacatcgaggattactacat<br>ccattgggtgcaacaggcccctggcaaagggctggaatggatgggaaggatcgaccccga<br>gaatgacgagactaagtacggcccgatcttccaaggacgggtgaccatcactgcagacactt<br>caaccaacaccgtctacatggaactctcctcgctgcgctccgaggacaccgccgtgtactact<br>gtgctttcagaggaggagtctactggggacagggaacgaccgtgaccgtcagctcaaccact<br>accccagcaccgaggccacccaccccggctcctaccatcgcctcccagcctctgtccctgcg<br>tccggaggcatgtagacccgcagctggtggggccgtgcatacccggggtcttgacttcgcct<br>gcgatatctacatttgggcccctctggctggtacttgcggggtcctgctgctttcactcgtgatca<br>ctctttactgtaagcgcggtcggaagaagctgctgtacatctttaagcaacccttcatgaggcct<br>gtgcagactactcaagaggaggacggctgttcatgccggttcccagaggaggaggaaggcg<br>gctgcgaactgcgcgtgaaattcagccgcagcgcagatgctccagcctacaagcaggggca<br>gaaccagctctacaacgaactcaatcttggtcggagagaggagtacgacgtgctggacaagc<br>ggagaggacgggacccagaaatgggcgggaagccgcgcagaaagaatccccaagaggg<br>cctgtacaacgagctccaaaaggataagatggcagaagcctatagcgagattggtatgaaag<br>gggaacgcagaagaggcaaaggccacgacggactgtaccagggactcagcaccgccacc<br>aaggacacctatgacgctcttcacatgcaggccctgccgcctcgg |
| CAR 2 - Full - aa | 49 | malpvtalllplalllhaarpdvvmtqspdslavslgeratinc**kssqslldsdgktyln**wlq<br>qkpgqppkrlis**lvsklds**gvpdrfsgsgsgtdftltisslqaedvavyyc**wqgthfpgt**fg<br>ggtkveikggggsggggsggggsggggseiqlvqsgaevkkpgatvkisckgsgfnied<br>**yyih**wvqqapgkglewmg**ridpendetkygpifqg**rvtitadtstntvymelsslrse**d**<br>tavyyca**frggvy**wgqgttvtvsstttpaprpptpaptiasqplslrpeacrpaaggavhtrg<br>ldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrk<br>npqeglynelqkdkmaeayseigmkgerrrgkghdglyqglstatkdtydalhmqalppr |
| | | CAR 3 |
| CAR3 scFv domain | 50 | eiqlvqsgaevkkpgeslrisckgsgfniedyyihwvrqmpgkglewmgridpendetk<br>ygpifqghvtisadtsintvylqwsslkasdtamyycafrggvywgqgttvtvssggggsg<br>gggsggggsggggsdvvmtqsplslpvtlgqpasisckssqslldsdgktylnwlqqrpg<br>qsprrlislvskldsgvpdrfsgsgsgtdftlkisrveaedvgvyycwqgthfpgtfgggtkv<br>eik |
| CAR3 scFv domain nt | 51 | gagattcagctggtccaaagcggcgcagaagtgaaaaagccaggggaatcgttgcgcatca<br>gctgtaaaggttccggcttcaacatcgaggactattacatccattgggtgcggcagatgccag<br>gaaaggggctggaatggatgggacggattgacccggagaacgacgaaaccaagtacggac<br>cgatctttcaaggacacgtgactatctccgccgacaccagcatcaatacggtgtacctccaatg<br>gtcctcactcaaggcctcggataccgcgatgtactactgcgcgttcagaggaggcgtctactg<br>gggacaagggactactgtgactgtctcatcaggaggtggaggaagcggaggaggtggctcg<br>ggcggaggtggatcgggaggaggagggtccgatgtggtgatgacccagtccccactgtcgc<br>tcccggtgaccctcggacagcctgctagcatctcgtgcaaatcctcgcaatccctgctggactc<br>ggacggaaaaacgtacctcaattggctgcagcagcgccctggccagagcccgagaaggctt<br>atctcgctggtgtcaaagctggatagcggtgtgcccgaccggttcagcggctcagggtcagg<br>aaccgatttcaccttgaagatctcccgcgtggaagccgaagatgtcggagtctactactgctgg<br>cagggtactcacttcccggggacctttggtggcggcactaaggtcgagattaag |
| CAR 3 - Soluble scFv - nt | 52 | atggccctccctgtcaccgccctgctgcttccgctggctcttctgctccacgccgctcggcccg<br>agattcagctggtccaaagcggcgcagaagtgaaaaagccaggggaatcgttgcgcatcag<br>ctgtaaaggttccggcttcaacatcgaggactattacatccattgggtgcggcagatgccagga<br>aaggggctggaatggatgggacggattgacccggagaacgacgaaaccaagtacggaccg<br>atctttcaaggacacgtgactatctccgccgacaccagcatcaatacggtgtacctccaatggt<br>cctcactcaaggcctcggataccgcgatgtactactgcgcgttcagaggaggcgtctactggg<br>gacaagggactactgtgactgtctcatcaggaggtggaggaagcggaggaggtggctcggg<br>cggaggtggatcgggaggaggagggtccgatgtggtgatgacccagtccccactgtcgctc<br>ccggtgaccctcggacagcctgctagcatctcgtgcaaatcctcgcaatccctgctggactcg |

TABLE 2-continued

Humanized EGFRvIII CAR Constructs

| Name | SEQ ID NO: | Sequence |
| --- | --- | --- |
| | | gacggaaaaacgtacctcaattggctgcagcagcgccctggccagagcccgagaaggctta<br>tctcgctggtgtcaaagctggatagcggtgtgcccgaccggttcagcggctcagggtcagga<br>accgatttcaccttgaagatctcccgcgtggaagccgaagatgtcggagtctactactgctggc<br>agggtactcacttcccggggacctttggtggcggcactaaggtcgagattaagggctcacacc<br>atcatcaccatcaccaccac |
| CAR 3 - Soluble scFv - aa | 53 | malpvtalllplalllhaarpeiqlvqsgaevkkpgeslrisckgsgfniedyyihwvrqmp<br>gkglewmgridpendetkygpifqghvtisadtsintvylqwsslkasdtamyycafrgg<br>vywgqgttvtvssggggsggggsggggsggggsdvvmtqsplslpvtlgqpasisckss<br>qslldsdgktylnwlqqrpgqsprrlislvskldsgvpdrfsgsgsgtdftlkisrveaedvgv<br>yycwqgthfpgtfgggtkveikgshhhhhhhh |
| CAR 3 - Full - nt | 54 | atggccctccctgtcaccgccctgctgcttccgctggctcttctgctccacgccgctcggcccg<br>aaatccagctggtgcaaagcggagccgaggtgaagaagcccggagaatccctgcgcatctc<br>gtgtaagggttccggctttaacatcgaggattactacatccactgggtgagacagatgccggg<br>caaaggtctggaatggatgggccgcatcgacccggagaacgacgaaaccaaatacggacc<br>aatcttccaaggacatgtgactatttccgcggatacctccatcaacactgtctacttgcagtgga<br>gctcgctcaaggcgtcggataccgccatgtactactgcgcattcagaggaggtgtgtactggg<br>gccagggcactacggtcaccgtgtcctcgggaggtggagggtcaggaggcggaggctcgg<br>gcggtggaggatcaggcggaggaggaagcgatgtggtcatgactcaatccccactgtcact<br>gcctgtcactctggggcaaccggcttccatctcatgcaagtcaagccaatcgctgctcgactcc<br>gacggaaaaacctacctcaattggcttcagcagcgcccaggccagtcgcctcggaggctgat<br>ctcactcgtgtcgaagcttgactccggggtgccggatcggtttagcggaagcggatcgggga<br>ccgacttcacgttgaagattagccgggtggaagccgaggacgtgggagtctattactgctggc<br>aggggacccacttcccggggactttcggaggaggcaccaaagtcgagattaagaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 3 - Full-aa | 55 | malpvtalllplalllhaarpeiqlvqsgaevkkpgeslrisckgsgfnie**dyyih**wvrqmp<br>gkglewmg**ridpendetkygpifqg**hvtisadtsintvylqwsslkasdtamyycaf**rg**<br>**gvy**wgqgttvtvssggggsggggsggggsggggsdvvmtqsplslpvtlgqpasisc**ks**<br>**sqslldsdgktyln**wlqqrpgqsprrlis**lvsklds**gvpdrfsgsgsgtdftlkisrveaedv<br>gvyyc**wqgthfpgt**fgggtkveiktttpaprpptpaptiasqplslrpeacrpaaggavhtr<br>gldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprr<br>knpqeglynelqkdkmaeayseigmkgerrrgkghdglyqglstatkdtydalhmqalp<br>pr |
| | | CAR 4 |
| CAR4 scFv domain | 56 | dvvmtqsplslpvtlgqpasisckssqslldsdgktylnwlqqrpgqsprrlislvskldsgv<br>pdrfsgsgsgtdftlkisrveaedvgvyycwqgthfpgtfgggtkveikggggsggggsg<br>gggsggggseiqlvqsgaevkkpgeslrisckgsgfniedyyihwvrqmpgkglewmg<br>ridpendetkygpifqghvtisadtsintvylqwsslkasdtamyycafrggvywgqgttv<br>tvss |
| CAR4 scFv domain nt | 57 | gacgtcgtcatgacccagagcccgctgtcactgcctgtgaccctgggccagccggcgtccat<br>tagctgcaaatcctcgcaatccctgctcgactcagacggaaaaacgtacttgaactggctccaa<br>cagcgccctgggcaatccccaaggcggcttatctcactcgtcagcaagctcgatagcggtgtc<br>ccagacagattttcgggctcgggatcgggcactgatttcactctgaagatctcgcgggtggaa<br>gccgaggatgtgggagtgtactattgctggcagggcactcacttccccgggacgtttggcgg<br>aggaactaaggtcgagatcaaaggaggaggtggatcaggcggaggtgggagcggaggag<br>gaggaagcggtggtggaggttccgaaatccagctggtgcaatcaggagccgaggtgaaga<br>agccgggagaatccctgcgcatctcgtgcaagggctcgggcttcaacatcgaggattactac<br>atccactgggtgcggcagatgccgggaaaggggttggaatggatgggacgcattgacccgg<br>aaaatgatgaaaccaaatacggcccaatcttccaaggccacgtgaccattagcgctgacactt<br>ccatcaacaccgtgtaccttcagtggtcctcactgaaggcgtcggacactgccatgtactactg<br>tgcattcagaggaggggtctactggggacagggcaccaccgtgaccgtgagctcc |
| CAR4 - Soluble scFv - nt | 58 | atggccctccctgtcaccgccctgctgcttccgctggctcttctgctccacgccgctcggcccg<br>acgtcgtcatgacccagagcccgctgtcactgcctgtgaccctgggccagccggcgtccatta<br>gctgcaaatcctcgcaatccctgctcgactcagacggaaaaacgtacttgaactggctccaac<br>agcgccctgggcaatccccaaggcggcttatctcactcgtcagcaagctcgatagcggtgtcc<br>cagacagattttcgggctcgggatcgggcactgatttcactctgaagatctcgcgggtggaag<br>ccgaggatgtgggagtgtactattgctggcagggcactcacttccccgggacgtttggcgga<br>ggaactaaggtcgagatcaaaggaggaggtggatcaggcggaggtgggagcggaggagg |

TABLE 2-continued

| Humanized EGFRvIII CAR Constructs | | |
|---|---|---|
| Name | SEQ ID NO: | Sequence |
| | | aggaagcggtggtggaggttccgaaatccagctggtgcaatcaggagccgaggtgaagaa<br>gccgggagaatccctgcgcatctcgtgcaagggctcgggcttcaacatcgaggattactacat<br>ccactgggtgcggcagatgccgggaaaggggttggaatggatgggacgcattgacccgga<br>aaatgatgaaaccaaatacgggccaatcttccaaggccacgtgaccattagcgctgacacttc<br>catcaacaccgtgtaccttcagtggtcctcactgaaggcgtcggacactgccatgtactactgt<br>gcattcagaggaggggtctactggggacagggcaccaccgtgaccgtgagctccggctcgc<br>atcaccatcatcaccaccatcac |
| CAR4 - Soluble scFv - aa | 59 | malpvtalllplalllhaarpdvvmtqsplslpvtlgqpasisckssqslldsdgktylnwlqq<br>rpgqsprrlislvskldsgvpdrfsgsgsgtdftlkisrveaedvgvyycwqgthfpgtfggg<br>tkveikggggsggggsggggsggggseiqlvqsgaevkkpgeslrisckgsgfniedyyi<br>hwvrqmpgkglewmgridpendetkygpifqghvtisadtsintvylqwsslkasdtam<br>yycafrggvywgqgttvtvssgshhhhhhhh |
| CAR 4 - Full - nt | 60 | atggccctccctgtcaccgccctgctgcttccgctggctcttctgctccacgccgctcggcccg<br>acgtcgtcatgacccaatcccctctctccctgccggtcaccctgggtcagccggcgtcgatctc<br>atgcaaaagctcacagtccctgctggattcggacggaaaaacctacttgaactggctccaaca<br>gaggccgggtcagtcccctcgcagactgatctcgctggtgagcaagctcgactcgggtgtgc<br>cggatcggttctccgggtcaggatcgggcaccgactttacgctcaagatttcgagagtggagg<br>ccgaggatgtgggagtgtactattgctggcagggcacgcatttccccgggacctttggaggc<br>gggactaaggtggaaatcaagggaggtggcggatcaggcggaggaggcagcggcggag<br>gtggatcaggaggcggagggtcagagatccagctggtccaaagcggagcagaggtgaaga<br>agccaggcgagtcccttcgcatttcgtgcaaagggagcggcttcaacattgaagattactacat<br>ccactgggtgcggcaaatgccaggaaagggtctggaatggatgggacggatcgacccaga<br>aaatgatgaaactaagtacggaccgatcttccaaggacacgtcactatctccgcggacacttc<br>gatcaacaccgtgtacctccagtggagcagcttgaaagcctccgacaccgctatgtactactgt<br>gccttccgcggaggagtctactggggacaggggactactgtgaccgtgtcgtccaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 4 - Full - aa | 61 | malpvtalllplalllhaarpdvvmtqsplslpvtlgqpasisc**kssqslldsdgktyln**wlq<br>qrpgqsprrlis**lvsklds**gvpdrfsgsgsgtdftlkisrveaedvgvyyc**wqgthfpgt**fg<br>ggtkveikggggsggggsggggsggggseiqlvqsgaevkkpgeslrisckgsgfnie**dy**<br>**yih**wvrqmpgkglewmg**ridpendetkygpifqg**hvtisadtsintvylqwsslkasd<br>tamyycaf**rggvy**wgqgttvtvsstttpaprpptpaptiasqplslrpeacrpaaggavhtr<br>gldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprr<br>knpqeglynelqkdkmaeayseigmkgerrrgkghdglyqglstatkdtydalhmqalp<br>pr |
| | | CAR 5 |
| CAR5 scFv domain | 62 | eiqlvqsgaevkkpgatvkisckgsgfniedyyihwvqqapgkglewmgridpendet<br>kygpifqgrvtitadtstntvymelsslrsedtavyycafrggvywgqgttvtvssggggsg<br>gggsggggsggggsdvvmtqsplslpvtlgqpasisckssqslldsdgktylnwlqqrpg<br>qsprrlislvskldsgvpdrfsgsgsgtdftlkisrveaedvgvyycwqgthfpgtfgggtkv<br>eik |
| CAR5 scFv domain nt | 63 | gaaatccagctcgtgcagagcggagccgaggtcaagaaaccgggtgctaccgtgaagattt<br>catgcaagggatcgggcttcaacatcgaggattactacatccactgggtgcagcaggcacca<br>ggaaaaggacttgaatggatgggccggatcgacccggaaaatgacgagactaagtacggcc<br>ctatcttccaaggacgggtgacgatcaccgcagacactagcaccaacaccgtctatatggaac<br>tctcgtccctgaggtccgaagatactgccgtgtactactgtgcgtttcgcggaggtgtgtactgg<br>ggacagggtaccaccgtcaccgtgtcatcgggcggtggaggctccggtggaggagggtca<br>ggaggcggtggaagcggaggaggcggcagcgacgtggtcatgactcaatcgccgctgtcg<br>ctgcccgtcactctgggacaacccgcgtccatcagctgcaaatcctcgcagtcactgcttgact<br>ccgatggaaagacctacctcaactggctgcagcaacgcccaggccaatccccaagacgcct<br>gatctcgttggtgtcaaagctggactcaggggtgccggaccggttctccgggagcgggtcgg<br>gcacggatttcactctcaagatctccagagtggaagccgaggatgtgggagtctactactgct<br>ggcagggaacccatttccctggaacttttggcggaggaactaaggtcgagattaaa |
| CAR5- Soluble scFv-nt | 64 | atggccctccctgtcaccgccctgctgcttccgctggctcttctgctccacgccgctcggcccg<br>aaatccagctcgtgcagagcggagccgaggtcaagaaaccgggtgctaccgtgaagatttca<br>tgcaagggatcgggcttcaacatcgaggattactacatccactgggtgcagcaggcaccagg<br>aaaaggacttgaatggatgggccggatcgacccggaaaatgacgagactaagtacggccct<br>atcttccaaggacgggtgacgatcaccgcagacactagcaccaacaccgtctatatggaactc |

TABLE 2-continued

| Humanized EGFRvIII CAR Constructs | | |
|---|---|---|
| Name | SEQ ID NO: | Sequence |
| | | tcgtccctgaggtccgaagatactgccgtgtactactgtgcgtttcgcggaggtgtgtactggg<br>gacagggtaccaccgtcaccgtgtcatcgggcggtggaggctccggtggaggagggtcag<br>gaggcggtggaagcggaggaggcggcagcgacgtggtcatgactcaatcgccgctgtcgc<br>tgcccgtcactctgggacaacccgcgtccatcagctgcaaatcctcgcagtcactgcttgactc<br>cgatggaaagacctacctcaactggctgcagcaacgcccaggccaatccccaagacgcctg<br>atctcgttggtgtcaaagctggactcaggggtgccggaccggttctccgggagcgggtcggg<br>cacggatttcactctcaagatctccagagtggaagccgaggatgtgggagtctactactgctg<br>gcagggaacccatttccctggaacttttggcggaggaactaaggtcgagattaaagggagcc<br>accatcatcatcaccaccaccac |
| CAR5 - Soluble scFv - aa | 65 | malpvtalllplalllhaarpeiqlvqsgaevkkpgatvkisckgsgfniedyyihwvqqap<br>gkglewmgridpendetkygpifqgrvtitadtstntvymelsslrsedtavyycafrggvy<br>wgqgttvtvssggggsggggsggggsggggsdvvmtqsplslpvtlgqpasisckssqsl<br>ldsdgktylnwlqqrpgqsprrlislvskldsgvpdrfsgsgsgtdftlkisrveaedvgvyy<br>cwqgthfpgtfgggtkveikgshhhhhhhh |
| CAR 5 - Full - nt | 66 | atggccctccctgtcaccgccctgctgcttccgctggctcttctgctccacgccgctcggcccg<br>aaatccagctcgtgcagagcggagccgaggtcaagaaacccgggtgctaccgtgaagatttca<br>tgcaagggatcgggcttcaacatcgaggattactacatccactgggtgcagcaggcaccagg<br>aaaaggacttgaatggatgggccggatcgacccggaaaatgacgagactaagtacggccct<br>atcttccaaggacgggtgacgatcaccgcagacactagcaccaacaccgtctatatggaactc<br>tcgtccctgaggtccgaagatactgccgtgtactactgtgcgtttcgcggaggtgtgtactggg<br>gacagggtaccaccgtcaccgtgtcatcgggcggtggaggctccggtggaggagggtcag<br>gaggcggtggaagcggaggaggcggcagcgacgtggtcatgactcaatcgccgctgtcgc<br>tgcccgtcactctgggacaacccgcgtccatcagctgcaaatcctcgcagtcactgcttgactc<br>cgatggaaagacctacctcaactggctgcagcaacgcccaggccaatccccaagacgcctg<br>atctcgttggtgtcaaagctggactcaggggtgccggaccggttctccgggagcgggtcggg<br>cacggatttcactctcaagatctccagagtggaagccgaggatgtgggagtctactactgctg<br>gcagggaacccatttccctggaacttttggcggaggaactaaggtcgagattaaaaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 5- Full-aa | 67 | malpvtalllplalllhaarpeiqlvqssaevkkpsatvkiscksssfnie**dyyih**wvqqap<br>gkglewmg**ridpendetkygpifqg**rvtitadtstntvymelsslrsedtavyycaf**rgg**<br>**vy**wgqgttvtvssggggsggggsggggsggggsdvvmtqsplslpvtlgqpasisc**kss**<br>**qslldsdgktyln**wlqqrpgqsprrlis**lvsklds**gvpdrfsgsgsgtdftlkisrveaedvg<br>vyyc**wqgthfpgt**fgggtkveiktttpaprpptpaptiasqplslrpeacrpaaggavhtrg<br>ldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrk<br>npqeglynelqkdkmaeayseigmkgerrrgkghdglyqglstatkdtydalhmqalppr |
| CAR 6 | | |
| CAR6 scFv domain | 68 | eiqlvqsgaevkkpgeslrisckgsgfniedyyihwvrqmpgkglewmgridpendetk<br>ygpifqghvtisadtsintvylqwsslkasdtamyycafrggvywgqgttvtvssggggsg<br>gggsggggsggggsdvvmtqspdslavslgeratinckssqslldsdgktylnwlqqkpg<br>qppkrlislvskldsgvpdrfsgsgsgtdftltisslqaedvavyycwqgthfpgtfgggtkv<br>eik |
| CAR6 scFv domain nt | 69 | gaaatccagctggtgcagtcaggcgccgaggtcaagaagccgggagagtcgctgagaatct<br>cgtgcaagggctcggggttcaacatcgaggactactacattcactgggtcaggcagatgccg<br>ggaaagggactggaatggatgggccggatcgacccagaaaatgacgaaaccaaatacggg<br>ccgatttttcaaggccacgtgactatcagcgcagacacgagcatcaacactgtctacctccagt<br>ggtcctcgcttaaggccagcgataccgctatgtactactgcgcattcagaggcggggtgtact<br>ggggacaaggaaccactgtgaccgtgagcagcggaggtggcggctcgggaggaggtggg<br>agcggaggaggaggttccggcggtggaggatcagatgtcgtgatgacccagtccccggact<br>ccctcgctgtctcactgggcgagcgcgcgaccatcaactgcaaatcgagccagtcgctgttg<br>gactccgatggaaagacttatctgaattggctgcaacagaaaccaggacaacctcccaagcg<br>gctcatctcgcttgtgtcaaaactcgattcgggagtgccagaccgcttctcggggtccgggag<br>cggaactgactttactttgaccatttcctcactgcaagcggaggatgtggccgtgtattactgttg<br>gcagggcacgcatttccctggaaccttcggtggcggaactaaggtggaaatcaag |
| CAR6 - Soluble scFv - nt | 70 | atggccctccctgtcaccgccctgctgcttccgctggctcttctgctccacgccgctcggcccg<br>aaatccagctggtgcagtcaggcgccgaggtcaagaagccgggagagtcgctgagaatctc<br>gtgcaagggctcggggttcaacatcgaggactactacattcactgggtcaggcagatgccgg |

TABLE 2-continued

Humanized EGFRvIII CAR Constructs

| Name | SEQ ID NO: | Sequence |
|---|---|---|
| | | gaaagggactggaatggatgggccggatcgacccagaaaatgacgaaaccaaatacgggc<br>cgatttttcaaggccacgtgactatcagcgcagacacgagcatcaacactgtctacctccagtg<br>gtcctcgcttaaggccagcgataccgctatgtactactgcgcattcagaggcggggtgtactg<br>gggacaaggaaccactgtgaccgtgagcagcggaggtggcggctcgggaggaggtggga<br>gcggaggaggaggttccggcggtggaggatcagatgtcgtgatgacccagtccccggactc<br>cctcgctgtctcactgggcgagcgcgcgaccatcaactgcaaatcgagccagtcgctgttgg<br>actccgatggaaagacttatctgaattggctgcaacagaaaccaggacaacctcccaagcgg<br>ctcatctcgcttgtgtcaaaactcgattcgggagtgccagaccgcttctcggggtccgggagc<br>ggaactgactttactttgaccatttcctcactgcaagcggaggatgtggccgtgtattactgttgg<br>cagggcacgcatttccctggaaccttcggtggcggaactaaggtggaaatcaagggatcaca<br>ccaccatcatcaccatcaccaccat |
| CAR6 - Soluble scFv - aa | 71 | malpvtalllplalllhaarpeiqlvqsgaevkkpgeslrisckgsgfniedyyihwvrqmp<br>gkglewmgridpendetkygpifqghvtisadtsintvylqwsslkasdtamyycafrgg<br>vywgqgttvtvssggggsggggsggggsggggsdvvmtqspdslavslgeratinckss<br>qslldsdgktylnwlqqkpgqppkrlislvskldsgvpdrfsgsgsgtdftltisslqaedvav<br>yycwqgthfpgtfgggtkveikgshhhhhhhh |
| CAR6 - Full - nt | 72 | atggccctccctgtcaccgccctgctgcttccgctggctcttctgctccacgccgctcggcccg<br>agattcagctcgtgcaatcgggagcggaagtcaagaagccaggagagtccttgcggatctca<br>tgcaagggtagcggctttaacatcgaggattactacatccactgggtgaggcagatgccggg<br>gaagggactcgaatggatgggacggatcgacccagaaaacgacgaaactaagtacggtcc<br>gatcttccaaggccatgtgactattagcgccgatacttcaatcaataccgtgtatctgcaatggtc<br>ctcattgaaagcctcagataccgcgatgtactactgtgctttcagaggaggggtctactgggga<br>cagggaactaccgtgactgtctcgtccggcggaggcgggtcaggaggtggcggcagcgga<br>ggaggagggtccggcggaggtgggtccgacgtcgtgatgacccagagccctgacagcctg<br>gcagtgagcctgggcgaaagagctaccattaactgcaaatcgtcgcagagcctgctggactc<br>ggacggaaaaacgtacctcaattggctgcagcaaaagcctggccagccaccgaagcgcctt<br>atctcactggtgtcgaagctggattcgggagtgcccgatcgcttctccggctcgggatcgggt<br>actgacttcaccctcactatctcctcgcttcaagcagaggacgtggccgtctactactgctggca<br>gggaacccactttccgggaaccttcggcggagggacgaaagtggagatcaagaccactacc<br>ccagcaccgaggccacccaccccggctcctaccatcgcctcccagcctctgtccctgcgtcc<br>ggaggcatgtagacccgcagctggtggggccgtgcatacccggggtcttgacttcgcctgcg<br>atatctacatttgggcccctctggctgg-<br>tacttgcggggtcctgctgctttcactcgtgatcactct<br>ttactgtaagcgcggtcggaagaagctgctgtacatctttaagcaacccttcatgaggcctgtg<br>cagactactcaagaggaggacggctgttcatgccggttcccagaggaggaggaaggcggct<br>gcgaactgcgcgtgaaattcagccgcagcgcagatgctccagcctacaagcaggggcaga<br>accagctctacaacgaactcaatcttggtcggagagaggagtacgacgtgctggacaagcgg<br>agaggacgggacccagaaatgggcgggaagccgcgcagaaagaatccccaagagggcct<br>gtacaacgagctccaaaaggataagatggcagaagcctatagcgagattggtatgaaaggg<br>gaacgcagaagaggcaaaggccacgacggactgtaccagggactcagcaccgccaccaa<br>ggacacctatgacgctcttcacatgcaggccctgccgcctcgg |
| CAR6 - Full - aa | 73 | malpvtalllplalllhaarpeiqlvqsgaevkkpgeslrisckgsgfnie**dyyih**wvrqmp<br>gkglewmg**ridpendetkygpifqg**hvtisadtsintvylqwsslkasdtamyycaf**rg**<br>**gvy**wgqgttvtvssggggsggggsggggsggggsdvvmtqspdslavslgeratinc**ks**<br>**sqslldsdgktyln**wlqqkpgqppkrlis**lvsklds**gvpdrfsgsgsgtdftltisslqaedv<br>avyyc**wqgthfpgt**fgggtkveiktttpaprpptpaptiasqplslrpeacrpaaggavhtr<br>gldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprr<br>knpqeglynelqkdkmaeayseigmkgerrrgkghdglyqglstatkdtydalhmqalp<br>pr |
| | | CAR 7 |
| CAR7 scFv domain | 74 | dvvmtqspdslavslgeratinckssqslldsdgktylnwlqqkpgqppkrlislvskldsg<br>vpdrfsgsgsgtdftltisslqaedvavyycwqgthfpgtfgggtkveikggggsggggsg<br>gggsggggseiqlvqsgaevkkpgeslrisckgsgfniedyyihwvrqmpgkglewmg<br>ridpendetkygpifqghvtisadtsintvylqwsslkasdtamyycafrggvywgqgttv<br>tvss |
| CAR7 scFv domain nt | 75 | gacgtggtgatgacccaatcgccagattccctggcagtgtccctgggcgaacgcgccactatt<br>aactgcaaatcgtcacagtccttgcttgattccgacggaaagacctacctcaattggctccagc<br>agaagccaggacaaccgccaaagagactgatctccctggtgtcaaagctggactcgggagt<br>gcctgatcggttctcgggtagcgggagcggcaccgacttcactctgaccatctcgtcactcca<br>ggctgaggacgtggccgtgtattactgttggcagggtactcactttccgggcactttcggaggc<br>ggcaccaaggtggagattaaaggaggaggcggaagcggaggtggaggatcgggaggtgg<br>tgggagcggcggaggagggagcgagatccagctcgtccaatcgggagcggaagtgaaga<br>agcccggagagtcacttagaatctcatgcaaggggtcgggcttcaacatcgaggattactaca<br>tccattgggtccgccagatgcctggtaaaggactggaatggatggggaggattgacccggaa<br>aacgacgaaactaagtacggaccgatctttcaagggcacgtgactatctccgctgatacctca<br>atcaatactgtctacctccagtggtcctcgctgaaagcaagcgacaccgcgatgtactactgcg<br>ccttccggggaggagtgtactggggccaaggcaccacggtcacggtcagctcc |

TABLE 2-continued

| Humanized EGFRvIII CAR Constructs | | |
|---|---|---|
| Name | SEQ ID NO: | Sequence |
| CAR7 - Soluble scFv - nt | 76 | atggccctccctgtcaccgccctgctgcttccgctggctcttctgctccacgccgctcggcccg<br>acgtggtgatgacccaatcgccagattccctggcagtgtccctgggcgaacgcgccactatta<br>actgcaaatcgtcacagtccttgcttgattccgacggaaagacctacctcaattggctccagca<br>gaagccaggacaaccgccaaagagactgatctccctggtgtcaaagctggactcgggagtg<br>cctgatcggttctcgggtagcgggagcggcaccgacttcactctgaccatctcgtcactccag<br>gctgaggacgtggccgtgtattactgttggcagggtactcactttccgggcactttcggaggcg<br>gcaccaaggtggagattaaaggaggaggcggaagcggaggtggaggatcgggaggtggt<br>gggagcggcggaggagggagcgagatccagctcgtccaatcgggagcggaagtgaagaa<br>gcccggagagtcacttagaatctcatgcaaggggtcgggcttcaacatcgaggattactacat<br>ccattgggtccgccagatgcctggtaaaggactggaatggatggggaggattgacccggaa<br>aacgacgaaactaagtacggaccgatctttcaagggcacgtgactatctccgctgatacctca<br>atcaatactgtctacctccagtggtcctcgctgaaagcaagcgacaccgcgatgtactactgcg<br>ccttccggggaggagtgtactggggccaaggcaccacggtcacggtcagctccggctccca<br>tcaccaccaccatcaccatcatcac |
| CAR7 - Soluble scFv - aa | 77 | malpvtalllplalllhaarpdvvmtqspdslavslgeratinckssqslldsdgktylnwlqq<br>kpgqppkrlislvskldsgvpdrfsgsgsgtdftltisslqaedvavyycwqgthfpgtfggg<br>tkveikggggsggggsggggsggggseiqlvqsgaevkkpgeslrisckgsgfniedyyi<br>hwvrqmpgkglewmgridpendetkygpifqghvtisadtsintvylqwsslkasdtam<br>yycafrggvywgqgttvtvssgshhhhhhhh |
| CAR 7 Full - nt | 78 | atggccctccctgtcaccgccctgctgcttccgctggctcttctgctccacgccgctcggcccg<br>acgtggtgatgactcagtcgcctgactcgctggctgtgtcccttggagagcgggccactatca<br>attgcaagtcatcccagtcgctgctggattccgacgggaaaacctacctcaattggctgcagca<br>aaaaccgggacagcctccaaagcggctcatcagcctggtgtccaagttggacagcggcgtg<br>ccagaccgcttctccggttcgggaagcggtactgatttcacgctgaccatctcatccctccaag<br>cggaggatgtggcagtctactactgttggcagggcacgcattttccgggcacttttggaggag<br>ggaccaaggtcgaaatcaagggaggaggtggctcgggcggaggaggctcgggaggagg<br>aggatcaggaggcggtggaagcgagattcaactggtccagagcggcgcagaagtcaagaa<br>gccgggtgaatcgctcagaatctcgtgcaaaggatcgggattcaacatcgaggactactacat<br>tcactgggtcagacaaatgccgggcaaagggctggaatggatggggaggatcgaccccga<br>aaacgatgaaaccaagtacggaccaatcttccaagggcacgtgaccatttcggcggacacct<br>caatcaacactgtgtacctccagtggagctcacttaaggccagcgataccgccatgtactattg<br>cgctttccgcggaggggtgtactggggacagggcactactgtgaccgtgtcatccaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 7 Full - aa | 79 | malpvtalllplalllhaarpdvvmtqspdslavslgeratinc**kssqslldsdgktyln**wlq<br>qkpgqppkrlis**lvsklds**gvpdrfsgsgsgtdftltisslqaedvavyyc**wqgthfpgt**fg<br>ggtkveikggggsggggsggggsggggseiqlvqsgaevkkpgeslrisckgsgfnie**dy**<br>**yih**wvrqmpgkglewmg**ridpendetkygpifqg**hvtisadtsintvylqwsslkasd<br>tamyycaf**rggvy**wgqgttvtvssttpaprpptpaptiasqplslrpeacrpaaggavhtr<br>gldfacdiyiwaplagtcgvlllslvitlyckrgrkkllyifkqpfmrpvqttqeedgcscrfp<br>eeeeggcelrvkfsrsadapaykqgqnqlynelnlgrreeydvldkrrgrdpemggkprr<br>knpqeglynelqkdkmaeayseigmkgerrrgkghdglyqglstatkdtydalhmqalp<br>pr |
| CAR 8 | | |
| CAR8 scFv domain | 80 | dvvmtqsplslpvtlgqpasisckssqslldsdgktylnwlqqrpgqsprrlislvskldsgv<br>pdrfsgsgsgtdftlkisrveaedvgvyycwqgthfpgtfgggtkveikggggsggggsg<br>gggsggggseiqlvqsgaevkkpgatvkisckgsgfniedyyihwvqqapgkglewm<br>gridpendetkygpifqgrvtitadtstntvymelsslrsedtavyycafrggvywgqgttvt<br>vss |
| CAR8 scFv domain nt | 81 | gatgtggtcatgacgcagtcaccactgtccctccccgtgacccttggacagccagcgtcgatt<br>agctgcaagtcatcccaatccctgctcgattcggatggaaagacctatctcaactggctgcagc<br>aaagacccggtcagagccctaggagactcatctcgttggtgtcaaagctggacagcggagtg<br>ccggaccggttttccggttcgggatcggggacggacttcactctgaagatttcacgggtggaa<br>gctgaggatgtgggagtgtactactgctggcagggaacccatttccctggcacttttggcgga<br>ggaactaaggtcgaaatcaagggaggaggtggctcgggaggaggcggatcgggcggagg<br>cgggagcggcggaggagggtccgaaatccaacttgtccagtcaggagccgaagtgaagaa<br>accgggagccaccgtcaaaatcagctgtaagggatcgggattcaatatcgaggactactacat<br>ccactgggtgcagcaagctccgggcaaaggactggagtggatggggcgcatcgacccaga |

TABLE 2-continued

| Name | SEQ ID NO: | Sequence |
|---|---|---|
| Humanized EGFRvIII CAR Constructs | | |
| | | gaacgacgaaaccaaatacggcccgatcttccaagggcgggtgaccatcaccgcggacac<br>ctcaactaacactgtgtacatggagctgagctccctgcgctccgaagatactgcagtctactact<br>gcgccttccgcggtggtgtgtactggggacagggcaccactgtgactgtcagctcg |
| CAR8 - Soluble scFv - nt | 82 | atggccctccctgtcaccgccctgctgcttccgctggctcttctgctccacgccgctcggcccg<br>atgtggtcatgacgcagtcaccactgtccctccccgtgacccttggacagccagcgtcgatta<br>gctgcaagtcatcccaatccctgctcgattcggatggaaagacctatctcaactggctgcagca<br>aagacccggtcagagccctaggagactcatctcgttggtgtcaaagctggacagcggagtgc<br>cggaccggttttccggttcgggatcggggacggacttcactctgaagatttcacgggtggaag<br>ctgaggatgtgggagtgtactactgctggcagggaacccatttccctggcacttttggcggag<br>gaactaaggtcgaaatcaagggaggaggtggctcgggaggaggcggatcgggcggaggc<br>gggagcggcggaggagggtccgaaatccaacttgtccagtcaggagccgaagtgaagaaa<br>ccgggagccaccgtcaaaatcagctgtaagggatcgggattcaatatcgaggactactacatc<br>cactgggtgcagcaagctccgggcaaaggactggagtggatggggcgcatcgacccagag<br>aacgacgaaaccaaatacggcccgatcttccaagggcgggtgaccatcaccgcggacacct<br>caactaacactgtgtacatggagctgagctccctgcgctccgaagatactgcagtctactactg<br>cgccttccgcggtggtgtgtactggggacagggcaccactgtgactgtcagctcggggtccc<br>accatcatcaccaccaccatcac |
| CAR8 - Soluble scFv - aa | 83 | malpvtalllplalllhaarpdvvmtqsplslpvtlgqpasisckssqslldsdgktylnwlqq<br>rpgqsprrlislvskldsgvpdrfsgsgsgtdftlkisrveaedvgvyycwqgthfpgtfggg<br>tkveikggggsggggsggggsggggseiqlvqsgaevkkpgatvkisckgsgfniedyyi<br>hwvqqapgkglewmgridpendetkygpifqgrvtitadtstntvymelsslrsedtavy<br>ycafrggvywgqgttvtvssgshhhhhhhh |
| CAR 8 - Full - nt | 84 | atggccctccctgtcaccgccctgctgcttccgctggctcttctgctccacgccgctcggcccg<br>atgtggtcatgacgcagtcaccactgtccctccccgtgacccttggacagccagcgtcgatta<br>gctgcaagtcatcccaatccctgctcgattcggatggaaagacctatctcaactggctgcagca<br>aagacccggtcagagccctaggagactcatctcgttggtgtcaaagctggacagcggagtgc<br>cggaccggttttccggttcgggatcggggacggacttcactctgaagatttcacgggtggaag<br>ctgaggatgtgggagtgtactactgctggcagggaacccatttccctggcacttttggcggag<br>gaactaaggtcgaaatcaagggaggaggtggctcgggaggaggcggatcgggcggaggc<br>gggagcggcggaggagggtccgaaatccaacttgtccagtcaggagccgaagtgaagaaa<br>ccgggagccaccgtcaaaatcagctgtaagggatcgggattcaatatcgaggactactacatc<br>cactgggtgcagcaagctccgggcaaaggactggagtggatggggcgcatcgacccagag<br>aacgacgaaaccaaatacggcccgatcttccaagggcgggtgaccatcaccgcggacacct<br>caactaacactgtgtacatggagctgagctccctgcgctccgaagatactgcagtctactactg<br>cgccttccgcggtggtgtgtactggggacagggcaccactgtgactgtcagctcgaccactac<br>cccagcaccgaggccacccaccccggctcctaccatcgcctcccagcctctgtccctgcgtc<br>cggaggcatgtagacccgcagctggtggggccgtgcatacccggggtcttgacttcgcctgc<br>gatatctacatttgggcccctctggctggtacttgcggggtcctgctgctttcactcgtgatcact<br>ctttactgtaagcgcggtcggaagaagctgctgtacatctttaagcaacccttcatgaggcctgt<br>gcagactactcaagaggaggacggctgttcatgccggttcccagaggaggaggaaggcgg<br>ctgcgaactgcgcgtgaaattcagccgcagcgcagatgctccagcctacaagcaggggcag<br>aaccagctctacaacgaactcaatcttggtcggagagaggagtacgacgtgctggacaagcg<br>gagaggacgggacccagaaatgggcgggaagccgcgcagaaagaatccccaagagggc<br>ctgtacaacgagctccaaaaggataagatggcagaagcctatagcgagattggtatgaaagg<br>ggaacgcagaagaggcaaaggccacgacggactgtaccagggactcagcaccgccacca<br>aggacacctatgacgctcttcacatgcaggccctgccgcctcgg |
| CAR 8 - Full - aa | 85 | malpvtalllplalllhaarpdvvmtqsplslpvtlgqpasisc**ksscislldsdgktyln**wlq<br>qrpgqsprrlis**lvsklds**gvpdrfsgsgsgtdftlkisrveaedvgvyyc**wqgthfpgt**fg<br>ggtkveikggggsggggsggggsggggseiqlvqsgaevkkpgatvkisckgsgfnie**d**<br>**yyih**wvqqapgkglewmg**ridpendetkygpifqg**rvtitadtstntvymelsslrsed<br>tavyycaf**rggvy**wgqgttvtvsstttpaprpptpaptiasqplslrpeacrpaaggavhtrg<br>ldfacdiyiwaplagtcgvlllslvitlyckrgrkkllyifkqpfmrpvqttqeedgcscrfpe<br>eeeggcelrvkfsrsadapaykqgqnqlynelnlgrreeydvldkrrgrdpemggkprrk<br>npqeglynelqkdkmaeayseigmkgerrrgkghdglyqglstatkdtydalhmqalppr |
| CAR 9 Mouse anti-EGFRvIII clone 3C10 | | |
| CAR9 scFv domain | 86 | eiqlqqsgaelvkpgasvklsctgsgfniedyyihwvkqrteqglewigridpendetkyg<br>pifqgratitadtssntvylqlssltsedtavyycafrggvywgpgttltvssggggsggggsg<br>gggshmdvvmtqspltlsvaigqsasisckssqslldsdgktylnwllqrpgqspkrlislv<br>skldsgvpdrftgsgsgtdftlrisrveaedlgiyycwqgthfpgtfgggtkleik |
| CAR9 scFv domain nt | 98 | gagatccagctccaacagagcggagccgaactggtcaaaccgggagcgtcggtgaagttgt<br>catgcactggatcgggcttcaacatcgaggattactacatccactgggtcaagcaacgcaccg<br>agcaggggctggaatggatcggacggatcgaccccgaaaacgatgaaaccaagtacgggc<br>ctatcttccaaggacgggccaccattacggctgacacgtcaagcaataccgtctacctccagct<br>ttccagcctgacctccgaggacactgccgtgtactactgcgccttcagaggaggcgtgtactg<br>gggaccaggaaccactttgaccgtgtccagcggaggcggtggatcaggaggaggaggctc<br>aggcggtggcggctcgcacatggacgtggtcatgactcagtccccgctgaccctgtcggtgg<br>caattggacagagcgcatccatctcgtgcaagagctcacagtcgctgctggattccgacggaa |

TABLE 2-continued

| Name | SEQ ID NO: | Sequence |
|---|---|---|
| Humanized EGFRvIII CAR Constructs | | |
| | | agacttatctgaactggctgctccaaagaccagggcaatcaccgaaacgccttatctccctggt<br>gtcgaaactcgactcgggtgtgccggatcggtttaccggtagcgggtccggcacggacttca<br>ctctccgcatttcgagggtggaagcggaggatctcgggatctactactgttggcagggaaccc<br>acttccctgggacttttggaggcggaactaagctggaaatcaag |
| CAR9 - Soluble scFv - nt | 87 | atggccctccctgtcaccgccctgctgcttccgctggctcttctgctccacgccgctcggcccg<br>agatccagctccaacagagcggagccgaactggtcaaaccgggagcgtcggtgaagttgtc<br>atgcactggatcgggcttcaacatcgaggattactacatccactgggtcaagcaacgcaccga<br>gcaggggctggaatggatcggacggatcgaccccgaaaacgatgaaaccaagtacgggcc<br>tatcttccaaggacgggccaccattacggctgacacgtcaagcaataccgtctacctccagctt<br>tccagcctgacctccgaggacactgccgtgtactactgcgccttcagaggaggcgtgtactgg<br>ggaccaggaaccactttgaccgtgtccagcggaggcggtggatcaggaggaggaggctca<br>ggcggtggcggctcgcacatggacgtggtcatgactcagtccccgctgaccctgtcggtggc<br>aattggacagagcgcatccatctcgtgcaagagctcacagtcgctgctggattccgacggaaa<br>gacttatctgaactggctgctccaaagaccagggcaatcaccgaaacgccttatctccctggtg<br>tcgaaactcgactcgggtgtgccggatcggtttaccggtagcgggtccggcacggacttcact<br>ctccgcatttcgagggtggaagcggaggatctcgggatctactactgttggcagggaaccca<br>cttccctgggacttttggaggcggaactaagctggaaatcaagggtagccatcaccatcacca<br>ccaccatcat |
| CAR9 - Soluble scFv - aa | 88 | malpvtalllplalllhaarpeiqlqqsgaelvkpgasvklsctgsgfniedyyihwvkqrte<br>qglewigridpendetkygpifqgratitadtssntvylqlssltsedtavyycafrggvywg<br>pgttltvssggggsggggsggggshmdvvmtqspltlsvaigqsasisckssqslldsdgkt<br>ylnwllqrpgqspkrlislvskldsgvpdrftgsgsgtdftlrisrveaedlgiyycwqgthfp<br>gtfgggtkleikgshhhhhhhh |
| CAR 9 - Full - nt | 89 | atggccctccctgtcaccgccctgctgcttccgctggctcttctgctccacgccgctcggcccg<br>agatccagctccaacagagcggagccgaactggtcaaaccgggagcgtcggtgaagttgtc<br>atgcactggatcgggcttcaacatcgaggattactacatccactgggtcaagcaacgcaccga<br>gcaggggctggaatggatcggacggatcgaccccgaaaacgatgaaaccaagtacgggcc<br>tatcttccaaggacgggccaccattacggctgacacgtcaagcaataccgtctacctccagctt<br>tccagcctgacctccgaggacactgccgtgtactactgcgccttcagaggaggcgtgtactgg<br>ggaccaggaaccactttgaccgtgtccagcggaggcggtggatcaggaggaggaggctca<br>ggcggtggcggctcgcacatggacgtggtcatgactcagtccccgctgaccctgtcggtggc<br>aattggacagagcgcatccatctcgtgcaagagctcacagtcgctgctggattccgacggaaa<br>gacttatctgaactggctgctccaaagaccagggcaatcaccgaaacgccttatctccctggtg<br>tcgaaactcgactcgggtgtgccggatcggtttaccggtagcgggtccggcacggacttcact<br>ctccgcatttcgagggtggaagcggaggatctcgggatctactactgttggcagggaaccca<br>cttccctgggacttttggaggcggaactaagctggaaatcaagaccactaccccagcaccga<br>ggccacccaccccggctcctaccatcgcctcccagcctctgtccctgcgtccggaggcatgta<br>gacccgcagctggtggggccgtgcatacccggggtcttgacttcgcctgcgatatctacatttg<br>ggcccctctggctggtacttgcggggtcctgctgctttcactcgtgatcactctttactgtaagcg<br>cggtcggaagaagctgctgtacatctttaagcaacccttcatgaggcctgtgcagactactcaa<br>gaggaggacggctgttcatgccggttcccagaggaggaggaaggcggctgcgaactgcgc<br>gtgaaattcagccgcagcgcagatgctccagcctacaagcaggggcagaaccagctctaca<br>acgaactcaatcttggtcggagagaggagtacgacgtgctggacaagcggagaggacggg<br>acccagaaatgggcgggaagccgcgcagaaagaatccccaagagggcctgtacaacgag<br>ctccaaaaggataagatggcagaagcctatagcgagattggtatgaaaggggaacgcagaa<br>gaggcaaaggccacgacggactgtaccagggactcagcaccgccaccaaggacacctatg<br>acgctcttcacatgcaggccctgccgcctcgg |
| CAR 9- Full-aa | 90 | malpvtalllplalllhaarpeiqlqqsgaelvkpgasvklsctgsgfnie**dyyih**wvkqrte<br>qglewig**ridpendetkygpifqg**ratitadtssntvylqlssltsedtavyyca**frggvy**w<br>gpgttltvssggggsggggsggggshmdvvmtqspltlsvaigqsasisc**kssqslldsdg**<br>**ktyln**wllqrpgqspkrlis**lvsklds**gvpdrftgsgsgtdftlrisrveaedlgiyyc**wqgt**<br>**hfpgt**fgggtklei0tlyckrgrkkllyifkqpfmrpvqttqeedgcscrfpeeeeggcelrv<br>kfsrsadapaykqgqnqlynelnlgrreeydvldkrrgrdpemggkprrknpqeglynel<br>qkdkmaeayseigmkgerrrgkghdglyqglstatkdtydalhmqalppr |
| CAR10 Anti-EGFRvIII clone 139 | | |
| CAR10 scFv domain | 91 | diqmtqspsslsasvgdrvtitcrasqgirnnlawyqqkpgkapkrliyaasnlqsgvpsrft<br>gsgsgteftlivsslqpedfatyyclqhhsypltsgggtkveikrtgstsgsgkpgsgegsev<br>qvlesggglvqpggslrlscaasgftfssyamswvrqapgkglewvsaisgsggstnyads<br>vkgrftisrdnskntlylqmnslraedtavyycagssgwseywgqgtlvtvss |
| CAR9 scFv domain nt | 92 | gatatccaaatgactcagagcccttcatccctgagcgccagcgtcggagacagggtgaccat<br>cacgtgccgggcatcccaaggcattagaaataacttggcgtggtatcagcaaaaaccaggaa<br>aggccccgaagcgcctgatctacgcggcctccaaccttcagtcaggagtgccctcgcgcttc<br>accgggagcggtagcggaactgagtttacccttatcgtgtcgtccctgcagccagaggacttc<br>gcgacctactactgcctccagcatcactcgtacccgttgacttcgggaggcggaaccaaggtc<br>gaaatcaaacgcactggctcgacgtcagggtccggtaaaccgggatcgggagaaggatcg<br>gaagtccaagtgctggagagcggaggcggactcgtgcaacctggcgggtcgctgcggctc<br>agctgtgccgcgtcgggttttactttcagctcgtacgctatgtcatgggtgcggcaggctccgg |

TABLE 2-continued

Humanized EGFRvIII CAR Constructs

| Name | SEQ ID NO: | Sequence |
|---|---|---|
| | | gaaaggggctggaatgggtgtccgctatttccggctcgggtggaagcaccaattacgccgac<br>tccgtgaagggacgcttcaccatctcacgggataactccaagaatactctgtacctccagatga<br>actcgctgagagccgaggacaccgcagtgtactactgcgcagggtcaagcggctggtccga<br>atactggggacagggcaccctcgtcactgtcagctcc |
| CAR10 - Soluble scFv - nt | 93 | atggccctccctgtcaccgccctgctgcttccgctggctcttctgctccacgccgctcggcccg<br>atatccaaatgactcagagcccttcatccctgagcgccagcgtcggagacagggtgaccatc<br>acgtgccgggcatcccaaggcattagaaataacttggcgtggtatcagcaaaaaccaggaaa<br>ggccccgaagcgcctgatctacgcggcctccaaccttcagtcaggagtgccctcgcgcttca<br>ccgggagcggtagcggaactgagtttacccttatcgtgtcgtccctgcagccagaggacttcg<br>cgacctactactgcctccagcatcactcgtacccgttgacttcgggaggcggaaccaaggtcg<br>aaatcaaacgcactggctcgacgtcagggtccggtaaaccgggatcgggagaaggatcgga<br>agtccaagtgctggagagcggaggcggactcgtgcaacctggcgggtcgctgcggctcag<br>ctgtgccgcgtcgggttttactttcagctcgtacgctatgtcatgggtgcggcaggctccggga<br>aaggggctggaatgggtgtccgctatttccggctcgggtggaagcaccaattacgccgactc<br>cgtgaagggacgcttcaccatctcacgggataactccaagaatactctgtacctccagatgaa<br>ctcgctgagagccgaggacaccgcagtgtactactgcgcagggtcaagcggctggtccgaa<br>tactggggacagggcaccctcgtcactgtcagctcccatcaccatcaccaccaccatcac |
| CAR10 - Soluble scFv-aa | 94 | malpvtalllplalllhaarpdiqmtqspsslsasvgdrvtitcrasqgirnnlawyqqkpgk<br>apkrliyaasnlqsgvpsrftgsgsgteftlivsslqpedfatyyclqhhsypltsgggtkveik<br>rtgstsgsgkpgsgegsevqvlesggglvqpggslrlscaasgftfssyamswvrqapgkg<br>lewvsaisgsggstnyadsvkgrftisrdnskntlylqmnslraedtavyycagssgwsey<br>wgqgtlvtvsshhhhhhhh |
| CAR 10 Full - nt | 95 | atggccctccctgtcaccgccctgctgcttccgctggctcttctgctccacgccgctcggcccg<br>atatccaaatgactcagagcccttcatccctgagcgccagcgtcggagacagggtgaccatc<br>acgtgccgggcatcccaaggcattagaaataacttggcgtggtatcagcaaaaaccaggaaa<br>ggccccgaagcgcctgatctacgcggcctccaaccttcagtcaggagtgccctcgcgcttca<br>ccgggagcggtagcggaactgagtttacccttatcgtgtcgtccctgcagccagaggacttcg<br>cgacctactactgcctccagcatcactcgtacccgttgacttcgggaggcggaaccaaggtcg<br>aaatcaaacgcactggctcgacgtcagggtccggtaaaccgggatcgggagaaggatcgga<br>agtccaagtgctggagagcggaggcggactcgtgcaacctggcgggtcgctgcggctcag<br>ctgtgccgcgtcgggttttactttcagctcgtacgctatgtcatgggtgcggcaggctccggga<br>aaggggctggaatgggtgtccgctatttccggctcgggtggaagcaccaattacgccgactc<br>cgtgaagggacgcttcaccatctcacgggataactccaagaatactctgtacctccagatgaa<br>ctcgctgagagccgaggacaccgcagtgtactactgcgcagggtcaagcggctggtccgaa<br>tactggggacagggcaccctcgtcactgtcagctccaccactaccccagcaccgaggccac<br>ccaccccggctcctaccatcgcctcccagcctctgtccctgcgtccggaggcatgtagacccg<br>cagctggtggggccgtgcatacccggggtcttgacttcgcctgcgatatctacatttgggcccc<br>tctggctggtacttgcggggtcctgctgctttcactcgtgatcactctttactgtaagcgcggtcg<br>gaagaagctgctgtacatctttaagcaacccttcatgaggcctgtgcagactactcaagagga<br>ggacggctgttcatgccggttcccagaggaggaggaaggcggctgcgaactgcgcgtgaa<br>attcagccgcagcgcagatgctccagcctacaagcaggggcagaaccagctctacaacgaa<br>ctcaatcttggtcggagagaggagtacgacgtgctggacaagcggagaggacgggaccca<br>gaaatgggcgggaagccgcgcagaaagaatccccaagagggcctgtacaacgagctccaa<br>aaggataagatggcagaagcctatagcgagattggtatgaaaggggaacgcagaagaggc<br>aaaggccacgacggactgtaccagggactcagcaccgccaccaaggacacctatgacgctc<br>ttcacatgcaggccctgccgcctcgg |
| CAR 10 Full - aa | 96 | malpvtalllplalllhaarpdiqmtqspsslsasvgdrvtitcrasqgirnnlawyqqkpgk<br>apkrliyaasnlqsgvpsrftgsgsgteftlivsslqpedfatyyclqhhsypltsgggtkveik<br>rtgstsgsgkpgsgegsevqvlesggglvqpggslrlscaasgftfssyamswvrqapgkg<br>lewvsaisgsggstnyadsvkgrftisrdnskntlylqmnslraedtavyycagssgwsey<br>wgqgtlvtvsstttpaprpptpaptiasqplslrpeacrpaaggavhtrgldfacdiyiwapla<br>gtcgvlllslvitlyckrgrkkllyifkqpfmrpvqttqeedgcscrfpeeeeggcelrvkfsrs<br>adapaykqgqnqlynelnlgrreeydvldkrrgrdpemggkprrknpqeglynelqkdk<br>maeayseigmkgerrrgkghdglyqglstatkdtydalhmqalppr |

The CAR scFv fragments were then cloned into lentiviral vectors to create a full length CAR construct in a single coding frame, and using the EF1 alpha promoter for expression (SEP ID NO: 97).

EF1 alpha promoter (SEQ ID NO: 97)

GTGAGGCTCCGGTGCCCGTCAGTGGGCAGAGCGCACATCGCCCACAGTCC

CCGAGAAGTTGGGGGGAGGGGTCGGCAATTGAACCGGTGCCTAGAGAAGG

-continued

TGGCGCGGGGTAAACTGGGAAAGTGATGTCGTGTACTGGCTCCGCCTTTT

TCCCGAGGGTGGGGGAGAACCGTATATAAGTGCAGTAGTCGCCGTGAACG

TTCTTTTTCGCAACGGGTTTGCCGCCAGAACACAGGTAAGTGCCGTGTGT

GGTTCCCGCGGGCCTGGCCTCTTTACGGGTTATGGCCCTTGCGTGCCTTG

AATTACTTCCACCTGGCTGCAGTACGTGATTCTTGATCCCGAGCTTCGGG

-continued

```
TTGGAAGTGGGTGGGAGAGTTCGAGGCCTTGCGCTTAAGGAGCCCCTTCG

CCTCGTGCTTGAGTTGAGGCCTGGCCTGGGCGCTGGGGCCGCCGCGTGCG

AATCTGGTGGCACCTTCGCGCCTGTCTCGCTGCTTTCGATAAGTCTCTAG

CCATTTAAAATTTTTGATGACCTGCTGCGACGCTTTTTTTCTGGCAAGAT

AGTCTTGTAAATGCGGGCCAAGATCTGCACACTGGTATTTCGGTTTTTGG

GGCCGCGGGCGGCGACGGGGCCCGTGCGTCCCAGCGCACATGTTCGGCGA

GGCGGGGCCTGCGAGCGCGGCCACCGAGAATCGGACGGGGGTAGTCTCAA

GCTGGCCGGCCTGCTCTGGTGCCTGGCCTCGCGCCGCCGTGTATCGCCCC

GCCCTGGGCGGCAAGGCTGGCCCGGTCGGCACCAGTTGCGTGAGCGGAAA

GATGGCCGCTTCCCGGCCCTGCTGCAGGGAGCTCAAAATGGAGGACGCGG

CGCTCGGGAGAGCGGGCGGGTGAGTCACCCACACAAAGGAAAAGGGCCTT

TCCGTCCTCAGCCGTCGCTTCATGTGACTCCACGGAGTACCGGGCGCCGT

CCAGGCACCTCGATTAGTTCTCGAGCTTTTGGAGTACGTCGTCTTTAGGT

TGGGGGGAGGGGTTTTATGCGATGGAGTTTCCCCACACTGAGTGGGTGGA

GACTGAAGTTAGGCCAGCTTGGCACTTGATGTAATTCTCCTTGGAATTTG

CCCTTTTTGAGTTTGGATCTTGGTTCATTCTCAAGCCTCAGACAGTGGTT

CAAAGTTTTTTTCTTCCATTTCAGGTGTCGTGA.
```

Surface Expression of CAR9, CAR10 and Select Humanized EGFRvIII CAR Constructs and Staining by FACS The following experiments showed that there appears to be an affinity difference for EGFRvIII based in vitro binding studies in both Jurkat cells and primary T cells.

Jurkat E6 cells were electroporated with either CAR9 vector or CAR10 vector using Amaxa Cell Line Nucleofector Kit V (Lonza, Colgne AG, Germany) and program X-001. One day after the transfection, $0.5\times10^6$ cells were placed into each well of a V-shape 96 well plate (Greiner Bio-One, Germany) in 0.2 ml FACS buffer (DPBS buffer containing 5% FBS) and incubated for 10 minutes at room temperature. Cells were then spun down and resuspended in 0.2 ml of the FACS buffer with different concentrations of EGFRvIII-Fc or EGFRwt-Fc and incubated at 4° C. for 30 minutes. Cells were then washed with FACS buffer three times, and incubated with 0.2 ml of the FACS buffer with 2 μl of PE anti-human IgG Fc (Jackson ImmunoResearch Laboratories, West Grove, Pa.) for 30 minutes at 4° C. in the dark. After washing with 0.2 ml of FACS buffer three times, cells were analyzed on a LSRII (BD Biosciences, San Jose, Calif.) machine using the FACSDiva software (BD Biosciences, San Jose, Calif.). Immunofluorescence staining was analyzed as the relative log fluorescence of live cells, and the percentage of the PE positive cells were measured.

Figure 12A:
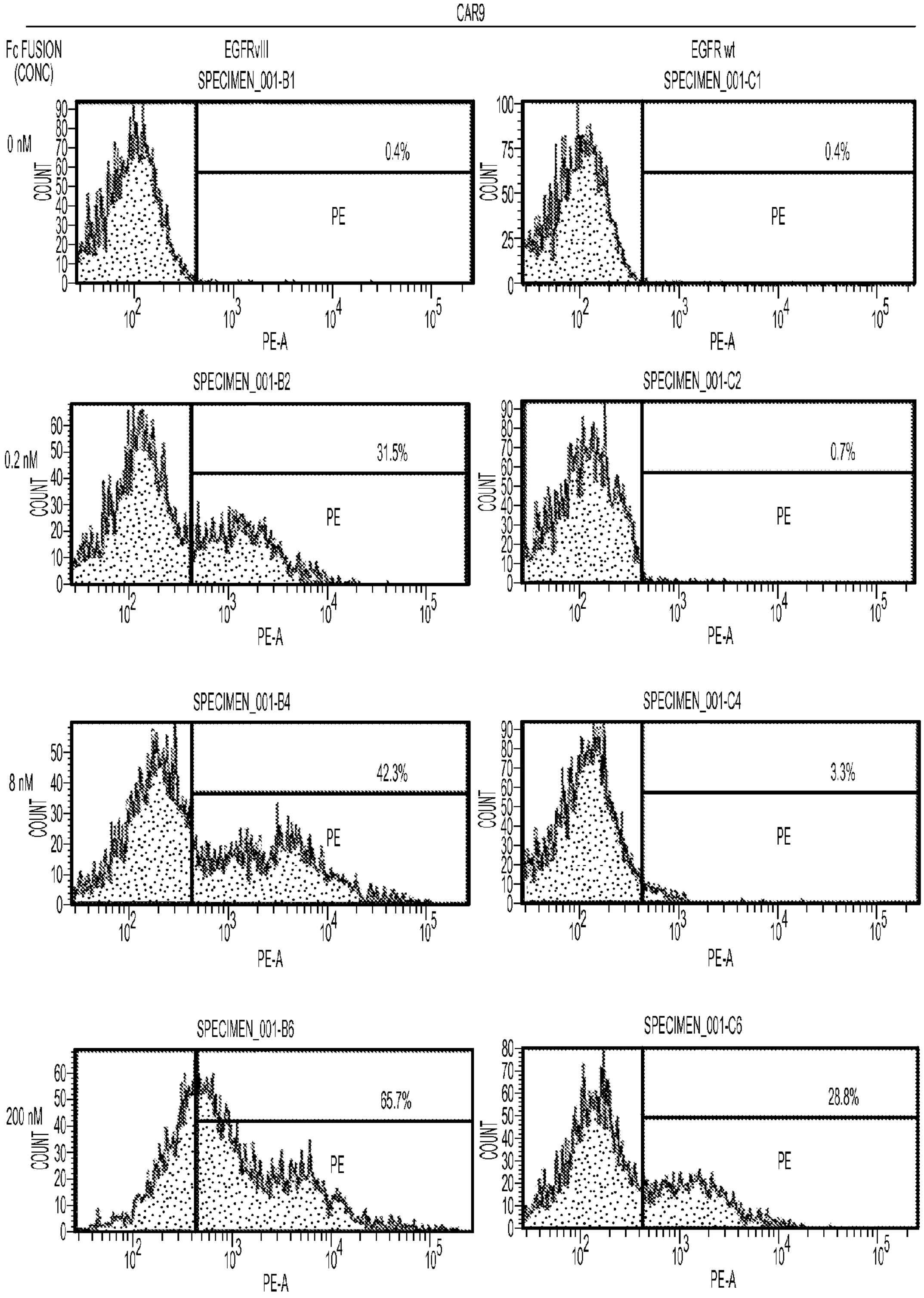
FIGS. 12A and 12B are graphs comparing the specificity of murine CAR9 and human CAR10 for EGFRvIII and wild type EGFR in transient transfection of Jurkat cells and detection with Fc fusion proteins.
Figure 12B:
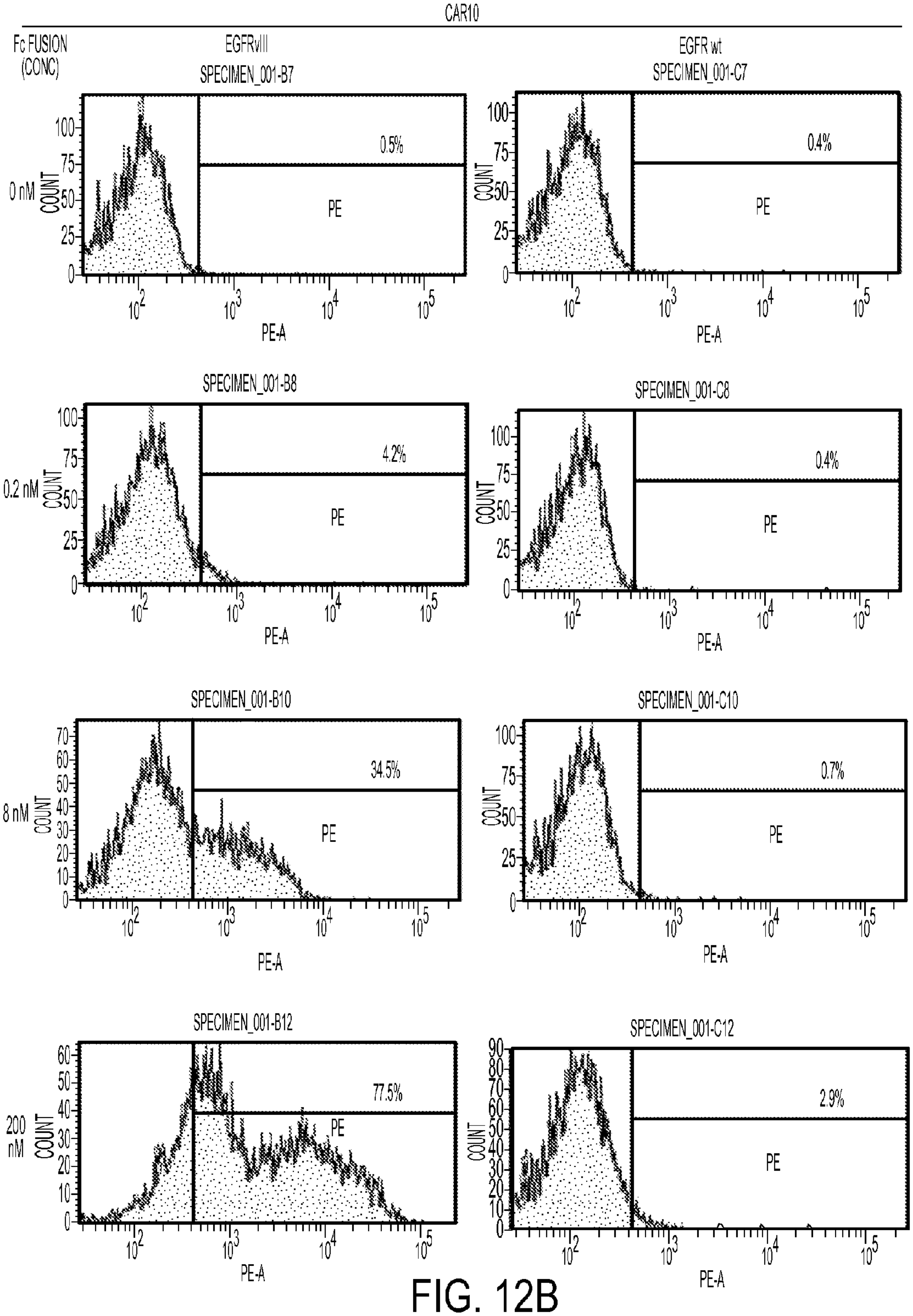

As shown in FIGS. 12A and 12B, binding of the CAR9 expressed in Jurkat cells to EGFRvIII-Fc fusion protein is approximately 1000 fold stronger than to wild type EGFR-Fc. Furthermore, the CART construct expressing CAR10 exhibits a significantly lower (~40 fold) binding to EGFRvIII compared to CAR9. This suggests that although murine CAR9 binds to EGFRvIII, it still retains some binding to wild type EGFR. Moreover, it strongly indicates that CAR9 has a higher binding affinity for EGFRvIII than the CAR10 construct.

Further experiments in primary T cells yielded similar results. Briefly, primary human CD3+ T cells were stimulated with anti-CD3/CD28 beads for 24 hrs and then transduced with lentiviral vectors encoding either CAR9, CAR10, CAR6 or a control CAR at a MOI of 3:1. Included in the experiment was also a mock transduced T cell population. These cells were expanded for about 8-9 days in culture until they started to rest down. At this point, 0.5×106 cells were placed into each well of a V-shape 96 well plate. The cells were washed one time with PBS and stained with Live/Dead reagent (1:1000 in PBS) for 30 min on ice. Cells were then washed twice with FACS buffer and incubated with 1 μg/ml biotinylated EGFRvIII or EGFR wt protein for 30 min on ice. Cells were then washed two times and incubated with 0.2 ml of FACS buffer with 1:1000 dilution of streptavidin-PE for 15 min on ice. After washing twice with FACS buffer, cells were analyzed on a LSRII. Immunofluorescence staining was analyzed as the relative log fluorescence of live cells and the percentage of the PE positive cells were measured in conjunction with the geometric mean of the positive population.

Figure 13:
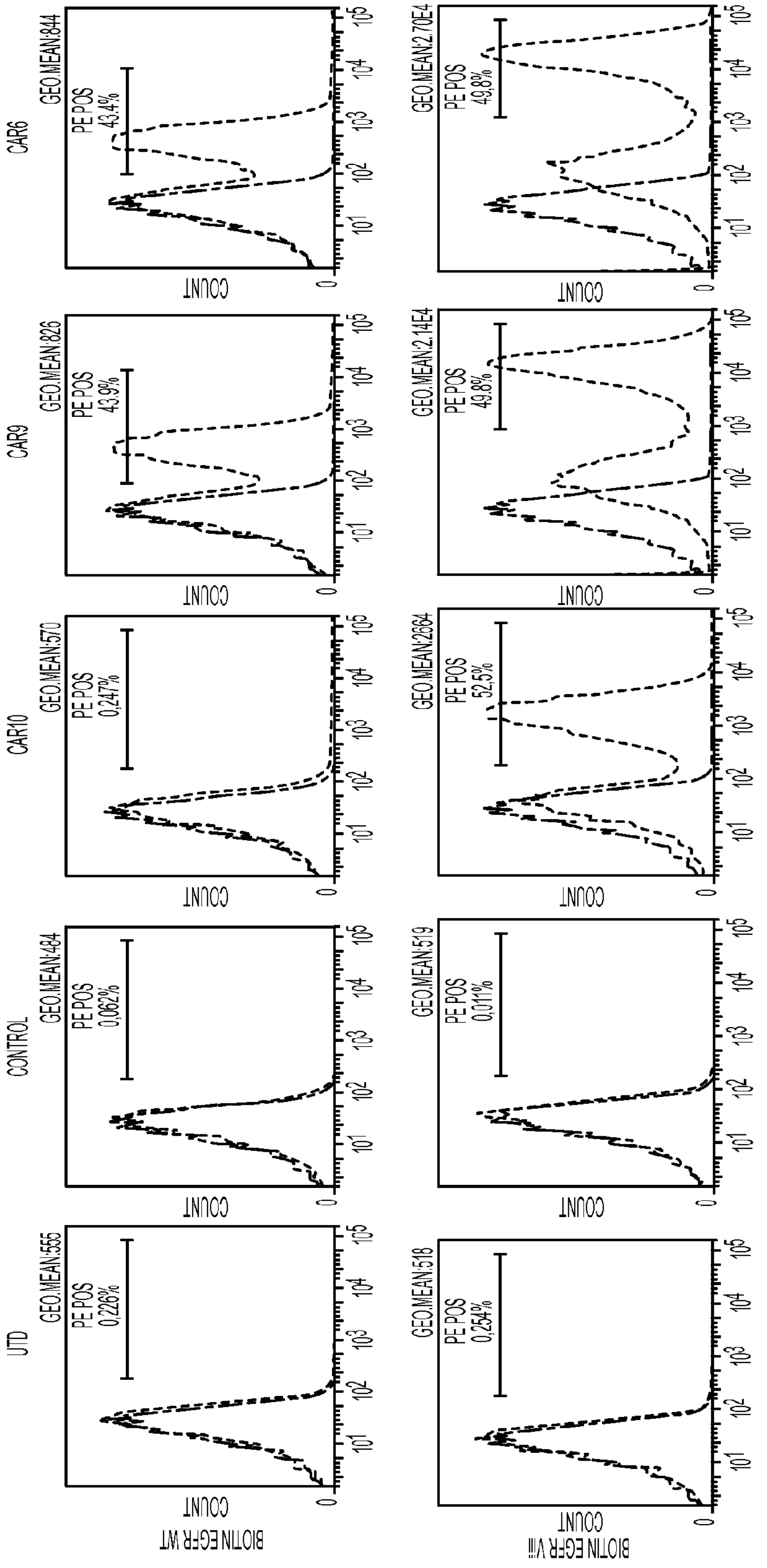
FIG. 13 is a graph showing primary T cell transduction of donor T cells with the humanized EGFRvIII CAR constructs mCAR19 (control), CAR10, CAR9, and CAR6, stained with saturating amounts of EGFRvIII.

As shown in FIG. 13, the CAR9 and CAR6 CARs show a 10-fold higher geometric mean (21K for CAR9, 27K for CAR6) for EGFRvIII binding than the CAR10 (only 2K) when saturating amounts of EGFRvIII protein are used for detection, even though all constructs transduce equivalently (~50% transduction efficiency for all). Similarly, the specificity for EGFR wt protein is about 10-fold lower, as depicted by the log shift downwards for the staining with EGFR wt protein. This provides additional support to the findings in the Jurkat cells above that indicate CAR9 and CAR6 have a stronger affinity for EGFRvIII protein compared to CAR10 when expressed in primary T cells and suggest they will be more efficacious in the clinic.

Functional analysis of the panel of humanized CAR constructs was conducted as described in Example 8.

Example 8

Analysis of Humanized EGFRvIII-Specific CAR Constructs in T Cells

To evaluate the feasibility of targeting EGFRvIII via a CAR technology, the humanized EGFRvIII scFv fragments were cloned into a lentiviral CAR expression vector with the CD3zeta chain and the 4-1BB costimulatory molecule in two different configurations. The optimal construct is selected based on the quantity and quality of the effector T cell response of EGFRvIII CAR transduced T cells in response to EGFRvIII+ and EGFR wt targets. Effector T cell responses include, but are not limited to, cellular expansion, proliferation, doubling, cytokine production and target cell killing or cytolytic activity (degranulation).

Materials and Methods

Generation of Jurkat Reporter Cell Line for Initial Characterization of CAR Function As an alternative to primary T cell transduction and activation, a Jurkat-NFAT reporter cell line can be used to evaluate the functional activity of CAR constructs. The Jurkat T cell line (E6-1) was transfected with a NFAT-luciferase reporter construct and a stable, clonal cell line (JNL) was selected for further characterization based on strong induction of the NFAT reporter following PMA and ionomycin stimulation. The JNL cells are transduced with lentiviral vectors at a MOI of 5:1 and then expanded for 5-7 days. Before using in an assay, the percentage of cells transduced (expressing the EGFRvIII CAR on the cell surface) and their relative fluorescence intensity of that expression are determined by flow cytometric analysis on an LSRII. From the histogram plots, the relative expression levels of the CARs can be examined by comparing percentage transduced with their relative fluorescent intensity.

Evaluating T Cell Activation of Humanized EGFRvIII-Specific CAR JNL Cells

To evaluate T cell activation in the JNL reporter cell line, JNL or CAR-transduced JNL cells are plated at 50,000 cells per well in a 96 well black plate with a clear bottom. Target cells (BHK parental cells or BHK cells engineered to express either EGFRvIIII or EGFR wt) are added to the wells to create effector to target (E:T) ratios of 1:2, 1:1, 1:0.3, 1:0.1, 1:0.03, 1:01, and 1:0.003. PMA and ionomycin are used as a positive control for activation. Cells are incubated at 37 C for 16-24 hrs. At the end of the incubation, an equal volume of Bright-Glo Luciferase assay reagent is added to each well. The plate is incubated at room temperature for 10 minutes and then luminescence is measured using a luminometer.

Generation of Redirected Humanized EGFRvIII-Specific CAR T Cells

The humanized EGFRvIII-specific CAR lentiviral transfer vectors are used to produce the genomic material packaged into the VSVg psuedotyped lentiviral particles. Lentiviral transfer vector DNA is mixed with the three packaging components of VSVg, gag/pol and rev in combination with lipofectamine reagent to transfect them together in to 293T cells. After 24 and 48 hr, the media is collected, filtered and concentrated by ultracentrifugation or chromatography. The resulting viral preparation is stored at −80 C. The number of transducing units is determined by titration on SupT1 cells.

Redirected EGFRvIII-specific CART cells are produced by activating fresh T cells by engaging with CD3×28 beads for 24hrs and then adding the appropriate number of transducing units to obtain the desired percentage of transduced T cells. These modified T cells are allowed to expand until they become rested and come down in size (~300 fl) at which point they are cryopreserved for later analysis. The cell numbers and sizes are measured using a Coulter multisizer III. Before cryopreserving, percentage of cells transduced (expressing the EGFRvIII-specific CAR on the cell surface) and their relative fluorescence intensity of that expression are determined by flow cytometric analysis on an LSRII. From the histogram plots, the relative expression levels of the CARs can be examined by comparing percentage transduced with their relative fluorescent intensity.

Evaluating Cytolytic Activity, Proliferation Capabilities and Cytokine Secretion of Humanized EGFRvIII Redirected CAR T Cells.

To evaluate the functional abilities of humanized EGFRvIII-specific CAR T cells to kill, proliferate and secrete cytokines, the cells are thawed and allowed to recover overnight. In addition to the humanized constructs, the murine CAR9 was used for comparative purposes while SS1-BBz was used as non-targeting expressed CAR for background CAR/T cell effect. For this flow based cytotoxicity assay, the target cells are stained with CSFE to quantitate their presence. The target cells were also stained for EGFRvIII expression to confirm similar target antigens levels. The cytolytic activities of EGFRvIII CAR T cells are measured at a titration of effector:target cell ratios of 10:1, 3:1, 1:1, 0.3:1 and 0:1 where effectors were defined as T cells expressing the anti-EGFRvIII CAR. Assays were initiated by mixing an appropriate number of T cells with a constant number of targets cells. After 4 or 16hrs, total volume of each mixture was removed and each well washed. The T cells were stained for CD3 and all cells stained with live/dead marker 7AAD. After the final wash, the pelleted cells were re-suspended in a specific volume with a predetermined number of counting beads. Cell staining data was collected by LSRII flow cytometry and analyzed with FlowJo software using beads to quantitate results.

For measuring cell proliferation and cytokine production of humanized CAR-EGFRvIII T cells, cells were thawed and allowed to recover overnight. In addition to the humanized CAR-EGFRvIII, the murine CARS was used for comparative purposes while SS1-BBz was used as a non-targeting expressed CAR for background CAR/T cell effect. The T cells were directed towards U87, an astrocytoma-derived glioblastoma cell line expressing or not expressing EGFRvIII. In addition, CD3×28 beads were used to evaluate the potential of T cells to respond to the second round of endogenous immunological signals. To analyze proliferation, T cells were stained with CSFE. The proliferation was the dilution of the CSFE stain reflecting the separation of the parental markings now into two daughter cells. The assay tested only an effector:target ratios of 1:1 and 1:0 where effectors were defined as total T cells (CD4 and 8) normalized to express the anti-EGFRvIII chimeric receptor at a common percentage. The assay was done in duplicate and 24 hrs after mixing of the cells. Supernatant was removed for cytokine production. After 5 days, T cells were stained for live/dead with Live/Dead Violet (Invitrogen), then stained for CAR expression and phenotyped as either CD4 or CD8 cells. After the final wash, the pelleted cells were re-suspended in a specific volume with a predetermined number of BD counting beads. Cell staining data was collected by LSRII flow cytometry and analyzed with FlowJo software using beads to quantitate results. Total cell counts were determined by number of cells counted relative to a specific number of beads multiplied by the fraction of beads yet to be counted.

Results

Jurkat Reporter Assay to Test the Ability of the Humanized CART-EGFRvIII Cells to Recognize EGFRvIII Target Cells.

Figure 14:
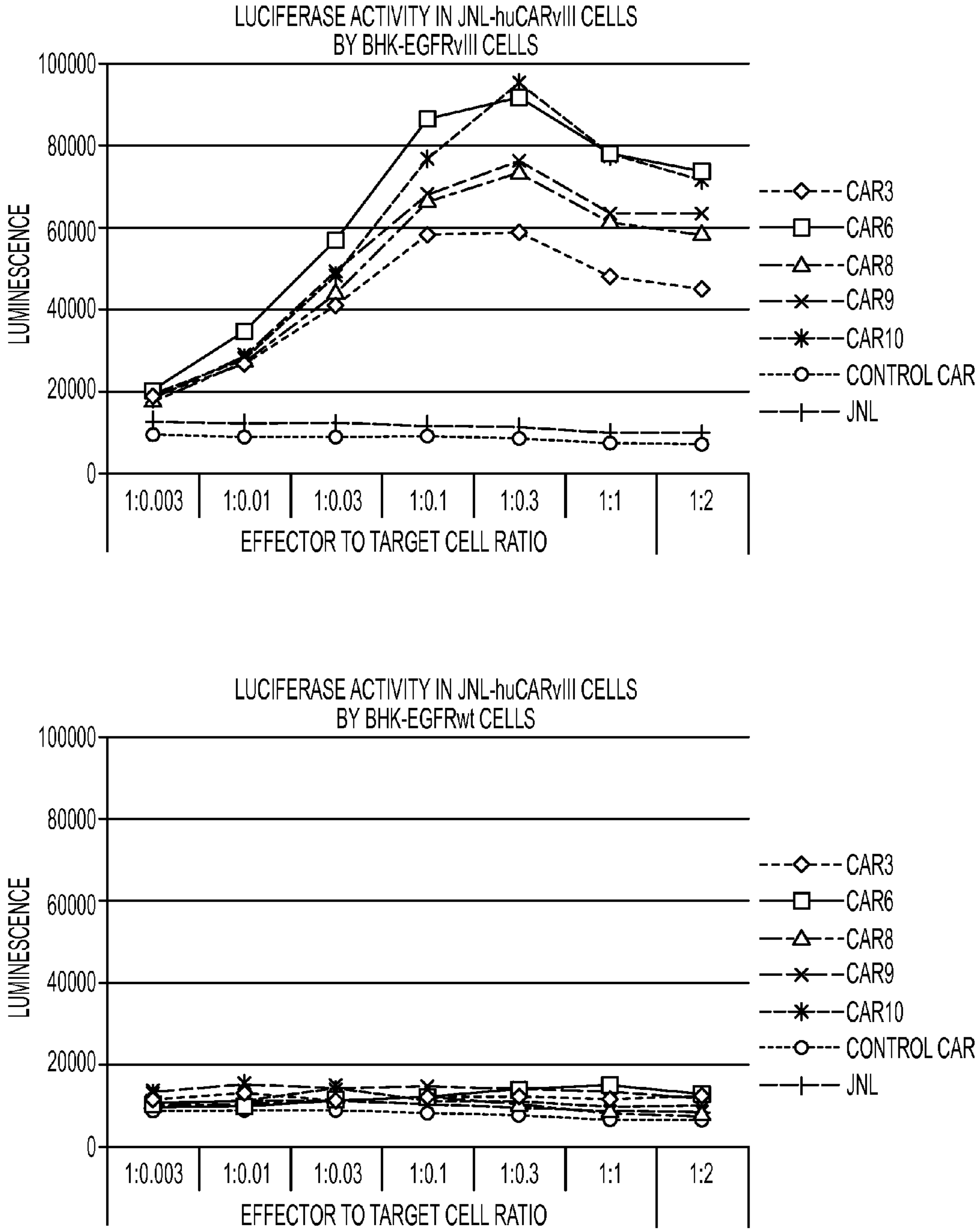
FIG. 14 is a graph showing the luciferase activity of humanized EGFRvIII CAR constructs by BHK-EGFRvIII but not wild type cells.

The ability of CART constructs to induce activation following target engagement was measured with the JNL reporter cell line. The JNL cell line is engineered with a NFAT-Luciferase reporter construct which is induced following target engagement of the CAR. JNL cells were transduced with the various CAR-EGFRvIII constructs (CAR9, CAR3, CAR6, CAR8 and CAR10). Transduction efficiency was assessed by flow cytometry and was shown to be about 45-52% for all the constructs. The JNL-CAR-EGFRvIII cells were then stimulated with seven different E:T ratios using three different target cells (BHK parental, BHK-EGFRvIII or BHK-EGFR wt). JNL parental cells and JNL cells expressing a control CAR were included as additional controls. The results in FIG. 14 show significant target induced activation can occur at ratios as low as 1:0.01 for all constructs tested and CAR6 and CAR10 induce the most activation at the higher E:T ratios. No significant activation was observed with the EGFR wt expressing cells or by the control CAR expressing JNL cells. These data demonstrate specificity of the CAR constructs for EGFRvIII target and lack of cross-reactivity to EGFR wt target.

Transduction and Expansion of Primary Human T Cells with the Humanized EGFRvIII CAR Constructs CD3+ T cells were obtained from apheresis products or whole blood from healthy donors. As described above, T cells were stimulated with CD3×CD28 beads for 24 hrs and then transduced with concentrated lentiviral supernatants at a MOI of 3. Cells were expanded in culture for 8-10 days.

Cell surface expressions of humanized EGFRvIII CARs are comparable and their expression level very similar to murine CAR9. The overlay of histograms plotting the cell surface expression staining pattern of each humanized EGFRvIII-specific CAR transduced T cells and the mean fluorescent intensity (MFI) calculated from these profiles correlates well with the percentage of cells transduced.

Figure 15:
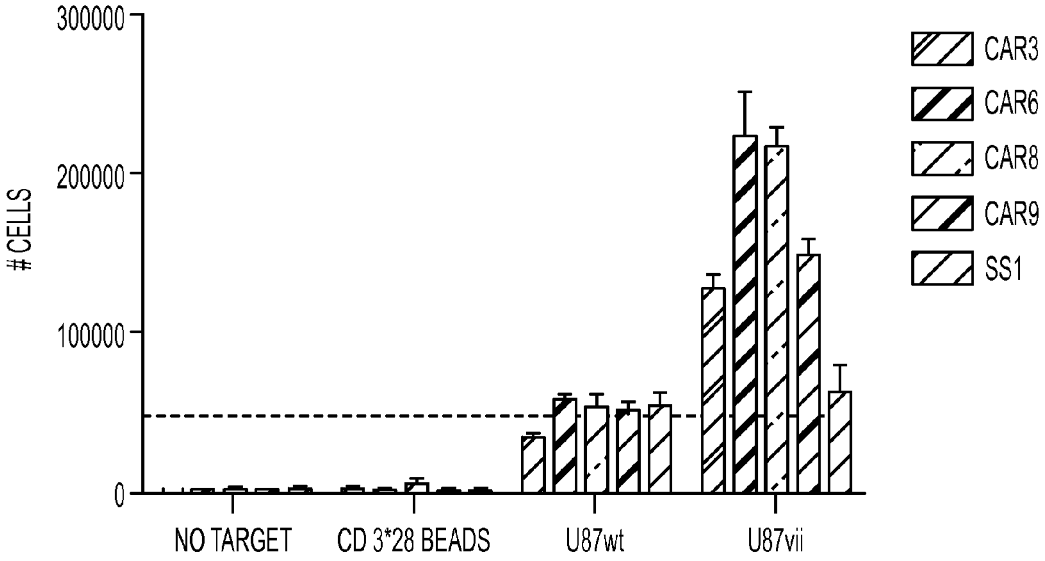
FIG. 15 is a graph showing that the humanized EGFRvIII CAR constructs proliferate in response to U87vIII challenge with no background proliferation to wild type EGFR.

Proliferation Assay to Test the Ability of EGFRvIII Target Cells to Stimulate Humanized EGFRvIII CART Cells The ability of EGFRvIII specific CAR T cells to proliferate in response to target engagement was evaluated in a proliferation assay. Subpopulations were enumerated by flow cytometry. Donor T cells were transduced with either humanized CARs, murine CAR9 or SS1 (mesothelin targeting). CARs were mixed 1:1 or 1:0 with target cells and cocultured for 5 days. FIG. 15 shows the ability of ND407 EGFRvIII CAR T cells to proliferate in an antigen specific manner. The dash bar indicates the number of T cells seeded and comparatively, no increase in T cell numbers were detected targeting U87 while engagement with U87-EGFRvIII induced proliferation which was specific to EGFRvIII CAR T cell populations. The relative response for ND407 indicated that CAR6 and CAR8 are more robust than CAR9 or CAR3. The result of CD3×28 beads indicates their stimulation was not enough to drive proliferation on a second round of activation, similar to no stimulation at all.

Figure 16:
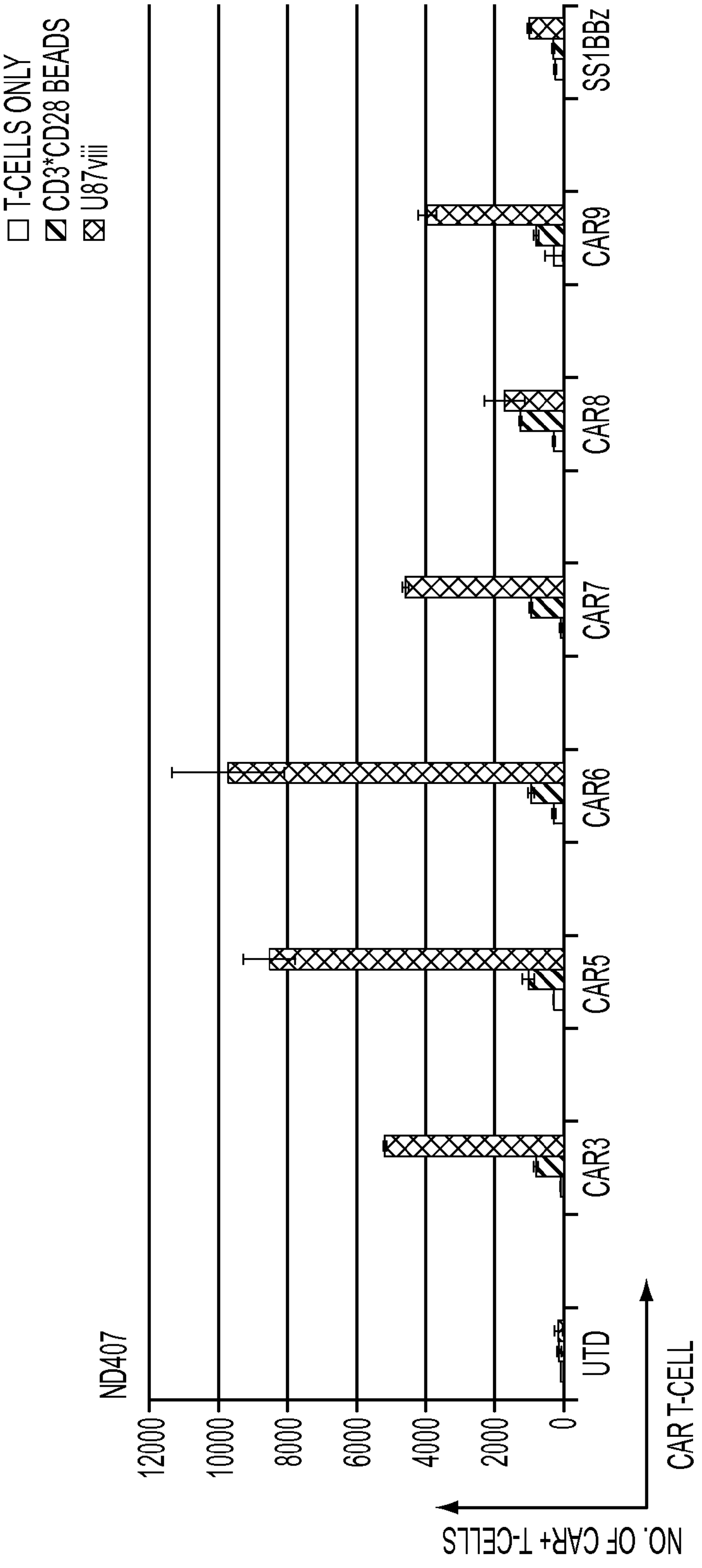
FIG. 16 is a graph showing that the humanized EGFRvIII CAR constructs proliferate in vitro in the presence of U87vIII challenge.

ND407 T cells were used to screen different huEGFRvIII CARs for their ability to preferentially expand CAR+ T cells. FIG. 16 shows CARS and CAR6 consistently having the strongest CAR+ expansion in each donor. CAR+ increase is a result of a successful engagement with target, proliferation and survival of activation induced cell death of antigen recognition.

Killing Assay to Test the Ability of the Humanized EGFRvIII CART Cells to Kill EGFRvIII Target Cells The ability of EGFRvIII specific CAR T cells to kill targets was tested in a Chromium release assay. The human glioblastoma cell line, U-87MG, was engineered to express either EGFR wild type receptor or the EGFRvIII mutant. These engineered cell lines served as the targets for the killing assay. Three effector CAR T cells were used to determine the specificity of killing target cells; 1) human T cells transduced to express murine 3C10 (CAR9), 2) human T cells transduced to express a humanized version of the murine 3C10, referred to as CAR6 and 3) human T cells transduced with a CAR specific for mesothelin, SS1. All effector cells were normalized to express 30% CAR+ transduction. Target cells were labeled with chromium-51 and washed immediately prior to coculture. The effectors and targets were mixed together at the indicated ratios (E:T) and allowed to incubate for 4 hours.

Figure 17:
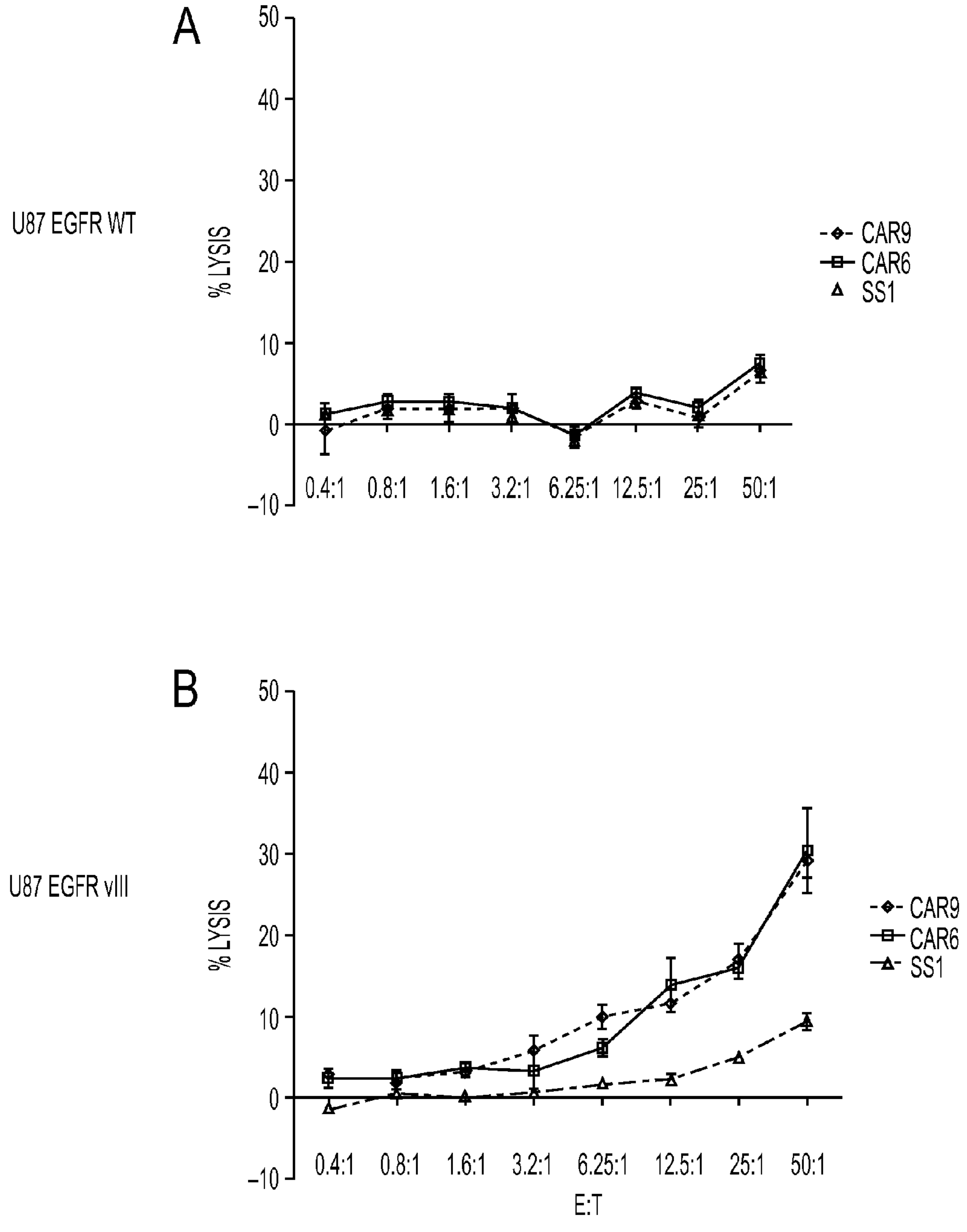
FIG. 17 is a graph showing a 4 hour 51-Chromium release tumor killing assay in which the humanized EGFRvIII CAR construct, 2173 (CAR6) and CAR9 specifically kills EGFRvIII expressing but not wild type EGFR cells.

The results in FIG. 17 (A) shows that CAR T cells mixed with U-87 cells expressing the wild type EGFR receptor showed no cell killing above background up to E:T of 50:1. However, the results in FIG. 17 (B) show that in contrast, EGFRvIII specific CAR T cells, CAR9 or CAR6, mixed with U-87 cells expressing EGFRvIII showed specific killing at E:T ratios of 6.25:1 up to 50:1. No significant killing was observed when the mesothelin specific CAR T cells were used as effectors. These data demonstrate the specific on target killing of target cells expressing EGFRvIII by CAR9 and CAR6 T cells, but no killing of cells expressing wild type EGFR or by a non-specific CAR T cell, SS1.

Cytokine Assay to Test the Ability of the Humanized EGFRvIII CART Cells to Promote an Anti-Tumor Response and Demonstrate Specificity The ability of EGFRvIII specific CAR T cells to induce cytokine in response to target engagement was evaluated in a co-culture assay. CAR T cells were co-cultured with target expressing cells for 18-24 hrs at various target:effector ratios (0.3:1, 1:1, 3:1 and 10:1). Target cells included U87 cells expressing the EGFR wt endogenous protein (U87 wt), U87 cells overexpressing EGFRvIII (U87-vIII), BHK (baby hamster kidney cells) parental cells, BHK cells overexpressing human EGFR wt protein (BHK wt), or BHK cells overexpressing human EGFRvIII protein (BHK-vIII). After 18-24 hrs, supernatants were removed from the cultures and cytokines analyzed using a Cytometric Bead Assay (CBA). The results clearly demonstrated that 1) CAR6 and CAR9 T cells induced similar levels of IFNg in response to EGFRvIII-expressing cells and 2) that neither CAR T cell population induced IFNg in response to EGFR wt expressing cells. Importantly, these data together with the killing and proliferation data indicate CAR6 and CAR9 show functional specificity for EGFRvIII and have the capability to promote an anti-tumor immune response.

Example 9

Humanized Anti-EGFRvIII CART Cells Reduce Tumor Burden in Mice

Humanized anti-EGFRvIII CAR T cells were shown to reduce tumor burden in vivo in mice. For example, #2173 (CAR6) humanized anti-EGFRvIII chimeric antigen receptor (CAR) lentivirally-transduced human T lymphocytes were delivered intravenously in xenogeneic immune-compromised NOD/SCID/common-gamma chain−/− mice treated established U87vIII glioma tumors in vivo. Control mice with 5 day established U87vIII subcutaneous flank tumors receiving donor-matched non-CAR transduced T cells' tumors grew rapidly, both by direct subcutaneous tumor measurement using calipers (max length×max width), and by photon emission measured by Spectrum in vivo imaging system (IVIS). In treated mice receiving even low numbers (0.5-1×$10^6$) of CAR6 transduced cells, tumor growth was markedly reduced in mice in a dose-dependent manner.

Figure 18:
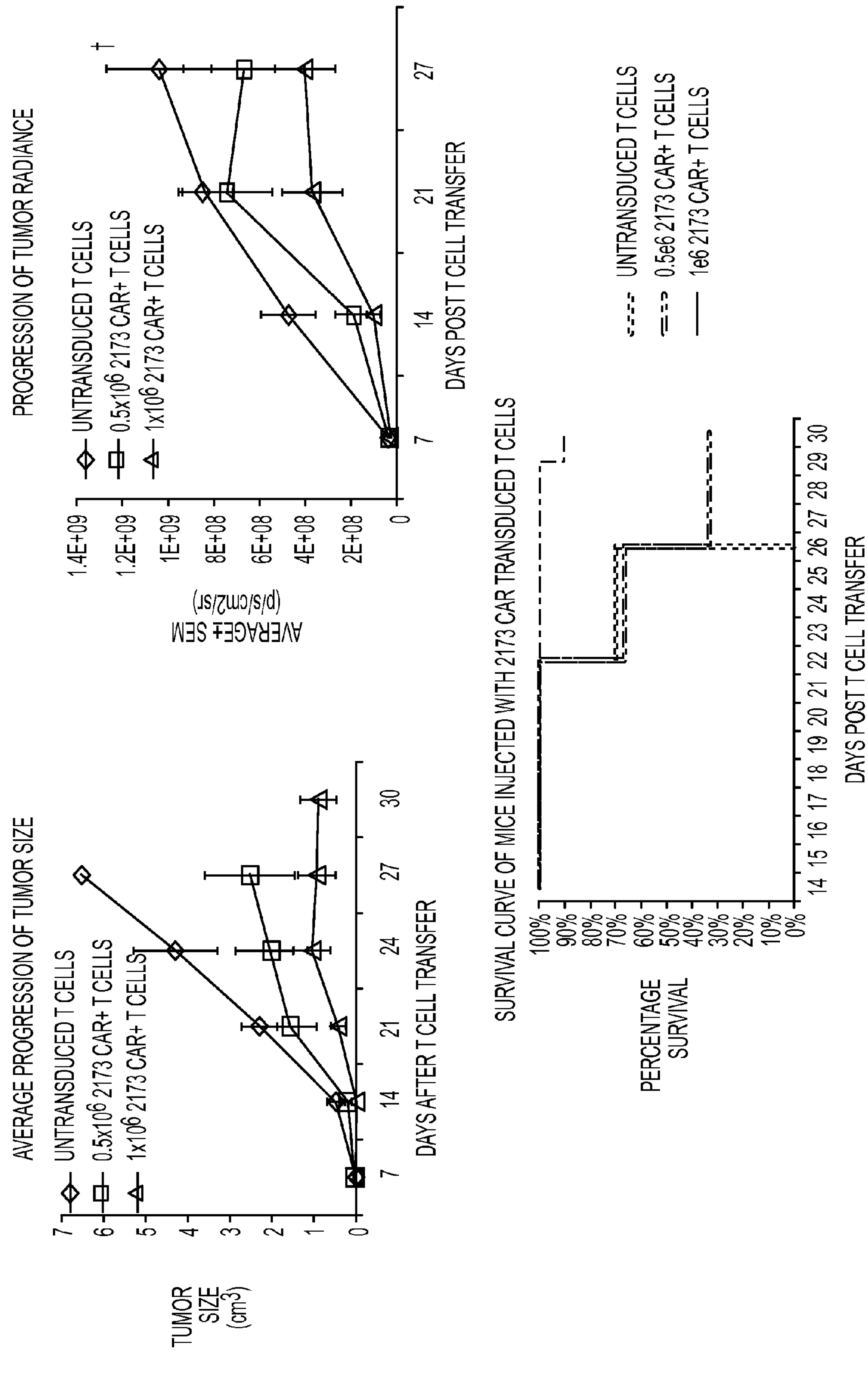
FIG. 18 is a graph showing progression of tumor size ($cm^3$, upper left panel) and progression of tumor radiance average ($p/s/cm^2/sr$, upper right panel), and Kaplan-meier survival curve (lower) in vivo in mice treated with CAR+ T cells transduced with the humanized EGFRvIII CAR contruct (CAR6).

In this example, 1×$10^6$ U87vIII human gliomas expressing EGFRvIII, GFP+Luc+ were washed and injected subcutaneously in 100 μL saline in the flanks of 30 NSG immune-compromised mice (N=10/group). Human T cells were stimulated with anti-CD3/28 coated beads and lentivirally transduced with humanized EGFRvIII CAR scFv #2173 (CAR6). Following transduction, ex vivo expansion and bead removal, CAR transduced T cells (~50% CAR+ by flow cytometry) were washed and injected in 100 μL saline via tail vein 5 days after tumor implantation. Tumor growth was evaluated by caliper measurement (upper left), and luciferin-induced photon emission (upper right). Measurements were started 7 days after T cell transfer and 12 days after tumor injection. SEM is shown in FIG. 18 (N=10 mice/group). Survival of each group is plotted by Kaplan Meier curves in FIG. 18 (lower). All mice receiving control T cells died by day 26, with group receiving 0.5×$10^6$ and 1.0×$10^6$ CAR6 T-cells at 30% and 90% survival, respectively as of experimental day 30.

Equivalents

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. An isolated nucleic acid molecule encoding a chimeric antigen receptor (CAR), wherein said CAR comprises an anti-EGFRvIII binding domain, a transmembrane domain, and an intracellular signaling domain comprising a primary signaling domain, a costimulatory domain, or both a primary signaling domain and a costimulatory domain, wherein the encoded anti-EGFRvIII binding domain comprises an amino acid sequence with greater than 99% sequence identity to SEQ ID NO:68 comprising:

(a) a heavy chain immunoglobulin variable region comprising:

(i) a CDR1 comprising the sequence DYYIH (SEQ ID NO: 22);

(ii) a CDR2 comprising the sequence RIDPENDETKYGPIFQG (SEQ ID NO: 23); and (iii) a CDR3 comprising the sequence RGGVY (SEQ ID NO: 24); and (b) a light chain immunoglobulin variable region comprising:

(i) a CDR1 comprising the sequence KSSQSLLDSDGKTYLN (SEQ ID NO: 26);

(ii) a CDR2 comprising the sequence LVSKLDS (SEQ ID NO: 27); and (iii) a CDR3 comprising the sequence WQGTHFPGT (SEQ ID NO: 28).

2. The isolated nucleic acid molecule of claim 1, wherein the nucleic acid sequence encoding the anti-EGFRvIII binding domain comprises a nucleotide sequence with greater than 99% sequence identity to SEQ ID NO: 69.

3. The isolated nucleic acid molecule of claim 1, wherein the encoded CAR comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

4. The isolated nucleic acid molecule of claim 1, wherein the encoded transmembrane domain comprises the sequence of SEQ ID NO: 15; an amino acid sequence comprises at least one modification but not more than 20 modifications of the amino acid sequence of SEQ ID NO:15; or a sequence with greater than 95% identity to the amino acid sequence of SEQ ID NO:15.

5. The isolated nucleic acid molecule of claim 1, wherein the nucleic acid sequence encoding the transmembrane domain comprises the sequence of SEQ ID NO:8, or a sequence with greater than 95% identity thereof.

6. The isolated nucleic acid molecule of claim 1, wherein the encoded anti-EGFRvIII binding domain is connected to the transmembrane domain by a hinge region.

7. The isolated nucleic acid molecule of claim 6, wherein the encoded hinge region comprises SEQ ID NO:14, or a sequence with greater than 95% identity thereof.

8. The isolated nucleic acid molecule of claim 6, wherein the nucleic acid sequence encoding the hinge region comprises the sequence of SEQ ID NO:7, or a sequence with greater than 95% identity thereof.

9. The isolated nucleic acid molecule of claim 1, wherein the encoded intracellular signaling domain comprises a costimulatory domain and a primary signaling domain.

10. The isolated nucleic acid molecule of claim 9, wherein the encoded costimulatory domain comprises a functional signaling domain of a protein selected from the group consisting of OX40, CD27, CD28, CDS, ICAM-1, LFA-1 (CD11a/CD18), ICOS (CD278), and 4-1BB (CD137).

11. The isolated nucleic acid molecule of claim 9, wherein the encoded costimulatory domain comprises the sequence of SEQ ID NO:16; an amino acid sequence which comprises at least one modification but not more than 20 modifications of the amino acid sequence of SEQ ID NO:16; or a sequence with greater than 95% identity to the amino acid sequence of SEQ ID NO:16.

12. The isolated nucleic acid molecule of claim 9, wherein the nucleic acid sequence encoding the costimulatory domain comprises the sequence of SEQ ID NO:9, or a sequence with greater than 95% identity thereof.

13. The isolated nucleic acid molecule of claim 1, wherein the encoded intracellular signaling domain comprises a functional signaling domain of 4-1BB and a functional signaling domain of CD3 zeta.

14. The isolated nucleic acid molecule of claim 1, wherein:

the encoded costimulatory domain comprises the sequence of SEQ ID NO: 16; an amino acid sequence having at least one modification but not more than 20 modifications of the amino acid sequence of SEQ ID NO: 16; or a sequence with greater than 95% identity to the amino acid sequence of SEQ ID NO: 16, and the encoded primary signaling domain comprises the sequence of SEQ ID NO: 17 or SEQ ID NO:99; an amino acid sequence having at least one modification but not more than 20 modifications of the amino acid sequence of SEQ ID NO:17 or SEQ ID NO:99 or a sequence with greater than 95% identity to the amino acid sequence of SEQ ID NO:17 or SEQ ID NO:99.

15. The isolated nucleic acid molecule of claim 1, wherein the encoded intracellular signaling domain comprises the sequence of SEQ ID NO: 16 and the sequence of SEQ ID NO: 17 or SEQ ID NO:99, wherein the sequences comprising the intracellular signaling domain are expressed in the same frame and as a single polypeptide chain.

16. The isolated nucleic acid molecule of claim 1, wherein the nucleic acid sequence encoding the intracellular signaling domain comprises the sequence of SEQ ID NO:9, or a sequence with greater than 95% identify thereof, and/or the sequence of SEQ ID NO:10 or SEQ ID NO:100, or a sequence with greater than 95% identity thereof.

17. The isolated nucleic acid molecule of claim 1, further comprising a leader sequence.

18. The isolated nucleic acid molecule of claim 17, wherein the leader sequence comprises SEQ ID NO: 13.

19. A vector comprising a nucleic acid molecule of claim 1.

20. The vector of claim 19, wherein the vector is selected from the group consisting of a DNA, a RNA, a plasmid, a lentivirus vector, adenoviral vector, and a retrovirus vector.

21. The vector of claim 19, further comprising a promoter.

22. The vector of claim 21, wherein the promoter is an EF-1 promoter.

23. The vector of claim 22, wherein the EF-1 promoter comprises the sequence of SEQ ID NO: 97.

24. The vector of claim 19, wherein the vector is an in vitro transcribed vector.

25. The vector of claim 19, wherein the nucleic acid sequence in the vector further comprises a poly(A) tail.

26. The vector of claim 19, wherein the nucleic acid sequence in the vector further comprises a 3'UTR.

27. An isolated cell comprising the vector of claim 19.

28. The cell of claim 27, wherein the cell is a T cell.

29. The cell of claim 28, wherein the T cell is a CD8+T cell.

30. The cell of claim 27, wherein the cell is a human cell.

31. A method of making a cell comprising transducing a T cell with a vector of claim 19.

32. A method of generating a population of RNA-engineered cells comprising introducing an in vitro transcribed RNA or synthetic RNA into a cell, where the RNA comprises the nucleic acid molecule of claim 1.

33. The isolated nucleic acid molecule of claim 1, wherein the encoded intracellular signaling domain comprises a primary signaling domain.

34. The isolated nucleic acid molecule of claim 1, wherein the encoded intracellular signaling domain comprises a costimulatory domain.

35. The isolated nucleic acid molecule of claim 1, wherein the nucleic acid sequence encoding the CAR comprises the nucleotide sequence of SEQ ID NO:72, or a nucleic acid sequence having greater than 99% identity thereof.

36. The isolated nucleic acid molecule of claim 1, wherein the encoded CAR comprises the amino acid sequence of SEQ ID NO:73, or an amino acid sequence having greater than 99% identity thereof.

37. The isolated nucleic acid molecule of claim 1, wherein the encoded anti-EGFRvIII binding domain comprises the sequence of SEQ ID NO:68.

38. The isolated nucleic acid molecule of claim 2, wherein the nucleic acid sequence encoding the anti-EGFRvIII binding domain comprises the nucleotide sequence of SEQ ID NO:69.

* * * * *

SEQUENCE LISTING

```
<160> NUMBER OF SEQ ID NOS: 127

<210> SEQ ID NO 1
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Leu Pro Val Thr Ala Leu Leu Leu Pro Leu Ala Leu Leu Leu
1               5                   10                  15

His Ala Ala Arg Pro Gly Ser Glu Ile Gln Leu Gln Gln Ser Gly Ala
            20                  25                  30

Glu Leu Val Lys Pro Gly Ala Ser Val Lys Leu Ser Cys Thr Gly Ser
        35                  40                  45

Gly Phe Asn Ile Glu Asp Tyr Tyr Ile His Trp Val Lys Gln Arg Thr
    50                  55                  60

Glu Gln Gly Leu Glu Trp Ile Gly Arg Ile Asp Pro Glu Asn Asp Glu
65                  70                  75                  80

Thr Lys Tyr Gly Pro Ile Phe Gln Gly Arg Ala Thr Ile Thr Ala Asp
                85                  90                  95

Thr Ser Ser Asn Thr Val Tyr Leu Gln Leu Ser Ser Leu Thr Ser Glu
            100                 105                 110

Asp Thr Ala Val Tyr Tyr Cys Ala Phe Arg Gly Gly Val Tyr Trp Gly
        115                 120                 125

Pro Gly Thr Thr Leu Thr Val Ser Ser Gly Gly Gly Gly Ser Gly Gly
    130                 135                 140

Gly Gly Ser Gly Gly Gly Gly Ser His Met Asp Val Val Met Thr Gln
145                 150                 155                 160

Ser Pro Leu Thr Leu Ser Val Ala Ile Gly Gln Ser Ala Ser Ile Ser
                165                 170                 175

Cys Lys Ser Ser Gln Ser Leu Leu Asp Ser Asp Gly Lys Thr Tyr Leu
            180                 185                 190

Asn Trp Leu Leu Gln Arg Pro Gly Gln Ser Pro Lys Arg Leu Ile Ser
        195                 200                 205

Leu Val Ser Lys Leu Asp Ser Gly Val Pro Asp Arg Phe Thr Gly Ser
    210                 215                 220

Gly Ser Gly Thr Asp Phe Thr Leu Arg Ile Ser Arg Val Glu Ala Glu
225                 230                 235                 240

Asp Leu Gly Ile Tyr Tyr Cys Trp Gln Gly Thr His Phe Pro Gly Thr
                245                 250                 255

Phe Gly Gly Gly Thr Lys Leu Glu Ile Lys Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350
```

```
Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Lys Arg Gly
    370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu
                405                 410                 415

Glu Glu Gly Gly Cys Glu Leu Arg Val Lys Phe Ser Arg Ser Ala Asp
            420                 425                 430

Ala Pro Ala Tyr Lys Gln Gly Gln Asn Gln Leu Tyr Asn Glu Leu Asn
        435                 440                 445

Leu Gly Arg Arg Glu Glu Tyr Asp Val Leu Asp Lys Arg Arg Gly Arg
    450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
                485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg
    530                 535


<210> SEQ ID NO 2
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Leu Pro Val Thr Ala Leu Leu Leu Pro Leu Ala Leu Leu Leu
1               5                   10                  15

His Ala Ala Arg Pro Gly Ser Glu Ile Gln Leu Gln Gln Ser Gly Ala
            20                  25                  30

Glu Leu Val Lys Pro Gly Ala Ser Val Lys Leu Ser Cys Thr Gly Ser
        35                  40                  45

Gly Phe Asn Ile Glu Asp Tyr Tyr Ile His Trp Val Lys Gln Arg Thr
    50                  55                  60

Glu Gln Gly Leu Glu Trp Ile Gly Arg Ile Asp Pro Glu Asn Asp Glu
65                  70                  75                  80

Thr Lys Tyr Gly Pro Ile Phe Gln Gly Arg Ala Thr Ile Thr Ala Asp
                85                  90                  95

Thr Ser Ser Asn Thr Val Tyr Leu Gln Leu Ser Ser Leu Thr Ser Glu
            100                 105                 110

Asp Thr Ala Val Tyr Tyr Cys Ala Phe Arg Gly Gly Val Tyr Trp Gly
        115                 120                 125

Pro Gly Thr Thr Leu Thr Val Ser Ser Gly Gly Gly Gly Ser Gly Gly
    130                 135                 140

Gly Gly Ser Gly Gly Gly Gly Ser His Met Asp Val Val Met Thr Gln
145                 150                 155                 160

Ser Pro Leu Thr Leu Ser Val Ala Ile Gly Gln Ser Ala Ser Ile Ser
                165                 170                 175
```

-continued

```
Cys Lys Ser Ser Gln Ser Leu Leu Asp Ser Asp Gly Lys Thr Tyr Leu
            180                 185                 190

Asn Trp Leu Leu Gln Arg Pro Gly Gln Ser Pro Lys Arg Leu Ile Ser
        195                 200                 205

Leu Val Ser Lys Leu Asp Ser Gly Val Pro Asp Arg Phe Thr Gly Ser
    210                 215                 220

Gly Ser Gly Thr Asp Phe Thr Leu Arg Ile Ser Arg Val Glu Ala Glu
225                 230                 235                 240

Asp Leu Gly Ile Tyr Tyr Cys Trp Gln Gly Thr His Phe Pro Gly Thr
                245                 250                 255

Phe Gly Gly Gly Thr Lys Leu Glu Ile Lys Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 3
<211> LENGTH: 488
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Ala Leu Pro Val Thr Ala Leu Leu Leu Pro Leu Ala Leu Leu Leu
1               5                   10                  15

His Ala Ala Arg Pro Gly Ser Asp Ile Gln Met Thr Gln Ser Pro Ser
            20                  25                  30

Ser Leu Ser Ala Ser Val Gly Asp Arg Val Thr Ile Thr Cys Arg Ala
```

-continued

```
        35                  40                  45

Ser Gln Gly Ile Arg Asn Asn Leu Ala Trp Tyr Gln Gln Lys Pro Gly
    50                  55                  60

Lys Ala Pro Lys Arg Leu Ile Tyr Ala Ala Ser Asn Leu Gln Ser Gly
65                  70                  75                  80

Val Pro Ser Arg Phe Thr Gly Ser Gly Ser Gly Thr Glu Phe Thr Leu
                85                  90                  95

Ile Val Ser Ser Leu Gln Pro Glu Asp Phe Ala Thr Tyr Tyr Cys Leu
            100                 105                 110

Gln His His Ser Tyr Pro Leu Thr Ser Gly Gly Gly Thr Lys Val Glu
        115                 120                 125

Ile Lys Arg Thr Gly Ser Thr Ser Gly Ser Gly Lys Pro Gly Ser Gly
    130                 135                 140

Glu Gly Ser Glu Val Gln Val Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ala Met Ser Trp Val Arg Gln Ala Pro Gly Lys Gly Leu
            180                 185                 190

Glu Trp Val Ser Ala Ile Ser Gly Ser Gly Gly Ser Thr Asn Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Gly Ser Ser Gly Trp Ser Glu Tyr Trp Gly Gln Gly
                245                 250                 255

Thr Leu Val Thr Val Ser Ser Ala Ser Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460
```

```
Leu Tyr Gln Gly Leu Ser Thr Ala Thr Lys Asp Thr Tyr Asp Ala Leu
465                 470                 475                 480

His Met Gln Ala Leu Pro Pro Arg
                485


<210> SEQ ID NO 4
<211> LENGTH: 729
<212> TYPE: DNA
<213> ORGANISM: Mus sp.

<400> SEQUENCE: 4

gagattcagc tgcagcaatc tggggcagaa cttgtgaagc caggggcctc agtcaagctg      60

tcctgcacag gttctggctt caacattgaa gactactata ttcactgggt gaagcagagg     120

actgaacagg gcctggaatg gattggaagg attgatcctg agaatgatga aactaaatat     180

ggcccaatat tccagggcag ggccactata acagcagaca catcctccaa cacagtctac     240

ctgcaactca gcagcctgac atctgaggac actgccgtct attactgtgc ctttcgcggt     300

ggagtctact gggggccagg aaccactctc acagtctcct caggaggtgg tggttccggt     360

ggtggtggtt ccggaggtgg tggttcacat atggatgttg tgatgaccca gtctccactc     420

actctatcgg ttgccattgg acaatcagcc tccatctctt gcaagtcaag tcagagcctc     480

ttagatagtg atggaaagac atatttgaat tggttgttac agaggccagg ccagtctcca     540

aagcgcctaa tctctctggt gtctaaactg gactctggag tccctgacag gttcactggc     600

agtggatcag ggacagattt cacactgaga atcagcagag tggaggctga ggatttggga     660

atttattatt gctggcaagg tacacatttt cctgggacgt tcggtggagg gaccaagctg     720

gagataaaa                                                             729


<210> SEQ ID NO 5
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

gacatccaga tgacccagag ccctagcagc ctgagcgcca gcgtgggcga cagagtgacc      60

atcacctgtc gggccagcca gggcatcaga aacaacctgg cctggtatca gcagaagccc     120

ggcaaggccc ccaagagact gatctacgct gccagcaatc tgcagagcgg cgtgcccagc     180

agattcaccg gaagcggctc cggcaccgag ttcaccctga tcgtgtccag cctgcagccc     240

gaggacttcg ccacctacta ctgcctgcag caccacagct accctctgac cagcggcgga     300

ggcaccaagg tggagatcaa gcggaccggc agcaccagcg gcagcggcaa gcctggcagc     360

ggcgagggaa gcgaggtcca ggtgctggaa tctggcggcg gactggtgca gcctggcggc     420

agcctgagac tgagctgtgc cgccagcggc ttcaccttca gcagctacgc catgtcttgg     480

gtccggcagg ctcctggaaa gggcctggaa tgggtgtccg ccatcagcgg ctctggcggc     540

tccaccaact acgccgacag cgtgaagggc cggttcacca tcagccggga caacagcaag     600

aacaccctgt atctgcagat gaacagcctg agagccgagg acaccgccgt gtactactgt     660

gccggcagca gcgggtggag cgagtactgg ggccagggca cactggtcac agtgtctagc     720


<210> SEQ ID NO 6
<211> LENGTH: 63
```

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
atggccttac cagtgaccgc cttgctcctg ccgctggcct tgctgctcca cgccgccagg 60
ccg 63

<210> SEQ ID NO 7
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
atctacatct gggcgccctt ggccgggact tgtggggtcc ttctcctgtc actggttatc 60
accctttact gc 72

<210> SEQ ID NO 9
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 10
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
agagtgaagt tcagcaggag cgcagacgcc cccgcgtaca agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 11
<211> LENGTH: 243
<212> TYPE: PRT
<213> ORGANISM: Mus sp.

<400> SEQUENCE: 11

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
    50                  55                  60

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
            100                 105                 110

Ser Ser Gly Gly Gly Gly Ser Gly Gly Gly Gly Ser Gly Gly Gly Gly
        115                 120                 125

Ser His Met Asp Val Val Met Thr Gln Ser Pro Leu Thr Leu Ser Val
    130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Arg Ile Ser Arg Val Glu Ala Glu Asp Leu Gly Ile Tyr Tyr Cys
    210                 215                 220

Trp Gln Gly Thr His Phe Pro Gly Thr Phe Gly Gly Gly Thr Lys Leu
225                 230                 235                 240

Glu Ile Lys

<210> SEQ ID NO 12
<211> LENGTH: 240
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65 70 75 80

Glu Asp Phe Ala Thr Tyr Tyr Cys Leu Gln His His Ser Tyr Pro Leu
85 90 95

Thr Ser Gly Gly Gly Thr Lys Val Glu Ile Lys Arg Thr Gly Ser Thr
100 105 110

Ser Gly Ser Gly Lys Pro Gly Ser Gly Glu Gly Ser Glu Val Gln Val
115 120 125

Leu Glu Ser Gly Gly Gly Leu Val Gln Pro Gly Gly Ser Leu Arg Leu
130 135 140

Ser Cys Ala Ala Ser Gly Phe Thr Phe Ser Ser Tyr Ala Met Ser Trp
145 150 155 160

Val Arg Gln Ala Pro Gly Lys Gly Leu Glu Trp Val Ser Ala Ile Ser
165 170 175

Gly Ser Gly Gly Ser Thr Asn Tyr Ala Asp Ser Val Lys Gly Arg Phe
180 185 190

Thr Ile Ser Arg Asp Asn Ser Lys Asn Thr Leu Tyr Leu Gln Met Asn
195 200 205

Ser Leu Arg Ala Glu Asp Thr Ala Val Tyr Tyr Cys Ala Gly Ser Ser
210 215 220

Gly Trp Ser Glu Tyr Trp Gly Gln Gly Thr Leu Val Thr Val Ser Ser
225 230 235 240

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Met Ala Leu Pro Val Thr Ala Leu Leu Leu Pro Leu Ala Leu Leu Leu
1 5 10 15

His Ala Ala Arg Pro
20

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 17
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 18
<211> LENGTH: 1605
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18
atggccttac cagtgaccgc cttgctcctg ccgctggcct tgctgctcca cgccgccagg 60
ccgggatccg agattcagct gcagcaatct ggggcagaac ttgtgaagcc aggggcctca 120
gtcaagctgt cctgcacagg ttctggcttc aacattgaag actactatat tcactgggtg 180
aagcagagga ctgaacaggg cctggaatgg attggaagga ttgatcctga gaatgatgaa 240
actaaatatg gcccaatatt ccagggcagg gccactataa cagcagacac atcctccaac 300
acagtctacc tgcaactcag cagcctgaca tctgaggaca ctgccgtcta ttactgtgcc 360
tttcgcggtg gagtctactg gggccagga accactctca cagtctcctc aggaggtggt 420
ggttccggtg gtggtggttc cggaggtggt ggttcacata tggatgttgt gatgacccag 480
tctccactca ctctatcggt tgccattgga caatcagcct ccatctcttg caagtcaagt 540
cagagcctct tagatagtga tggaaagaca tatttgaatt ggttgttaca gaggccaggc 600
cagtctccaa agcgcctaat ctctctggtg tctaaactgg actctggagt ccctgacagg 660
ttcactggca gtggatcagg gacagatttc acactgagaa tcagcagagt ggaggctgag 720
gatttgggaa tttattattg ctggcaaggt acacattttc ctgggacgtt cggtggaggg 780
accaagctgg agataaaagc tagcaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgatt tttgggtgct ggtggtggtt 960
ggtggagtcc tggcttgcta tagcttgcta gtaacagtgg cctttattat tttctgggtg 1020
aggagtaaga ggagcaggct cctgcacagt gactacatga acatgactcc ccgccgcccc 1080
gggcccaccc gcaagcatta ccagccctat gccccaccac gcgacttcgc agcctatcgc 1140
tccaaacggg gcagaaagaa actcctgtat atattcaaac aaccatttat gagaccagta 1200
caaactactc aagaggaaga tggctgtagc tgccgatttc cagaagaaga agaaggagga 1260
tgtgaactga gagtgaagtt cagcaggagc gcagacgccc ccgcgtacaa gcagggccag 1320
aaccagctct ataacgagct caatctagga cgaagagagg agtacgatgt tttggacaag 1380
agacgtggcc gggaccctga gatgggggga aagccgagaa ggaagaaccc tcaggaaggc 1440
ctgtacaatg aactgcagaa agataagatg gcggaggcct acagtgagat tgggatgaaa 1500
ggcgagcgcc ggaggggcaa ggggcacgat ggcctttacc agggtctcag tacagccacc 1560
aaggacacct acgacgccct tcacatgcag gccctgcccc ctcgc 1605

<210> SEQ ID NO 19
<211> LENGTH: 1473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
atggccttac cagtgaccgc cttgctcctg ccgctggcct tgctgctcca cgccgccagg 60
ccgggatccg agattcagct gcagcaatct ggggcagaac ttgtgaagcc aggggcctca 120
gtcaagctgt cctgcacagg ttctggcttc aacattgaag actactatat tcactgggtg 180
aagcagagga ctgaacaggg cctggaatgg attggaagga ttgatcctga gaatgatgaa 240
actaaatatg gcccaatatt ccagggcagg gccactataa cagcagacac atcctccaac 300
acagtctacc tgcaactcag cagcctgaca tctgaggaca ctgccgtcta ttactgtgcc 360
tttcgcggtg gagtctactg gggccagga accactctca cagtctcctc aggaggtggt 420
ggttccggtg gtggtggttc cggaggtggt ggttcacata tggatgttgt gatgacccag 480
tctccactca ctctatcggt tgccattgga caatcagcct ccatctcttg caagtcaagt 540
cagagcctct tagatagtga tggaaagaca tatttgaatt ggttgttaca gaggccaggc 600
cagtctccaa agcgcctaat ctctctggtg tctaaactgg actctggagt ccctgacagg 660
ttcactggca gtggatcagg gacagatttc acactgagaa tcagcagagt ggaggctgag 720
gatttgggaa tttattattg ctggcaaggt acacattttc ctgggacgtt cggtggaggg 780
accaagctgg agataaaagc tagcaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg caaacggggc 1020
agaaagaaac tcctgtatat attcaaacaa ccatttatga gaccagtaca aactactcaa 1080
gaggaagatg gctgtagctg ccgatttcca gaagaagaag aaggaggatg tgaactgaga 1140
gtgaagttca gcaggagcgc agacgccccc gcgtacaagc agggccagaa ccagctctat 1200
aacgagctca atctaggacg aagagaggag tacgatgttt tggacaagag acgtggccgg 1260
gaccctgaga tgggggggaaa gccgagaagg aagaaccctc aggaaggcct gtacaatgaa 1320
ctgcagaaag ataagatggc ggaggcctac agtgagattg ggatgaaagg cgagcgccgg 1380
aggggcaagg ggcacgatgg cctttaccag ggtctcagta cagccaccaa ggacacctac 1440
gacgcccttc acatgcaggc cctgccccct cgc 1473

<210> SEQ ID NO 20
<211> LENGTH: 1465
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20
atggccttac cagtgaccgc cttgctcctg ccgctggcct tgctgctcca cgccgccagg 60
ccgggatccg acatccagat gacccagagc cctagcagcc tgagcgccag cgtgggcgac 120
agagtgacca tcacctgtcg ggccagccag ggcatcagaa acaacctggc ctggtatcag 180
cagaagcccg gcaaggcccc caagagactg atctacgctg ccagcaatct gcagagcggc 240
gtgcccagca gattcaccgg aagcggctcc ggcaccgagt tcaccctgat cgtgtccagc 300
ctgcagcccg aggacttcgc cacctactac tgcctgcagc accacagcta ccctctgacc 360
agcggcggag gcaccaaggt ggagatcaag cggaccggca gcaccagcgg cagcggcaag 420
cctggcagcg gcgagggaag cgaggtccag gtgctggaat ctggcggcgg actggtgcag 480
cctggcggca gcctgagact gagctgtgcc gccagcggct tcaccttcag cagctacgcc 540
atgtcttggg tccggcaggc tcctggaaag ggcctggaat gggtgtccgc catcagcggc 600
tctggcggct ccaccaacta cgccgacagc gtgaagggcc ggttcaccat cagccgggac 660
aacagcaaga acaccctgta tctgcagatg aacagcctga gagccgagga caccgccgtg 720
tactactgtg ccggcagcag cgggtggagc gagtactggg gccagggcac actggtcaca 780
gtgtctagcg ctagcaccac gacgccagcg ccgcgaccac caacaccggc gcccaccatc 840
gcgtcgcagc ccctgtccct gcgcccagag gcgtgccggc cagcggcggg gggcgcagtg 900
cacacgaggg ggctggactt cgcctgtgat atctacatct gggcgccctt ggccgggact 960
tgtggggtcc ttctcctgtc actggttatc accctttact gcaaacgggg cagaaagaaa 1020
ctcctgtata tattcaaaca accatttatg agaccagtac aaactactca agaggaagat 1080
ggctgtagct gccgatttcc agaagaagaa gaaggaggat gtgaactgag agtgaagttc 1140
agcaggagcg cagacgcccc cgcgtacaag cagggccaga accagctcta taacgagctc 1200
aatctaggac gaagagagga gtacgatgtt ttggacaaga gacgtggccg ggaccctgag 1260
atggggggaa agccgagaag gaagaaccct caggaaggcc tgtacaatga actgcagaaa 1320
gataagatgg cggaggccta cagtgagatt gggatgaaag gcgagcgccg gaggggcaag 1380
gggcacgatg gcctttacca gggtctcagt acagccacca aggacaccta cgacgccctt 1440
cacatgcagg ccctgccccc tcgct 1465

<210> SEQ ID NO 21
<211> LENGTH: 114
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Glu Ile Gln Leu Gln Gln Ser Gly Ala Glu Leu Val Lys Pro Gly Ala
1 5 10 15

Ser Val Lys Leu Ser Cys Thr Gly Ser Gly Phe Asn Ile Glu Asp Tyr
20 25 30

Tyr Ile His Trp Val Lys Gln Arg Thr Glu Gln Gly Leu Glu Trp Ile
35 40 45

Gly Arg Ile Asp Pro Glu Asn Asp Glu Thr Lys Tyr Gly Pro Ile Phe
50 55 60

Gln Gly Arg Ala Thr Ile Thr Ala Asp Thr Ser Ser Asn Thr Val Tyr
65 70 75 80

Leu Gln Leu Ser Ser Leu Thr Ser Glu Asp Thr Ala Val Tyr Tyr Cys
85 90 95

Ala Phe Arg Gly Gly Val Tyr Trp Gly Pro Gly Thr Thr Leu Thr Val
100 105 110

Ser Ser

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Asp Tyr Tyr Ile His
1 5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Arg Ile Asp Pro Glu Asn Asp Glu Thr Lys Tyr Gly Pro Ile Phe Gln
1 5 10 15

Gly

<210> SEQ ID NO 24
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 24

```
Arg Gly Gly Val Tyr
1               5
```

<210> SEQ ID NO 25
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Val Val Met Thr Gln Ser Pro Leu Thr Leu Ser Val Ala Ile Gly
1               5                   10                  15

Gln Ser Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Ile Tyr Tyr Cys Trp Gln Gly
                85                  90                  95

Thr His Phe Pro Gly Thr Phe Gly Gly Gly Thr Lys Leu Glu Ile Lys
            100                 105                 110
```

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Lys Ser Ser Gln Ser Leu Leu Asp Ser Asp Gly Lys Thr Tyr Leu Asn
1               5                   10                  15
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Leu Val Ser Lys Leu Asp Ser
1               5
```

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Gln Gly Thr His Phe Pro Gly Thr
1 5

<210> SEQ ID NO 29
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Glu Ile Gln Leu Gln Gln Ser Gly Ala Glu Leu Val Lys Pro Gly Ala
1 5 10 15

Ser Val Lys Leu Ser Cys Thr Gly Ser Gly Phe Asn Ile Glu Asp Tyr
20 25 30

Tyr Ile His Trp Val Lys Gln Arg Thr Glu Gln Gly Leu Glu Trp Ile
35 40 45

Gly Arg Ile Asp Pro Glu Asn Asp Glu Thr Lys Tyr Gly Pro Ile Phe
50 55 60

Gln Gly Arg Ala Thr Ile Thr Ala Asp Thr Ser Ser Asn Thr Val Tyr
65 70 75 80

Leu Gln Leu Ser Ser Leu Thr Ser Glu Asp Thr Ala Val Tyr Tyr Cys
85 90 95

Ala Phe Arg Gly Gly Val Tyr Trp Gly Pro Gly Thr Thr Leu Thr Val
100 105 110

Ser Ser

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Gly Phe Asn Ile Glu Asp Tyr
1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Asp Pro Glu Asn Asp Glu
1 5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Arg Gly Gly Val Tyr 1 5

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Asp Val Val Met Thr Gln Ser Pro Leu Thr Leu Ser Val Ala Ile Gly
1 5 10 15

Gln Ser Ala Ser Ile Ser Cys Lys Ser Ser Gln Ser Leu Leu Asp Ser
20 25 30

Asp Gly Lys Thr Tyr Leu Asn Trp Leu Leu Gln Arg Pro Gly Gln Ser
35 40 45

Pro Lys Arg Leu Ile Ser Leu Val Ser Lys Leu Asp Ser Gly Val Pro
50 55 60

Asp Arg Phe Thr Gly Ser Gly Ser Gly Thr Asp Phe Thr Leu Arg Ile
65 70 75 80

Ser Arg Val Glu Ala Glu Asp Leu Gly Ile Tyr Tyr Cys Trp Gln Gly
85 90 95

Thr His Phe Pro Gly Thr Phe Gly Gly Gly Thr Lys Leu Glu Ile Lys
100 105 110

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ser Gln Ser Leu Leu Asp Ser Asp Gly Lys Thr Tyr
1 5 10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Leu Val Ser
1

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Thr His Phe Pro Gly
1 5

<210> SEQ ID NO 37
<211> LENGTH: 5

<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Gly Gly Gly Gly Ser
1               5
```

<210> SEQ ID NO 38
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 39
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
gaaatccagc tggtccaatc gggagctgag gtcaagaagc cgggagccac cgtcaagatc     60
tcatgcaagg ggtcgggatt caacatcgag gactactaca ttcactgggt gcagcaagct    120
ccgggaaaag gcctggaatg gatgggcaga atcgacccag aaaacgacga aactaagtac    180
ggaccgattt tccaaggaag agtgactatc accgccgata cttcaaccaa taccgtctac    240
atggaactga gctcgctccg gtccgaagat actgcagtgt attactgtgc ctttcgcgga    300
ggggtgtact ggggccaagg aactactgtc actgtctcgt caggaggcgg agggtcggga    360
ggaggcggga gcggaggcgg tggctcgggt ggcggaggaa gcgacgtggt gatgacccag    420
tccccggact ccctcgccgt gagcctcgga gagagggcga ctatcaattg caagtcgtcc    480
cagtcacttc tggattccga tggtaaaacg tacctcaact ggctgcagca aaagccaggg    540
cagccaccca aacggttgat ctcccttgtg tccaaactgg atagcggagt gcctgaccgc    600
ttctcgggtt ccggtagcgg gaccgacttc accctgacga tcagctcact gcaggcggag    660
gacgtggcag tgtactactg ctggcaggga acccacttcc ctggcacctt tggaggtggc    720
accaaggtgg agatcaag                                                  738
```

<210> SEQ ID NO 40
<211> LENGTH: 831
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40

```
atggccctcc ctgtcaccgc cctgctgctt ccgctggctc ttctgctcca cgccgctcgg     60
cccgaaatcc agctggtcca atcgggagct gaggtcaaga agccgggagc caccgtcaag    120
atctcatgca aggggtcggg attcaacatc gaggactact acattcactg ggtgcagcaa    180
gctccgggaa aaggcctgga atggatgggc agaatcgacc cagaaaacga cgaaactaag    240
tacggaccga ttttccaagg aagagtgact atcaccgccg atacttcaac caataccgtc    300
tacatggaac tgagctcgct ccggtccgaa gatactgcag tgtattactg tgcctttcgc    360
ggaggggtgt actggggcca aggaactact gtcactgtct cgtcaggagg cggagggtcg    420
ggaggaggcg ggagcggagg cggtggctcg ggtggcggag gaagcgacgt ggtgatgacc    480
cagtccccgg actccctcgc cgtgagcctc ggagagaggg cgactatcaa ttgcaagtcg    540
tcccagtcac ttctggattc cgatggtaaa acgtacctca actggctgca gcaaaagcca    600
gggcagccac ccaaacggtt gatctccctt gtgtccaaac tggatagcgg agtgcctgac    660
cgcttctcgg gttccggtag cgggaccgac ttcaccctga cgatcagctc actgcaggcg    720
gaggacgtgg cagtgtacta ctgctggcag ggaacccact tccctggcac ctttggaggt    780
ggcaccaagg tggagatcaa gggatcgcac caccatcacc atcatcatca c             831
```

<210> SEQ ID NO 41
<211> LENGTH: 277
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Met Ala Leu Pro Val Thr Ala Leu Leu Leu Pro Leu Ala Leu Leu Leu

-continued

```
1               5                   10                  15

His Ala Ala Arg Pro Glu Ile Gln Leu Val Gln Ser Gly Ala Glu Val
            20                  25                  30

Lys Lys Pro Gly Ala Thr Val Lys Ile Ser Cys Lys Gly Ser Gly Phe
        35                  40                  45

Asn Ile Glu Asp Tyr Tyr Ile His Trp Val Gln Gln Ala Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly Arg Val Thr Ile Thr Ala Asp Thr Ser
                85                  90                  95

Thr Asn Thr Val Tyr Met Glu Leu Ser Ser Leu Arg Ser Glu Asp Thr
            100                 105                 110

Ala Val Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Leu Leu Asp Ser Asp Gly Lys Thr Tyr
            180                 185                 190

Leu Asn Trp Leu Gln Gln Lys Pro Gly Gln Pro Pro Lys Arg Leu Ile
        195                 200                 205

Ser Leu Val Ser Lys Leu Asp Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Trp Gln Gly Thr His Phe Pro Gly
                245                 250                 255

Thr Phe Gly Gly Gly Thr Lys Val Glu Ile Lys Gly Ser His His His
            260                 265                 270

His His His His His
        275


<210> SEQ ID NO 42
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

atggccctcc ctgtcaccgc cctgctgctt ccgctggctc ttctgctcca cgccgctcgg      60

cccgagatcc agctggtgca gtcgggagct gaagtcaaaa agcctggcgc aaccgtcaag     120

atctcgtgca aaggatcagg gttcaacatc gaggactact acatccattg ggtgcaacag     180

gcacccggaa aaggcctgga gtggatgggg aggattgacc cagaaaatga cgaaaccaag     240

tacggaccga tcttccaagg acgggtgacc atcacggctg acacttccac taacaccgtc     300

tacatggaac tctcgagcct tcgctcggaa gataccgcgg tgtactactg cgcctttaga     360

ggtggagtct actggggaca agggactacc gtcaccgtgt cgtcaggtgg cggaggatca     420

ggcggaggcg gctccggtgg aggaggaagc ggaggaggtg gctccgacgt ggtgatgacg     480
```

```
cagtcaccgg actccttggc ggtgagcctg ggtgaacgcg ccactatcaa ctgcaagagc    540
tcccagagct tgctggactc cgatggaaag acttatctca attggctgca acagaagcct    600
ggccagccgc caaagagact catctcactg gtgagcaagc tggatagcgg agtgccagat    660
cggttttcgg gatcgggctc aggcaccgac ttcaccctga ctatttcctc cctccaagcc    720
gaggatgtgg ccgtctacta ctgttggcag gggactcact tcccggggac cttcggtgga    780
ggcactaagg tggagatcaa aaccactacc ccagcaccga ggccacccac cccggctcct    840
accatcgcct cccagcctct gtccctgcgt ccggaggcat gtagacccgc agctggtggg    900
gccgtgcata cccggggtct tgacttcgcc tgcgatatct acatttgggc ccctctggct    960
ggtacttgcg gggtcctgct gctttcactc gtgatcactc tttactgtaa gcgcggtcgg   1020
aagaagctgc tgtacatctt taagcaaccc ttcatgaggc ctgtgcagac tactcaagag   1080
gaggacggct gttcatgccg gttcccagag gaggaggaag gcggctgcga actgcgcgtg   1140
aaattcagcc gcagcgcaga tgctccagcc tacaagcagg ggcagaacca gctctacaac   1200
gaactcaatc ttggtcggag agaggagtac gacgtgctgg acaagcggag aggacgggac   1260
ccagaaatgg gcgggaagcc gcgcagaaag aatccccaag agggcctgta caacgagctc   1320
caaaaggata agatggcaga agcctatagc gagattggta tgaaagggga acgcagaaga   1380
ggcaaaggcc acgacggact gtaccaggga ctcagcaccg ccaccaagga cacctatgac   1440
gctcttcaca tgcaggccct gccgcctcgg                                    1470
```

```
<210> SEQ ID NO 43
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Ala Thr Val Lys Ile Ser Cys Lys Gly Ser Gly Phe
        35                  40                  45

Asn Ile Glu Asp Tyr Tyr Ile His Trp Val Gln Gln Ala Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly Arg Val Thr Ile Thr Ala Asp Thr Ser
                85                  90                  95

Thr Asn Thr Val Tyr Met Glu Leu Ser Ser Leu Arg Ser Glu Asp Thr
            100                 105                 110

Ala Val Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Asp Ser Leu Ala Val Ser Leu Gly Glu Arg Ala Thr Ile
                165                 170                 175
```

Asn Cys Lys Ser Ser Gln Ser Leu Leu Asp Ser Asp Gly Lys Thr Tyr
180 185 190

Leu Asn Trp Leu Gln Gln Lys Pro Gly Gln Pro Pro Lys Arg Leu Ile
195 200 205

Ser Leu Val Ser Lys Leu Asp Ser Gly Val Pro Asp Arg Phe Ser Gly
210 215 220

Ser Gly Ser Gly Thr Asp Phe Thr Leu Thr Ile Ser Ser Leu Gln Ala
225 230 235 240

Glu Asp Val Ala Val Tyr Tyr Cys Trp Gln Gly Thr His Phe Pro Gly
245 250 255

Thr Phe Gly Gly Gly Thr Lys Val Glu Ile Lys Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 44
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Asp Val Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asp Ser
20 25 30

Asp Gly Lys Thr Tyr Leu Asn Trp Leu Gln Gln Lys Pro Gly Gln Pro
35 40 45

-continued

```
Pro Lys Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245
```

<210> SEQ ID NO 45
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
gatgtcgtga tgacccagtc cccagactcc ctcgcagtgt ccttgggaga acgggccacc     60

atcaactgca aatcgagcca gtcactgctg gactcagacg gaaagaccta cctcaactgg    120

ctgcagcaga agcctggcca gccaccgaag cgcctgatct ccctggtgtc caagctggac    180

tcgggcgtcc cggacaggtt tagcggtagc ggctcgggaa ccgacttcac tctgaccatt    240

agctcgctcc aagctgaaga tgtggcggtc tactactgct ggcaggggac ccacttcccc    300

gggacctttg gcggaggaac taaagtcgaa atcaaaggag gaggcggatc aggtggagga    360

ggcagcggag gaggagggag cggcggtggc ggctccgaaa ttcaacttgt gcaatccggt    420

gccgaggtga agaaacctgg tgccactgtc aagatctcgt gtaagggatc gggattcaat    480

atcgaggact actacatcca ctgggtgcaa caggcgccag gaaagggatt ggagtggatg    540

ggtcgcatcg acccggaaaa cgatgagact aagtacggac cgatcttcca aggccgggtc    600

acgatcactg cggatacctc cactaatacc gtgtatatgg agctctcgtc actgagaagc    660

gaagatacgg ccgtgtacta ctgcgcattc agaggaggtg tgtactgggg ccagggaact    720

actgtgaccg tgtcgtcg                                                  738
```

<210> SEQ ID NO 46

```
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

atggccctcc ctgtcaccgc cctgctgctt ccgctggctc ttctgctcca cgccgctcgg     60

cccgatgtcg tgatgaccca gtccccagac tccctcgcag tgtccttggg agaacgggcc    120

accatcaact gcaaatcgag ccagtcactg ctggactcag acggaaagac ctacctcaac    180

tggctgcagc agaagcctgg ccagccaccg aagcgcctga tctccctggt gtccaagctg    240

gactcgggcg tcccggacag gtttagcggt agcggctcgg gaaccgactt cactctgacc    300

attagctcgc tccaagctga agatgtggcg gtctactact gctggcaggg gacccacttc    360

cccgggacct ttggcggagg aactaaagtc gaaatcaaag gaggaggcgg atcaggtgga    420

ggaggcagcg gaggaggagg gagcggcggt ggcggctccg aaattcaact tgtgcaatcc    480

ggtgccgagg tgaagaaacc tggtgccact gtcaagatct cgtgtaaggg atcgggattc    540

aatatcgagg actactacat ccactgggtg caacaggcgc caggaaaggg attggagtgg    600

atgggtcgca tcgacccgga aaacgatgag actaagtacg gaccgatctt ccaaggccgg    660

gtcacgatca ctgcggatac ctccactaat accgtgtata tggagctctc gtcactgaga    720

agcgaagata cggccgtgta ctactgcgca ttcagaggag gtgtgtactg gggccaggga    780

actactgtga ccgtgtcgtc ggggtcacat caccaccatc atcatcacca c             831


<210> SEQ ID NO 47
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Leu Leu Asp Ser Asp Gly Lys Thr Tyr Leu Asn Trp Leu Gln Gln
    50                  55                  60

Lys Pro Gly Gln Pro Pro Lys Arg Leu Ile Ser Leu Val Ser Lys Leu
65                  70                  75                  80

Asp Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Trp Gln Gly Thr His Phe Pro Gly Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Ala Thr Val Lys Ile Ser Cys Lys
```

-continued

```
                165                 170                 175

Gly Ser Gly Phe Asn Ile Glu Asp Tyr Tyr Ile His Trp Val Gln Gln
            180                 185                 190

Ala Pro Gly Lys Gly Leu Glu Trp Met Gly Arg Ile Asp Pro Glu Asn
        195                 200                 205

Asp Glu Thr Lys Tyr Gly Pro Ile Phe Gln Gly Arg Val Thr Ile Thr
    210                 215                 220

Ala Asp Thr Ser Thr Asn Thr Val Tyr Met Glu Leu Ser Ser Leu Arg
225                 230                 235                 240

Ser Glu Asp Thr Ala Val Tyr Tyr Cys Ala Phe Arg Gly Gly Val Tyr
                245                 250                 255

Trp Gly Gln Gly Thr Thr Val Thr Val Ser Ser Gly Ser His His His
            260                 265                 270

His His His His His
        275


<210> SEQ ID NO 48
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

atggccctcc ctgtcaccgc cctgctgctt ccgctggctc ttctgctcca cgccgctcgg     60

cccgacgtgg tcatgactca aagcccagat tccttggctg tctcccttgg agaaagagca    120

acgatcaatt gcaaaagctc gcagtccctg ttggactccg atggaaaaac ctacctcaac    180

tggctgcagc agaagccggg acaaccacca aagcggctga tttccctcgt gtccaagctg    240

gacagcggcg tgccggatcg cttctcgggc agcggctcgg gaaccgattt tactctcact    300

atttcgtcac tgcaagcgga ggacgtggcg gtgtattact gctggcaggg cactcacttc    360

ccgggtactt ttggtggagg taccaaagtc gaaatcaagg gtggaggcgg gagcggagga    420

ggcgggtcgg gaggaggagg atcgggtggc ggaggctcag aaatccagct ggtgcagtca    480

ggtgccgaag tgaagaagcc tggggccacg gtgaagatct cgtgcaaggg gagcggattc    540

aacatcgagg attactacat ccattgggtg caacaggccc ctggcaaagg gctggaatgg    600

atgggaagga tcgaccccga gaatgacgag actaagtacg gcccgatctt ccaaggacgg    660

gtgaccatca ctgcagacac ttcaaccaac accgtctaca tggaactctc ctcgctgcgc    720

tccgaggaca ccgccgtgta ctactgtgct ttcagaggag gagtctactg gggacaggga    780

acgaccgtga ccgtcagctc aaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380
```

-continued ggcaaaggcc acgacggact gtaccaggga ctcagcaccg ccaccaagga cacctatgac 1440
gctcttcaca tgcaggccct gccgcctcgg 1470

<210> SEQ ID NO 49
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Asp Ser Leu
20 25 30

Ala Val Ser Leu Gly Glu Arg Ala Thr Ile Asn Cys Lys Ser Ser Gln
35 40 45

Ser Leu Leu Asp Ser Asp Gly Lys Thr Tyr Leu Asn Trp Leu Gln Gln
50 55 60

Lys Pro Gly Gln Pro Pro Lys Arg Leu Ile Ser Leu Val Ser Lys Leu
65 70 75 80

Asp Ser Gly Val Pro Asp Arg Phe Ser Gly Ser Gly Ser Gly Thr Asp
85 90 95

Phe Thr Leu Thr Ile Ser Ser Leu Gln Ala Glu Asp Val Ala Val Tyr
100 105 110

Tyr Cys Trp Gln Gly Thr His Phe Pro Gly Thr Phe Gly Gly Gly Thr
115 120 125

Lys Val Glu Ile Lys Gly Gly Gly Gly Ser Gly Gly Gly Gly Ser Gly
130 135 140

Gly Gly Gly Ser Gly Gly Gly Gly Ser Glu Ile Gln Leu Val Gln Ser
145 150 155 160

Gly Ala Glu Val Lys Lys Pro Gly Ala Thr Val Lys Ile Ser Cys Lys
165 170 175

Gly Ser Gly Phe Asn Ile Glu Asp Tyr Tyr Ile His Trp Val Gln Gln
180 185 190

Ala Pro Gly Lys Gly Leu Glu Trp Met Gly Arg Ile Asp Pro Glu Asn
195 200 205

Asp Glu Thr Lys Tyr Gly Pro Ile Phe Gln Gly Arg Val Thr Ile Thr
210 215 220

Ala Asp Thr Ser Thr Asn Thr Val Tyr Met Glu Leu Ser Ser Leu Arg
225 230 235 240

Ser Glu Asp Thr Ala Val Tyr Tyr Cys Ala Phe Arg Gly Gly Val Tyr
245 250 255

Trp Gly Gln Gly Thr Thr Val Thr Val Ser Ser Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 50
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

Glu Ile Gln Leu Val Gln Ser Gly Ala Glu Val Lys Lys Pro Gly Glu
1 5 10 15

Ser Leu Arg Ile Ser Cys Lys Gly Ser Gly Phe Asn Ile Glu Asp Tyr
20 25 30

Tyr Ile His Trp Val Arg Gln Met Pro Gly Lys Gly Leu Glu Trp Met
35 40 45

Gly Arg Ile Asp Pro Glu Asn Asp Glu Thr Lys Tyr Gly Pro Ile Phe
50 55 60

Gln Gly His Val Thr Ile Ser Ala Asp Thr Ser Ile Asn Thr Val Tyr
65 70 75 80

Leu Gln Trp Ser Ser Leu Lys Ala Ser Asp Thr Ala Met Tyr Tyr Cys
85 90 95

Ala Phe Arg Gly Gly Val Tyr Trp Gly Gln Gly Thr Thr Val Thr Val
100 105 110

Ser Ser Gly Gly Gly Gly Ser Gly Gly Gly Gly Ser Gly Gly Gly Gly
115 120 125

Ser Gly Gly Gly Gly Ser Asp Val Val Met Thr Gln Ser Pro Leu Ser
130 135 140

Leu Pro Val Thr Leu Gly Gln Pro Ala Ser Ile Ser Cys Lys Ser Ser
145 150 155 160

Gln Ser Leu Leu Asp Ser Asp Gly Lys Thr Tyr Leu Asn Trp Leu Gln
165 170 175

Gln Arg Pro Gly Gln Ser Pro Arg Arg Leu Ile Ser Leu Val Ser Lys
180 185 190

Leu Asp Ser Gly Val Pro Asp Arg Phe Ser Gly Ser Gly Ser Gly Thr
195 200 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245

<210> SEQ ID NO 51
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gagattcagc tggtccaaag cggcgcagaa gtgaaaaagc caggggaatc gttgcgcatc 60
agctgtaaag gttccggctt caacatcgag gactattaca tccattgggt gcggcagatg 120
ccaggaaagg ggctggaatg gatgggacgg attgacccgg agaacgacga aaccaagtac 180
ggaccgatct ttcaaggaca cgtgactatc tccgccgaca ccagcatcaa tacggtgtac 240
ctccaatggt cctcactcaa ggcctcggat accgcgatgt actactgcgc gttcagagga 300
ggcgtctact ggggacaagg gactactgtg actgtctcat caggaggtgg aggaagcgga 360
ggaggtggct cgggcggagg tggatcggga ggaggagggt ccgatgtggt gatgacccag 420
tccccactgt cgctcccggt gaccctcgga cagcctgcta gcatctcgtg caaatcctcg 480
caatccctgc tggactcgga cggaaaaacg tacctcaatt ggctgcagca gcgccctggc 540
cagagcccga gaaggcttat ctcgctggtg tcaaagctgg atagcggtgt gcccgaccgg 600
ttcagcggct cagggtcagg aaccgatttc accttgaaga tctcccgcgt ggaagccgaa 660
gatgtcggag tctactactg ctggcagggt actcacttcc cggggacctt tggtggcggc 720
actaaggtcg agattaag 738

<210> SEQ ID NO 52
<211> LENGTH: 831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atggccctcc ctgtcaccgc cctgctgctt ccgctggctc ttctgctcca cgccgctcgg 60
cccgagattc agctggtcca aagcggcgca gaagtgaaaa agccagggga atcgttgcgc 120
atcagctgta aaggttccgg cttcaacatc gaggactatt acatccattg ggtgcggcag 180
atgccaggaa aggggctgga atggatggga cggattgacc cggagaacga cgaaaccaag 240
tacggaccga tctttcaagg acacgtgact atctccgccg acaccagcat caatacggtg 300
tacctccaat ggtcctcact caaggcctcg gataccgcga tgtactactg cgcgttcaga 360
ggaggcgtct actggggaca agggactact gtgactgtct catcaggagg tggaggaagc 420
ggaggaggtg gctcgggcgg aggtggatcg ggaggaggag ggtccgatgt ggtgatgacc 480
cagtccccac tgtcgctccc ggtgaccctc ggacagcctg ctagcatctc gtgcaaatcc 540
tcgcaatccc tgctggactc ggacggaaaa acgtacctca attggctgca gcagcgccct 600
ggccagagcc cgagaaggct tatctcgctg gtgtcaaagc tggatagcgg tgtgcccgac 660
cggttcagcg gctcagggtc aggaaccgat ttcaccttga agatctcccg cgtggaagcc 720
gaagatgtcg gagtctacta ctgctggcag ggtactcact tcccggggac ctttggtggc 780
ggcactaagg tcgagattaa gggctcacac catcatcacc atcaccacca c 831

<210> SEQ ID NO 53
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Met Ala Leu Pro Val Thr Ala Leu Leu Leu Pro Leu Ala Leu Leu Leu
1 5 10 15

His Ala Ala Arg Pro Glu Ile Gln Leu Val Gln Ser Gly Ala Glu Val
20 25 30

Lys Lys Pro Gly Glu Ser Leu Arg Ile Ser Cys Lys Gly Ser Gly Phe
35 40 45

Asn Ile Glu Asp Tyr Tyr Ile His Trp Val Arg Gln Met Pro Gly Lys
50 55 60

Gly Leu Glu Trp Met Gly Arg Ile Asp Pro Glu Asn Asp Glu Thr Lys
65 70 75 80

Tyr Gly Pro Ile Phe Gln Gly His Val Thr Ile Ser Ala Asp Thr Ser
85 90 95

Ile Asn Thr Val Tyr Leu Gln Trp Ser Ser Leu Lys Ala Ser Asp Thr
100 105 110

Ala Met Tyr Tyr Cys Ala Phe Arg Gly Gly Val Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Gly Gly Gly Gly Ser Asp Val Val Met Thr
145 150 155 160

Gln Ser Pro Leu Ser Leu Pro Val Thr Leu Gly Gln Pro Ala Ser Ile
165 170 175

Ser Cys Lys Ser Ser Gln Ser Leu Leu Asp Ser Asp Gly Lys Thr Tyr
180 185 190

Leu Asn Trp Leu Gln Gln Arg Pro Gly Gln Ser Pro Arg Arg Leu Ile
195 200 205

Ser Leu Val Ser Lys Leu Asp Ser Gly Val Pro Asp Arg Phe Ser Gly
210 215 220

Ser Gly Ser Gly Thr Asp Phe Thr Leu Lys Ile Ser Arg Val Glu Ala
225 230 235 240

Glu Asp Val Gly Val Tyr Tyr Cys Trp Gln Gly Thr His Phe Pro Gly
245 250 255

Thr Phe Gly Gly Gly Thr Lys Val Glu Ile Lys Gly Ser His His His
260 265 270

His His His His His
275

<210> SEQ ID NO 54
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atggccctcc ctgtcaccgc cctgctgctt ccgctggctc ttctgctcca cgccgctcgg     60
cccgaaatcc agctggtgca aagcggagcc gaggtgaaga agcccggaga atccctgcgc    120
atctcgtgta agggttccgg ctttaacatc gaggattact acatccactg ggtgagacag    180
atgccgggca aaggtctgga atggatgggc cgcatcgacc cggagaacga cgaaaccaaa    240
tacggaccaa tcttccaagg acatgtgact atttccgcgg atacctccat caacactgtc    300
tacttgcagt ggagctcgct caaggcgtcg gataccgcca tgtactactg cgcattcaga    360
ggaggtgtgt actggggcca gggcactacg gtcaccgtgt cctcgggagg tggagggtca    420
ggaggcggag gctcgggcgg tggaggatca ggcggaggag gaagcgatgt ggtcatgact    480
caatccccac tgtcactgcc tgtcactctg ggcaaccgg cttccatctc atgcaagtca     540
agccaatcgc tgctcgactc cgacggaaaa acctacctca attggcttca gcagcgccca    600
ggccagtcgc ctcggaggct gatctcactc gtgtcgaagc ttgactccgg ggtgccggat    660
cggtttagcg gaagcggatc ggggaccgac ttcacgttga agattagccg ggtggaagcc    720
gaggacgtgg gagtctatta ctgctggcag gggacccact tcccggggac tttcggagga    780
ggcaccaaag tcgagattaa gaccactacc ccagcaccga ggccacccac cccggctcct    840
accatcgcct cccagcctct gtccctgcgt ccggaggcat gtagacccgc agctggtggg    900
gccgtgcata cccggggtct tgacttcgcc tgcgatatct acatttgggc ccctctggct    960
ggtacttgcg gggtcctgct gctttcactc gtgatcactc tttactgtaa gcgcggtcgg   1020
aagaagctgc tgtacatctt taagcaaccc ttcatgaggc ctgtgcagac tactcaagag   1080
gaggacggct gttcatgccg gttcccagag gaggaggaag gcggctgcga actgcgcgtg   1140
aaattcagcc gcagcgcaga tgctccagcc tacaagcagg ggcagaacca gctctacaac   1200
gaactcaatc ttggtcggag agaggagtac gacgtgctgg acaagcggag aggacgggac   1260
ccagaaatgg gcgggaagcc gcgcagaaag aatccccaag agggcctgta caacgagctc   1320
caaaaggata agatggcaga agcctatagc gagattggta tgaaagggga acgcagaaga   1380
ggcaaaggcc acgacggact gtaccaggga ctcagcaccg ccaccaagga cacctatgac   1440
gctcttcaca tgcaggccct gccgcctcgg                                    1470
```

<210> SEQ ID NO 55
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

```
Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Glu Ser Leu Arg Ile Ser Cys Lys Gly Ser Gly Phe
        35                  40                  45

Asn Ile Glu Asp Tyr Tyr Ile His Trp Val Arg Gln Met Pro Gly Lys
    50                  55                  60

Gly Leu Glu Trp Met Gly Arg Ile Asp Pro Glu Asn Asp Glu Thr Lys
65                  70                  75                  80
```

-continued

```
Tyr Gly Pro Ile Phe Gln Gly His Val Thr Ile Ser Ala Asp Thr Ser
                85                  90                  95

Ile Asn Thr Val Tyr Leu Gln Trp Ser Ser Leu Lys Ala Ser Asp Thr
            100                 105                 110

Ala Met Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Leu Ser Leu Pro Val Thr Leu Gly Gln Pro Ala Ser Ile
                165                 170                 175

Ser Cys Lys Ser Ser Gln Ser Leu Leu Asp Ser Asp Gly Lys Thr Tyr
            180                 185                 190

Leu Asn Trp Leu Gln Gln Arg Pro Gly Gln Ser Pro Arg Arg Leu Ile
        195                 200                 205

Ser Leu Val Ser Lys Leu Asp Ser Gly Val Pro Asp Arg Phe Ser Gly
    210                 215                 220

Ser Gly Ser Gly Thr Asp Phe Thr Leu Lys Ile Ser Arg Val Glu Ala
225                 230                 235                 240

Glu Asp Val Gly Val Tyr Tyr Cys Trp Gln Gly Thr His Phe Pro Gly
                245                 250                 255

Thr Phe Gly Gly Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 56
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245
```

<210> SEQ ID NO 57
<211> LENGTH: 738
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57

```
gacgtcgtca tgacccagag cccgctgtca ctgcctgtga ccctgggcca gccggcgtcc      60

attagctgca aatcctcgca atccctgctc gactcagacg gaaaaacgta cttgaactgg     120

ctccaacagc gccctgggca atccccaagg cggcttatct cactcgtcag caagctcgat     180

agcggtgtcc cagacagatt ttcgggctcg ggatcgggca ctgatttcac tctgaagatc     240

tcgcgggtgg aagccgagga tgtgggagtg tactattgct ggcagggcac tcacttcccc     300
```

gggacgtttg gcggaggaac taaggtcgag atcaaaggag gaggtggatc aggcggaggt 360
gggagcggag gaggaggaag cggtggtgga ggttccgaaa tccagctggt gcaatcagga 420
gccgaggtga agaagccggg agaatccctg cgcatctcgt gcaagggctc gggcttcaac 480
atcgaggatt actacatcca ctgggtgcgg cagatgccgg gaaaggggtt ggaatggatg 540
ggacgcattg acccggaaaa tgatgaaacc aaatacgggc caatcttcca aggccacgtg 600
accattagcg ctgacacttc catcaacacc gtgtaccttc agtggtcctc actgaaggcg 660
tcggacactg ccatgtacta ctgtgcattc agaggagggg tctactgggg acagggcacc 720
accgtgaccg tgagctcc 738

<210> SEQ ID NO 58
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
atggccctcc ctgtcaccgc cctgctgctt ccgctggctc ttctgctcca cgccgctcgg 60
cccgacgtcg tcatgaccca gagcccgctg tcactgcctg tgaccctggg ccagccggcg 120
tccattagct gcaaatcctc gcaatccctg ctcgactcag acggaaaaac gtacttgaac 180
tggctccaac agcgccctgg gcaatcccca aggcggctta tctcactcgt cagcaagctc 240
gatagcggtg tcccagacag atttcgggc tcgggatcgg gcactgattt cactctgaag 300
atctcgcggg tggaagccga ggatgtggga gtgtactatt gctggcaggg cactcacttc 360
cccgggacgt ttggcggagg aactaaggtc gagatcaaag gaggaggtgg atcaggcgga 420
ggtgggagcg gaggaggagg aagcggtggt ggaggttccg aaatccagct ggtgcaatca 480
ggagccgagg tgaagaagcc gggagaatcc ctgcgcatct cgtgcaaggg ctcgggcttc 540
aacatcgagg attactacat ccactgggtg cggcagatgc cgggaaaggg gttggaatgg 600
atgggacgca ttgacccgga aaatgatgaa accaaatacg ggccaatctt ccaaggccac 660
gtgaccatta gcgctgacac ttccatcaac accgtgtacc ttcagtggtc ctcactgaag 720
gcgtcggaca ctgccatgta ctactgtgca ttcagaggag gggtctactg gggacagggc 780
accaccgtga ccgtgagctc cggctcgcat caccatcatc accaccatca c 831

<210> SEQ ID NO 59
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Leu Ser Leu
20 25 30

Pro Val Thr Leu Gly Gln Pro Ala Ser Ile Ser Cys Lys Ser Ser Gln
35 40 45

Ser Leu Leu Asp Ser Asp Gly Lys Thr Tyr Leu Asn Trp Leu Gln Gln
50 55 60

-continued

```
Arg Pro Gly Gln Ser Pro Arg Arg Leu Ile Ser Leu Val Ser Lys Leu
65                  70                  75                  80

Asp Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Trp Gln Gly Thr His Phe Pro Gly Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Glu Ser Leu Arg Ile Ser Cys Lys
                165                 170                 175

Gly Ser Gly Phe Asn Ile Glu Asp Tyr Tyr Ile His Trp Val Arg Gln
            180                 185                 190

Met Pro Gly Lys Gly Leu Glu Trp Met Gly Arg Ile Asp Pro Glu Asn
        195                 200                 205

Asp Glu Thr Lys Tyr Gly Pro Ile Phe Gln Gly His Val Thr Ile Ser
    210                 215                 220

Ala Asp Thr Ser Ile Asn Thr Val Tyr Leu Gln Trp Ser Ser Leu Lys
225                 230                 235                 240

Ala Ser Asp Thr Ala Met Tyr Tyr Cys Ala Phe Arg Gly Gly Val Tyr
                245                 250                 255

Trp Gly Gln Gly Thr Thr Val Thr Val Ser Ser Gly Ser His His His
            260                 265                 270

His His His His His
        275


<210> SEQ ID NO 60
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

atggccctcc ctgtcaccgc cctgctgctt ccgctggctc ttctgctcca cgccgctcgg     60

cccgacgtcg tcatgaccca atcccctctc tccctgccgg tcaccctggg tcagccggcg    120

tcgatctcat gcaaaagctc acagtccctg ctggattcgg acggaaaaac ctacttgaac    180

tggctccaac agaggccggg tcagtcccct cgcagactga tctcgctggt gagcaagctc    240

gactcgggtg tgccggatcg gttctccggg tcaggatcgg gcaccgactt tacgctcaag    300

atttcgagag tggaggccga ggatgtggga gtgtactatt gctggcaggg cacgcatttc    360

cccgggacct ttggaggcgg gactaaggtg gaaatcaagg gaggtggcgg atcaggcgga    420

ggaggcagcg gcggaggtgg atcaggaggc ggagggtcag agatccagct ggtccaaagc    480

ggagcagagg tgaagaagcc aggcgagtcc cttcgcattt cgtgcaaagg gagcggcttc    540

aacattgaag attactacat ccactgggtg cggcaaatgc caggaaaggg tctggaatgg    600

atgggacgga tcgacccaga aaatgatgaa actaagtacg gaccgatctt ccaaggacac    660

gtcactatct ccgcggacac ttcgatcaac accgtgtacc tccagtggag cagcttgaaa    720

gcctccgaca ccgctatgta ctactgtgcc ttccgcggag gagtctactg gggacagggg    780
```

```
actactgtga ccgtgtcgtc caccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470


<210> SEQ ID NO 61
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Lys Ser Ser Gln
        35                  40                  45

Ser Leu Leu Asp Ser Asp Gly Lys Thr Tyr Leu Asn Trp Leu Gln Gln
    50                  55                  60

Arg Pro Gly Gln Ser Pro Arg Arg Leu Ile Ser Leu Val Ser Lys Leu
65                  70                  75                  80

Asp Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Trp Gln Gly Thr His Phe Pro Gly Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Glu Ser Leu Arg Ile Ser Cys Lys
                165                 170                 175

Gly Ser Gly Phe Asn Ile Glu Asp Tyr Tyr Ile His Trp Val Arg Gln
            180                 185                 190

Met Pro Gly Lys Gly Leu Glu Trp Met Gly Arg Ile Asp Pro Glu Asn
        195                 200                 205

Asp Glu Thr Lys Tyr Gly Pro Ile Phe Gln Gly His Val Thr Ile Ser
    210                 215                 220

Ala Asp Thr Ser Ile Asn Thr Val Tyr Leu Gln Trp Ser Ser Leu Lys
225                 230                 235                 240
```

Ala Ser Asp Thr Ala Met Tyr Tyr Cys Ala Phe Arg Gly Gly Val Tyr
245 250 255

Trp Gly Gln Gly Thr Thr Val Thr Val Ser Ser Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

Glu Leu Asn Leu Gly Arg Arg Glu Glu Tyr Asp Val Leu Asp Lys Arg
405 410 415

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg
485 490

<210> SEQ ID NO 62
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Glu Ile Gln Leu Val Gln Ser Gly Ala Glu Val Lys Lys Pro Gly Ala
1 5 10 15

Thr Val Lys Ile Ser Cys Lys Gly Ser Gly Phe Asn Ile Glu Asp Tyr
20 25 30

Tyr Ile His Trp Val Gln Gln Ala Pro Gly Lys Gly Leu Glu Trp Met
35 40 45

Gly Arg Ile Asp Pro Glu Asn Asp Glu Thr Lys Tyr Gly Pro Ile Phe
50 55 60

Gln Gly Arg Val Thr Ile Thr Ala Asp Thr Ser Thr Asn Thr Val Tyr
65 70 75 80

Met Glu Leu Ser Ser Leu Arg Ser Glu Asp Thr Ala Val Tyr Tyr Cys
85 90 95

Ala Phe Arg Gly Gly Val Tyr Trp Gly Gln Gly Thr Thr Val Thr Val

```
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 63
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
gaaatccagc tcgtgcagag cggagccgag gtcaagaaac cgggtgctac cgtgaagatt      60

tcatgcaagg gatcgggctt caacatcgag gattactaca tccactgggt gcagcaggca     120

ccaggaaaag gacttgaatg gatgggccgg atcgacccgg aaaatgacga gactaagtac     180

ggccctatct tccaaggacg ggtgacgatc accgcagaca ctagcaccaa caccgtctat     240

atggaactct cgtccctgag gtccgaagat actgccgtgt actactgtgc gtttcgcgga     300

ggtgtgtact ggggacaggg taccaccgtc accgtgtcat cgggcggtgg aggctccggt     360

ggaggagggt caggaggcgg tggaagcgga ggaggcggca gcgacgtggt catgactcaa     420

tcgccgctgt cgctgcccgt cactctggga caacccgcgt ccatcagctg caaatcctcg     480

cagtcactgc ttgactccga tggaaagacc tacctcaact ggctgcagca acgcccaggc     540

caatccccaa gacgcctgat ctcgttggtg tcaaagctgg actcaggggt gccggaccgg     600

ttctccggga gcgggtcggg cacggatttc actctcaaga tctccagagt ggaagccgag     660

gatgtgggag tctactactg ctggcaggga acccatttcc ctggaacttt tggcggagga     720

actaaggtcg agattaaa                                                   738
```

<210> SEQ ID NO 64
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
atggccctcc ctgtcaccgc cctgctgctt ccgctggctc ttctgctcca cgccgctcgg      60
```

```
cccgaaatcc agctcgtgca gagcggagcc gaggtcaaga aaccgggtgc taccgtgaag    120

atttcatgca agggatcggg cttcaacatc gaggattact acatccactg ggtgcagcag    180

gcaccaggaa aaggacttga atggatgggc cggatcgacc cggaaaatga cgagactaag    240

tacggcccta tcttccaagg acgggtgacg atcaccgcag acactagcac caacaccgtc    300

tatatggaac tctcgtccct gaggtccgaa gatactgccg tgtactactg tgcgtttcgc    360

ggaggtgtgt actggggaca gggtaccacc gtcaccgtgt catcgggcgg tggaggctcc    420

ggtggaggag ggtcaggagg cggtggaagc ggaggaggcg gcagcgacgt ggtcatgact    480

caatcgccgc tgtcgctgcc cgtcactctg ggacaacccg cgtccatcag ctgcaaatcc    540

tcgcagtcac tgcttgactc cgatggaaag acctacctca actggctgca gcaacgccca    600

ggccaatccc caagacgcct gatctcgttg gtgtcaaagc tggactcagg ggtgccggac    660

cggttctccg ggagcgggtc gggcacggat ttcactctca agatctccag agtggaagcc    720

gaggatgtgg gagtctacta ctgctggcag ggaacccatt tccctggaac ttttggcgga    780

ggaactaagg tcgagattaa agggagccac catcatcatc accaccacca c             831
```

<210> SEQ ID NO 65
<211> LENGTH: 277
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Ala Thr Val Lys Ile Ser Cys Lys Gly Ser Gly Phe
        35                  40                  45

Asn Ile Glu Asp Tyr Tyr Ile His Trp Val Gln Gln Ala Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly Arg Val Thr Ile Thr Ala Asp Thr Ser
                85                  90                  95

Thr Asn Thr Val Tyr Met Glu Leu Ser Ser Leu Arg Ser Glu Asp Thr
            100                 105                 110

Ala Val Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Leu Ser Leu Pro Val Thr Leu Gly Gln Pro Ala Ser Ile
                165                 170                 175

Ser Cys Lys Ser Ser Gln Ser Leu Leu Asp Ser Asp Gly Lys Thr Tyr
            180                 185                 190

Leu Asn Trp Leu Gln Gln Arg Pro Gly Gln Ser Pro Arg Arg Leu Ile
        195                 200                 205

Ser Leu Val Ser Lys Leu Asp Ser Gly Val Pro Asp Arg Phe Ser Gly
    210                 215                 220
```

```
Ser Gly Ser Gly Thr Asp Phe Thr Leu Lys Ile Ser Arg Val Glu Ala
225                 230                 235                 240

Glu Asp Val Gly Val Tyr Tyr Cys Trp Gln Gly Thr His Phe Pro Gly
                245                 250                 255

Thr Phe Gly Gly Gly Thr Lys Val Glu Ile Lys Gly Ser His His His
            260                 265                 270

His His His His His
        275
```

<210> SEQ ID NO 66
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atggccctcc ctgtcaccgc cctgctgctt ccgctggctc ttctgctcca cgccgctcgg     60

cccgaaatcc agctcgtgca gagcggagcc gaggtcaaga aaccgggtgc taccgtgaag    120

atttcatgca agggatcggg cttcaacatc gaggattact acatccactg ggtgcagcag    180

gcaccaggaa aaggacttga atggatgggc cggatcgacc cggaaaatga cgagactaag    240

tacggcccta tcttccaagg acgggtgacg atcaccgcag acactagcac caacaccgtc    300

tatatggaac tctcgtccct gaggtccgaa gatactgccg tgtactactg tgcgtttcgc    360

ggaggtgtgt actggggaca gggtaccacc gtcaccgtgt catcgggcgg tggaggctcc    420

ggtggaggag ggtcaggagg cggtggaagc ggaggaggcg gcagcgacgt ggtcatgact    480

caatcgccgc tgtcgctgcc cgtcactctg ggacaacccg cgtccatcag ctgcaaatcc    540

tcgcagtcac tgcttgactc cgatggaaag acctacctca actggctgca gcaacgccca    600

ggccaatccc caagacgcct gatctcgttg gtgtcaaagc tggactcagg ggtgccggac    660

cggttctccg ggagcgggtc gggcacggat ttcactctca agatctccag agtggaagcc    720

gaggatgtgg gagtctacta ctgctggcag ggaacccatt tccctggaac ttttggcgga    780

ggaactaagg tcgagattaa aaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

<210> SEQ ID NO 67
<211> LENGTH: 490
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 67

Met Ala Leu Pro Val Thr Ala Leu Leu Leu Pro Leu Ala Leu Leu Leu
1 5 10 15

His Ala Ala Arg Pro Glu Ile Gln Leu Val Gln Ser Gly Ala Glu Val
20 25 30

Lys Lys Pro Gly Ala Thr Val Lys Ile Ser Cys Lys Gly Ser Gly Phe
35 40 45

Asn Ile Glu Asp Tyr Tyr Ile His Trp Val Gln Gln Ala Pro Gly Lys
50 55 60

Gly Leu Glu Trp Met Gly Arg Ile Asp Pro Glu Asn Asp Glu Thr Lys
65 70 75 80

Tyr Gly Pro Ile Phe Gln Gly Arg Val Thr Ile Thr Ala Asp Thr Ser
85 90 95

Thr Asn Thr Val Tyr Met Glu Leu Ser Ser Leu Arg Ser Glu Asp Thr
100 105 110

Ala Val Tyr Tyr Cys Ala Phe Arg Gly Gly Val Tyr Trp Gly Gln Gly
115 120 125

Thr Thr Val Thr Val Ser Ser Gly Gly Gly Gly Ser Gly Gly Gly Gly
130 135 140

Ser Gly Gly Gly Gly Ser Gly Gly Gly Gly Ser Asp Val Val Met Thr
145 150 155 160

Gln Ser Pro Leu Ser Leu Pro Val Thr Leu Gly Gln Pro Ala Ser Ile
165 170 175

Ser Cys Lys Ser Ser Gln Ser Leu Leu Asp Ser Asp Gly Lys Thr Tyr
180 185 190

Leu Asn Trp Leu Gln Gln Arg Pro Gly Gln Ser Pro Arg Arg Leu Ile
195 200 205

Ser Leu Val Ser Lys Leu Asp Ser Gly Val Pro Asp Arg Phe Ser Gly
210 215 220

Ser Gly Ser Gly Thr Asp Phe Thr Leu Lys Ile Ser Arg Val Glu Ala
225 230 235 240

Glu Asp Val Gly Val Tyr Tyr Cys Trp Gln Gly Thr His Phe Pro Gly
245 250 255

Thr Phe Gly Gly Gly Thr Lys Val Glu Ile Lys Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala
305 310 315 320

Gly Thr Cys Gly Val Leu Leu Leu Ser Leu Val Ile Thr Leu Tyr Cys
325 330 335

Lys Arg Gly Arg Lys Lys Leu Leu Tyr Ile Phe Lys Gln Pro Phe Met
340 345 350

Arg Pro Val Gln Thr Thr Gln Glu Glu Asp Gly Cys Ser Cys Arg Phe
355 360 365

Pro Glu Glu Glu Glu Gly Gly Cys Glu Leu Arg Val Lys Phe Ser Arg
370 375 380

Ser Ala Asp Ala Pro Ala Tyr Lys Gln Gly Gln Asn Gln Leu Tyr Asn
385 390 395 400

```
Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 68
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 69
<211> LENGTH: 738
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 69
gaaatccagc tggtgcagtc aggcgccgag gtcaagaagc cgggagagtc gctgagaatc 60
tcgtgcaagg gctcggggtt caacatcgag gactactaca ttcactgggt caggcagatg 120
ccgggaaagg gactggaatg gatgggccgg atcgacccag aaaatgacga aaccaaatac 180
gggccgattt ttcaaggcca cgtgactatc agcgcagaca cgagcatcaa cactgtctac 240
ctccagtggt cctcgcttaa ggccagcgat accgctatgt actactgcgc attcagaggc 300
ggggtgtact ggggacaagg aaccactgtg accgtgagca gcggaggtgg cggctcggga 360
ggaggtggga gcggaggagg aggttccggc ggtggaggat cagatgtcgt gatgacccag 420
tccccggact ccctcgctgt ctcactgggc gagcgcgcga ccatcaactg caaatcgagc 480
cagtcgctgt tggactccga tggaaagact tatctgaatt ggctgcaaca gaaaccagga 540
caacctccca agcggctcat ctcgcttgtg tcaaaactcg attcgggagt gccagaccgc 600
ttctcggggt ccgggagcgg aactgacttt actttgacca tttcctcact gcaagcggag 660
gatgtggccg tgtattactg ttggcagggc acgcatttcc ctggaacctt cggtggcgga 720
actaaggtgg aaatcaag 738

<210> SEQ ID NO 70
<211> LENGTH: 834
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
atggccctcc ctgtcaccgc cctgctgctt ccgctggctc ttctgctcca cgccgctcgg 60
cccgaaatcc agctggtgca gtcaggcgcc gaggtcaaga agccgggaga gtcgctgaga 120
atctcgtgca agggctcggg gttcaacatc gaggactact acattcactg ggtcaggcag 180
atgccgggaa agggactgga atggatgggc cggatcgacc cagaaaatga cgaaaccaaa 240
tacgggccga tttttcaagg ccacgtgact atcagcgcag acacgagcat caacactgtc 300
tacctccagt ggtcctcgct taaggccagc gataccgcta tgtactactg cgcattcaga 360
ggcggggtgt actggggaca aggaaccact gtgaccgtga gcagcggagg tggcggctcg 420
ggaggaggtg ggagcggagg aggaggttcc ggcggtggag gatcagatgt cgtgatgacc 480
cagtccccgg actccctcgc tgtctcactg ggcgagcgcg cgaccatcaa ctgcaaatcg 540
agccagtcgc tgttggactc cgatggaaag acttatctga attggctgca acagaaacca 600
ggacaacctc ccaagcggct catctcgctt gtgtcaaaac tcgattcggg agtgccagac 660
cgcttctcgg ggtccgggag cggaactgac tttactttga ccatttcctc actgcaagcg 720
gaggatgtgg ccgtgtatta ctgttggcag ggcacgcatt tccctggaac cttcggtggc 780
ggaactaagg tggaaatcaa gggatcacac caccatcatc accatcacca ccat 834

<210> SEQ ID NO 71
<211> LENGTH: 278
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 71

Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Glu Ser Leu Arg Ile Ser Cys Lys Gly Ser Gly Phe
        35                  40                  45

Asn Ile Glu Asp Tyr Tyr Ile His Trp Val Arg Gln Met Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly His Val Thr Ile Ser Ala Asp Thr Ser
                85                  90                  95

Ile Asn Thr Val Tyr Leu Gln Trp Ser Ser Leu Lys Ala Ser Asp Thr
            100                 105                 110

Ala Met Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Leu Leu Asp Ser Asp Gly Lys Thr Tyr
            180                 185                 190

Leu Asn Trp Leu Gln Gln Lys Pro Gly Gln Pro Pro Lys Arg Leu Ile
        195                 200                 205

Ser Leu Val Ser Lys Leu Asp Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Trp Gln Gly Thr His Phe Pro Gly
                245                 250                 255

Thr Phe Gly Gly Gly Thr Lys Val Glu Ile Lys Gly Ser His His His
            260                 265                 270

His His His His His His
        275


<210> SEQ ID NO 72
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

atggccctcc ctgtcaccgc cctgctgctt ccgctggctc ttctgctcca cgccgctcgg      60

cccgagattc agctcgtgca atcgggagcg gaagtcaaga agccaggaga gtccttgcgg     120

atctcatgca agggtagcgg ctttaacatc gaggattact acatccactg ggtgaggcag     180

atgccgggga agggactcga atggatggga cggatcgacc cagaaaacga cgaaactaag     240
```

```
tacggtccga tcttccaagg ccatgtgact attagcgccg atacttcaat caataccgtg    300

tatctgcaat ggtcctcatt gaaagcctca gataccgcga tgtactactg tgctttcaga    360

ggaggggtct actggggaca gggaactacc gtgactgtct cgtccggcgg aggcgggtca    420

ggaggtggcg gcagcggagg aggagggtcc ggcggaggtg ggtccgacgt cgtgatgacc    480

cagagccctg acagcctggc agtgagcctg ggcgaaagag ctaccattaa ctgcaaatcg    540

tcgcagagcc tgctggactc ggacggaaaa acgtacctca attggctgca gcaaaagcct    600

ggccagccac cgaagcgcct tatctcactg gtgtcgaagc tggattcggg agtgcccgat    660

cgcttctccg gctcgggatc gggtactgac ttcaccctca ctatctcctc gcttcaagca    720

gaggacgtgg ccgtctacta ctgctggcag ggaacccact ttccgggaac cttcggcgga    780

gggacgaaag tggagatcaa gaccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140

aaattcagcc gcagcgcaga tgctccagcc tacaagcagg ggcagaacca gctctacaac   1200

gaactcaatc ttggtcggag agaggagtac gacgtgctgg acaagcggag aggacgggac   1260

ccagaaatgg gcgggaagcc gcgcagaaag aatccccaag agggcctgta caacgagctc   1320

caaaaggata agatggcaga agcctatagc gagattggta tgaaagggga acgcagaaga   1380

ggcaaaggcc acgacggact gtaccaggga ctcagcaccg ccaccaagga cacctatgac   1440

gctcttcaca tgcaggccct gccgcctcgg                                    1470
```

```
<210> SEQ ID NO 73
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ala Leu Pro Val Thr Ala Leu Leu Leu Pro Leu Ala Leu Leu Leu
1               5                   10                  15

His Ala Ala Arg Pro Glu Ile Gln Leu Val Gln Ser Gly Ala Glu Val
            20                  25                  30

Lys Lys Pro Gly Glu Ser Leu Arg Ile Ser Cys Lys Gly Ser Gly Phe
        35                  40                  45

Asn Ile Glu Asp Tyr Tyr Ile His Trp Val Arg Gln Met Pro Gly Lys
    50                  55                  60

Gly Leu Glu Trp Met Gly Arg Ile Asp Pro Glu Asn Asp Glu Thr Lys
65                  70                  75                  80

Tyr Gly Pro Ile Phe Gln Gly His Val Thr Ile Ser Ala Asp Thr Ser
                85                  90                  95

Ile Asn Thr Val Tyr Leu Gln Trp Ser Ser Leu Lys Ala Ser Asp Thr
            100                 105                 110

Ala Met Tyr Tyr Cys Ala Phe Arg Gly Gly Val Tyr Trp Gly Gln Gly
        115                 120                 125

Thr Thr Val Thr Val Ser Ser Gly Gly Gly Gly Ser Gly Gly Gly Gly
```

```
    130                 135                 140

Ser Gly Gly Gly Gly Ser Gly Gly Gly Gly Ser Asp Val Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Leu Leu Asp Ser Asp Gly Lys Thr Tyr
            180                 185                 190

Leu Asn Trp Leu Gln Gln Lys Pro Gly Gln Pro Pro Lys Arg Leu Ile
        195                 200                 205

Ser Leu Val Ser Lys Leu Asp Ser Gly Val Pro Asp Arg Phe Ser Gly
    210                 215                 220

Ser Gly Ser Gly Thr Asp Phe Thr Leu Thr Ile Ser Ser Leu Gln Ala
225                 230                 235                 240

Glu Asp Val Ala Val Tyr Tyr Cys Trp Gln Gly Thr His Phe Pro Gly
                245                 250                 255

Thr Phe Gly Gly Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 74
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

```
Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Asp Gly Lys Thr Tyr Leu Asn Trp Leu Gln Gln Lys Pro Gly Gln Pro
        35                  40                  45

Pro Lys Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245
```

<210> SEQ ID NO 75
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 75

```
gacgtggtga tgacccaatc gccagattcc ctggcagtgt ccctgggcga acgcgccact      60

attaactgca aatcgtcaca gtccttgctt gattccgacg gaaagaccta cctcaattgg     120

ctccagcaga agccaggaca accgccaaag agactgatct ccctggtgtc aaagctggac     180

tcgggagtgc ctgatcggtt ctcgggtagc gggagcggca ccgacttcac tctgaccatc     240

tcgtcactcc aggctgagga cgtggccgtg tattactgtt ggcagggtac tcactttccg     300

ggcactttcg gaggcggcac caaggtggag attaaaggag gaggcggaag cggaggtgga     360

ggatcgggag gtggtgggag cggcggagga gggagcgaga tccagctcgt ccaatcggga     420

gcggaagtga agaagcccgg agagtcactt agaatctcat gcaaggggtc gggcttcaac     480

atcgaggatt actacatcca ttgggtccgc cagatgcctg gtaaaggact ggaatggatg     540

gggaggattg acccggaaaa cgacgaaact aagtacggac cgatctttca agggcacgtg     600
```

-continued actatctccg ctgatacctc aatcaatact gtctacctcc agtggtcctc gctgaaagca 660
agcgacaccg cgatgtacta ctgcgccttc cggggaggag tgtactgggg ccaaggcacc 720
acggtcacgg tcagctcc 738

<210> SEQ ID NO 76
<211> LENGTH: 834
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 76
atggccctcc ctgtcaccgc cctgctgctt ccgctggctc ttctgctcca cgccgctcgg 60
cccgacgtgg tgatgaccca atcgccagat tccctggcag tgtccctggg cgaacgcgcc 120
actattaact gcaaatcgtc acagtccttg cttgattccg acggaaagac ctacctcaat 180
tggctccagc agaagccagg acaaccgcca aagagactga tctccctggt gtcaaagctg 240
gactcgggag tgcctgatcg gttctcgggt agcgggagcg gcaccgactt cactctgacc 300
atctcgtcac tccaggctga ggacgtggcc gtgtattact gttggcaggg tactcacttt 360
ccgggcactt tcggaggcgg caccaaggtg gagattaaag gaggaggcgg aagcggaggt 420
ggaggatcgg gaggtggtgg gagcggcgga ggagggagcg agatccagct cgtccaatcg 480
ggagcggaag tgaagaagcc cggagagtca cttagaatct catgcaaggg gtcgggcttc 540
aacatcgagg attactacat ccattgggtc cgccagatgc ctggtaaagg actggaatgg 600
atggggagga ttgacccgga aaacgacgaa actaagtacg gaccgatctt tcaagggcac 660
gtgactatct ccgctgatac ctcaatcaat actgtctacc tccagtggtc ctcgctgaaa 720
gcaagcgaca ccgcgatgta ctactgcgcc ttccggggag gagtgtactg gggccaaggc 780
accacggtca cggtcagctc cggctcccat caccaccacc atcaccatca tcac 834

<210> SEQ ID NO 77
<211> LENGTH: 278
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 77

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Asp Ser Leu
20 25 30

Ala Val Ser Leu Gly Glu Arg Ala Thr Ile Asn Cys Lys Ser Ser Gln
35 40 45

Ser Leu Leu Asp Ser Asp Gly Lys Thr Tyr Leu Asn Trp Leu Gln Gln
50 55 60

Lys Pro Gly Gln Pro Pro Lys Arg Leu Ile Ser Leu Val Ser Lys Leu
65 70 75 80

Asp Ser Gly Val Pro Asp Arg Phe Ser Gly Ser Gly Ser Gly Thr Asp
85 90 95

Phe Thr Leu Thr Ile Ser Ser Leu Gln Ala Glu Asp Val Ala Val Tyr
100 105 110

Tyr Cys Trp Gln Gly Thr His Phe Pro Gly Thr Phe Gly Gly Gly Thr
115 120 125

```
Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Glu Ser Leu Arg Ile Ser Cys Lys
                165                 170                 175

Gly Ser Gly Phe Asn Ile Glu Asp Tyr Tyr Ile His Trp Val Arg Gln
            180                 185                 190

Met Pro Gly Lys Gly Leu Glu Trp Met Gly Arg Ile Asp Pro Glu Asn
        195                 200                 205

Asp Glu Thr Lys Tyr Gly Pro Ile Phe Gln Gly His Val Thr Ile Ser
    210                 215                 220

Ala Asp Thr Ser Ile Asn Thr Val Tyr Leu Gln Trp Ser Ser Leu Lys
225                 230                 235                 240

Ala Ser Asp Thr Ala Met Tyr Tyr Cys Ala Phe Arg Gly Gly Val Tyr
                245                 250                 255

Trp Gly Gln Gly Thr Thr Val Thr Val Ser Ser Gly Ser His His His
            260                 265                 270

His His His His His His
        275
```

<210> SEQ ID NO 78
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
atggccctcc ctgtcaccgc cctgctgctt ccgctggctc ttctgctcca cgccgctcgg     60

cccgacgtgg tgatgactca gtcgcctgac tcgctggctg tgtcccttgg agagcgggcc    120

actatcaatt gcaagtcatc ccagtcgctg ctggattccg acgggaaaac ctacctcaat    180

tggctgcagc aaaaaccggg acagcctcca aagcggctca tcagcctggt gtccaagttg    240

gacagcggcg tgccagaccg cttctccggt tcgggaagcg gtactgattt cacgctgacc    300

atctcatccc tccaagcgga ggatgtggca gtctactact gttggcaggg cacgcatttt    360

ccgggcactt ttggaggagg gaccaaggtc gaaatcaagg gaggaggtgg ctcgggcgga    420

ggaggctcgg gaggaggagg atcaggaggc ggtggaagcg agattcaact ggtccagagc    480

ggcgcagaag tcaagaagcc gggtgaatcg ctcagaatct cgtgcaaagg atcgggattc    540

aacatcgagg actactacat tcactgggtc agacaaatgc cgggcaaagg gctggaatgg    600

atggggagga tcgaccccga aaacgatgaa accaagtacg gaccaatctt ccaagggcac    660

gtgaccattt cggcggacac ctcaatcaac actgtgtacc tccagtggag ctcacttaag    720

gccagcgata ccgccatgta ctattgcgct ttccgcggag ggtgtactg gggacagggc    780

actactgtga ccgtgtcatc caccactacc ccagcaccga ggccacccac cccggctcct    840

accatcgcct cccagcctct gtccctgcgt ccggaggcat gtagacccgc agctggtggg    900

gccgtgcata cccggggtct tgacttcgcc tgcgatatct acatttgggc ccctctggct    960

ggtacttgcg gggtcctgct gctttcactc gtgatcactc tttactgtaa gcgcggtcgg   1020

aagaagctgc tgtacatctt taagcaaccc ttcatgaggc ctgtgcagac tactcaagag   1080

gaggacggct gttcatgccg gttcccagag gaggaggaag gcggctgcga actgcgcgtg   1140
```

aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320
caaaaggata agatggcaga agcctatagc gagattggta tgaaagggga acgcagaaga 1380
ggcaaaggcc acgacggact gtaccaggga ctcagcaccg ccaccaagga cacctatgac 1440
gctcttcaca tgcaggccct gccgcctcgg 1470

<210> SEQ ID NO 79
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Asp Ser Leu
20 25 30

Ala Val Ser Leu Gly Glu Arg Ala Thr Ile Asn Cys Lys Ser Ser Gln
35 40 45

Ser Leu Leu Asp Ser Asp Gly Lys Thr Tyr Leu Asn Trp Leu Gln Gln
50 55 60

Lys Pro Gly Gln Pro Pro Lys Arg Leu Ile Ser Leu Val Ser Lys Leu
65 70 75 80

Asp Ser Gly Val Pro Asp Arg Phe Ser Gly Ser Gly Ser Gly Thr Asp
85 90 95

Phe Thr Leu Thr Ile Ser Ser Leu Gln Ala Glu Asp Val Ala Val Tyr
100 105 110

Tyr Cys Trp Gln Gly Thr His Phe Pro Gly Thr Phe Gly Gly Gly Thr
115 120 125

Lys Val Glu Ile Lys Gly Gly Gly Gly Ser Gly Gly Gly Gly Ser Gly
130 135 140

Gly Gly Gly Ser Gly Gly Gly Gly Ser Glu Ile Gln Leu Val Gln Ser
145 150 155 160

Gly Ala Glu Val Lys Lys Pro Gly Glu Ser Leu Arg Ile Ser Cys Lys
165 170 175

Gly Ser Gly Phe Asn Ile Glu Asp Tyr Tyr Ile His Trp Val Arg Gln
180 185 190

Met Pro Gly Lys Gly Leu Glu Trp Met Gly Arg Ile Asp Pro Glu Asn
195 200 205

Asp Glu Thr Lys Tyr Gly Pro Ile Phe Gln Gly His Val Thr Ile Ser
210 215 220

Ala Asp Thr Ser Ile Asn Thr Val Tyr Leu Gln Trp Ser Ser Leu Lys
225 230 235 240

Ala Ser Asp Thr Ala Met Tyr Tyr Cys Ala Phe Arg Gly Gly Val Tyr
245 250 255

Trp Gly Gln Gly Thr Thr Val Thr Val Ser Ser Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr

```
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 80
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Ala Thr Val Lys Ile Ser Cys Lys Gly Ser Gly Phe Asn
145                 150                 155                 160
```

-continued

```
Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245
```

<210> SEQ ID NO 81
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gatgtggtca tgacgcagtc accactgtcc ctccccgtga cccttggaca gccagcgtcg     60

attagctgca agtcatccca atccctgctc gattcggatg gaaagaccta tctcaactgg    120

ctgcagcaaa gacccggtca gagccctagg agactcatct cgttggtgtc aaagctggac    180

agcggagtgc cggaccggtt ttccggttcg ggatcgggga cggacttcac tctgaagatt    240

tcacgggtgg aagctgagga tgtgggagtg tactactgct ggcagggaac ccatttccct    300

ggcacttttg gcggaggaac taaggtcgaa atcaagggag gaggtggctc gggaggaggc    360

ggatcgggcg gaggcgggag cggcggagga gggtccgaaa tccaacttgt ccagtcagga    420

gccgaagtga agaaaccggg agccaccgtc aaaatcagct gtaagggatc gggattcaat    480

atcgaggact actacatcca ctgggtgcag caagctccgg gcaaaggact ggagtggatg    540

ggggcgcatcg acccagagaa cgacgaaacc aaatacggcc cgatcttcca agggcgggtg    600

accatcaccg cggacacctc aactaacact gtgtacatgg agctgagctc cctgcgctcc    660

gaagatactg cagtctacta ctgcgccttc cgcggtggtg tgtactgggg acagggcacc    720

actgtgactg tcagctcg                                                  738
```

<210> SEQ ID NO 82
<211> LENGTH: 831
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

```
atggccctcc ctgtcaccgc cctgctgctt ccgctggctc ttctgctcca cgccgctcgg     60

cccgatgtgg tcatgacgca gtcaccactg tccctccccg tgacccttgg acagccagcg    120

tcgattagct gcaagtcatc ccaatccctg ctcgattcgg atggaaagac ctatctcaac    180

tggctgcagc aaagacccgg tcagagccct aggagactca tctcgttggt gtcaaagctg    240

gacagcggag tgccggaccg gttttccggt tcgggatcgg ggacggactt cactctgaag    300

atttcacggg tggaagctga ggatgtggga gtgtactact gctggcaggg aacccatttc    360

cctggcactt ttggcggagg aactaaggtc gaaatcaagg gaggaggtgg ctcgggagga    420
```

```
ggcggatcgg gcggaggcgg gagcggcgga ggagggtccg aaatccaact tgtccagtca    480

ggagccgaag tgaagaaacc gggagccacc gtcaaaatca gctgtaaggg atcgggattc    540

aatatcgagg actactacat ccactgggtg cagcaagctc cgggcaaagg actggagtgg    600

atggggcgca tcgacccaga gaacgacgaa accaaatacg gcccgatctt ccaagggcgg    660

gtgaccatca ccgcggacac ctcaactaac actgtgtaca tggagctgag ctccctgcgc    720

tccgaagata ctgcagtcta ctactgcgcc ttccgcggtg gtgtgtactg gggacagggc    780

accactgtga ctgtcagctc ggggtcccac catcatcacc accaccatca c             831
```

<210> SEQ ID NO 83
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Leu Gly Gln Pro Ala Ser Ile Ser Cys Lys Ser Ser Gln
        35                  40                  45

Ser Leu Leu Asp Ser Asp Gly Lys Thr Tyr Leu Asn Trp Leu Gln Gln
    50                  55                  60

Arg Pro Gly Gln Ser Pro Arg Arg Leu Ile Ser Leu Val Ser Lys Leu
65                  70                  75                  80

Asp Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Trp Gln Gly Thr His Phe Pro Gly Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Ala Thr Val Lys Ile Ser Cys Lys
                165                 170                 175

Gly Ser Gly Phe Asn Ile Glu Asp Tyr Tyr Ile His Trp Val Gln Gln
            180                 185                 190

Ala Pro Gly Lys Gly Leu Glu Trp Met Gly Arg Ile Asp Pro Glu Asn
        195                 200                 205

Asp Glu Thr Lys Tyr Gly Pro Ile Phe Gln Gly Arg Val Thr Ile Thr
    210                 215                 220

Ala Asp Thr Ser Thr Asn Thr Val Tyr Met Glu Leu Ser Ser Leu Arg
225                 230                 235                 240

Ser Glu Asp Thr Ala Val Tyr Tyr Cys Ala Phe Arg Gly Gly Val Tyr
                245                 250                 255

Trp Gly Gln Gly Thr Thr Val Thr Val Ser Ser Gly Ser His His His
            260                 265                 270

His His His His His
        275
```

<210> SEQ ID NO 84
<211> LENGTH: 1470
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 84
atggccctcc ctgtcaccgc cctgctgctt ccgctggctc ttctgctcca cgccgctcgg 60
cccgatgtgg tcatgacgca gtcaccactg tccctccccg tgacccttgg acagccagcg 120
tcgattagct gcaagtcatc ccaatccctg ctcgattcgg atggaaagac ctatctcaac 180
tggctgcagc aaagacccgg tcagagccct aggagactca tctcgttggt gtcaaagctg 240
gacagcggag tgccggaccg gttttccggt tcgggatcgg ggacggactt cactctgaag 300
atttcacggg tggaagctga ggatgtggga gtgtactact gctggcaggg aacccatttc 360
cctggcactt ttggcggagg aactaaggtc gaaatcaagg gaggaggtgg ctcgggagga 420
ggcggatcgg gcggaggcgg gagcggcgga ggagggtccg aaatccaact tgtccagtca 480
ggagccgaag tgaagaaacc gggagccacc gtcaaaatca gctgtaaggg atcgggattc 540
aatatcgagg actactacat ccactgggtg cagcaagctc cgggcaaagg actggagtgg 600
atggggcgca tcgacccaga gaacgacgaa accaaatacg gcccgatctt ccaagggcgg 660
gtgaccatca ccgcggacac ctcaactaac actgtgtaca tggagctgag ctccctgcgc 720
tccgaagata ctgcagtcta ctactgcgcc ttccgcggtg gtgtgtactg ggacagggc 780 accactgtga ctgtcagctc gaccactacc ccagcaccga ggccacccac cccggctcct 840
accatcgcct cccagcctct gtccctgcgt ccggaggcat gtagacccgc agctggtggg 900
gccgtgcata cccggggtct tgacttcgcc tgcgatatct acatttgggc ccctctggct 960
ggtacttgcg gggtcctgct gctttcactc gtgatcactc tttactgtaa gcgcggtcgg 1020
aagaagctgc tgtacatctt taagcaaccc ttcatgaggc ctgtgcagac tactcaagag 1080
gaggacggct gttcatgccg gttcccagag gaggaggaag gcggctgcga actgcgcgtg 1140
aaattcagcc gcagcgcaga tgctccagcc tacaagcagg ggcagaacca gctctacaac 1200
gaactcaatc ttggtcggag agaggagtac gacgtgctgg acaagcggag aggacgggac 1260
ccagaaatgg gcgggaagcc gcgcagaaag aatccccaag agggcctgta caacgagctc 1320
caaaaggata agatggcaga agcctatagc gagattggta tgaaagggga acgcagaaga 1380
ggcaaaggcc acgacggact gtaccaggga ctcagcaccg ccaccaagga cacctatgac 1440
gctcttcaca tgcaggccct gccgcctcgg 1470

<210> SEQ ID NO 85
<211> LENGTH: 490
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Met Ala Leu Pro Val Thr Ala Leu Leu Leu Pro Leu Ala Leu Leu Leu
1 5 10 15

His Ala Ala Arg Pro Asp Val Val Met Thr Gln Ser Pro Leu Ser Leu
20 25 30

-continued

```
Pro Val Thr Leu Gly Gln Pro Ala Ser Ile Ser Cys Lys Ser Ser Gln
        35                  40                  45

Ser Leu Leu Asp Ser Asp Gly Lys Thr Tyr Leu Asn Trp Leu Gln Gln
    50                  55                  60

Arg Pro Gly Gln Ser Pro Arg Arg Leu Ile Ser Leu Val Ser Lys Leu
65                  70                  75                  80

Asp Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Trp Gln Gly Thr His Phe Pro Gly Thr Phe Gly Gly Gly Thr
        115                 120                 125

Lys Val Glu Ile Lys Gly Gly Gly Gly Ser Gly Gly Gly Gly Ser Gly
    130                 135                 140

Gly Gly Gly Ser Gly Gly Gly Gly Ser Glu Ile Gln Leu Val Gln Ser
145                 150                 155                 160

Gly Ala Glu Val Lys Lys Pro Gly Ala Thr Val Lys Ile Ser Cys Lys
                165                 170                 175

Gly Ser Gly Phe Asn Ile Glu Asp Tyr Tyr Ile His Trp Val Gln Gln
            180                 185                 190

Ala Pro Gly Lys Gly Leu Glu Trp Met Gly Arg Ile Asp Pro Glu Asn
        195                 200                 205

Asp Glu Thr Lys Tyr Gly Pro Ile Phe Gln Gly Arg Val Thr Ile Thr
    210                 215                 220

Ala Asp Thr Ser Thr Asn Thr Val Tyr Met Glu Leu Ser Ser Leu Arg
225                 230                 235                 240

Ser Glu Asp Thr Ala Val Tyr Tyr Cys Ala Phe Arg Gly Gly Val Tyr
                245                 250                 255

Trp Gly Gln Gly Thr Thr Val Thr Val Ser Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Lys Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
```

```
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 86
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
    50                  55                  60

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
            100                 105                 110

Ser Ser Gly Gly Gly Gly Ser Gly Gly Gly Gly Ser Gly Gly Gly Gly
        115                 120                 125

Ser His Met Asp Val Val Met Thr Gln Ser Pro Leu Thr Leu Ser Val
    130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Arg Ile Ser Arg Val Glu Ala Glu Asp Leu Gly Ile Tyr Tyr Cys
    210                 215                 220

Trp Gln Gly Thr His Phe Pro Gly Thr Phe Gly Gly Gly Thr Lys Leu
225                 230                 235                 240

Glu Ile Lys


<210> SEQ ID NO 87
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

atggccctcc ctgtcaccgc cctgctgctt ccgctggctc ttctgctcca cgccgctcgg     60
```

-continued

```
cccgagatcc agctccaaca gagcggagcc gaactggtca aaccgggagc gtcggtgaag    120

ttgtcatgca ctggatcggg cttcaacatc gaggattact acatccactg ggtcaagcaa    180

cgcaccgagc aggggctgga atggatcgga cggatcgacc ccgaaaacga tgaaaccaag    240

tacgggccta tcttccaagg acgggccacc attacggctg acacgtcaag caataccgtc    300

tacctccagc tttccagcct gacctccgag gacactgccg tgtactactg cgccttcaga    360

ggaggcgtgt actggggacc aggaaccact ttgaccgtgt ccagcggagg cggtggatca    420

ggaggaggag gctcaggcgg tggcggctcg cacatggacg tggtcatgac tcagtccccg    480

ctgaccctgt cggtggcaat tggacagagc gcatccatct cgtgcaagag ctcacagtcg    540

ctgctggatt ccgacggaaa gacttatctg aactggctgc tccaaagacc agggcaatca    600

ccgaaacgcc ttatctccct ggtgtcgaaa ctcgactcgg gtgtgccgga tcggtttacc    660

ggtagcgggt ccggcacgga cttcactctc cgcatttcga gggtggaagc ggaggatctc    720

gggatctact actgttggca gggaacccac ttccctggga cttttggagg cggaactaag    780

ctggaaatca agggtagcca tcaccatcac caccaccatc at                      822
```

<210> SEQ ID NO 88
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Met Ala Leu Pro Val Thr Ala Leu Leu Leu Pro Leu Ala Leu Leu Leu
1               5                   10                  15

His Ala Ala Arg Pro Glu Ile Gln Leu Gln Gln Ser Gly Ala Glu Leu
            20                  25                  30

Val Lys Pro Gly Ala Ser Val Lys Leu Ser Cys Thr Gly Ser Gly Phe
        35                  40                  45

Asn Ile Glu Asp Tyr Tyr Ile His Trp Val Lys Gln Arg Thr Glu Gln
    50                  55                  60

Gly Leu Glu Trp Ile Gly Arg Ile Asp Pro Glu Asn Asp Glu Thr Lys
65                  70                  75                  80

Tyr Gly Pro Ile Phe Gln Gly Arg Ala Thr Ile Thr Ala Asp Thr Ser
                85                  90                  95

Ser Asn Thr Val Tyr Leu Gln Leu Ser Ser Leu Thr Ser Glu Asp Thr
            100                 105                 110

Ala Val Tyr Tyr Cys Ala Phe Arg Gly Gly Val Tyr Trp Gly Pro Gly
        115                 120                 125

Thr Thr Leu Thr Val Ser Ser Gly Gly Gly Gly Ser Gly Gly Gly Gly
    130                 135                 140

Ser Gly Gly Gly Gly Ser His Met Asp Val Val Met Thr Gln Ser Pro
145                 150                 155                 160

Leu Thr Leu Ser Val Ala Ile Gly Gln Ser Ala Ser Ile Ser Cys Lys
                165                 170                 175

Ser Ser Gln Ser Leu Leu Asp Ser Asp Gly Lys Thr Tyr Leu Asn Trp
            180                 185                 190

Leu Leu Gln Arg Pro Gly Gln Ser Pro Lys Arg Leu Ile Ser Leu Val
        195                 200                 205

Ser Lys Leu Asp Ser Gly Val Pro Asp Arg Phe Thr Gly Ser Gly Ser
    210                 215                 220
```

```
Gly Thr Asp Phe Thr Leu Arg Ile Ser Arg Val Glu Ala Glu Asp Leu
225                 230                 235                 240

Gly Ile Tyr Tyr Cys Trp Gln Gly Thr His Phe Pro Gly Thr Phe Gly
                245                 250                 255

Gly Gly Thr Lys Leu Glu Ile Lys Gly Ser His His His His His His
            260                 265                 270

His His
```

<210> SEQ ID NO 89
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
atggccctcc ctgtcaccgc cctgctgctt ccgctggctc ttctgctcca cgccgctcgg     60

cccgagatcc agctccaaca gagcggagcc gaactggtca aaccgggagc gtcggtgaag    120

ttgtcatgca ctggatcggg cttcaacatc gaggattact acatccactg ggtcaagcaa    180

cgcaccgagc aggggctgga atggatcgga cggatcgacc ccgaaaacga tgaaaccaag    240

tacgggccta tcttccaagg acgggccacc attacggctg acacgtcaag caataccgtc    300

tacctccagc tttccagcct gacctccgag gacactgccg tgtactactg cgccttcaga    360

ggaggcgtgt actggggacc aggaaccact ttgaccgtgt ccagcggagg cggtggatca    420

ggaggaggag gctcaggcgg tggcggctcg cacatggacg tggtcatgac tcagtccccg    480

ctgaccctgt cggtggcaat tggacagagc gcatccatct cgtgcaagag ctcacagtcg    540

ctgctggatt ccgacggaaa gacttatctg aactggctgc tccaaagacc agggcaatca    600

ccgaaacgcc ttatctccct ggtgtcgaaa ctcgactcgg gtgtgccgga tcggtttacc    660

ggtagcgggt ccggcacgga cttcactctc cgcatttcga gggtggaagc ggaggatctc    720

gggatctact actgttggca gggaacccac ttccctggga cttttggagg cggaactaag    780

ctggaaatca agaccactac cccagcaccg aggccaccca ccccggctcc taccatcgcc    840

tcccagcctc tgtccctgcg tccggaggca tgtagacccg cagctggtgg ggccgtgcat    900

acccggggtc ttgacttcgc ctgcgatatc tacatttggg cccctctggc tggtacttgc    960

ggggtcctgc tgctttcact cgtgatcact ctttactgta agcgcggtcg gaagaagctg   1020

ctgtacatct ttaagcaacc cttcatgagg cctgtgcaga ctactcaaga ggaggacggc   1080

tgttcatgcc ggttcccaga ggaggaggaa ggcggctgcg aactgcgcgt gaaattcagc   1140

cgcagcgcag atgctccagc ctacaagcag gggcagaacc agctctacaa cgaactcaat   1200

cttggtcgga gagaggagta cgacgtgctg gacaagcgga gaggacggga cccagaaatg   1260

ggcgggaagc cgcgcagaaa gaatccccaa gagggcctgt acaacgagct ccaaaaggat   1320

aagatggcag aagcctatag cgagattggt atgaaagggg aacgcagaag aggcaaaggc   1380

cacgacggac tgtaccaggg actcagcacc gccaccaagg acacctatga cgctcttcac   1440

atgcaggccc tgccgcctcg g                                               1461
```

<210> SEQ ID NO 90
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Met Ala Leu Pro Val Thr Ala Leu Leu Leu Pro Leu Ala Leu Leu Leu
1               5                   10                  15

His Ala Ala Arg Pro Glu Ile Gln Leu Gln Gln Ser Gly Ala Glu Leu
            20                  25                  30

Val Lys Pro Gly Ala Ser Val Lys Leu Ser Cys Thr Gly Ser Gly Phe
        35                  40                  45

Asn Ile Glu Asp Tyr Tyr Ile His Trp Val Lys Gln Arg Thr Glu Gln
    50                  55                  60

Gly Leu Glu Trp Ile Gly Arg Ile Asp Pro Glu Asn Asp Glu Thr Lys
65                  70                  75                  80

Tyr Gly Pro Ile Phe Gln Gly Arg Ala Thr Ile Thr Ala Asp Thr Ser
                85                  90                  95

Ser Asn Thr Val Tyr Leu Gln Leu Ser Ser Leu Thr Ser Glu Asp Thr
            100                 105                 110

Ala Val Tyr Tyr Cys Ala Phe Arg Gly Gly Val Tyr Trp Gly Pro Gly
        115                 120                 125

Thr Thr Leu Thr Val Ser Ser Gly Gly Gly Gly Ser Gly Gly Gly Gly
    130                 135                 140

Ser Gly Gly Gly Gly Ser His Met Asp Val Val Met Thr Gln Ser Pro
145                 150                 155                 160

Leu Thr Leu Ser Val Ala Ile Gly Gln Ser Ala Ser Ile Ser Cys Lys
                165                 170                 175

Ser Ser Gln Ser Leu Leu Asp Ser Asp Gly Lys Thr Tyr Leu Asn Trp
            180                 185                 190

Leu Leu Gln Arg Pro Gly Gln Ser Pro Lys Arg Leu Ile Ser Leu Val
        195                 200                 205

Ser Lys Leu Asp Ser Gly Val Pro Asp Arg Phe Thr Gly Ser Gly Ser
    210                 215                 220

Gly Thr Asp Phe Thr Leu Arg Ile Ser Arg Val Glu Ala Glu Asp Leu
225                 230                 235                 240

Gly Ile Tyr Tyr Cys Trp Gln Gly Thr His Phe Pro Gly Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400
```

```
Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 91
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Val
        115                 120                 125

Leu Glu Ser Gly Gly Gly Leu Val Gln Pro Gly Gly Ser Leu Arg Leu
    130                 135                 140

Ser Cys Ala Ala Ser Gly Phe Thr Phe Ser Ser Tyr Ala Met Ser Trp
145                 150                 155                 160

Val Arg Gln Ala Pro Gly Lys Gly Leu Glu Trp Val Ser Ala Ile Ser
                165                 170                 175

Gly Ser Gly Gly Ser Thr Asn Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Gly Ser Ser
    210                 215                 220

Gly Trp Ser Glu Tyr Trp Gly Gln Gly Thr Leu Val Thr Val Ser Ser
225                 230                 235                 240


<210> SEQ ID NO 92
<211> LENGTH: 720
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 92
gatatccaaa tgactcagag cccttcatcc ctgagcgcca gcgtcggaga cagggtgacc 60
atcacgtgcc gggcatccca aggcattaga aataacttgg cgtggtatca gcaaaaacca 120
ggaaaggccc cgaagcgcct gatctacgcg gcctccaacc ttcagtcagg agtgccctcg 180
cgcttcaccg ggagcggtag cggaactgag tttaccctta tcgtgtcgtc cctgcagcca 240
gaggacttcg cgacctacta ctgcctccag catcactcgt acccgttgac ttcgggaggc 300
ggaaccaagg tcgaaatcaa acgcactggc tcgacgtcag ggtccggtaa accgggatcg 360
ggagaaggat cggaagtcca agtgctggag agcggaggcg gactcgtgca acctggcggg 420
tcgctgcggc tcagctgtgc cgcgtcgggt tttactttca gctcgtacgc tatgtcatgg 480
gtgcggcagg ctccgggaaa ggggctggaa tgggtgtccg ctatttccgg ctcgggtgga 540
agcaccaatt acgccgactc cgtgaaggga cgcttcacca tctcacggga taactccaag 600
aatactctgt acctccagat gaactcgctg agagccgagg acaccgcagt gtactactgc 660
gcagggtcaa gcggctggtc cgaatactgg ggacagggca ccctcgtcac tgtcagctcc 720

<210> SEQ ID NO 93
<211> LENGTH: 807
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 93
atggccctcc ctgtcaccgc cctgctgctt ccgctggctc ttctgctcca cgccgctcgg 60
cccgatatcc aaatgactca gagcccttca tccctgagcg ccagcgtcgg agacagggtg 120
accatcacgt gccgggcatc ccaaggcatt agaaataact tggcgtggta tcagcaaaaa 180
ccaggaaagg ccccgaagcg cctgatctac gcggcctcca accttcagtc aggagtgccc 240
tcgcgcttca ccgggagcgg tagcggaact gagtttaccc ttatcgtgtc gtccctgcag 300
ccagaggact tcgcgaccta ctactgcctc cagcatcact cgtacccgtt gacttcggga 360
ggcggaacca aggtcgaaat caaacgcact ggctcgacgt cagggtccgg taaaccggga 420
tcgggagaag gatcggaagt ccaagtgctg gagagcggag gcggactcgt gcaacctggc 480
gggtcgctgc ggctcagctg tgccgcgtcg ggttttactt tcagctcgta cgctatgtca 540
tgggtgcggc aggctccggg aaaggggctg gaatgggtgt ccgctatttc cggctcgggt 600
ggaagcacca attacgccga ctccgtgaag ggacgcttca ccatctcacg ggataactcc 660
aagaatactc tgtacctcca gatgaactcg ctgagagccg aggacaccgc agtgtactac 720
tgcgcagggt caagcggctg gtccgaatac tggggacagg gcaccctcgt cactgtcagc 780
tcccatcacc atcaccacca ccatcac 807

<210> SEQ ID NO 94
<211> LENGTH: 269
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

-continued

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser His His His His His His His His
            260                 265
```

<210> SEQ ID NO 95
<211> LENGTH: 1452
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
atggccctcc ctgtcaccgc cctgctgctt ccgctggctc ttctgctcca cgccgctcgg      60

cccgatatcc aaatgactca gagcccttca tccctgagcg ccagcgtcgg agacagggtg     120

accatcacgt gccgggcatc ccaaggcatt agaaataact tggcgtggta tcagcaaaaa     180

ccaggaaagg ccccgaagcg cctgatctac gcggcctcca accttcagtc aggagtgccc     240

tcgcgcttca ccgggagcgg tagcggaact gagtttaccc ttatcgtgtc gtccctgcag     300

ccagaggact tcgcgaccta ctactgcctc cagcatcact cgtacccgtt gacttcggga     360

ggcggaacca aggtcgaaat caaacgcact ggctcgacgt cagggtccgg taaaccggga     420

tcgggagaag gatcggaagt ccaagtgctg gagagcggag gcggactcgt gcaacctggc     480
```

-continued

```
gggtcgctgc ggctcagctg tgccgcgtcg ggttttactt tcagctcgta cgctatgtca    540

tgggtgcggc aggctccggg aaaggggctg gaatgggtgt ccgctatttc cggctcgggt    600

ggaagcacca attacgccga ctccgtgaag ggacgcttca ccatctcacg ggataactcc    660

aagaatactc tgtacctcca gatgaactcg ctgagagccg aggacaccgc agtgtactac    720

tgcgcagggt caagcggctg gtccgaatac tggggacagg gcaccctcgt cactgtcagc    780

tccaccacta ccccagcacc gaggccaccc accccggctc ctaccatcgc ctcccagcct    840

ctgtccctgc gtccggaggc atgtagaccc gcagctggtg gggccgtgca tacccggggt    900

cttgacttcg cctgcgatat ctacatttgg gcccctctgg ctggtacttg cggggtcctg    960

ctgctttcac tcgtgatcac tctttactgt aagcgcggtc ggaagaagct gctgtacatc   1020

tttaagcaac ccttcatgag gcctgtgcag actactcaag aggaggacgg ctgttcatgc   1080

cggttcccag aggaggagga aggcggctgc gaactgcgcg tgaaattcag ccgcagcgca   1140

gatgctccag cctacaagca ggggcagaac cagctctaca acgaactcaa tcttggtcgg   1200

agagaggagt acgacgtgct ggacaagcgg agaggacggg acccagaaat gggcgggaag   1260

ccgcgcagaa agaatcccca agagggcctg tacaacgagc tccaaaagga taagatggca   1320

gaagcctata gcgagattgg tatgaaaggg gaacgcagaa gaggcaaagg ccacgacgga   1380

ctgtaccagg gactcagcac cgccaccaag gacacctatg acgctcttca catgcaggcc   1440

ctgccgcctc gg                                                       1452


<210> SEQ ID NO 96
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Gly Ile Arg Asn Asn Leu Ala Trp Tyr Gln Gln Lys Pro Gly Lys Ala
    50                  55                  60

Pro Lys Arg Leu Ile Tyr Ala Ala Ser Asn Leu Gln Ser Gly Val Pro
65                  70                  75                  80

Ser Arg Phe Thr Gly Ser Gly Ser Gly Thr Glu Phe Thr Leu Ile Val
                85                  90                  95

Ser Ser Leu Gln Pro Glu Asp Phe Ala Thr Tyr Tyr Cys Leu Gln His
            100                 105                 110

His Ser Tyr Pro Leu Thr Ser Gly Gly Gly Thr Lys Val Glu Ile Lys
        115                 120                 125

Arg Thr Gly Ser Thr Ser Gly Ser Gly Lys Pro Gly Ser Gly Glu Gly
    130                 135                 140

Ser Glu Val Gln Val Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Tyr Ala Met Ser Trp Val Arg Gln Ala Pro Gly Lys Gly Leu Glu Trp
```

```
            180                 185                 190

Val Ser Ala Ile Ser Gly Ser Gly Gly Ser Thr Asn Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Gly Ser Ser Gly Trp Ser Glu Tyr Trp Gly Gln Gly Thr Leu
                245                 250                 255

Val Thr Val Ser Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Lys Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg
```

```
<210> SEQ ID NO 97
<211> LENGTH: 1183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

gtgaggctcc ggtgcccgtc agtgggcaga gcgcacatcg cccacagtcc ccgagaagtt      60

gggggaggg gtcggcaatt gaaccggtgc ctagagaagg tggcgcgggg taaactggga     120

aagtgatgtc gtgtactggc tccgcctttt tcccgagggt gggggagaac cgtatataag     180

tgcagtagtc gccgtgaacg ttctttttcg caacgggttt gccgccagaa cacaggtaag     240

tgccgtgtgt ggttcccgcg ggcctggcct ctttacgggt tatggccctt gcgtgccttg     300
```

-continued

```
aattacttcc acctggctgc agtacgtgat tcttgatccc gagcttcggg ttggaagtgg    360

gtgggagagt tcgaggcctt gcgcttaagg agccccttcg cctcgtgctt gagttgaggc    420

ctggcctggg cgctggggcc gccgcgtgcg aatctggtgg caccttcgcg cctgtctcgc    480

tgctttcgat aagtctctag ccatttaaaa tttttgatga cctgctgcga cgcttttttt    540

ctggcaagat agtcttgtaa atgcgggcca agatctgcac actggtattt cggtttttgg    600

ggccgcgggc ggcgacgggg cccgtgcgtc ccagcgcaca tgttcggcga ggcggggcct    660

gcgagcgcgg ccaccgagaa tcggacgggg gtagtctcaa gctggccggc ctgctctggt    720

gcctggcctc gcgccgccgt gtatcgcccc gccctgggcg gcaaggctgg cccggtcggc    780

accagttgcg tgagcggaaa gatggccgct tcccggccct gctgcaggga gctcaaaatg    840

gaggacgcgg cgctcgggag agcgggcggg tgagtcaccc acacaaagga aaagggcctt    900

tccgtcctca gccgtcgctt catgtgactc cacggagtac cgggcgccgt ccaggcacct    960

cgattagttc tcgagctttt ggagtacgtc gtctttaggt tggggggagg ggttttatgc   1020

gatggagttt ccccacactg agtgggtgga gactgaagtt aggccagctt ggcacttgat   1080

gtaattctcc ttggaatttg ccctttttga gtttggatct tggttcattc tcaagcctca   1140

gacagtggtt caaagttttt ttcttccatt tcaggtgtcg tga                     1183


<210> SEQ ID NO 98
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

gagatccagc tccaacagag cggagccgaa ctggtcaaac cgggagcgtc ggtgaagttg     60

tcatgcactg gatcgggctt caacatcgag gattactaca tccactgggt caagcaacgc    120

accgagcagg ggctggaatg gatcggacgg atcgaccccg aaaacgatga aaccaagtac    180

gggcctatct tccaaggacg ggccaccatt acggctgaca cgtcaagcaa taccgtctac    240

ctccagcttt ccagcctgac ctccgaggac actgccgtgt actactgcgc cttcagagga    300

ggcgtgtact ggggaccagg aaccactttg accgtgtcca gcggaggcgg tggatcagga    360

ggaggaggct caggcggtgg cggctcgcac atggacgtgg tcatgactca gtccccgctg    420

accctgtcgg tggcaattgg acagagcgca tccatctcgt gcaagagctc acagtcgctg    480

ctggattccg acggaaagac ttatctgaac tggctgctcc aaagaccagg gcaatcaccg    540

aaacgcctta tctccctggt gtcgaaactc gactcgggtg tgccggatcg gtttaccggt    600

agcgggtccg gcacggactt cactctccgc atttcgaggg tggaagcgga ggatctcggg    660

atctactact gttggcaggg aacccacttc cctgggactt ttggaggcgg aactaagctg    720

gaaatcaag                                                            729


<210> SEQ ID NO 99
<211> LENGTH: 112
<212> TYPE: PRT
<213> ORGANISM: Homo sapiens

<400> SEQUENCE: 99

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
```

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 100
<211> LENGTH: 336
<212> TYPE: DNA
<213> ORGANISM: Homo sapiens

<400> SEQUENCE: 100

agagtgaagt tcagcaggag cgcagacgcc cccgcgtacc agcagggcca gaaccagctc      60

tataacgagc tcaatctagg acgaagagag gagtacgatg ttttggacaa gagacgtggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggtctca gtacagccac caaggacacc     300

tacgacgccc ttcacatgca ggccctgccc cctcgc                               336


<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Glu Glu Lys Lys Gly Asn Tyr Val Val Thr Asp His Cys
1               5                   10


<210> SEQ ID NO 102
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 103
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 103
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 104
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Met
225                 230

<210> SEQ ID NO 105
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gagagcaagt acggccctcc ctgcccccct tgccctgccc ccgagttcct gggcggaccc    60
agcgtgttcc tgttcccccc caagcccaag gacaccctga tgatcagccg gacccccgag   120

-continued gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 106
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

Arg Trp Pro Glu Ser Pro Lys Ala Gln Ala Ser Ser Val Pro Thr Ala
1 5 10 15

Gln Pro Gln Ala Glu Gly Ser Leu Ala Lys Ala Thr Thr Ala Pro Ala
20 25 30

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys
165 170 175

Leu Ser Leu Asn Leu Leu Ala Ser Ser Asp Pro Pro Glu Ala Ala Ser
180 185 190

Trp Leu Leu Cys Glu Val Ser Gly Phe Ser Pro Pro Asn Ile Leu Leu
195 200 205

Met Trp Leu Glu Asp Gln Arg Glu Val Asn Thr Ser Gly Phe Ala Pro
210 215 220

Ala Arg Pro Pro Pro Gln Pro Gly Ser Thr Thr Phe Trp Ala Trp Ser
225 230 235 240

Val Leu Arg Val Pro Ala Pro Pro Ser Pro Gln Pro Ala Thr Tyr Thr
245 250 255

Cys Val Val Ser His Glu Asp Ser Arg Thr Leu Leu Asn Ala Ser Arg
260 265 270

Ser Leu Glu Val Ser Tyr Val Thr Asp His
275 280

<210> SEQ ID NO 107
<211> LENGTH: 847
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgcccca 480 cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Gly Gly Gly Gly Ser Gly Gly Gly Gly Ser
1 5 10

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
ggtggcggag gttctggagg tggaggttcc 30

<210> SEQ ID NO 110
<211> LENGTH: 30
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1, 2, 3, 4, 5, or 6
      "Gly Gly Gly Gly Ser" repeating units
<220> FEATURE:
<223> OTHER INFORMATION: See specification as filed for detailed
      description of substitutions and preferred embodiments

<400> SEQUENCE: 110

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 111
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa                                     150


<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gly Gly Ser
1


<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Gly Gly Gly Ser Gly Gly Gly Gly Ser Gly Gly Gly Gly Ser Gly
1               5                   10                  15

Gly Gly Gly Ser
            20


<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114
```

```
Gly Gly Gly Gly Ser Gly Gly Gly Gly Ser Gly Gly Gly Gly Ser
1               5                   10                  15


<210> SEQ ID NO 115
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass between 50 and
      5,000 nucleotides
<220> FEATURE:
<223> OTHER INFORMATION: See specification as filed for detailed
      description of substitutions and preferred embodiments

<400> SEQUENCE: 115

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa aaaaaaaaaa aaaaaaaaaa    420

aaaaaaaaaa aaaaaaaaaa aaaaaaaaaa aaaaaaaaaa aaaaaaaaaa aaaaaaaaaa    480

aaaaaaaaaa aaaaaaaaaa aaaaaaaaaa aaaaaaaaaa aaaaaaaaaa aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaaaaaaaa aaaaaaaaaa aaaaaaaaaa aaaaaaaaaa aaaaaaaaaa    720

aaaaaaaaaa aaaaaaaaaa aaaaaaaaaa aaaaaaaaaa aaaaaaaaaa aaaaaaaaaa    780

aaaaaaaaaa aaaaaaaaaa aaaaaaaaaa aaaaaaaaaa aaaaaaaaaa aaaaaaaaaa    840

aaaaaaaaaa aaaaaaaaaa aaaaaaaaaa aaaaaaaaaa aaaaaaaaaa aaaaaaaaaa    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaaaaaaaaa   1020

aaaaaaaaaa aaaaaaaaaa aaaaaaaaaa aaaaaaaaaa aaaaaaaaaa aaaaaaaaaa   1080

aaaaaaaaaa aaaaaaaaaa aaaaaaaaaa aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680
```

-continued

```
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
```

aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 116
<211> LENGTH: 2000
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(2000)
<223> OTHER INFORMATION: This sequence may encompass between 50 and
2,000 nucleotides

<400> SEQUENCE: 116
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900

-continued aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa 2000

<210> SEQ ID NO 117
<211> LENGTH: 100
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 117
tttttttttt tttttttttt tttttttttt tttttttttt tttttttttt tttttttttt 60
tttttttttt tttttttttt tttttttttt tttttttttt 100

<210> SEQ ID NO 118
<211> LENGTH: 5000
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(5000)
<223> OTHER INFORMATION: This sequence may encompass between 50 and
5,000 nucleotides

<400> SEQUENCE: 118
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300

-continued

```
tttttttttt tttttttttt tttttttttt tttttttttt tttttttttt tttttttttt    360
tttttttttt tttttttttt tttttttttt tttttttttt tttttttttt tttttttttt    420
tttttttttt tttttttttt tttttttttt tttttttttt tttttttttt tttttttttt    480
tttttttttt tttttttttt tttttttttt tttttttttt tttttttttt tttttttttt    540
tttttttttt tttttttttt tttttttttt tttttttttt tttttttttt tttttttttt    600
tttttttttt tttttttttt tttttttttt tttttttttt tttttttttt tttttttttt    660
tttttttttt tttttttttt tttttttttt tttttttttt tttttttttt tttttttttt    720
tttttttttt tttttttttt tttttttttt tttttttttt tttttttttt tttttttttt    780
tttttttttt tttttttttt tttttttttt tttttttttt tttttttttt tttttttttt    840
tttttttttt tttttttttt tttttttttt tttttttttt tttttttttt tttttttttt    900
tttttttttt tttttttttt tttttttttt tttttttttt tttttttttt tttttttttt    960
tttttttttt tttttttttt tttttttttt tttttttttt tttttttttt tttttttttt   1020
tttttttttt tttttttttt tttttttttt tttttttttt tttttttttt tttttttttt   1080
tttttttttt tttttttttt tttttttttt tttttttttt tttttttttt tttttttttt   1140
tttttttttt tttttttttt tttttttttt tttttttttt tttttttttt tttttttttt   1200
tttttttttt tttttttttt tttttttttt tttttttttt tttttttttt tttttttttt   1260
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
```

-continued

```
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
tttttttttt tttttttttt tttttttttt tttttttttt tttttttttt tttttttttt   3720
tttttttttt tttttttttt tttttttttt tttttttttt tttttttttt tttttttttt   3780
tttttttttt tttttttttt tttttttttt tttttttttt tttttttttt tttttttttt   3840
tttttttttt tttttttttt tttttttttt tttttttttt tttttttttt tttttttttt   3900
tttttttttt tttttttttt tttttttttt tttttttttt tttttttttt tttttttttt   3960
tttttttttt tttttttttt tttttttttt tttttttttt tttttttttt tttttttttt   4020
tttttttttt tttttttttt tttttttttt tttttttttt tttttttttt tttttttttt   4080
tttttttttt tttttttttt tttttttttt tttttttttt tttttttttt tttttttttt   4140
tttttttttt tttttttttt tttttttttt tttttttttt tttttttttt tttttttttt   4200
tttttttttt tttttttttt tttttttttt tttttttttt tttttttttt tttttttttt   4260
tttttttttt tttttttttt tttttttttt tttttttttt tttttttttt tttttttttt   4320
tttttttttt tttttttttt tttttttttt tttttttttt tttttttttt tttttttttt   4380
tttttttttt tttttttttt tttttttttt tttttttttt tttttttttt tttttttttt   4440
tttttttttt tttttttttt tttttttttt tttttttttt tttttttttt tttttttttt   4500
tttttttttt tttttttttt tttttttttt tttttttttt tttttttttt tttttttttt   4560
tttttttttt tttttttttt tttttttttt tttttttttt tttttttttt tttttttttt   4620
tttttttttt tttttttttt tttttttttt tttttttttt tttttttttt tttttttttt   4680
tttttttttt tttttttttt tttttttttt tttttttttt tttttttttt tttttttttt   4740
tttttttttt tttttttttt tttttttttt tttttttttt tttttttttt tttttttttt   4800
tttttttttt tttttttttt tttttttttt tttttttttt tttttttttt tttttttttt   4860
tttttttttt tttttttttt tttttttttt tttttttttt tttttttttt tttttttttt   4920
tttttttttt tttttttttt tttttttttt tttttttttt tttttttttt tttttttttt   4980
tttttttttt tttttttttt                                               5000
```

<210> SEQ ID NO 119
<211> LENGTH: 5000
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(5000)
<223> OTHER INFORMATION: This sequence may encompass between 100 and 5,000 nucleotides

<400> SEQUENCE: 119
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920

```
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
```

aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 120
<211> LENGTH: 400
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(400)
<223> OTHER INFORMATION: This sequence may encompass between 100 and 400
nucleotides
<220> FEATURE:
<223> OTHER INFORMATION: See specification as filed for detailed
description of substitutions and preferred embodiments

<400> SEQUENCE: 120
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa 400

<210> SEQ ID NO 121
<211> LENGTH: 487
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Met Val Leu Leu Val Thr Ser Leu Leu Leu Cys Glu Leu Pro His Pro
1 5 10 15

Ala Phe Leu Ile Ile Pro Asp Ile Gln Met Thr Gln Ser Pro Ser Ser
20 25 30

Leu Ser Ala Ser Val Gly Asp Arg Val Ile Ile Ile Cys Arg Ala Ser
35 40 45

```
Gln Gly Ile Arg Asn Asn Leu Ala Trp Tyr Gln Gln Lys Pro Gly Lys
    50                  55                  60

Ala Pro Lys Arg Leu Ile Tyr Ala Ala Ser Asn Leu Gln Ser Gly Val
65                  70                  75                  80

Pro Ser Arg Phe Thr Gly Ser Gly Ser Gly Thr Glu Phe Thr Leu Ile
                85                  90                  95

Val Ser Ser Leu Gln Pro Glu Asp Phe Ala Thr Tyr Tyr Cys Leu Gln
            100                 105                 110

His His Ser Tyr Pro Leu Thr Ser Gly Gly Gly Thr Lys Val Glu Ile
        115                 120                 125

Lys Phe Thr Gly Ser Thr Ser Gly Ser Gly Lys Pro Gly Ser Gly Glu
    130                 135                 140

Gly Ser Glu Val Gln Val Leu Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Ser Tyr Ala Met Ser Trp Val Arg Gln Ala Pro Gly Lys Gly Leu Glu
            180                 185                 190

Trp Val Ser Ala Ile Ser Gly Ser Gly Gly Ser Thr Asn Tyr Ala Asp
        195                 200                 205

Ser Val Lys Gly Arg Phe Thr Ile Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Gly Ser Ser Gly Trp Ser Glu Tyr Trp Gly Gln Gly Thr
                245                 250                 255

Leu Val Thr Val Ser Ser Ala Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
```

465 470 475 480

Met Gln Ala Leu Pro Pro Arg
485

<210> SEQ ID NO 122
<211> LENGTH: 114
<212> TYPE: PRT
<213> ORGANISM: Mus musculus

<400> SEQUENCE: 122

Glu Ile Gln Leu Gln Gln Ser Gly Ala Glu Leu Val Lys Pro Gly Ala
1 5 10 15

Ser Val Lys Leu Ser Cys Thr Gly Ser Gly Phe Asn Ile Glu Asp Tyr
20 25 30

Tyr Ile His Trp Val Lys Gln Arg Thr Glu Gln Gly Leu Glu Trp Ile
35 40 45

Gly Arg Ile Asp Pro Glu Asn Asp Glu Thr Lys Tyr Gly Pro Ile Phe
50 55 60

Gln Gly Arg Ala Thr Ile Thr Ala Asp Thr Ser Ser Asn Thr Val Tyr
65 70 75 80

Leu Gln Leu Ser Ser Leu Thr Ser Glu Asp Thr Ala Val Tyr Tyr Cys
85 90 95

Ala Phe Arg Gly Gly Val Tyr Trp Gly Pro Gly Thr Thr Leu Thr Val
100 105 110

Ser Ser

<210> SEQ ID NO 123
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Glu Ile Gln Leu Val Gln Ser Gly Ala Glu Val Lys Lys Pro Gly Ala
1 5 10 15

Thr Val Lys Ile Ser Cys Lys Gly Ser Gly Phe Asn Ile Glu Asp Tyr
20 25 30

Tyr Ile His Trp Val Gln Gln Ala Pro Gly Lys Gly Leu Glu Trp Met
35 40 45

Gly Arg Ile Asp Pro Glu Asn Asp Glu Thr Lys Tyr Gly Pro Ile Phe
50 55 60

Gln Gly Arg Val Thr Ile Thr Ala Asp Thr Ser Thr Asn Thr Val Tyr
65 70 75 80

Met Glu Leu Ser Ser Leu Arg Ser Glu Asp Thr Ala Val Tyr Tyr Cys
85 90 95

Ala Phe Arg Gly Gly Val Tyr Trp Gly Gln Gly Thr Thr Val Thr Val
100 105 110

Ser Ser

<210> SEQ ID NO 124
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser

<210> SEQ ID NO 125
<211> LENGTH: 112
<212> TYPE: PRT
<213> ORGANISM: Mus musculus

<400> SEQUENCE: 125

Asp Val Val Met Thr Gln Ser Pro Leu Thr Leu Ser Val Ala Ile Gly
1               5                   10                  15

Gln Ser Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Ile Tyr Tyr Cys Trp Gln Gly
                85                  90                  95

Thr His Phe Pro Gly Thr Phe Gly Gly Gly Thr Lys Leu Glu Ile Lys
            100                 105                 110

<210> SEQ ID NO 126
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110


<210> SEQ ID NO 127
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Asp Gly Lys Thr Tyr Leu Asn Trp Leu Gln Gln Lys Pro Gly Gln Pro
        35                  40                  45

Pro Lys Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110
```